(12) United States Patent
Matsuya et al.

(10) Patent No.: US 9,085,540 B2
(45) Date of Patent: Jul. 21, 2015

(54) PYRAZINECARBOXAMIDE COMPOUND

(71) Applicant: Astellas Pharma Inc., Tokyo (JP)

(72) Inventors: Takahiro Matsuya, Tokyo (JP); Yutaka Kondoh, Tokyo (JP); Itsuro Shimada, Tokyo (JP); Shigetoshi Kikuchi, Tokyo (JP); Maiko Iida, Tokyo (JP); Kenichi Onda, Tokyo (JP); Hiroki Fukudome, Tokyo (JP); Yukihiro Takemoto, Tokyo (JP); Nobuaki Shindou, Tokyo (JP); Hideki Sakagami, Tokyo (JP); Hisao Hamaguchi, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 13/990,006

(22) PCT Filed: Jan. 15, 2013

(86) PCT No.: PCT/JP2013/050579
§ 371 (c)(1),
(2) Date: May 28, 2013

(87) PCT Pub. No.: WO2013/108754
PCT Pub. Date: Jul. 25, 2013

(65) Prior Publication Data
US 2014/0323463 A1 Oct. 30, 2014

(30) Foreign Application Priority Data
Jan. 17, 2012 (JP) .................. 2012-007525

(51) Int. Cl.
*A61K 31/497* (2006.01)
*C07D 241/24* (2006.01)
*C07D 403/12* (2006.01)
*C07D 401/14* (2006.01)
*C07D 401/12* (2006.01)
*C07D 471/10* (2006.01)
*C07D 491/113* (2006.01)
*C07D 405/14* (2006.01)
*C07D 413/14* (2006.01)
*C07D 403/14* (2006.01)
*C07D 405/12* (2006.01)
*C07D 241/28* (2006.01)
*C07D 451/06* (2006.01)
*C07D 487/08* (2006.01)
*C07D 487/10* (2006.01)
*C07D 413/12* (2006.01)

(52) U.S. Cl.
CPC ............ *C07D 241/24* (2013.01); *C07D 241/28* (2013.01); *C07D 401/12* (2013.01); *C07D 401/14* (2013.01); *C07D 403/12* (2013.01); *C07D 403/14* (2013.01); *C07D 405/12* (2013.01); *C07D 405/14* (2013.01); *C07D 413/12* (2013.01); *C07D 413/14* (2013.01); *C07D 451/06* (2013.01); *C07D 471/10* (2013.01); *C07D 487/08* (2013.01); *C07D 487/10* (2013.01); *C07D 491/113* (2013.01)

(58) Field of Classification Search
CPC ... C07D 401/12; C07D 401/14; C07D 403/14
See application file for complete search history.

(56) References Cited

U.S. PATENT DOCUMENTS

| 2002/0173509 A1 | 11/2002 | Himmelsbach et al. |
| 2005/0059678 A1 | 3/2005 | Wissner et al. |
| 2005/0250761 A1 | 11/2005 | Fakhoury et al. |
| 2010/0029610 A1 | 2/2010 | Singh et al. |
| 2010/0179120 A1 | 7/2010 | Lee et al. |
| 2012/0040968 A1 | 2/2012 | Shimada et al. |
| 2012/0094999 A1 | 4/2012 | Gray et al. |
| 2013/0137709 A1 | 5/2013 | Gray et al. |

FOREIGN PATENT DOCUMENTS

| WO | WO 02/50043 A1 | 6/2002 |
| WO | WO 2005/028443 A2 | 3/2005 |
| WO | WO 2005/034955 A1 | 4/2005 |
| WO | WO 2005/107758 A1 | 11/2005 |
| WO | WO 2008/117050 A1 | 10/2008 |
| WO | WO 2008/150118 A2 | 12/2008 |
| WO | WO 2009/051822 A1 | 4/2009 |
| WO | WO 2009/158571 A1 | 12/2009 |

(Continued)

OTHER PUBLICATIONS

Office Action issued on Jan. 14, 2014 in the corresponding Japanese Patent Application No. 2013-513321 (with English Translation).

(Continued)

*Primary Examiner* — Brian McDowell
(74) *Attorney, Agent, or Firm* — Oblon, McClelland, Maier & Neustadt, L.L.P.

(57) ABSTRACT

Compounds of formula (I):

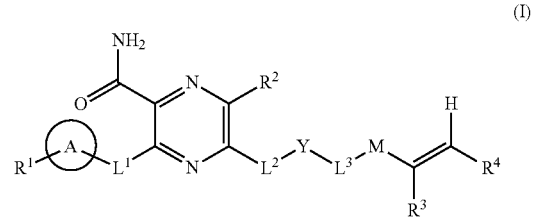

in which the variables are defined herein, are useful for the treatment of cancer in patients which express the EGFR T790M mutation.

19 Claims, 12 Drawing Sheets

(56) References Cited

FOREIGN PATENT DOCUMENTS

| WO | WO 2010/123870 A1 | 10/2010 |
|----|-------------------|---------|
| WO | 2010 128659 | 11/2010 |
| WO | 2010 129053 | 11/2010 |
| WO | WO 2010/128659 | 11/2010 |
| WO | WO 2010/129053 | 11/2010 |
| WO | WO 2011/090760 A1 | 7/2011 |
| WO | WO 2011/140338 A1 | 11/2011 |

OTHER PUBLICATIONS

Office Action issued on Feb. 18, 2014 in the corresponding Japanese Patent Application No. 2013-513321 (with English Translation).
International Search Report Issued Mar. 5, 2013 in PCT/JP13/50579 Filed Jan. 15, 2013 (with Translation of Category).
International Search Report issued Mar. 5, 2013, in International Application No. PCT/JP2013/050579 (English translation only).
Wenjun Zhou, et al., "Novel mutant-selective EGFR kinase inhibitors against EGFR T790M", Nature (08622), vol. 462, No. 7276, Dec. 31, 2009, pp. 1070-1074.
Eunice L. Kwak, et al., "Irreversible inhibitors of the EGF receptor may circumvent acquired resistance to gefitinib", PNAS, vol. 102, No. 21, May 24, 2005, pp. 7665-7670.
Eskens Falm, et al., "A phase I dose escalation study of BIBW 2992, an irreversible dual inhibitor of epidermal growth factor receptor I (EGFR) and 2 (HER2) tyrosine kinase in a 2-week on, 2-week off schedule in patients with advanced solid tumours", British Journal of Cancer, vol. 98, 2008, pp. 80-85.
D. Li, et al,, "BIBW2992, an irreversible EGFR/HER2 inhibitor highly effective in preclinical lung cancer models", Oncogene, vol. 27, 2008, pp. 4702-4711.
Jeffrey A. Engelman, et al., "PF00299804, an Irreversible Pan-ERBB Inhibitor, Is Effective in Lung Cancer Models with EGFR and ERBB2 Mutations that Are Resistant to Gefitinib", Cancer Research, vol. 67, No. 24, 2007, pp. 11924-11932.
WHO Drug Information, vol. 24, No. 2, 2010, pp. 132.

PYRAZINECARBOXAMIDE COMPOUND

CROSS REFERENCES TO RELATED APPLICATIONS

This application is a 371 of International Patent Application No. PCT/JP13/050579, filed on Jan. 15, 2013, and claims priority to Japanese Patent Application No. 2012-007525, filed on Jan. 17, 2012.

TECHNICAL FIELD

The present invention relates to a pyrazinecarboxamide compound which is useful as an active ingredient of a pharmaceutical composition, for example, a pharmaceutical composition for treating cancer.

BACKGROUND ART

Lung cancer is caused by disordered proliferation of tracheal, bronchial, or alveolar cells as a result of loss of their normal functions. The number of people who have died of lung cancer is the largest of the total of cancer deaths, accounting for 17% of the total death, and about 1.3 million people worldwide die of lung cancer per year.

Treatments for lung cancer are roughly divided into surgical operation (surgical therapy), anticancer agents (chemotherapy) and radioactive irradiation (radiation therapy), but the effectiveness of treatment will vary depending on the tissue type of lung cancer. For example, although a definite diagnosis of lung cancer is made by a pathologist based on his cytohistopathological diagnosis on a microscope specimen, small cell lung cancer, which constitutes about 20% of lung cancer cases, has often reached an advanced stage at the time of discovery because it generally has a high grade of malignancy and will rapidly grow and spread and will often metastasize to other organs. For this reason, chemotherapy or radiation therapy is often used for treatment of this cancer, but the prognosis is poor because small cell lung cancer will often recur although it is relatively sensitive to these therapies. On the other hand, in the case of non-small cell lung cancer, which constitutes the remainder of about 80%, surgical therapy is considered for use until a certain stage, but there is little opportunity to use surgical operation in the subsequent stages where chemotherapy or radiation therapy is mainly used for treatment. Therefore, chemotherapy is an important choice for treatment of any type of lung cancer.

EGFR (Epidermal Growth Factor Receptor) is a receptor type tyrosine kinase recognizing epidermal growth factor (EGF) as a ligand, and plays an important role in differentiation, development, proliferation, and survival of cells in normal tissues. It has been hitherto reported that EGFR is overexpressed in various malignant tumors (Journal of Cellular Physiology Vol. 194, No. 1, p. 13, 2003), and causes acceleration of cell proliferation and division of cancer cells, metastasis, or the like (Endocrine-Related Cancer, Vol. 8, No. 1, p. 11, 2001). Further, it is thought that the overexpression of EGFR is a factor resulting in poor prognosis (Journal of Clinical Oncology, Vol. 21, No. 20, p. 3798, 2003).

It is known that in some patients with non-small cell lung cancer (NSCLC), cancer cells have mutation for constitutive activation of the kinase activity of EGFR, such as mutation of leucine to arginine at the position 858 (L858R mutation) and deletion mutation of the exon 19 of EGFR, and gefitinib and erlotinib, which are inhibitors of the tyrosine kinase activity of EGFR, exhibit high effectiveness (Proc. Natl. Acad. Sci. USA Vol. 101, No. 36, p. 13306, 2004; and Science Vol. 304, p. 1497, 2004). However, resistance to these inhibitors is shown in many patients after treatment. It is known that secondary mutation in EGFR occurs in about half of these patients with resistance and threonine is replaced with methionine at the position 790 (T790M mutation), and a recombinant enzyme of EGFR having T790M mutation introduced thereinto or cells of H1975 or the like which endogenously have T790M mutation exhibit substantial resistance to gefitinib and erlotinib (Cancer Res. Vol. 67, No. 13, p. 6253, 2007, Oncogene Vol. 28, p. S24, 2009). In addition, it has been reported that an irreversible inhibitor of an EGFR T790M mutation kinase inhibits the proliferation of cell lines expressing EGFR T790M mutation, and regresses the tumor volume in an EGFR resistant mutation (T790M/L858R) model mouse (Non-Patent Document 1).

It has been reported that a compound represented by the following formula (A) has an irreversible inhibitory activity on an EGFR T790M mutation kinase (Patent Document 1 and Non-Patent Document 1), and the inhibitory activity on an EGFR T790M mutation kinase of a pyrimidine compound disclosed as Compound 2-2 (WZ4002) has been disclosed.

[Chem. 1]

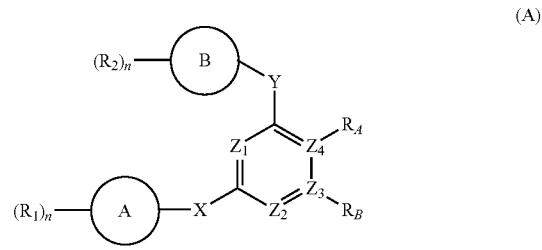

(A)

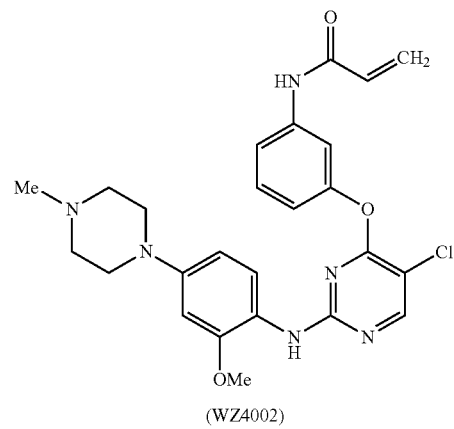

Compound 2-2

(WZ4002)

(For the symbols in the formulae, refer to the corresponding publications)

It has been reported that the pyrimidine compounds represented by the following formula (B) (Patent Documents 2 and 4), the formula (C) (Patent Documents 3 and 5), and the formula (D) (Patent Documents 3 and 5) have an inhibitory activity on various kinases containing EGFR, and an EGFR T790M mutation kinase, and it is also described that the pyrimidine compounds are useful for treatment of cancer.

[Chem. 2]

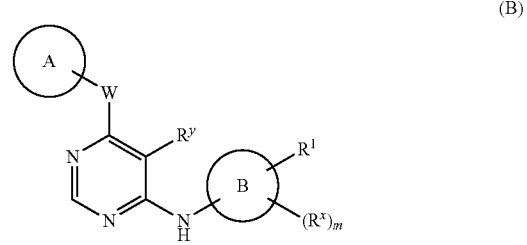

(B)

-continued

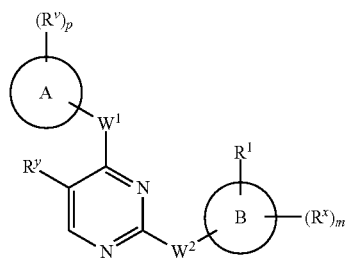
(C)

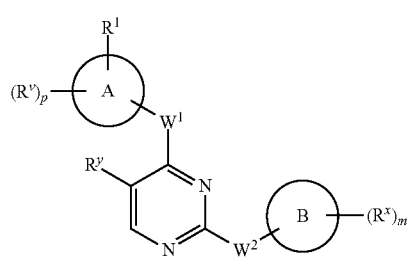
(D)

(For the symbols in the formulae, refer to each of the publications)

It has been reported that a compound having a pyrazine ring represented by the following formula (E) has an inhibitory activity on JAK and Trk among the tyrosine kinases, and is useful for treatment of myeloproliferative diseases or cancer (Patent Document 6).

[Chem. 3]

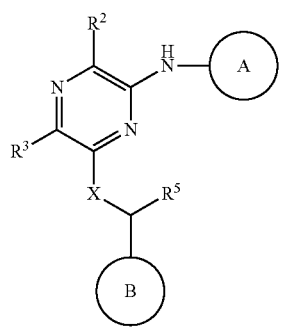
(E)

(wherein Ring A represents a 5- to 6-membered heteroaryl ring which may be substituted with one or more $R^1$'s, $R^1$ represents $C_{1-6}$ alkyl or the like, Ring B represents a carbocycle or heterocycle which may be substituted with one or more $R^6$'s, $R^6$ represents $C_{1-6}$ alkyl, —N($R^{6a}$)C(O)$R^{6b}$, or the like, $R^{6a}$ represents H, $C_{1-6}$ alkyl, or the like, $R^{6b}$ represents $C_{1-6}$ alkyl, $C_{2-6}$ alkenyl, or the like, $R^2$ represents —C(O)N($R^{2a}$)$_2$ or the like, $R^{2a}$ represents H, $C_{1-6}$ alkyl, or the like, $R^3$ represents $C_{1-6}$ alkyl or the like, X represents —O— or the like, and $R^5$ represents $C_{1-6}$ alkyl or the like. For the other symbols in the formulae, refer to the corresponding publication.)

However, there is no disclosure of an action on an EGFR T790M mutation or an EGFR kinase in the Document above, and further, the pyrazinecarboxamide compound represented by the formula (I) as described later according to the present invention has a different structure from that of the compound of the formula (E) in $L^2$.

It has been reported that a compound represented by the following formula (F) has an inhibitory activity on an EGFR and a mutation EGFR kinase including T790M mutation, and an inhibitory activity on an EGFR T790M mutation kinase of a pyrimidine compound disclosed as Compound XIII-1 has been described (Patent Document 7).

[Chem. 4]

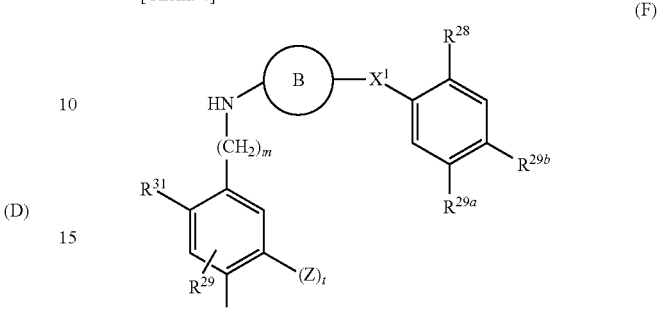
(F)

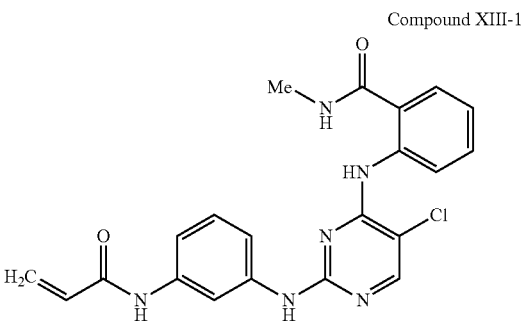
Compound XIII-1

(wherein $X^1$ represents —O—, —NH—, or the like, B represents pyridine-2,4-diyl, pyrimidine-2,4-diyl, or the like, and m represents 0 or 1. For the other symbols, refer to the corresponding publication.)

It has been reported that a compound represented by the following formula (G) inhibits the activity of a Her-2 kinase and an EGFR kinase (Patent Documents 8 and 9). Further, it has been reported that a compound represented as HKI-272 of the following formula (also called neratinib) has a proliferation inhibitory activity on EGFR T790M mutation cell lines (Non-Patent Document 2).

[Chem. 5]

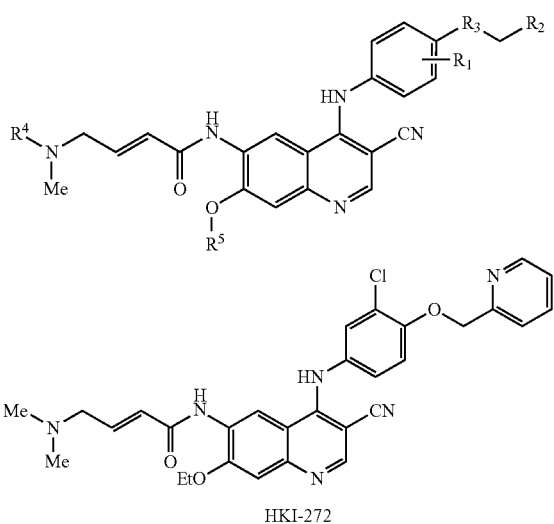
(G)

HKI-272

(For the symbols in the formulae, refer to the corresponding publications).

Furthermore, it has been reported that a compound represented by the following formula (H) has an inhibitory activity on an EGFR and a mutation EGFR kinase including T790M mutation (Patent Document 10). Further, an inhibitory activity on EGFR and mutation EGFR kinases of a compound represented as BIBW2992 (also called afatinib) and an action on a cancer-bearing mouse with EGFR T790M mutation expressing cells have been reported (Non-Patent Documents 3 and 4).

[Chem. 6]

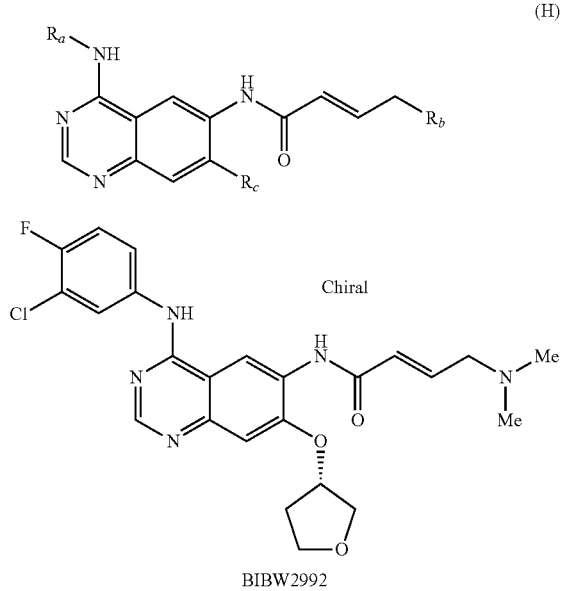

(For the symbols in the formulae, refer to the corresponding publications).

It has been reported that a compound represented by the following formula (J) has an inhibitory activity on an EGFR and a mutation EGFR kinase including T790M mutation (Patent Document 11). Further, it has been reported that a compound disclosed as PF-00299804 of the following formula (also called dacomitinib) has an inhibitory activity on an EGFR and mutation EGFR kinase and an action in a cancer-bearing mouse with EGFR T790M mutation expressing cells (Non-Patent Documents 5 and 6).

[Chem. 7]

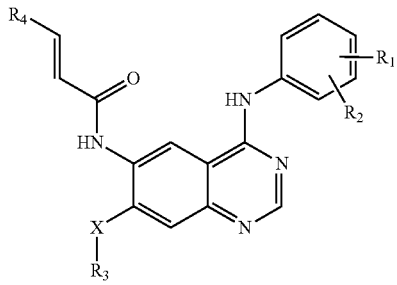

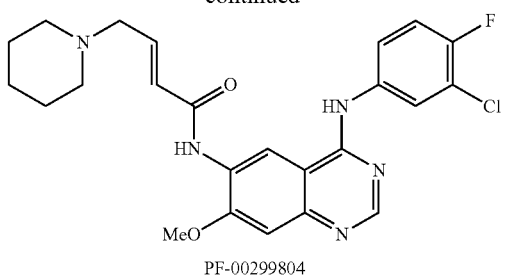

(For the symbols in the formulae, refer to the corresponding publications).

It has been reported that a pyrazinecarboxamide compound included in the following formula (K) has an inhibitory activity on ALK, RET, ROS, and FLT3 among the tyrosine kinases, and is useful for treatment of various cancers (Patent Document 12).

[Chem. 8]

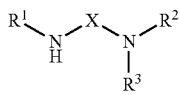

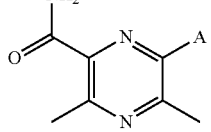

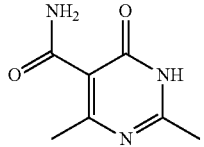

(wherein X represents a group of the formula (K-1) or the formula (K-2). For the other symbols, refer to the corresponding publication.)

However, there is no disclosure of an action on EGFR T790M mutation or EGFR kinase in the above-described documents, and further, the pyrazinecarboxamide compound represented by the following formula (I) according to the present invention has a different structure from that of the compound of the formula (K) in that a substituted vinyl group is bonded to $-L^2-Y-L^3-M$.

It has been reported that a quinazoline compound represented by the following formula (L) has an inhibitory activity on an EGFR and a mutation EGFR kinase including T790M mutation (Patent Document 13).

[Chem. 9]

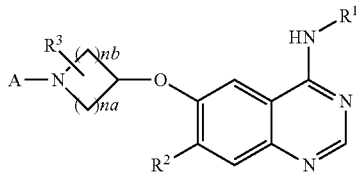

(wherein A represents acyl substituted with alkyne or alkene. For the details, refer to the corresponding publication.)

RELATED ART

Patent Documents

[Patent Document 1] Pamphlet of International Publication WO 2010/129053
[Patent Document 2] Pamphlet of International Publication WO 2009/051822
[Patent Document 3] Pamphlet of International Publication WO 2009/158571
[Patent Document 4] Pamphlet of International Publication WO 2010/123870
[Patent Document 5] Pamphlet of International Publication WO 2011/090760
[Patent Document 6] Pamphlet of International Publication WO 2008/117050
[Patent Document 7] Pamphlet of International Publication WO 2011/140338
[Patent Document 8] Pamphlet of International Publication WO 2005/028443
[Patent Document 9] Pamphlet of International Publication WO 2005/034955
[Patent Document 10] Pamphlet of International Publication WO 2002/050043
[Patent Document 11] Pamphlet of International Publication WO 2005/107758
[Patent Document 12] Pamphlet of International Publication WO 2010/128659
[Patent Document 13] Pamphlet of International Publication WO 2008/150118

Non-Patent Documents

[Non-Patent Document 1] Nature Vol. 462, No. 7276, p. 1070, 2009
[Non-Patent Document 2] Proc. Natl. Acad. Sci. USA Vol. 102, No. 21, p. 7665, 2005
[Non-Patent Document 3] Br. J. Cancer, Vol. 98, p. 80, 2008
[Non-Patent Document 4] Oncogene Vol. 27, p. 4702, 2008
[Non-Patent Document 5] Cancer Res. Vol. 67, No. 24, p. 11924, 2007
[Non-Patent Document 6] WHO Drug Information Vol. 24, No. 2, p. 132, 2010

DISCLOSURE OF INVENTION

Problems to be Solved by the Invention

A compound which is useful as an active ingredient of a pharmaceutical composition, for example, a pharmaceutical composition for treating EGFR T790M mutation positive cancer, is provided.

Means for Solving the Problems

The present inventors have extensively studied compounds which are useful as an active ingredient of a pharmaceutical composition for treating EGFR T790M mutation positive cancer, and as a result, they have found that pyrazinecarboxamide compounds of the formula (I) have an excellent inhibitory activity on an EGFR T790M mutation kinase and are useful as an active ingredient of a pharmaceutical composition for treating EGFR T790M mutation positive cancer, thereby completing the present invention.

That is, the present invention relates to a compound of the formula (I) or a salt thereof, and a pharmaceutical composition comprising a compound of the formula (I) or a salt thereof and an excipient:

[Chem. 10]

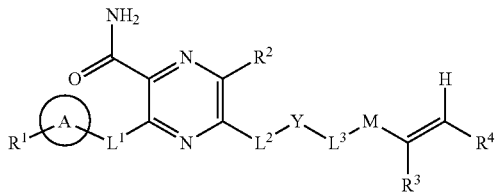

(wherein
$R^1$ represents lower alkyl which may be substituted, —O-lower alkyl which may be substituted, —$NH_2$, —NH-lower alkyl which may be substituted, —N(lower alkyl which may be substituted)$_2$, -$L^4$-cycloalkyl which may be substituted, -$L^4$-aryl which may be substituted, -$L^4$-aromatic heterocyclic group which may be substituted, or —O-non-aromatic heterocyclic group which may be substituted,
Ring A represents arene which may be substituted or aromatic heterocycle which may be substituted,
$L^1$ represents —O— or —NH—,
$R^2$ represents H, halogen, —OH, —$NR^5R^6$, —$CONH_2$, —CN, -$L^4$-cycloalkyl which may be substituted, -$L^4$-aryl which may be substituted, -$L^4$-aromatic heterocyclic group which may be substituted, -$L^4$-non-aromatic heterocyclic group which may be substituted, lower alkyl which may be substituted, lower alkenyl which may be substituted, or lower alkynyl which may be substituted,
$L^2$ represents —O—, —S(O)$_P$—, —NH—, —N(CH$_3$)—, —NHCH$_2$—, —NHCH$_2$CH$_2$—, —OCH$_2$—, or a bond,
Y represents Ring X or a bond,
Ring X represents cycloalkane which may be substituted, arene which may be substituted, an aromatic heterocycle which may be substituted, or a non-aromatic heterocycle which may be substituted,
$L^3$ represents —O—, —NH—, —N(lower alkyl which may be substituted)-, —N(cycloalkyl which may be substituted), -lower alkylene which may be substituted-, -lower alkylene which may be substituted-NH—, —NH-lower alkylene which may be substituted-, -lower alkylene which may be substituted-N(lower alkyl which may be substituted)-, —N(lower alkyl which may be substituted)-lower alkylene which may be substituted-, or a bond,
M represents —C(O)— or —S(O)$_2$—,
$R^3$ represents H or lower alkyl which may be substituted,
$R^4$ represents lower alkyl which may be substituted with one or more substituents selected from the group consisting of —OH, halogen, —$NH_2$, —NH-(lower alkyl which may be substituted), —N(lower alkyl which may be substituted)$_2$, and a non-aromatic heterocyclic group which may be substituted, or H,
$R^5$ and $R^6$ are the same as or different from each other, and represent H or lower alkyl which may be substituted,
$L^4$'s are the same as or different from each other, and represent lower alkylene which may be substituted-, —NH—, —O—, —O-lower alkylene which may be substituted-, -lower alkylene which may be substituted-O—, or a bond, and
p represents 0, 1, or 2.)

Furthermore, the present invention relates to a pharmaceutical composition for preventing and/or treating EGFR T790M mutation positive cancer, which comprises the compound of the formula (I) or a salt thereof. Further, the pharmaceutical composition contains an agent for preventing and/ or treating EGFR T790M mutation positive cancer, which comprises the compound of the formula (I) or a salt thereof.

Furthermore, the present invention relates to use of the compound of the formula (I) or a salt thereof for the manufacture of a pharmaceutical composition for preventing and/or treating EGFR T790M mutation positive cancer, use of the compound of the formula (I) or a salt thereof for the prevention and/or treatment of EGFR T790M mutation positive cancer, the compound of the formula (I) or a salt thereof for the prevention and/or treatment of EGFR T790M mutation positive cancer, and a method for preventing and/or treating EGFR T790M mutation positive cancer, comprising administering an effective amount of the compound of the formula (I) or a salt thereof to a subject. Further, the "subject" is a human or another animal in need of prevention and/or treatment thereof, and in a certain embodiment, it is a human in need of prevention and/or treatment thereof.

Effects of the Invention

The compound of the formula (I) or a salt thereof has an inhibitory activity on an EGFR T790M mutation kinase and an inhibitory activity on EGFR T790M mutation protein-dependent cell proliferation, and can be used as an active ingredient of a pharmaceutical composition for preventing and/or treating EGFR T790M mutation positive cancer, in another embodiment, EGFR T790M mutation positive lung cancer, in still another embodiment, EGFR T790M mutation positive non-small cell lung cancer, in further still another embodiment, EGFR T790M mutation protein positive cancer, and in further still another embodiment, EGFR T790M mutation protein positive lung cancer.

EMBODIMENTS FOR CARRYING OUT THE INVENTION

Figure 1:
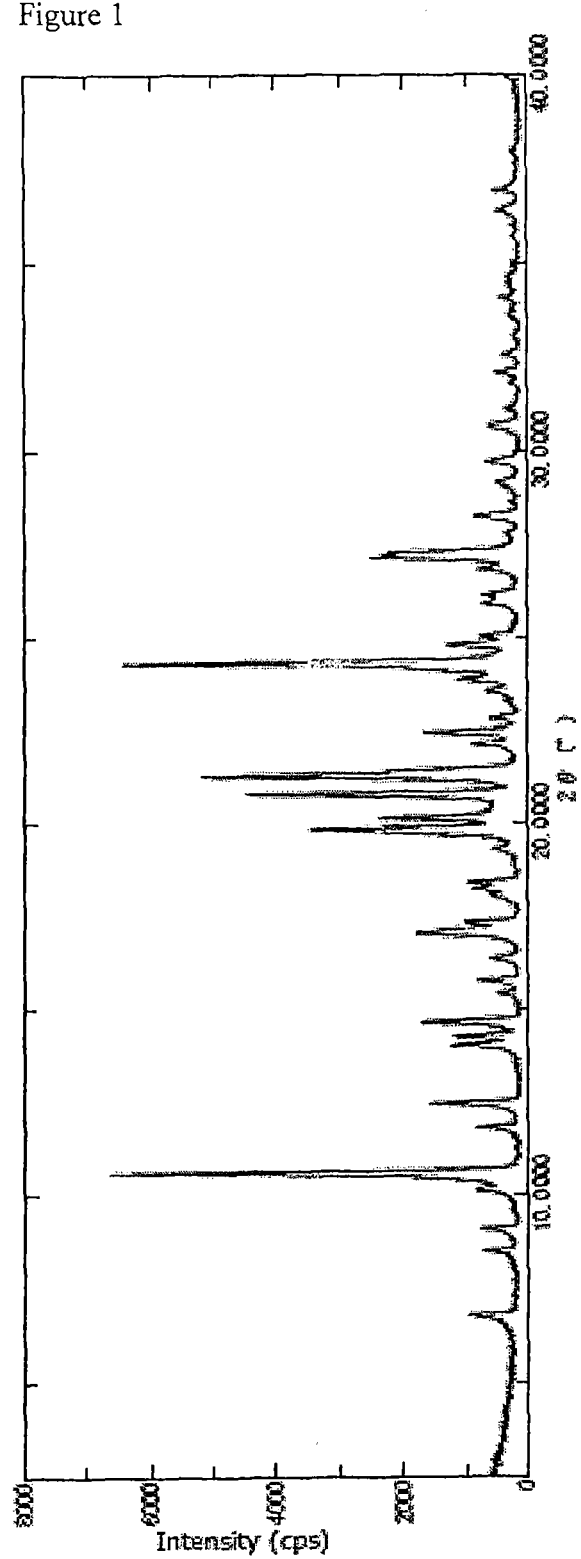
FIG. 1 shows a powder X-ray diffraction pattern of the compound of Example 254.

Hereinbelow, the present invention will be described in detail.

In the present specification, the "L858R mutation" refers to mutation in which a residue corresponding to the position 858 changes from leucine to arginine in a gene encoding wild type EGFR.

The "del19" denotes mutation in which an amino acid in the exon 19 region is deleted in a gene encoding EGFR. It denotes, for example, E746-A750 deletion mutation (mutation in which the residues corresponding to the position 746 to the position 750 are deleted, the same shall apply hereinafter), E746-T751 deletion mutation, E746-S752 deletion mutation, L747-E749 deletion mutation, L747-A750 deletion mutation, L747-T751 deletion mutation, L747-S752 deletion mutation, L747-P753 deletion mutation, S752-1759 deletion mutation, or the like. In a certain embodiment, it is E746-A750 deletion mutation.

The "T790M mutation" denotes mutation in which a residue corresponding to the position 790 changes from threonine to methionine in a gene encoding wild type EGFR.

The "EGFR T790M mutation kinase" is a kinase which has "T790M mutation" and may have mutation in another gene region encoding the EGFR. In a certain embodiment, it is a kinase which may have mutation for constitutively activating the kinase activity of EGFR such as the "L858R mutation" or "del1 9", and which has "T790M mutation". In another embodiment, it is a kinase which has a mutation of constitutively activating the kinase activity of EGFR as well as "T790M mutation", and in still another embodiment, a kinase which has "L858R mutation" or "del19" as well "T790M mutation".

In the present specification, there are some cases where an EGFR mutation kinase having both of "L858R mutation" and "T790M mutation" is described as "T790M/L858R mutation" or "T790M/L858R". Further, there are some cases where an EGFR mutation kinase having both mutations of the "del19" and the "T790M mutation" are described as "T790M/del19 mutation" or "T790M/del19".

The "lower alkyl" is linear or branched alkyl having 1 to 6 carbon atoms (hereinafter abbreviated as $C_{1-6}$), and examples thereof include methyl, ethyl, n-propyl, isopropyl, n-butyl, isobutyl, sec-butyl, tert-butyl, n-pentyl, n-hexyl, and the like. In another embodiment, the lower alkyl is $C_{1-4}$ alkyl, in a still other embodiment, methyl, and in further still another embodiment, ethyl, and in further still another embodiment, isopropyl.

The "lower alkenyl" is linear or branched $C_{2-6}$ alkenyl, and examples thereof include vinyl, propenyl, butenyl, pentenyl, 1-methylvinyl, 1-methyl-2-propenyl, 1,3-butadienyl, 1,3-pentadienyl, and the like. In another embodiment, the lower alkenyl is $C_{2-4}$ alkenyl, in a still other embodiment, vinyl, and in further still another embodiment, propenyl.

The "lower alkynyl" is linear or branched $C_{2-6}$ alkynyl, and examples thereof include ethynyl, propynyl, butynyl, pentynyl, 1-methyl-2-propynyl, 1,3-butadiinyl, 1,3-pentadiinyl, and the like. In another embodiment, the lower alkynyl is $C_{2-4}$ alkynyl, in a still other embodiment, ethynyl, and in further still another embodiment, propynyl.

The "lower alkylene" is linear or branched $C_{1-6}$ alkylene, and examples thereof include methylene, ethylene, trimethylene, tetramethylene, pentamethylene, hexamethylene, propylene, methylmethylene, ethylethylene, 1,2-dimethylethylene, 1,1,2,2-tetramethylethylene, and the like. In another embodiment, the lower alkylene is $C_{1-4}$ alkylene, in a still other embodiment, methylene, and in further still another embodiment, ethylene.

The "cycloalkane" is a $C_{3-10}$ saturated hydrocarbon ring, and may have a bridge, and examples thereof include cyclopropane, cyclobutane, cyclopentane, cyclohexane, cycloheptane, cyclooctane, adamantane, and the like. In another embodiment, the cycloalkane is $C_{3-6}$ cycloalkane, in a still other embodiment, cyclopropane, and in further still another embodiment, cyclohexane.

The "cycloalkyl" is a monovalent group of a "cycloalkane", and examples thereof include cyclopropyl, cyclobutyl, cyclopentyl, cyclohexyl, and the like. In another embodiment, the cycloalkyl is cyclopropyl, and in a still other embodiment, cyclohexyl.

The "arene" is a $C_{6-14}$ monocyclic to tricyclic aromatic hydrocarbon ring, and may be fused with a non-aromatic heterocycle or cycloalkane. Examples thereof include benzene, naphthalene, tetrahydronaphthalene, fluorene, indoline, 1,2,3,4-tetrahydroquinoline, and 3,4-dihydro-1,4-benzoxazine. In another embodiment, the arene is benzene, in a still other embodiment, 1,2,3,4-tetrahydroquinoline, and in further still another embodiment, 3,4-dihydro-1,4-benzoxazine.

The "aryl" is a monovalent group of an "arene", and examples thereof include phenyl, naphthyl, 5-tetrahydronaphthyl, 1-fluorenyl, indolyl, 1,2,3,4-tetrahydroquinolinyl, and 3,4-dihydro-1,4-benzoxazinyl. In another embodiment, the aryl is phenyl, in a still other embodiment, 1,2,3,4-tetrahydroquinolinyl, and in, a still other embodiment, 3,4-dihydro-1,4-benzoxazinyl.

The "aromatic heterocycle" is a 5- to 10-membered aromatic heterocycle containing 1 to 4 hetero atoms selected from the group consisting of nitrogen, oxygen, and sulfur, and examples thereof include pyridine, pyrrole, pyrazine, pyrimidine, pyridazine, imidazole, pyrazole, thiazole, oxazole, thiophene, furan, 1,2,4-oxadiazole, and the like. In another embodiment, the aromatic heterocycle is a 5- to 6-membered aromatic heterocycle containing 1 to 2 nitrogen atoms, and in a still other embodiment, pyridine, imidazole, pyrazole, or pyrimidine.

The "aromatic heterocyclic group" is a monovalent group of an "aromatic heterocycle", and examples thereof include pyridyl, pyrrolyl, pyrazinyl, pyrimidinyl, pyridazinyl, imidazolyl, pyrazolyl, thiazolyl, oxazolyl, thienyl, furyl, 1,2,4-oxadiazolyl, and the like. In another embodiment, the aromatic heterocyclic group is a 5- to 6-membered aromatic heterocyclic group containing 1 to 2 nitrogen atoms, and in a still other embodiment, pyridyl.

The "non-aromatic heterocycle" is a 3- to 10-membered non-aromatic heterocycle containing 1 to 4 hetero atoms selected from the group consisting of nitrogen, oxygen, and sulfur. It may be bridged with lower alkylene and may have an unsaturated bond in a part of the ring. Examples thereof include aziridine, azetidine, pyrrolidine, piperidine, azepane, diazepane, azocane, piperazine, homopiperazine, morpholine, oxazepane, thiomorpholine, thiazepane, 7-oxabicyclo[2.2.1]heptane, 2-azabicyclo[2.2.1]heptane, 2,5-diazabicyclo[2.2.1]heptane, 3-azabicyclo[3.2.1]octane, 8-azabicyclo[3.2.1]octane, 9-azabicyclo[3.3.1]nonane, 3,9-diazabicyclo[3.3.1]nonane, tetrahydropyran, tetrahydrofuran, dioxane, dioxolane, tetrahydrothiophene, tetrahydrothiopyran, dihydropyran, dihydropyrrole, dihydropyridine, tetrahydropyridine, tetrahydropyrazine, 2,7-diazaspiro[5.5]nonane, and the like. In another embodiment, the non-aromatic heterocycle is a 5- to 7-membered non-aromatic heterocycle containing the same or different 1 to 2 hetero atoms selected from the group consisting of nitrogen, oxygen, and sulfur, which may be bridged with lower alkylene, in a still other embodiment, a 5- to 7-membered non-aromatic heterocycle containing at least one nitrogen atom, which may be bridged with lower alkylene, in further still another embodiment, azetidine, pyrrolidine, piperidine, tetrahydropyridine, or 8-azabicyclo[3.2.1]octane, and in further still another embodiment, pyrrolidine, piperidine, or tetrahydropyridine.

The "non-aromatic heterocyclic group" is a monovalent group of a non-aromatic heterocycle or a 3- to 10-membered non-aromatic heterocycle containing the same or different 1 to 4 hetero atoms selected from the group consisting of nitrogen, oxygen, and sulfur. It may be bridged with lower alkylene, may have an unsaturated bond in a part of the ring, and may be combined with another non-aromatic heterocycle to form a spiro ring. Examples thereof include aziridinyl, azetidinyl, pyrrolidinyl, piperidinyl, azepanyl, diazepanyl, azocanyl, piperazinyl, homopiperazinyl, morpholinyl, oxazepanyl, thiomorpholinyl, thiazepanyl, tetrahydropyranyl, tetrahydrofuryl, dioxanyl, dioxolanyl, tetrahydrothienyl, tetrahydrothiopyranyl, 7-oxabicyclo[2.2.1]heptyl, 2-azabicyclo[2.2.1]heptyl, 2,5-diazabicyclo[2.2.1]heptyl, 3-azabicyclo[3.2.1]octyl, 8-azabicyclo[3.2.1]octyl, 9-azabicyclo[3.3.1]nonyl, 3,9-diazabicyclo[3.3.1]nonyl, dihydropyranyl, dihydropyrrolyl, dihydropyridyl, tetrahydropyridyl, tetrahydropyrazyl, 3,9-diazaspiro[5.5]undec-3-yl, 1,9-diazaspiro[5.5]undec-9-yl, 1,8-diazaspiro[4.5]dec-8-yl, and 1,4-dioxa-8-azaspiro[4.5]dec-8-yl. In another embodiment, the non-aromatic heterocyclic group is a 5- to 7-membered non-aromatic heterocyclic group containing the same or different 1 to 2 hetero atoms selected from the group consisting of nitrogen, oxygen, and sulfur, in a still other embodiment, a 5- to 7-membered non-aromatic heterocyclic group containing at least one nitrogen atom, in further still another embodiment, azepanyl, pyrrolidinyl, piperidinyl, piperazinyl, tetrahydropyridyl, or morpholinyl, and in further still another embodiment, pyrrolidinyl, piperidinyl, piperazinyl, or morpholinyl.

The "halogen" is —F, —Cl, —Br, or —I.

The expression "which may be substituted" means unsubstituted or substituted with 1 to 5 substituents. Further, in a case where it has a plurality of substituents, the substituents may be the same as or different from each other. Incidentally, the two lower alkyl groups on nitrogen, for example, in a case of the phrase "—N(lower alkyl which may be substituted)$_2$" may be the same or different lower alkyl groups. Further, the lower alkyl groups may be each substituted with the same substituent or with different substituents, or one or both of the lower alkyl groups may be unsubstituted.

Examples of the acceptable substituents in the "arene which may be substituted", "aryl which may be substituted", "aromatic heterocycle which may be substituted", "aromatic heterocyclic group which may be substituted", "cycloalkane which may be substituted", "cycloalkyl which may be substituted", "non-aromatic heterocycle which may be substituted", and "non-aromatic heterocyclic group which may be substituted", described in $R^1$, $R^2$, $R^4$, Ring A, and Ring X, include substituents selected from the group consisting of Group D1.

The Group D1 is a group consisting of:
(1) halogen,
(2) —OH, —O-lower alkyl and —O-cycloalkyl,
(3) —SH, —S-lower alkyl and —S-cycloalkyl,
(4) —S(O)-lower alkyl and —S(O)$_2$ lower alkyl
(5) —S(O)-cycloalkyl and —S(O)$_2$ cycloalkyl,
(6) —CN,
(7) —NO$_2$,
(8) —NH$_2$, —NH-(lower alkyl) and —N(lower alkyl)$_2$,
(9) —NH—C(O)-lower alkyl and —N(lower alkyl)-C(O)-lower alkyl,
(10) —C(O)-lower alkyl, —C(O)—O-lower alkyl,
(11) —C(O)—NH$_2$, —C(O)—NH-(lower alkyl) and —C(O)—N(lower alkyl)$_2$,

(12) —O—C(O)-lower alkyl,
(13) cycloalkyl,
(14) aryl which may be substituted with lower alkyl,
(15) aromatic heterocyclic group which may be substituted with lower alkyl,
(16) a non-aromatic heterocyclic group which may be substituted with a substituent selected from the group consisting of lower alkyl and non-aromatic heterocycles
(17) oxo, and
(18) lower alkyl, —O-lower alkyl, and lower alkenyl, each of which may be substituted with one or more substituents selected from the group consisting of the substituents described in (1) to (17) above.

In another embodiment, the Group D1 is a group consisting of:
(1) halogen,
(2) —OH and —O-lower alkyl,
(3) —CN,
(4) cycloalkyl
(5) aryl which may be substituted with lower alkyl
(6) aromatic heterocyclic group which may be substituted with lower alkyl,
(7) non-aromatic heterocyclic group which may be substituted with lower alkyl
(8) oxo, and
(9) lower alkyl, —O-lower alkyl, and lower alkenyl, each of which may be substituted with one or more substituents selected from the group consisting of the substituents described in (1) to (8) above.

In a still other embodiment, the Group D1 is a group consisting of:
(1) halogen,
(2) —O-lower alkyl,
(3) —CN
(4) cycloalkyl
(5) aryl
(6) aromatic heterocyclic group
(7) non-aromatic heterocyclic group which may be substituted with lower alkyl
(8) oxo, and
(9) lower alkyl which may be substituted with one or more halogen atoms.

Examples of the substituent in lower alkyl, lower alkenyl, lower alkynyl, or lower alkylene, which may be substituted, described in $R^1$, $R^2$, $L^2$, $L^3$, $R^3$, $R^4$, $R^5$, $R^6$ and $L^4$ include substituents selected from the group consisting of Group D2.

The Group D2 is a group consisting of:
(1) halogen,
(2) —OH, —O-lower alkyl and —O-cycloalkyl,
(3) —SH, —S-lower alkyl and —S-cycloalkyl,
(4) —S(O)-lower alkyl and —S(O)$_2$ lower alkyl
(5) —S(O)-cycloalkyl and —S(O)$_2$ cycloalkyl,
(6) —CN,
(7) —NO$_2$,
(8) —NH$_2$, —NH-(lower alkyl) and —N(lower alkyl)$_2$,
(9) —NH—C(O)-lower alkyl and —N(lower alkyl)-C(O)-lower alkyl,
(10) —C(O)-lower alkyl,
(11) —C(O)—NH$_2$, —C(O)—NH-(lower alkyl) and —C(O)—N(lower alkyl)$_2$,
(12) —O—C(O)-lower alkyl,
(13) cycloalkyl,
(14) aryl which may be substituted with lower alkyl,
(15) aromatic heterocyclic group which may be substituted with lower alkyl,
(16) non-aromatic heterocyclic group which may be substituted with lower alkyl, and
(17) —O-lower alkyl, each of which may be substituted with one or more substituents selected from the group consisting of the substituents described in (1) to (16) above.

In another embodiment, the Group D2 is a group consisting of:
(1) —OH and —O-lower alkyl,
(2) —CN,
(3) —NH$_2$, —NH-(lower alkyl) and —N(lower alkyl)$_2$,
(4) cycloalkyl,
(5) non-aromatic heterocyclic group which may be substituted with lower alkyl, and
(6) —O-lower alkyl, each of which may be substituted with one or more substituents selected from the group consisting of the substituents described in (1) to (5) above.

In a still other embodiment, the Group D2 is a group consisting of:
(1) —OH and —O-lower alkyl, and
(2) —N(lower alkyl)$_2$.

In another embodiment, the lower alkyl, lower alkenyl, lower alkynyl, or lower alkylene, which may be substituted, described in $R^1$, $R^2$, $L^2$, $L^3$, $R^3$, $R^4$, $R^5$, $R^6$ and $L^4$, is, in a certain embodiment, each of unsubstituted lower alkyl, unsubstituted lower alkenyl, unsubstituted lower alkynyl, or unsubstituted lower alkylene.

In another embodiment, examples of the acceptable substituent of the "lower alkyl which may be substituted" of $R^1$ include a non-aromatic heterocyclic group which may be substituted with lower alkyl, and in a still other embodiment, 4-methylpiperazin-1-yl and pyrrolidin-1-yl.

In another embodiment, examples of the acceptable substituent of the "—O-lower alkyl which may be substituted" of $R^1$ include a non-aromatic heterocyclic group, and in a still other embodiment, morpholin-4-yl.

In another embodiment, examples of the acceptable substituent of the "—NH-lower alkyl which may be substituted" and "—N(lower alkyl which may be substituted)$_2$" of $R^1$ include —O-lower alkyl and —N(lower alkyl)$_2$, and in a still other embodiment, methoxy and dimethylamino.

In another embodiment, examples of the acceptable substituent of the "-$L^4$-non-aromatic heterocyclic group which may be substituted" of $R^1$ include lower alkyl, cycloalkyl, a non-aromatic heterocyclic group which may be substituted with lower alkyl, and oxo, and in a still other embodiment, methyl, ethyl, cyclopropyl, morpholin-4-yl, 4-methylpiperazin-1-yl, and oxo.

In another embodiment, examples of the acceptable substituent of the "arene which may be substituted" and the "aromatic heterocycle which may be substituted" of Ring A include lower alkyl which may be substituted with halogen, —O-lower alkyl which may be substituted with halogen, halogen, cyano, aryl, and an aromatic heterocyclic group, and in a still other embodiment, methyl, trifluoromethyl, methoxy, fluoro, chloro, bromo, cyano, phenyl, and pyridyl.

In another embodiment, examples of the acceptable substituent of the "lower alkyl which may be substituted" of $R^2$ include —OH.

In another embodiment, examples of the acceptable substituent of the "arene which may be substituted" of Ring X include lower alkyl which may be substituted with halogen and halogen, and in a still other embodiment, methyl, trifluoromethyl, fluoro, and chloro.

In another embodiment, examples of the acceptable substituent of the "non-aromatic heterocycle which may be substituted" of Ring X include lower alkyl which may be substituted with a group selected from the group consisting of phenyl and benzyloxy, aryl, and —OH.

In another embodiment, examples of the acceptable substituent of the "—N(lower alkyl which may be substituted)-" of $L^3$ include phenyl.

In another embodiment, examples of the acceptable substituent of the "-lower alkylene-NH—" of $L^3$ include phenyl.

Moreover, other embodiments of the "-$L^4$-cycloalkyl which may be substituted" of $R^1$, the "-$L^4$-aryl which may be substituted" of $R^1$, the "-$L^4$-aromatic heterocyclic group which may be substituted" of $R^1$, the "-$L^4$-cycloalkyl which may be substituted" of $R^2$, the "-$L^4$-aryl which may be substituted" of $R^2$, the "-$L^4$-aromatic heterocyclic group which may be substituted" of $R^2$, the "-$L^4$-non-aromatic heterocyclic group which may be substituted" of $R^2$, the "lower alkenyl which may be substituted" of $R^2$, the "lower alkynyl which may be substituted" of $R^2$, the "cycloalkane which may be substituted" of Ring X, the "aromatic heterocyclic compound which may be substituted" of Ring X, the "—N(cycloalkyl which may be substituted)-" of $L^3$, the "-lower alkylene which may be substituted-" of $L^3$, the "—NH-lower alkylene which may be substituted-" of $L^3$, the "-lower alkylene which may be substituted-N(lower alkyl which may be substituted)-" of $L^3$, the "—N(lower alkyl which may be substituted)-lower alkylene which may be substituted-" of $L^3$, the "lower alkyl which may be substituted" of $R^3$, the "—NH-(lower alkyl which may be substituted)" and the "—N(lower alkyl which may be substituted)$_2$" of $R^4$, the "non-aromatic heterocyclic group which may be substituted" of $R^4$, the "lower alkyl which may be substituted" of $R^5$ and $R^6$, the "-lower alkylene which may be substituted-" of $L^4$, the "—O-lower alkylene which may be substituted-" of $L^4$, and the "-lower alkylene which may be substituted-O—" of $L^4$ each include embodiments involving being unsubstituted.

Furthermore, unless specified otherwise, in the case where the symbols of the chemical formulae in the present specification are also used in other chemical formulae, the same symbols denote the same meanings.

Certain embodiments of the present invention are shown below.

(1) The compound or a salt thereof, wherein $R^1$ is lower alkyl which may be substituted, —O-lower alkyl which may be substituted, —NH$_2$, —NH-lower alkyl which may be substituted, —N(lower alkyl which may be substituted)$_2$, or -$L^4$-non-aromatic heterocyclic group which may be substituted; in another embodiment, the compound or a salt thereof, wherein $R^1$ is lower alkyl; —O-lower alkyl; —N(lower alkyl which may be substituted with —O-lower alkyl)$_2$; or a non-aromatic heterocyclic group which may be substituted with one or more substituents selected from the group consisting of a non-aromatic heterocyclic group which may be substituted with lower alkyl, lower alkyl and oxo; in a still other embodiment, the compound or a salt thereof, wherein $R^1$ is a non-aromatic heterocyclic group which may be substituted with one or more substituents selected from the group consisting of a non-aromatic heterocyclic group which may be substituted with lower alkyl, lower alkyl and oxo; in further still another embodiment, the compound or a salt thereof, wherein $R^1$ is piperidinyl which may be substituted with one or more lower alkyl groups; piperazinyl which may be substituted with one or more lower alkyl groups; or piperidinyl substituted with piperazinyl which may be substituted with lower alkyl; in further still another embodiment, the compound or a salt thereof, wherein $R^1$ is 4-methylpiperidin-1-yl, 4-methylpiperazin-1-yl, 4-ethylpiperazin-1-yl, 3,4-dimethylpiperazin-1-yl, or 4-(4-methylpiperazin-1-yl)piperidin-1-yl; in further still another embodiment, the compound or a salt thereof, wherein $R^1$ is 4-methylpiperazin-1-yl; in further still another embodiment, the compound or a salt thereof, wherein $R^1$ is 3,4-dimethylpiperazin-1-yl; and in further still another embodiment, the compound or a salt thereof, wherein $R^1$ is 4-(4-methylpiperazin-1-yl)piperidin-1-yl.

Furthermore, in a certain embodiment, in a case where Ring A is a 6-membered ring, when the atom on Ring A substituted with $L^1$ is at the position 1, $R^1$ is substituted at the position 3 or 4. In another embodiment, in a case where Ring A is a 6-membered ring, when the atom on Ring A substituted with $L^1$ is at the position 1, $R^1$ is substituted at the position 4.

(2) The compound or a salt thereof, wherein Ring A is benzene which may be substituted, a 5- to 6-membered aromatic heterocycle containing 1 to 2 nitrogen atoms, which may be substituted; in another embodiment, the compound or a salt thereof, wherein Ring A is benzene which may be substituted, pyrazole which may be substituted, imidazole which may be substituted, or pyrimidine which may be substituted; in a still other embodiment, the compound or a salt thereof, wherein Ring A is benzene which may be substituted with one or more substituents selected from the group consisting of lower alkyl which may be substituted with one or more halogen atoms, —O-lower alkyl, —CN, aryl, an aromatic heterocyclic group, and halogen, or pyrazole which may be substituted with lower alkyl which may be substituted with one or more halogen atoms; in further still another embodiment, the compound or a salt thereof, wherein Ring A is benzene which may be substituted with one or more substituents selected from the group consisting of lower alkyl which may be substituted with one or more halogen atoms, —O-lower alkyl, and halogen, or pyrazole which may be substituted with lower alkyl; in further still another embodiment, the compound or a salt thereof, wherein Ring A is benzene which may be substituted with a substituent selected from the group consisting of methyl and methoxy, or pyrazole; in further still another embodiment, the compound or a salt thereof, wherein Ring A is benzene which may be substituted with a substituent selected from the group consisting of methyl and methoxy; in further still another embodiment, the compound or a salt thereof, wherein Ring A is benzene which may be substituted with methyl; in further still another embodiment, the compound or a salt thereof, wherein Ring A is benzene substituted with methyl; in further still another embodiment, the compound or a salt thereof, wherein Ring A is benzene; in further still another embodiment, the compound or a salt thereof, wherein Ring A is pyrazole.

(3) The compound or a salt thereof, wherein $L^1$ is —NH—; and in another embodiment, the compound or a salt thereof, wherein $L^1$ is —O—.

(4) The compound or a salt thereof, wherein $R^2$ is H, cycloalkyl, or lower alkyl which may be substituted; in another embodiment, $R^2$ is H, or lower alkyl which may be substituted with —OH; in a still other embodiment, the compound or a salt thereof, wherein $R^2$ is lower alkyl; in further still another embodiment, the compound or a salt thereof, wherein $R^2$ is H, ethyl, or isopropyl; in further still another embodiment, the compound or a salt thereof, wherein $R^2$ is ethyl, or isopropyl; in further still another embodiment, the compound or a salt thereof, wherein $R^2$ is H; in further still another embodiment, the compound or a salt thereof, wherein $R^2$ is ethyl; and in further still another embodiment, the compound or a salt thereof, wherein $R^2$ is isopropyl.

(5) The compound or a salt thereof, wherein $L^2$ is —O—, —NH—, —S—, or a bond; in another embodiment, the compound or a salt thereof, wherein $L^2$ is —O— or a bond; in a still other embodiment, the compound or a salt thereof, wherein $L^2$ is —O—; in further still another embodiment, the compound or a salt thereof, wherein $L^2$ is a bond; and in further still another embodiment, the compound or a salt thereof, wherein $L^2$ is —NH—.

(6) The compound or a salt thereof, wherein Y is Ring X; in another embodiment, the compound or a salt thereof, wherein Y is a bond; in a still other embodiment, the compound or a salt thereof, wherein Ring X is a non-aromatic heterocycle which may be substituted, an aromatic heterocycle which may be substituted, cycloalkane which may be substituted, or a benzene ring which may be substituted; in further still another embodiment, the compound or a salt thereof, wherein Ring X is benzene, pyridine, tetrahydropyridine, azetidine, pyrrolidine, piperidine, piperazine, 8-azabicyclo[3.2.1]octane, or cyclohexane, each of which may be substituted with one or more substituents selected from halogen, —O-lower alkyl, lower alkyl which may be substituted with one or more halogen atoms and —CN; in further still another embodiment, the compound or a salt thereof, wherein Ring X is benzene, pyrrolidine, or piperidine, each of which may be substituted with one or more substituents selected from halogen and lower alkyl which may be substituted with one or more halogen atoms; in further still another embodiment, the compound or a salt thereof, wherein Ring X is benzene substituted with a group selected from the group consisting of methyl and fluoro, or pyrrolidine, or piperidine; in further still another embodiment, the compound or a salt thereof, wherein Ring X is benzene which may be substituted with one or more substituents selected from the group consisting of halogen and lower alkyl which may be substituted with one or more halogen atoms; in further still another embodiment, the compound or a salt thereof, wherein Ring X is benzene which may be substituted with a substituent selected from the group consisting of methyl and fluoro; in further still another embodiment, the compound or a salt thereof, wherein Ring X is benzene; in further still another embodiment, the compound or a salt thereof, wherein Ring X is pyrrolidine, or piperidine, each of which may be substituted with one or more substituents selected from the group consisting of halogen and lower alkyl which may be substituted with one or more halogen atoms; in further still another embodiment, the compound or a salt thereof, wherein Ring X is pyrrolidine or piperidine; in further still another embodiment, the compound or a salt thereof, wherein Ring X is pyrrolidine; and in further still another embodiment, the compound or a salt thereof, wherein Ring X is piperidine.

(7) The compound or a salt thereof, wherein $L^3$ is —NH—, —N(lower alkyl)-, or a bond; in another embodiment, the compound or a salt thereof, wherein $L^3$ is —NH— or a bond; in a still other embodiment, the compound or a salt thereof, wherein $L^3$ is —NH—; and in further still another embodiment, the compound or a salt thereof, wherein $L^3$ is a bond.

Further, in a certain embodiment, in a case where $L^2$ is other than a bond, Y is Ring X, and Ring X is a 5-membered ring or a 6-membered ring, and when the atom on Ring X substituted with $L^2$ is at the position 1, $L^3$ is substituted at the position 3. Further, in a certain embodiment, in a case where $L^2$ is a bond, Y is Ring X, and Ring X is a 6-membered ring, and when the atom on Ring X substituted with $L^2$ is at the position 1, $L^3$ is substituted at the position 4.

Furthermore, in a certain embodiment, M is substituted at the nitrogen atom of -$L^2$-Y-$L^3$-.

(8) In another embodiment, the compound or a salt thereof, wherein -$L^2$-Y-$L^3$- is —O-(1,3-phenylene which may be substituted with one or more substituents selected from the group consisting of lower alkyl and halogen)-NH—, piperidine-1,4-diyl (provided that M is substituted at the position 1 of piperidine), —O-pyrrolidine-1,3-diyl (provided that M is substituted at the position 1 of pyrrolidine), and —O-piperidine-1,3-diyl (provided that M is substituted at the position 1 of piperidine); in a still other embodiment, the compound or a salt thereof, wherein -$L^2$-Y-$L^3$- is —O-(1,3-phenylene which may be substituted with one or more substituents selected from the group consisting of lower alkyl and halogen)-NH—; in further still another embodiment, the compound or a salt thereof, wherein -$L^2$-Y-$L^3$- is —O-(1,3-phenylene which may be substituted with one or more substituents selected from the group consisting of methyl and fluoro)-NH—; in further still another embodiment, the compound or a salt thereof, wherein -$L^2$-Y-$L^3$- is piperidine-1,4-diyl (provided that M is substituted at the position 1 of piperidine); in further still another embodiment, the compound or a salt thereof, wherein -$L^2$-Y-$L^3$- is —O-pyrrolidine-1,3-diyl (provided that M is substituted at the position 1 of pyrrolidine); in and further still another embodiment, the compound or a salt thereof, wherein -$L^2$-Y-$L^3$- is —O-piperidine-1,3-diyl (provided that M is substituted at the position 1 of piperidine).

(9) The compound or a salt thereof, wherein M is —C(O)—; and in another embodiment, the compound or a salt thereof, wherein M is —S(O)$_2$—.

(10) The compound or a salt thereof, wherein $R^3$ is H or lower alkyl; and in another embodiment, the compound or a salt thereof, wherein $R^3$ is H.

(11) The compound or a salt thereof, wherein $R^4$ is lower alkyl which may be substituted with one or more substituents selected from the group consisting of halogen, —N(lower alkyl)$_2$, and a non-aromatic heterocyclic group, or H; in another embodiment, the compound or a salt thereof, wherein $R^4$ is dimethylaminomethyl or H; in a still other embodiment, the compound or a salt thereof, wherein $R^4$ is H; and in further still another embodiment, the compound or a salt thereof, wherein $R^4$ is dimethylaminomethyl.

(12) The compound or a salt thereof, which is a combination of any two or more of the embodiments of (1) to (11) as described above, which do not contradict to each other.

The compound or a salt thereof, which is a combination of any two or more of the embodiments of (1) to (11) as described above, which do not contradict to each other, is also included in the present invention, as described in (12) above, and the specific examples thereof also include the following embodiments.

(13) The compound or a salt thereof, wherein $R^2$ is H, halogen, —OH, —NR$^5$R$^6$, —CN, -$L^4$-cycloalkyl which may be substituted, -$L^4$-aryl which may be substituted, -$L^4$-aromatic heterocyclic group which may be substituted, -$L^4$-non-aromatic heterocyclic group which may be substituted, lower alkyl which may be substituted, lower alkenyl which may be substituted, or lower alkynyl which may be substituted, $L^2$ is —O—, —S(O)$_p$—, or a bond, and Y is Ring X.

(14) The compound or a salt thereof as described in (13), wherein $R^1$ is a non-aromatic heterocyclic group which may be substituted, $L^1$ is —NH—, $R^2$ is H or lower alkyl, and M is —C(O)—.

(15) The compound or a salt thereof as described in (14), wherein $R^1$ is piperazinyl which may be substituted, piperidinyl which may be substituted with lower alkyl, or piperidinyl substituted with piperazinyl which may be substituted with lower alkyl, Ring A is benzene which may be substituted with one or more substituents selected from the group consisting of halogen, lower alkyl which may be substituted with one or more halogen atoms, and —O-lower alkyl, pyrazole which may be substituted with lower alkyl, imidazole which may be substituted with lower alkyl or pyrimidine which may be substituted with lower alkyl, and $R^3$ and $R^4$ are each H.

(16) The compound or a salt thereof as described in (15), wherein $L^2$ is —O— or a bond, Ring X is an aromatic heterocycle, a non-aromatic heterocycle, cycloalkane, or benzene which may be substituted, and $L^3$ is —NH—, —N(lower alkyl)-, or a bond.

(17) The compound or a salt thereof as described in (16), wherein $L^2$ is —O—, Ring X is an aromatic heterocycle, or benzene which may be substituted, and $L^3$ is —NH— or —N(lower alkyl)-.

(18) The compound or a salt thereof as described in (16), wherein $L^2$ is —O—, Ring X is a non-aromatic heterocycle, and $L^3$ is a bond.

(19) The compound or a salt thereof as described in (16), wherein $L^2$ is a bond, Ring X is a non-aromatic heterocycle, and $L^3$ is a bond.

(20) The compound or a salt thereof as described in (17), wherein Ring X is benzene which may be substituted with lower alkyl, and $L^3$ is —NH—.

(21) The compound or a salt thereof as described in (18), wherein Ring X is pyrrolidine or piperidine.

(22) The compound or a salt thereof as described in (19), wherein Ring X is piperidine or tetrahydropyridine.

Examples of the specific compounds included in the present invention include the following compounds:

5-[3-(acryloylamino)phenoxy]-6-ethyl-3-{[4-(4-methylpiperazin-1-yl)phenyl]amino}pyrazine-2-carboxamide, 5-(3-{[(2E)-4-(dimethylamino)-2-butenoyl]amino}phenoxy)-6-ethyl-3-{[4-(4-methylpiperazin-1-yl)phenyl]amino}pyrazine-2-carboxamide, 5-[3-(acryloylamino)-2-methylphenoxy]-6-ethyl-3-{[4-(4-methylpiperazin-1-yl)phenyl]amino}pyrazine-2-carboxamide, 5-[3-(acryloylamino)phenoxy]-6-isopropyl-3-{[4-(4-methylpiperazin-1-yl)phenyl]amino}pyrazine-2-carboxamide, 5-(1-acryloylpiperidin-4-yl)-6-ethyl-3-({3-methyl-4-[4-(4-methylpiperazin-1-yl)piperidin-1-yl]phenyl}amino)pyrazine-2-carboxamide, 5-[3-(acryloylamino)phenoxy]-3-{[4-(4-methylpiperazin-1-yl)phenyl]amino}pyrazine-2-carboxamide, 5-[3-(acryloylamino)phenoxy]-6-ethyl-3-{[4-methoxy-3-(4-methylpiperazin-1-yl)phenyl]amino}pyrazine-2-carboxamide, 5-[3-(acryloylamino)phenoxy]-6-ethyl-3-{[4-(4-ethylpiperazin-1-yl)phenyl]amino}pyrazine-2-carboxamide, 5-{[(3R)-1-acryloylpyrrolidin-3-yl]oxy}-6-ethyl-3-({4-[4-(4-methylpiperazin-1-yl)piperidin-1-yl]phenyl}amino)pyrazine-2-carboxamide, 5-[3-(acryloylamino)phenoxy]-6-isopropyl-3-{[1-(1-methylpiperidin-4-yl)-1H-pyrazol-4-yl]amino}pyrazine-2-carboxamide, 5-[3-(acryloylamino)phenoxy]-3-({4-[(3S)-3,4-dimethylpiperazin-1-yl]phenyl}amino)-6-ethylpyrazine-2-carboxamide, 5-[3-(acryloylamino)phenoxy]-3-({4-[(3R)-3,4-dimethylpiperazin-1-yl]phenyl}amino)-6-ethylpyrazine-2-carboxamide, 5-(1-acryloylpiperidin-4-yl)-6-ethyl-3-({4-[4-(4-methylpiperazin-1-yl)piperidin-1-yl]phenyl}amino)pyrazine-2-carboxamide, 5-{[(3R)-1-acryloylpyrrolidin-3-yl]oxy}-6-ethyl-3-{[4-(4-methylpiperazin-1-yl)phenyl]amino}pyrazine-2-carboxamide, 5-{[(3R)-1-acryloylpiperidin-3-yl]oxy}-6-ethyl-3-({4-[4-(4-methylpiperazin-1-yl)piperidin-1-yl]phenyl}amino)pyrazine-2-carboxamide, 5-{[(3R)-1-acryloylpiperidin-3-yl]oxy}-6-ethyl-3-({3-methyl-4-[4-(4-methylpiperazin-1-yl)piperidin-1-yl]phenyl}amino)pyrazine-2-carboxamide, and 5-[5-(acryloylamino)-2-fluorophenoxy]-6-ethyl-3-{[4-(4-methylpiperazin-1-yl)phenyl]amino}pyrazine-2-carboxamide, and salts thereof.

The compound of the formula (I) may exist in the form of tautomers or geometrical isomers depending on the kind of substituents. In the present specification, the compound of the formula (I) shall be described in only one form of isomer, yet the present invention includes other isomers, isolated forms of the isomers, or a mixture thereof.

In addition, the compound of the formula (I) may have asymmetric carbon atoms or axial asymmetry in some cases, and correspondingly, it may exist in the form of optical isomers based thereon. The present invention includes both an isolated form of the optical isomers of the compound of the formula (I) or a mixture thereof.

Moreover, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and "Pharmaceutical Research and Development" (Hirokawa Publishing Company, 1990), Vol. 7, Molecular Design, 163-198.

Furthermore, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, ornithine, and the like, salts with various amino acids such as acetylleucine, and amino acid derivatives with ammonium salts.

In addition, the present invention also includes various hydrates or solvates, and polymorphic crystalline substances of the compound of the formula (I) and salts thereof. In addition, the present invention also includes compounds labeled with various radioactive or non-radioactive isotopes.

The compound of the formula (I) and a salt thereof can be prepared using the characteristics based on the basic structure or the type of substituents thereof and by applying various known synthesis methods. During the preparation, replacement of the relevant functional group with a suitable protective group (a group that can be easily converted into the relevant functional group) at the stage from starting material to an intermediate may be effective depending on the type of the functional group in the production technology in some cases. The protective group for such a functional group may include, for example, the protective groups described in "Greene's Protective Groups in Organic Synthesis (4th edition, 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, the prodrug of the compound of the formula (I) can be prepared by introducing a specific group at the stage from a starting material to an intermediate, or by carrying out the reaction using the obtained compound of the formula (I), as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the References appended in the present description. Further, the preparation methods of the present invention are not limited to the examples as shown below.

(Production Process 1)

[Chem. 11]

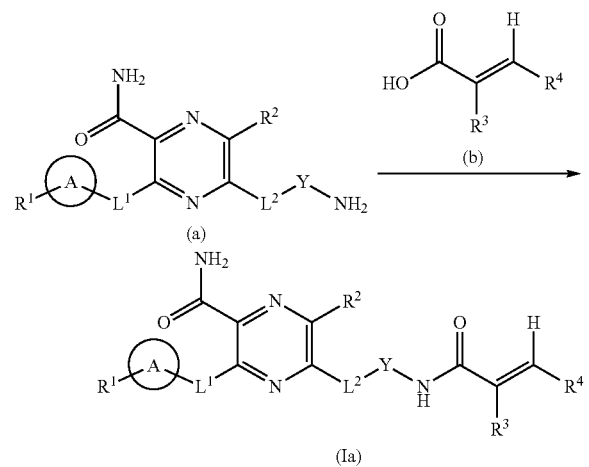

The present production process is a method for preparing a compound (Ia), which is the compound of the formula (I) of the present invention, wherein $L^3$ is NH and M is C=O, by subjecting a compound (a) to amidation.

The present reaction is carried out by using a compound (a) and a compound (b) in equivalent amounts, or either thereof in an excess amount, and stirring the mixture in a solvent which is inert to the reaction, in a range of from cooling to heating, preferably at −20° C. to 60° C., usually for 0.1 hours to 5 days, in the presence of a condensing agent. Examples of the solvent used herein are not particularly limited, but include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran, dioxane, dimethoxyethane, and the like, N,N-dimethylformamide, dimethylsulfoxide, ethyl acetate, acetonitrile, or water, and a mixture thereof. Examples of the condensing agent used herein are not particularly limited but include 1-(3-dimethylaminopropyl)-3-ethylcarbodiimide, dicyclohexylcarbodiimide, 1,1'-carbonyldiimidazole, diphenylphosphorylazide, and phosphorus oxychloride. It is preferable in some cases for the reaction to use an additive (such as 1-hydroxybenzotriazole). It is preferable in some cases for the progress of the reaction to use organic bases such as triethylamine, N,N-diisopropylethylamine, N-methylmorpholine, and the like, or inorganic bases such as potassium carbonate, sodium carbonate, potassium hydroxide, and the like.

In addition, a method in which a carboxylic acid (b) is converted into a reactive derivative, which is reacted with an amine (a), can also be used. Examples of the reactive derivative of the carboxylic acid include acid halides obtained by the reaction with a halogenating agent such as phosphorus oxychloride, thionyl chloride, oxalyl dichloride, and the like, mixed acid anhydrides obtained by the reaction with isobutyl chloroformate or the like, active esters obtained by condensation with 1-hydroxybenzotriazole or the like, and others. The reaction of the reactive derivative with the amine (a) can be carried out in a range of from cooling to heating, preferably at −20° C. to 60° C., in a solvent which is inert to the reaction, such as halogenated hydrocarbons, aromatic hydrocarbons, and ethers.

[Documents]

S. R. Sandler and W. Karo, "Organic Functional Group Preparations", $2^{nd}$ Ed., Vol. 1, Academic Press Inc., 1991

"Jikken Kagaku Kozo" (Courses in Experimental Chemistry) ($5^{th}$ Edition), edited by The Chemical Society of Japan, Vol. 16 (2005) (Maruzen)

(Production Process 2)

[Chem. 12]

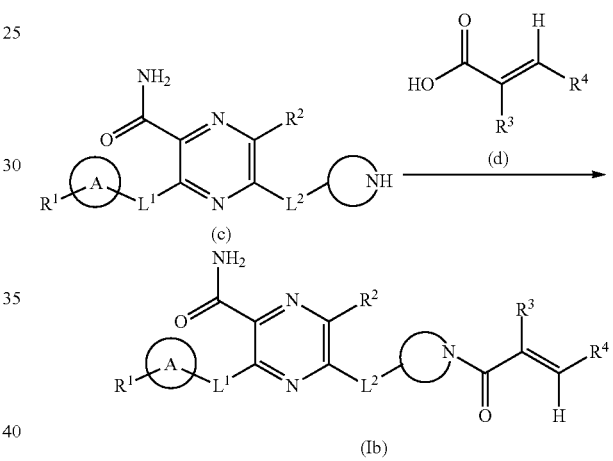

The present production process is a method for preparing a compound (Ib), which is the compound of the formula (I) the present invention, wherein Y is Ring X, Ring X is a non-aromatic heterocycle which may be substituted, having one or more nitrogen atoms, M is C=O, and $L^3$ is a bond, by subjecting the compound (c) to amidation in the similar manner to Production Process 1. The reaction condition is the same as in Production Process 1.

(Preparation of Starting Compound)

In the preparation method above, the starting compound can be prepared by using any of, for example, the methods below, the methods described in Preparation Examples as described later, known methods, or modified methods thereof.

(Starting Material Synthesis 1)

[Chem. 13]

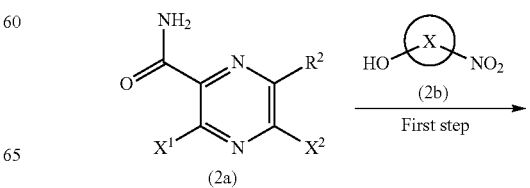

First step

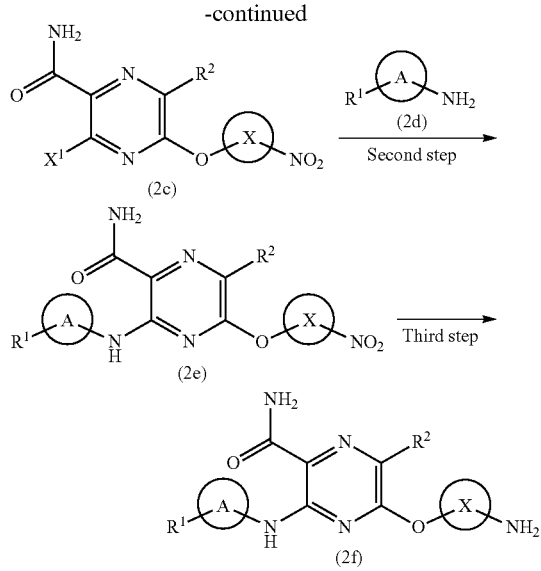

(wherein X¹ and X² each represent a leaving group).

The present production process is a method for preparing a compound (20, which is the starting compound (a) of Production Process 1, wherein $L^1$ is —NH—, $L^2$ is —O—, and Y is Ring X. Here, examples of the leaving group of X¹ and X² include halogen, methanesulfonyloxy, p-toluenesulfonyloxy groups, and the like.

(First Step)

The present step is a step of obtaining a compound (2c) by the ipso substitution reaction of a compound (2a) and a compound (2b).

The present step is carried out by using the compound (2a) and the compound (2b) in equivalent amounts, or either thereof in an excess amount, and stirring the mixture in a solvent which is inert to the reaction, or in the absence of a solvent, in a range of from cooling to heating and refluxing, preferably at 0° C. to 80° C., usually for 0.1 hours to 5 days. Examples of the solvent used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, N-methylpyrrolidone, ethyl acetate, acetonitrile, and a mixture thereof. It is preferable in some cases for the progress of the reaction to use organic bases such as triethylamine, N,N-diisopropylethylamine, and N-methylmorpholine, or inorganic bases such as potassium tert-butoxide, sodium hydride, potassium carbonate, sodium carbonate, potassium hydroxide, and the like.

[Documents]

S. R. Sandler and W. Karo, "Organic Functional Group Preparations", $2^{nd}$ Ed., Vol. 1, Academic Press Inc., 1991

"Jikken Kagaku Koza" (Courses in Experimental Chemistry) ($5^{th}$ Edition), edited by The Chemical Society of Japan, Vol. 14 (2005) (Maruzen)

(Second Step)

The present step is a step of obtaining a compound (2e) by the ipso substitution reaction of the compound (2c) and a compound (2d).

The reaction condition is the same as in the first step of Starting Material Synthesis 1. Further, it is preferable in some cases for the progress of the reaction to carry out the reaction at a higher temperature, for example, 180° C. or lower.

(Third Step)

The present step is a step of obtaining a compound (2f) by the hydrogenation reaction of the compound (2e).

In the present step, the compound (2e) is stirred in a solvent which is inert to the reaction, usually for 1 hour to 5 days, under a hydrogen atmosphere, in the presence of a metal catalyst. This reaction is usually carried out in a range from cooling to heating, and preferably at room temperature. Examples of the solvent used herein are not particularly limited, but include alcohols such as methanol, ethanol, 2-propanol, and the like, ethers such as diethyl ether, tetrahydrofuran, dioxane, dimethoxyethane, and the like, water, ethyl acetate, N,N-dimethylformamide, dimethyl sulfoxide, and a mixture thereof. As the metal catalyst, palladium catalysts such as palladium carbon, palladium black, palladium hydroxide, and the like, platinum catalysts such as a platinum plate, platinum oxide, and the like, nickel catalysts such as reduced nickel, Raney nickel, and the like, rhodium catalysts such as tetrakistriphenylphosphine chlororhodium and the like, or iron catalysts such as reduced iron and the like are suitably used. It is also possible to use an equivalent amount or an excess amount of the formic acid or ammonium formate with respect to the compound of the formula (I) instead of the hydrogen gas as a hydrogen source.

[Documents]

M. Hudlicky, "Reductions in Organic Chemistry, $2^{nd}$ Ed. (ACS Monograph: 188)", ACS, 1996

"Jikken Kagaku Koza" (Courses in Experimental Chemistry) ($5^{th}$ Edition), edited by The Chemical Society of Japan, Vol. 19 (2005) (Maruzen)

(Starting Material Synthesis 2)

[Chem. 14]

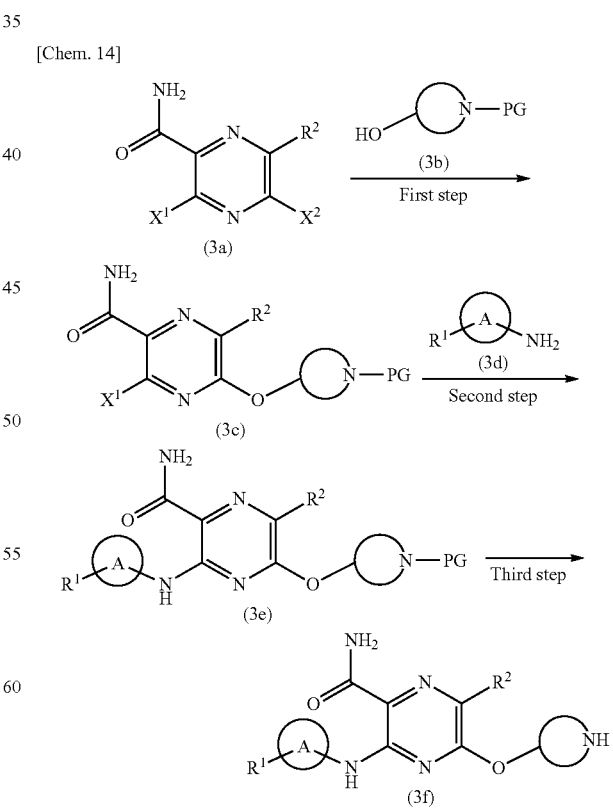

(wherein X¹ and X² each represent a leaving group. Further, PG represents a protective group.)

The present production process is a method for preparing a compound (3f), which is the starting compound (c) of Production Process 2, wherein $L^1$ is —NH— and $L^2$ is —O—.

(First Step)

The present step is a step of obtaining a compound (3c) by the ipso substitution reaction of the compound (3a) and the compound (3b).

The reaction condition is the same as in the first step of Starting Material Synthesis 1.

(Second Step)

The present step is a step of obtaining a compound (3e) by the ipso substitution reaction of the compound (3c) and the compound (3d).

The reaction condition is the same as in the first step of Starting Material Synthesis 1.

(Third Step)

The present step is a step of obtaining a compound (3f) by the deprotection reaction of the compound (3e).

The deprotection reaction can be carried out with reference to "Greene's Protective Groups in Organic Synthesis ($4^{th}$ edition, 2006)" as described above.

Further, if desired, the order of the first step and the second step can be reversed. In addition, there is a case where the preparation method such as the present production process can be employed for the compound in a case where $L^2$ represents a group other than —O—.

(Starting Material Synthesis 3)

[Chem. 15]

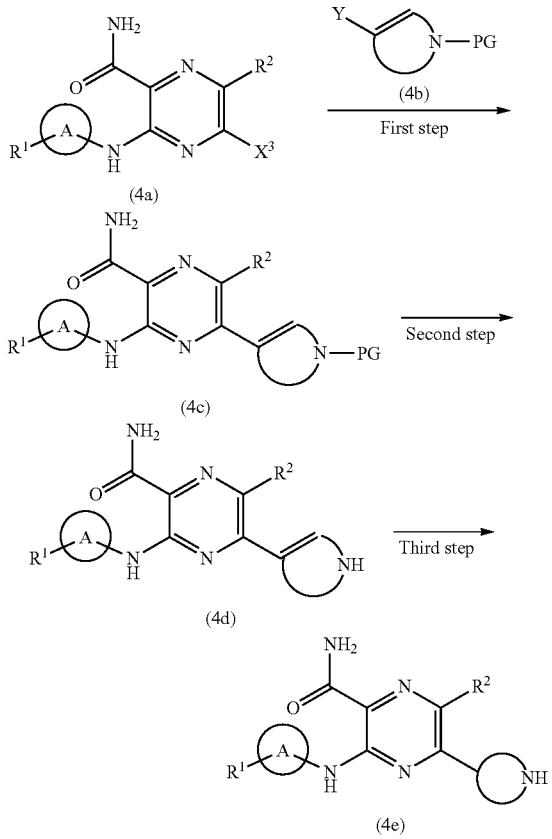

(wherein $X^3$ represents a leaving group, Y represents —B(OH)$_2$ or —B(OZ)OW, and PG represents a protective group. Here, Z and W are the same as or different from each other, and represent lower alkyl, or Z and W are combined to represent lower alkylene).

The present production process is a method for preparing a compound (4e), which is the starting compound (c) of Production Process 2, wherein $L^1$ is NH and $L^2$ is a bond. Here, examples of the leaving group represented by $X^3$ include halogen, methanesulfonyloxy, p-toluenesulfonyloxy, trifluoromethanesulfonyloxy groups, and the like.

(First Step)

The present step is a step of obtaining a compound (4c) by the coupling reaction of the compound (4a) and the compound (4b) prepared by the method described in the pamphlet of International Publication WO2010/128659 or a method equivalent thereto.

This reaction is carried out by using the compound (4a) and the compound (4b) in equivalent amounts, or either thereof in an excess amount, and stirring the mixture in a solvent which is inert to the reaction, in a range from at room temperature to heating and refluxing, usually for 0.1 hours to 5 days, in the presence of a base and a palladium catalyst. The present reaction is preferably carried out under an inert gas atmosphere. Examples of the solvent used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, dimethylsulfoxide, and a mixed solvent. As the base, inorganic bases such as sodium carbonate, potassium carbonate, sodium hydroxide, and the like are preferred. As the palladium catalyst, tetrakis(triphenylphosphine)palladium, dichlorobis(triphenylphosphine)palladium, palladium-1,1'-bis(diphenylphosphino)ferrocene chloride, or the like is preferred.

[Documents]

"Metal-Catalyzed Cross-Coupling Reactions", edited by A. d. Meijere and F. Diederich, Vol. 1, VCH Publishers Inc., 1997

"Jikken Kagaku Kozo" (Courses in Experimental Chemistry) ($5^{th}$ Edition), edited by The Chemical Society of Japan, Vol. 13 (2005) (Maruzen)

(Second Step)

The present step is a step of obtaining a compound (4d) by the deprotection reaction of the compound (4c).

The reaction condition is the same as in the third step of Starting Material Synthesis 2.

(Third Step)

The present step is a step of obtaining a compound (4e) by the hydrogenation reaction of the compound (4d).

The reaction condition is the same as in the third step of Starting Material Synthesis 1.

The compounds of the formula (I) can be isolated and purified as their free compounds, salts, hydrates, solvates, or polymorphic crystalline substances thereof. The salts of the compound of the formula (I) can be prepared by carrying out the treatment of a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemic products (for example, fractional crystallization for inducing diastereomer salts with optically active bases or acids, chromatography using a chiral column or the like, and others), and further, the isomers can also be prepared from an appropriate optically active starting compound.

The pharmacological activity of the compound of the formula (I) was confirmed by the tests shown below.

Test Example 1

Evaluation Test on Inhibitory Activity on EGFR T790M/L858R Mutation Kinase

The phosphorylation activity on the peptide substrate of EGFR was investigated using LabChip (trademark) Systems (Caliper Life Sciences, Inc.). For the enzyme, EGFR [T790M/L858R] (Carna Biosciences, Inc.) was used. The test compound was added to a reaction liquid containing the enzyme protein to give 8 stages of final concentrations ranging from 300 nM to 0.1 nM, followed by incubation for 2 hours. Then, the substrate and the ATP solution were added thereto, followed by reaction for 1 hour. An ATP concentration of 1000 μM was used. A reaction liquid containing the enzyme protein but no test compound (in which the DMSO alone was added as a solvent at 0.4% in place of the test compound) was prepared, followed by reaction in the same manner with or without ATP addition. Without addition of the test compound, the phosphorylation count without ATP addition and with ATP addition was assumed to be 100% inhibition and 0% inhibition, respectively. The concentration causing 50% inhibition ($IC_{50}$) was calculated for the test compound by a logistic regression method.

The $IC_{50}$ values of several Example Compounds of the present invention are shown in Table 1. Ex denotes Example No. of the test compound. Further, the $IC_{50}$ values of the compound of Example 546 in Patent Document 12 were 300 nM or more.

TABLE 1

| Ex | $IC_{50}$ (nM) |
|---|---|
| 1 | 1.3 |
| 3 | 1.4 |
| 15 | 1.2 |
| 22 | 1.5 |
| 24 | 1.1 |
| 26 | 1.1 |
| 42 | 1.2 |
| 43 | 1.4 |
| 54 | 1.7 |
| 56 | 1.3 |
| 63 | 1.8 |
| 64 | 1.7 |
| 69 | 1.3 |
| 73 | 1.2 |
| 79 | 1.3 |
| 80 | 1.2 |
| 82 | 1.5 |

Test Example 2

Evaluation Test on Inhibitory Activity on EGFR T790M/L858R Mutation Kinase- and EGFR T790M/del19 Mutation Kinase-Dependent Cell Proliferation The present test was carried out using Ba/F3 cells that had expressed an EGFR T790M/L858R mutation kinase and an EGFR T790M/del19 mutation kinase.

In a 96-well plate (Iwaki), Ba/F3 cells were seeded at 500 cells per well in an RPMI1640 medium (Invitrogen) containing 10% fetal bovine serum, followed by the addition of the test compound (final concentrations ranging from 1 μM to 0.1 nM) and DMSO which was a solvent of the test compound as a negative control. In the presence of 5% $CO_2$, the cells were cultured at 37° C. for 2 days. A cell counting reagent (Cell Titer-Glo; Promega) was added thereto, and the light emitting intensity was measured using a luminometer (Envison or ARVO; PerkinElmer Inc.). The measured values in the medium only and the negative control were assumed to be 100% inhibition and 0% inhibition, respectively. The inhibitory rate of the test compound was calculated and the concentration causing 50% inhibition ($IC_{50}$ value) was determined by a logistic regression method.

The $IC_{50}$ values of several compounds of the formula (I) are shown in Table 2. Ex denotes Example No.

TABLE 2

| Ex | T790M/L858R $IC_{50}$ (nM) | T790M/del19 $IC_{50}$ (nM) |
|---|---|---|
| 1 | 2.2 | 1.4 |
| 3 | 17 | 8.8 |
| 15 | 1.1 | 0.77 |
| 22 | 1.9 | 1.9 |
| 24 | 2.1 | 0.48 |
| 26 | 0.92 | 0.52 |
| 42 | 1.4 | 1.3 |
| 43 | 0.66 | 0.51 |
| 54 | 4.5 | 3.2 |
| 56 | 2.0 | 1.6 |
| 63 | 1.2 | 0.66 |
| 64 | 0.56 | 0.42 |
| 69 | 4.0 | 1.5 |
| 73 | 5.6 | 3.2 |

Test Example 3

Anti-Tumor Test on EGFR T790M Mutation-Expressing H1975 Cell Cancer-Bearing Mice $3 \times 10^6$ Cells of H1975 suspended in PBS were inoculated subcutaneously by injection to the back of 5-week old male Babble nude mice (Charles River Laboratories Japan, Inc.). After 10 days of the inoculation, the administration of the test compound was initiated. The test was carried out in the solvent group and the test compound groups, with 5 animals per group. The test compounds were each mixed in a solvent of 0.5% aqueous methyl cellulose solution or a mixed solvent of polyethyleneglycol:N-methylpyrrolidone=90:10, and administered orally at a dose of 10 mg/kg. Administrations were performed once a day for 14 days, and the body weight and the tumor diameter were measured roughly every other day. The tumor volume was calculated using the following formula.

[Tumor volume $(mm^3)$]=[Tumor major axis (mm)]×[Tumor minor axis (mm)]$^2$×0.5

The tumor volumes of the solvent group on the day of starting administration and the day of finishing administration of the test compound were assumed to be 100% inhibition and 0% inhibition, respectively, and the inhibitory rate of the test compound was calculated.

The inhibitory rates of Example Compounds of the present invention are shown in Table 3. Ex denotes Example No. of the test compound.

TABLE 3

| Ex | % |
|---|---|
| 1 | 24 |
| 15 | 41 |
| 22 | 65 |
| 24 | 100 |
| 54 | 74 |
| 64 | 28 |
| 79 | 30 |
| 80 | 27 |
| 82 | 84 |

As the results of Test Examples 1 to 2 above, it was confirmed that several Example Compounds of the present invention have inhibitory actions on EGFR T790M/L858R mutation kinase activity, and suppression actions on EGFR T790M/L858R mutation kinase- and T790M/del19 mutation kinase-dependent cell proliferation. Further, in Test Example 3, for the EGFR T790M mutation expressing cells cancer-bearing mice, the compounds have an anti-tumor action.

Therefore, the compound of the formula (I) or a salt thereof can be used for, for example, treatment of EGFR T790M mutation positive cancer, in another embodiment, EGFR T790M mutation positive lung cancer, in a still other embodiment, EGFR T790M mutation positive non-small cell lung cancer, in further still another embodiment, EGFR T790M mutation protein positive cancer, and in further still another embodiment, EGFR T790M mutation protein positive lung cancer, or the like.

From the standpoint that since the EGFR T790M mutation positive cancer exhibits resistance to the existing EGFR tyrosine kinase inhibitors such as gefitinib and erlotinib, in another embodiment, the compound of the formula (I) or a salt thereof of the present invention can be used for, for example, treatment of EGFR tyrosine kinase inhibitor-resistant cancer, in another embodiment, EGFR tyrosine kinase inhibitor-resistant lung cancer, and in a still other embodiment, EGFR tyrosine kinase inhibitor-resistant non-small cell lung cancer, or the like.

A pharmaceutical composition containing one or two or more kinds of the salt or compound of the formula (I) of the present invention can be prepared using excipients that are usually used in the art, that is, excipients for pharmaceutical preparations, carriers for pharmaceutical preparations, and the like according to the methods usually used.

Administration can be accomplished either by oral administration via tablets, pills, capsules, granules, powders, solutions, and the like, or parenteral administration, such as injections such as intraarticular, intravenous, and intramuscular injections, suppositories, ophthalmic solutions, eye ointments, transdermal liquid preparations, ointments, transdermal patches, transmucosal liquid preparations, transmucosal patches, and inhalers.

The solid composition for use in the oral administration according to the present invention is used in the form of tablets, powders, granules, or the like. In such a solid composition, one or more active ingredient(s) are mixed with at least one inactive excipien. In a conventional method, the composition may contain inactive additives, such as a lubricant, a disintegrating agent, a stabilizer, or a solubilization assisting agent. If necessary, tablets or pills may be coated with sugar or a film of a gastric-soluble or enteric coating substance.

The liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent, and a suspending agent, sweeteners, flavors, aromatics, or antiseptics.

The injections for parenteral administration include sterile aqueous or non-aqueous solutions, suspensions and emulsions. The aqueous solvent includes, for example, distilled water for injection and physiological saline. Examples of the non-aqueous solvent include alcohols such as ethanol. Such a composition may further contain a tonicity agent, an antiseptic, a moistening agent, an emulsifying agent, a dispersing agent, a stabilizer, or a solubilizing assisting agent. These are sterilized, for example, by filtration through a bacteria retaining filter, blending in of a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, poultices, sprays, lotions, eye drops, and eye ointments. The agents contain generally used ointment bases, lotion bases, aqueous or non-aqueous liquid preparations, suspensions, and emulsions.

As the transmucosal agents such as an inhaler and a transnasal agent, those in the form of a solid, liquid, or semi-solid state are used, and can be prepared in accordance with a conventionally known method. For example, a known excipient, and also a pH adjusting agent, an antiseptic, a surfactant, a lubricant, a stabilizer, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a known device or sprayer, such as a measured administration inhalation device. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, hydrofluoroalkane, and carbon dioxide.

Typically, in oral administration, the daily dose is appropriately from about 0.001 to 100 mg/kg, preferably from 0.1 to 30 mg/kg, and more preferably 0.1 to 10 mg/kg, per body weight, administered in one portion or in 2 to 4 separate portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

Although varying depending on administration routes, dosage forms, administration sites, or the types of excipients and additives, the pharmaceutical composition of the present invention contains 0.01 to 100% by weight, and in a certain embodiment, 0.01 to 50% by weight of one or more kinds of the compound of the formula (I) or a salt thereof, which is an active ingredient.

The compound of the formula (I) can be used in combination with various agents for treating or preventing the diseases, in which the compound of the formula (I) is considered effective. In general, when an anti-tumor agent is administered alone during chemotherapy for a tumor, particularly a malignant tumor, the anti-tumor agent has a limit in its effect in terms of side effects and the like, and thus often fails to produce a sufficient anti-tumor effect. For this reason, in clinical cases, multidrug therapy is used in which two or three or more drugs with different mechanisms of action are combined. By combining anti-tumor agents with different mechanisms of action, this combination therapy aims to reduce side effects or enhance the desired anti-tumor effect, for example, 1) to reduce the size of non-sensitive cell population, 2) to prevent or delay the development of drug resistance, 3) to disperse toxicity by combination of drugs with different toxicity levels, and the like. In such combination therapy, drugs may be administered simultaneously or separately in succession or at desired time intervals. Formulations for simultaneous administration may be in either mixed or have separate forms.

Examples of the drug which can be used in combination include chemotherapeutic agents such as an EGFR tyrosine kinase inhibitor, an alkylating agent, and an antimetabolite, immunotherapeutic agents, hormone therapeutic agents, cell proliferation factor inhibitors, and the like, and specifically, drugs such as gefitinib, erlotinib, cisplatin, carboplatin, paclitaxel, docetaxel, gemcitabine, irinotecan, vinorelbine, bevacizumab, pemetrexed, and the like.

EXAMPLES

Hereinbelow, the preparation methods for the compound of the formula (I) will be described in more detail with reference to Examples, but the present invention is not limited to the compounds described in the Examples below. Further, the production processes for the starting compounds will be each described in Preparation Examples. In addition, the preparation methods for the compound of the formula (I) are not limited to the preparation methods of the specific Examples shown below, but the compound of the formula (I) can be prepared by a combination of the preparation methods or a method that is apparent to a person skilled in the art.

Furthermore, the following abbreviations may be used in some cases in the Examples, Preparation Examples, and Tables below.

PEx: Preparation Example No., Ex: Example No., PSyn: Preparation Example No. prepared by the same method, Syn: Example No. prepared by the same method (e.g., E1 stands for Example 1), Str: Chemical structural formula (Me: methyl, Et: ethyl, iPr: isopropyl, OMe: methoxy, OEt: ethoxy, $NO_2$: nitro, $CF_3$: trifluoromethyl, CN: cyano, Boc: tert-butyloxycarbonyl, further, a compound denoted by "*" in the chemical structural formula represents that the compound is a single isomer having steric configuration of described structure. In addition, a compound having two or more asymmetric carbons which has stereochemical notation but no "*" indicates racemic mixture which relative configuration is only determined.), Data: Physicochemical Data, ESI+: m/z values in mass spectroscopy (Ionization ESI, representing [M+H]$^+$ unless otherwise specified), ESI−: m/z values in mass spectroscopy (Ionization ESI, representing [M−H]$^−$ unless otherwise specified), APCI/ESI+: APCI/ESI-MS[M+H]$^+$ (atmospheric pressure chemical ionization APCI, APCI/ESI: simultaneous measurement of APCI and ESI, representing [M+H]$^+$ unless otherwise specified), EI+: m/z values in mass spectroscopy (Ionization EI, representing (M)$^+$ unless otherwise specified), $^1$H-NMR (CDCl$_3$): peak δ (ppm) in 1H NMR in CDCl$_3$, 1H-NMR (DMSO-d6): peak δ (ppm) in 1H NMR in DMSO-d6, s: singlet (spectrum), d: doublet (spectrum), t: triplet (spectrum), q: quartet (spectrum), br: broad line (spectrum) (e.g.: br-s), m: multiplet (spectrum). Further, HCl in the structural formula represents monohydrochloride, 2HCl represents dihydrochloride, and 3HCl represents trihydrochloride.

RINT-TTRII was used in the measurement of powder X-ray diffraction according to the following conditions: X-ray tube: Cu; tube-current: 300 mA; tube-voltage: 50 kV; sampling width: 0.020°; scanning speed: 4°/min; wavelength: 1.54056 Å; range of measurement diffraction angles (2θ): 2.5-40°.

Moreover, in the present specification, nomenclature software such as ACD/Name (registered trademark, Advanced Chemistry Development, Inc.) is used in some cases for the nomenclature of the compound.

Furthermore, for the sake of convenience, a concentration mol/l is expressed as M.

For example, a 1 M aqueous sodium hydroxide solution means a 1 mol/l aqueous sodium hydroxide solution.

Preparation Example 1

A mixture of 3-nitrophenol (1 g), 3,5-dichloro-6-ethylpyrazine-2-carboxamide (1.74 g), diisopropylethylamine (2.63 mL), and dioxane (10 mL) was stirred at 80° C. overnight. To the reaction mixture was added water, and the precipitated solid was collected by filtration and then dried under reduced pressure to obtain 3-chloro-6-ethyl-5-(3-nitrophenoxy)pyrazine-2-carboxamide (1.68 g) as a white solid.

Preparation Example 2

A mixture of 3-chloro-6-ethyl-5-(3-nitrophenoxy)pyrazine-2-carboxamide (500 mg), 4-(4-methylpiperazin-1-yl)aniline (300 mg), methanesulfonic acid (201 μl), and N-methylpyrrolidone (2 mL) was heated in a microwave reaction device at 200° C. for 1 hour. To the reaction mixture was added 4-(4-methylpiperazin-1-yl)aniline (150 mg) and the mixture was heated at 200° C. for 30 minutes. To the reaction mixture was added a saturated aqueous sodium hydrogen carbonate solution, and the precipitated solid was collected by filtration and then dried. The obtained solid was purified by silica gel column chromatography (eluent; chloroform:methanol:28% aqueous ammonia=1:0:0-200:10:1) to obtain 6-ethyl-3-{[4-(4-methylpiperazin-1-yl)phenyl]amino}-5-(3-nitrophenoxy)pyrazine-2-carboxamide (308 mg) as a yellow solid.

Preparation Example 3

A mixture of 3-chloro-6-ethyl-5-(3-nitrophenoxy)pyrazine-2-carboxamide (400 mg), 4-[4-(4-methylpiperazin-1-yl)piperidin-1-yl]aniline (374 mg), trifluoroacetic acid (209 μL), and N-methylpyrrolidone (2.8 mL) was heated at 150° C. for 16 hours. To the reaction mixture was added a saturated aqueous sodium hydrogen carbonate solution, and the precipitated solid was collected by filtration, and then dried. The obtained solid was purified by silica gel column chromatography (eluent; chloroform:methanol:28% aqueous ammonia=1:0:0-200:10:1) to obtain 6-ethyl-3-({4-[4-(4-methylpiperazin-1-yl)piperidin-1-yl]phenyl}amino)-5-(3-nitrophenoxy)pyrazine-2-carboxamide (383 mg) as a brown solid.

Preparation Example 4

A mixture of 3-chloro-6-ethyl-5-(3-nitrophenoxy)pyrazine-2-carboxamide (300 mg), 2-(4-methylpiperazin-1-yl)pyrimidine-5-amine (198 mg), and diisopropylethylamine (318 µL) in N-methylpyrrolidone (1.5 mL) was heated at 120° C. for 18 hours. The reaction mixture was cooled, and then diluted with ethyl acetate, and the organic phase was washed with water and saturated brine. After drying over anhydrous sodium sulfate, the solvent was evaporated under reduced pressure. The residue was purified by silica gel column chromatography (eluent; chloroform:methanol:28% aqueous anunonia=1:0:0-95:4.5:0.5) to obtain 6-ethyl-3-{[2-(4-methylpiperazin-1-yl)pyrimidin-5-yl]amino}-5-(3-nitrophenoxy)pyrazine-2-carboxamide (234 mg) as a yellow solid.

Preparation Example 5

A mixture of 3-chloro-6-ethyl-5-(3-nitrophenoxy)pyrazine-2-carboxamide (300 mg), 2-methyl-4-(morpholin-4-yl)aniline (200 mg), diisopropylethylamine (330 µL), and N-methylpyrrolidone (2 mL) was reacted in a microwave reaction device at 180° C. for 2 hours. The reaction mixture was left to be cooled, and then 5 mL of water was added thereto. The precipitated solid was collected by filtration and purified by silica gel column chromatography (eluent; ethyl acetate:hexane=1:9-7:3) to obtain 6-ethyl-3-{[2-methyl-4-(morpholin-4-yl)phenyl]amino}-5-(3-nitrophenoxy)pyrazine-2-carboxamide (160 mg) as a brown solid.

Preparation Example 6

Under an argon atmosphere, a mixture of 3-chloro-6-ethyl-5-(3-nitrophenoxy)pyrazine-2-carboxamide (50 mg), 4-[(4-methylpiperazin-1-yl)methyl]aniline (48 mg), tris(dibenzylideneacetone)dipalladium (0) (14 mg), dicyclohexyl(2',4',6'-triisopropylbiphenyl-2-yl)phosphine (30 mg), cesium carbonate (101 mg), and dioxane (2 mL) was heated and refluxed for 4 hours. The reaction mixture was cooled and then diluted with ethyl acetate, and the organic phase was washed with water and saturated brine. After drying over anhydrous sodium sulfate, the solvent was evaporated under reduced pressure. The residue was purified by silica gel column chromatography (eluent; ethyl acetate:methanol:28% aqueous ammonia=95:4.5:0.5-90:9:1, chloroform: methanol=1:0-9:1) to obtain 6-ethyl-3-({4-[(4-methylpiperazin-1-yl)methyl]phenyl}amino)-5-(3-nitrophenoxy)pyrazine-2-carboxamide (14 mg) as a yellow oily substance.

Preparation Example 7

To a mixture of 6-ethyl-3-{[4-(4-methylpiperazin-1-yl)phenyl]amino}-5-(3-nitrophenoxy)pyrazine-2-carboxamide (300 mg) in ethanol (6 mL) and water (6 mL) were added ammonium chloride (672 mg) and iron powder (351 mg), followed by stirring at 60° C. for 6 hours. The reaction mixture was left to be cooled and then filtered through celite, and the solvent was evaporated under reduced pressure. To the residue was added a saturated aqueous sodium hydrogen carbonate solution, followed by extraction with chloroform. The organic phase was washed with saturated brine and dried over anhydrous magnesium sulfate, and then the solvent was evaporated under reduced pressure. The residue was purified by silica gel column chromatography (eluent; chloroform: methanol:28% aqueous ammonia=1:0:0-200:10:1). Diisopropyl ether was added thereto, and the solid was collected by filtration and then dried under reduced pressure to obtain 5-(3-aminophenoxy)-6-ethyl-3-{[4-(4-methylpiperazin-1-yl)phenyl]amino}pyrazine-2-carboxamide (125 mg).

Preparation Example 8

A mixture of 6-ethyl-3-{[4-(1-methylpiperidin-4-yl)phenyl]amino}-5-(3-nitrophenoxy)pyrazine-2-carboxamide (500 mg) in ethanol (10 mL) and water (10 mL) were heated to 80° C., and zinc powder (686 mg) and ammonium chloride (561 mg) were added thereto, followed by stirring at 80° C. for 3 hours. The reaction mixture was left to be cooled, and then a saturated aqueous sodium hydrogen carbonate solution was added thereto, followed by extraction with ethyl acetate. The organic phase was washed with saturated brine and dried over anhydrous magnesium sulfate, and then the solvent was evaporated under reduced pressure. The residue was purified by silica gel column chromatography (eluent; chloroform:methanol:28% aqueous ammonia=1:0:0-100:10:1) to obtain 5-(3-aminophenoxy)-6-ethyl-3-{[4-(1-methylpiperidin-4-yl)phenyl]amino}pyrazine-2-carboxamide (255 mg).

Preparation Example 9

To a mixture of 3-{[4-(4-methylpiperazin-1-yl)phenyl]amino}-5-(3-nitrophenoxy)-6-(prop-1-en-2-yl)pyrazine-2-carboxamide (1.13 g), ethanol (60 mL), and tetrahydrofuran (30 mL) was added 10% palladium-supported carbon (53% wet product) (1.23 g), followed by stirring for 6 hours under a hydrogen gas atmosphere (4 atm). The reaction mixture was filtered through celite and then the solvent was evaporated under reduced pressure. The obtained residue was purified by silica gel column chromatography (eluent; chloroform:methanol:28% aqueous ammonia=100:1:0.1-30:1:0.1) to obtain 5-(3-aminophenoxy)-6-isopropyl-3-{[4-(4-methylpiperazin-1-yl)phenyl]amino}pyrazine-2-carboxamide (702 mg) as a yellow solid.

Preparation Example 10

To a mixture of 6-ethyl-3-({4-[(4-methylpiperazin-1-yl)methyl]phenyl}amino)-5-(3-nitrophenoxy)pyrazine-2-carboxamide (112 mg) in ethanol (3 mL) and water (1 mL) were added iron chloride (III) hexahydrate (31 mg), activated carbon (60 mg), and hydrazine monohydrate (221 µL), followed by stirring at 80° C. for 2 hours. The reaction mixture was left to be cooled, and then water was added thereto. The insoluble matter was collected by filtration. To the obtained solid was added a solution in chloroform-methanol (10:1), and the insoluble matter was separated by filtration. The obtained filtrate was concentrated under reduced pressure to obtain 5-(3-aminophenoxy)-6-ethyl-3-({4-[(4-methylpiperazin-1-yl)methyl]phenyl}amino)pyrazine-2-carboxamide (46 mg) as a pale yellow solid.

Preparation Example 11

To a mixture of 6-ethyl-3-{[2-methyl-4-(morpholin-4-yl)phenyl]amino}-5-(3-nitrophenoxy)pyrazine-2-carboxamide (145 mg), ethanol (2 mL), and tetrahydrofuran (6 mL) was added 10% palladium-supported carbon (50% wet product) (30 mg), followed by stirring for 5 hours under a hydrogen gas atmosphere (1 atm). The reaction mixture was filtered through celite and then the solvent was evaporated under reduced pressure to obtain 5-(3-aminophenoxy)-6-ethyl-3-{[2-methyl-4-(morpholin-4-yl)phenyl]amino}pyrazine-2-carboxamide (135 mg) as a solid.

Preparation Example 12

To a mixture of 6-(2-hydroxypropan-2-yl)-3-{[4-(4-methylpiperazin-1-yl)phenyl]amino}-5-(3-nitrophenoxy)pyrazine-2-carboxamide (300 mg), tetrahydrofuran (6 mL), and methanol (12 mL) were added sodium dithionite (1.03 g), sodium hydrogen carbonate (993 mg), and water (13.5 mL), followed by stirring at room temperature for 30 minutes, and then stirring at 50° C. for 2 hours. To the reaction mixture was added chloroform-isopropanol (4:1), and then the organic phase was washed with water. The organic phase was dried over anhydrous sodium sulfate, and then the solvent was evaporated under reduced pressure. The residue was purified by silica gel column chromatography (NH2 type, eluent; chloroform:methanol:28% aqueous ammonia=50:1:0.1-20:1:0.1) to obtain 5-(3-aminophenoxy)-6-(2-hydroxypropan-2-yl)-3-{[4-(4-methylpiperazin-1-yl)phenyl]amino}pyrazine-2-carboxamide (27 mg) as a yellow solid.

Preparation Example 13

A mixture of 3-amino-2-fluorophenol (50 mg), 5-chloro-6-ethyl-3-{[4-(4-methylpiperazin-1-yl)phenyl]amino}pyrazine-2-carboxamide (162 mg), potassium carbonate (65 mg), and N-methylpyrrolidone (1 mL) was stirred at 100° C. for 2 hours. To the reaction mixture was added water-saturated brine (1:1), followed by extraction with ethyl acetate. The organic phase was dried over anhydrous sodium sulfate and then the solvent was evaporated under reduced pressure. The residue was purified by silica gel column chromatography (eluent; chloroform:methanol=1:0-9:1) to obtain 5-(3-amino-2-fluorophenoxy)-6-ethyl-3-{[4-(4-methylpiperazin-1-yl)phenyl]amino}pyrazine-2-carboxamide (126 mg) as a yellow solid.

Preparation Example 14

A mixture of 3-chloro-6-(2-hydroxypropan-2-yl)-5-(3-nitrophenoxy)pyrazine-2-carboxamide (1.48 g), 4-(4-methylpiperidin-1-yl)aniline (883 mg), trifluoroacetic acid (385 µL), and N-methylpyrrolidone (14.8 mL) was heated to 160° C. for 5 hours. To the reaction mixture were added water and a saturated aqueous sodium hydrogen carbonate solution, and the precipitated solid was collected by filtration and then dried. The obtained solid was purified by silica gel column chromatography (eluent; chloroform:methanol:28% aqueous ammonia=1:0:0-30:1:0.1) and washed with ethyl acetate to obtain 3-{[4-(4-methylpiperazin-1-yl)phenyl]amino}-5-(3-nitrophenoxy)-6-(prop-1-en-2-yl)pyrazine-2-carboxamide (1.15 g) as an orange solid.

Preparation Example 15

A mixture of 3-chloro-6-(2-hydroxypropan-2-yl)-5-(3-nitrophenoxy)pyrazine-2-carboxamide (300 mg), 1-(1-methylpiperidin-4-yl)-1H-pyrazol-4-amine (184 mg), diisopropylethylamine (291 µL), and N-methylpyrrolidone (3 mL) was reacted in a microwave reaction device at 180° C. for 2 hours. To the reaction mixture were added water and saturated brine, followed by extraction with ethyl acetate. The organic phase was dried over anhydrous sodium sulfate and the solvent was evaporated under reduced pressure. The obtained residue was purified by silica gel column chromatography (eluent; chloroform:methanol=1:0-9:1). The obtained solid was purified by silica gel column chromatography (NH2 type, eluent; chloroform:methanol=100:0-98:2) to obtain 3-{[1-(1-methylpiperidin-4-yl)-1H-pyrazol-4-yl]amino}-5-(3-nitrophenoxy)-6-(prop-1-en-2-yl)pyrazine-2-carboxamide (212 mg) as a yellow solid.

Preparation Example 16

A mixture of 3-chloro-6-(2-hydroxypropan-2-yl)-5-(3-nitrophenoxy)pyrazine-2-carboxamide (1 g), 4-(4-methylpiperazin-1-yl)aniline (542 mg), tris(dibenzylideneacetone)dipalladium (0) (130 mg), dicyclohexyl (2',4',6'-triisopropylbiphenyl-2-yl)phosphine (135 mg), potassium carbonate (1.29 g), and tert-butanol (5 mL) was stirred at 80° C. for 5 days. The reaction mixture was left to be cooled and then diluted with chloroform, and the insoluble matter was separated by filtration. The filtrate was concentrated and the obtained residue was purified by silica gel column chromatography (eluent; chloroform:methanol:28% aqueous ammonia=100:0:0-300:10:1) to obtain 6-(2-hydroxypropan-2-yl)-3-{[4-(4-methylpiperazin-1-yl)phenyl]amino}-5-(3-nitrophenoxy)pyrazine-2-carboxamide (303 mg) as a yellow solid.

Preparation Example 17

To a mixture of tert-butyl 4-(4-{[3-carbamoyl-6-(3-nitrophenoxy)pyrazin-2-yl]amino}phenyl)piperazine-1-carboxylate (1 g) and chloroform (30 mL) was added N-bromosuccinimide (349 mg), followed by stirring at room temperature for 30 minutes. Then, N-bromosuccinimide (100 mg) was added thereto, followed by further stirring at room temperature for 30 minutes. To the reaction mixture was added silica gel, and the solvent was evaporated under reduced pressure and then purified by silica gel column chromatography (eluent; chloroform) to obtain tert-butyl 4-(2-bromo-4-{[3-carbamoyl-6-(3-nitrophenoxy)pyrazin-2-yl]amino}phenyl)piperazine-1-carboxylate (682 mg) as a yellow solid.

Preparation Example 18

To a mixture of tert-butyl 4-(4-{[3-carbamoyl-6-(3-nitrophenoxy)pyrazin-2-yl]amino}phenyl)piperazine-1-carboxylate (1 g) and chloroform (30 mL) was added N-chlorosuccinimide (262 mg), and the reaction mixture was stirred at 50° C. for 15 hours and further, at 60° C. for 24 hours. To the reaction mixture was added silica gel, and the solvent was evaporated under reduced pressure and then purified by silica gel column chromatography (eluent; chloroform) to obtain tert-butyl 4-(4-{[3-carbamoyl-6-(3-nitrophenoxy)pyrazin-2-yl]amino}-2-chlorophenyl)piperazine-1-carboxylate (1.05 g) as a yellow solid.

Preparation Example 19

To a mixture of tert-butyl 4-(2-bromo-4-{[3-carbamoyl-6-(3-nitrophenoxy)pyrazin-2-yl]amino}phenyl)piperazine-1-carboxylate (682 mg) and 1,2-dichloroethane (7 mL) was added trifluoroacetic acid (3 mL) under ice-cooling, and followed by stirring at room temperature for 2 hours. The reaction mixture was concentrated under reduced pressure, then diluted with chloroform, and neutralized with a 10% aqueous potassium carbonate solution. After extracting with chloroform, the organic phase was dried over anhydrous magnesium sulfate. The solvent was evaporated under reduced pressure to obtain 3-{[3-bromo-4-(piperazin-1-yl)phenyl]amino}-5-(3-nitrophenoxy)pyrazine-2-carboxamide (523 mg) as a yellow amorphous substance.

Preparation Example 20

To a mixture of tert-butyl[3-({5-carbamoyl-3-ethyl-6-[4-(1-methyl-1,2,3,6-tetrahydropyridin-4-yl)phenoxy]pyrazin-2-yl}oxy)phenyl]carbamate (150 mg) and dichloromethane (3 mL) was added trifluoroacetic acid (421 µL), followed by stirring at room temperature for 2 hours. The mixture was neutralized with a saturated aqueous sodium hydrogen carbonate solution, extracted with ethyl acetate, and then the organic phase was washed with saturated brine, and dried over anhydrous sodium sulfate. The solvent was evaporated under reduced pressure. The obtained residue was purified by silica gel column chromatography (NH2 type, eluent; chloroform:methanol=1:0-95:5) to obtain 5-(3-aminophenoxy)-6-ethyl-3-[4-(1-methyl-1,2,3,6-tetrahydropyridin-4-yl)phenoxy]pyrazine-2-carboxamide (56 mg) as a colorless solid.

Preparation Example 21

To a mixture of 3-{[3-bromo-4-(piperazin-1-yl)phenyl]amino}-5-(3-nitrophenoxy)pyrazine-2-carboxamide (523 mg) and ethanol (5 mL)-tetrahydrofuran (15 mL) were added 1H-benzotriazole-1-methanol (159 mg) and sodium triacetoxyborohydride (323 mg), followed by stirring at room temperature for 6 hours, then diluting with chloroform, and washing with a saturated aqueous sodium hydrogen carbonate solution. After the organic phase was dried over anhydrous magnesium sulfate, the solvent was evaporated under reduced pressure and the residue was purified by silica gel column chromatography (eluent; chloroform:methanol:28% aqueous ammonia=1:0:0-50:1:0.1) to obtain 3-{[3-bromo-4-(4-methylpiperazin-1-yl)phenyl]amino}-5-(3-nitrophenoxy)pyrazine-2-carboxamide (447 mg) as a pale yellow solid.

Preparation Example 22

A mixture of 5-(3-aminophenoxy)-3-{[4-(1,4-dioxa-8-azaspiro[4.5]dec-8-yl)-3-methylphenyl]amino}-6-ethylpyrazine-2-carboxamide (840 mg) and 3 M hydrochloric acid (6 mL) was stirred at 80° C. for 5 hours, and then acetic acid (1.5 mL) was added thereto, followed by stirring at 80° C. overnight. The reaction mixture was left to be cooled, and then water (30 mL) was added thereto, followed by ice-cooling. The pH was adjusted to 9 by the addition of concentrated ammonia. The precipitated solid was collected by filtration and then dried under reduced pressure to obtain 5-(3-aminophenoxy)-6-ethyl-3-{[3-methyl-4-(4-oxopiperidin-1-yl)phenyl]amino}pyrazine-2-carboxamide (0.74 g) as a pale yellow solid.

Preparation Example 23

To a mixture of 3-{[3-bromo-4-(4-methylpiperazin-1-yl)phenyl]amino}-5-(3-nitrophenoxy)pyrazine-2-carboxamide (500 mg), and N-methylpyrrolidone (5 mL) were added pyridin-4-ylboronic acid (407 mg), tetrakistriphenylphosphine palladium (0) (164 mg), and a 2 M aqueous sodium carbonate solution (2.84 mL), followed by stirring in a microwave reaction device at 140° C. for 1 hour. To the reaction mixture was added water, followed by extraction with ethyl acetate. The organic phase was washed with saturated brine and dried over anhydrous magnesium sulfate, and then the solvent was evaporated under reduced pressure. The residue was purified by silica gel column chromatography (eluent: chloroform:methanol:28% aqueous ammonia=1:0:0-15:1:0.1) to obtain 3-{[4-(4-methylpiperazin-1-yl)-3-(pyridin-4-yl)phenyl]amino}-5-(3-nitrophenoxy)pyrazine-2-carboxamide (64 mg) as a yellow solid.

Preparation Example 24

To a mixture of 3-{[3-bromo-4-(4-methylpiperazin-1-yl)phenyl]amino}-5-(3-nitrophenoxy)pyrazine-2-carboxamide (645 mg) and pyridine (3.87 mL) was added cuprous cyanide (219 mg), followed by heating and refluxing for 5 hours. Cuprous cyanide (328 mg) was further added thereto, followed by heating and refluxing for 15 hours. The reaction mixture was left to be cooled, and then a mixed solvent (10:1:0.1) of chloroform:methanol:28% aqueous ammonia was added thereto. A saturated aqueous sodium hydrogen carbonate solution was further added thereto, followed by stirring, and then the insoluble matter was separated by filtration. The filtrate was subjected to liquid separation, and then the organic phase was dried over anhydrous magnesium sulfate. Then, the solvent was evaporated under reduced pressure. The obtained residue was purified by silica gel column chromatography (eluent: chloroform:methanol:28% aqueous ammonia=1:0:0-20:1:0.1) to obtain 3-{[3-cyano-4-(4-methylpiperazin-1-yl)phenyl]amino}-5-(3-nitrophenoxy)pyrazine-2-carboxamide (68 mg) as a yellow solid.

Preparation Example 25

A mixture of tert-butyl {3-[(5-carbamoyl-6-chloro-3-ethylpyrazin-2-yl)oxy]phenyl}carbamate (500 mg), 4-bromophenol (440 mg), potassium carbonate (440 mg), and N-methylpyrrolidone (5 mL) was reacted at 100° C. for 4 hours. The reaction mixture was left to be cooled, and then water-saturated brine (1:1) was added thereto, followed by extraction with ethyl acetate. Then, the organic phase was dried over anhydrous sodium sulfate and the solvent was evaporated under reduced pressure. The obtained residue was purified by silica gel column chromatography (eluent; chloroform:methanol=1:0-95:5, hexane:ethyl acetate=7:3-3:7) to obtain tert-butyl (3-{[6-(4-bromophenoxy)-5-carbamoyl-3-ethylpyrazin-2-yl]oxy}phenyl)carbamate (599 mg) as a colorless solid.

Preparation Example 26

To a mixture of tert-butyl (3-{[6-(4-bromophenoxy)-5-carbamoyl-3-ethylpyrazin-2-yl]oxy}phenyl)carbamate (540 mg), 1-methyl-4-(4,4,5,5-tetramethyl-1,3,2-dioxaborolan-2-yl)-1,2,3,6-tetrahydropyridine (273 mg), and N,N-dimethylformamide (10 mL) were added a 1,1'-bis(diphenylphosphino)ferrocene palladium (II) dichloride-dichloromethane complex (83 mg) and cesium carbonate (665 mg), followed by reacting at 80° C. for 1 hour. The reaction mixture was left to be cooled, and then ethyl acetate was added thereto. The mixture was washed with water and saturated brine and dried over anhydrous sodium sulfate, and then the solvent was evaporated under reduced pressure. The obtained residue was purified by silica gel column chromatography (eluent; chloroform:methanol=1:0-9:1) and silica gel column chromatography (NH2 type, eluent; chloroform:methanol=100:0-98:2) to obtain tert-butyl [3-({5-carbamoyl-3-ethyl-6-[4-(1-methyl-1,2,3,6-tetrahydropyridin-4-yl)phenoxy]pyrazin-2-yl}oxy)phenyl]carbamate (153 mg) as a pale yellow oily substance.

Preparation Example 27

A mixture of 3,5-dichloro-6-ethylpyrazine-2-carboxamide (420 mg), 4-[(2S)-2,4-dimethylpiperazin-1-yl]aniline (392 mg), diisopropylethylamine (665 µL), and dioxane (8.4 mL) was stirred at 110° C. overnight. To the reaction mixture was added water, followed by extraction with ethyl acetate. The organic phase was washed with saturated brine and dried over anhydrous magnesium sulfate, and then the solvent was evaporated under reduced pressure. The obtained residue was purified by silica gel column chromatography (eluent; chloroform:methanol=95:5) to obtain 5-chloro-3-({4-[(2S)-2,4- dimethylpiperazin-1-yl]phenyl}amino)-6-ethylpyrazine-2-carboxamide (560 mg) as a brown solid.

Preparation Example 28

To a mixture of tert-butyl 4-(4-nitro-1H-imidazol-1-yl)piperidine-1-carboxylate (700 mg) and ethyl acetate (5 ml) was added a 4 M hydrogen chloride ethyl acetate solution (5 mL), followed by stirring at room temperature for 3 hours. The reaction mixture was evaporated under reduced pressure, and then to the residue were added dichloromethane (3 mL), methanol (5 mL), tetrahydrofuran (3 ml), 1H-benzotriazol-1-yl methanol (705 mg), sodium triacetoxyborohydride (1 g), and sodium acetate (388 mg), followed by stirring at room temperature for 2 hours. To the reaction mixture was added a saturated aqueous sodium hydrogen carbonate solution, and silica gel (NH2 type) was added thereto. The solvent was evaporated under reduced pressure, and then the residue was purified by silica gel column chromatography (NH2 type, eluent; chloroform:methanol=100:0-98:2). To the obtained solid were added ethanol (10 mL) and 10% palladium-supported carbon (50% wet product) (201 mg), followed by stirring at room temperature for 1 hour under a hydrogen gas atmosphere (1 atm). The reaction mixture was filtered through celite and then the solvent was evaporated under reduced pressure. To the residue were added 3-chloro-6-ethyl-5-(3-nitrophenoxy)pyrazine-2-carboxamide (670 mg), diisopropylethylamine (647 µL), and N-methylpyrrolidone (3 mL), followed by stirring in a microwave reaction device at 180° C. for 2 hours. To the reaction mixture was added water-saturated brine (1:1), followed by extraction with ethyl acetate. The organic phase was dried over anhydrous sodium sulfate, and then the solvent was evaporated under reduced pressure. The residue was purified by silica gel column chromatography (eluent; chloroform:methanol=10:0-9:1, NH2 type: eluent; chloroform:methanol=100:0-95:5) to obtain 6-ethyl-3-{[1-(1-methylpiperidin-4-yl)-1H-imidazol-4-yl]amino}-5-(3-nitrophenoxy)pyrazine-2-carboxamide (144 mg) as a yellow solid.

Preparation Example 29

To a mixture of tert-butyl 3-hydroxypyrrolidine-1-carboxylate (1 g) and N,N-dimethylformamide (30 mL) was added 55% oily sodium hydride (233 mg) under ice-cooling. After stirring for 30 minutes under ice-cooling, 3,5-dichloro-6-ethylpyrazine-2-carboxamide (1.18 g) was added thereto, followed by further stirring for 1 hour under ice-cooling. The reaction mixture was poured into ice water, followed by extraction with ethyl acetate. The organic phase was washed with saturated brine and then dried over anhydrous magnesium sulfate, and the solvent was evaporated under reduced pressure. The obtained residue was purified by silica gel column chromatography (eluent: chloroform) to obtain tert-butyl 3-[(5-carbamoyl-6-chloro-3-ethylpyrazin-2-yl)oxy]pyrrolidine-1-carboxylate (795 mg) as a pale yellow solid.

Preparation Example 30

A mixture of tert-butyl 3-[(5-carbamoyl-6-chloro-3-ethylpyrazin-2-yl)oxy]pyrrolidine-1-carboxylate (790 mg), 4-(4-methylpiperazin-1-yl)aniline (448 mg), diisopropylethylamine (729 µL), and N,N-dimethylformamide (5.53 mL) was stirred at 120° C. for 22 hours. The reaction mixture was left to be cooled and then diluted with ethyl acetate, and the organic phase was washed with water, a saturated aqueous sodium hydrogen carbonate solution, and saturated brine in this order, and dried over anhydrous magnesium sulfate, and then the solvent was evaporated under reduced pressure. The obtained residue was purified by silica gel column chromatography (eluent; chloroform:methanol:28% aqueous ammonia=1:0:0-30:1:0.1), and then washed with diisopropyl ether to obtain tert-butyl 3-[(5-carbamoyl-3-ethyl-6-{[4-(4-methylpiperazin-1-yl)phenyl]amino}pyrazin-2-yl)oxy]pyrrolidine-1-carboxylate (355 mg) as a pale yellow solid.

Preparation Example 31

A mixture of tert-butyl (3R)-3-[(5-carbamoyl-6-chloro-3-ethylpyrazin-2-yl)oxy]pyrrolidine-1-carboxylate (90 mg), 4-[4-(4-methylpiperazin-1-yl)piperidin-1-yl]aniline (210 mg), diisopropylethylamine (140 µL), and N-methylpyrrolidone (500 µL) was reacted using a microwave reaction device at 150° C. for 2 hours. The reaction mixture was left to be cooled, and then water and diisopropyl ether were added thereto. The insoluble matter was collected by filtration to obtain tert-butyl (3R)-3-{[5-carbamoyl-3-ethyl-6-({4-[4-(4-methylpiperazin-1-yl)piperidin-1-yl]phenyl}amino)pyrazin-2-yl]oxy}pyrrolidine-1-carboxylate (101 mg) as a yellowish brown solid.

Preparation Example 32

A mixture of tert-butyl (3R)-3-{[5-carbamoyl-6-chloro-3-(2-hydroxypropan-2-yl)pyrazin-2-yl]oxy}pyrrolidine-1-carboxylate (300 mg), 4-[4-(4-methylpiperazin-1-yl)piperidin-1-yl]aniline (680 mg), diisopropylethylamine (400 µL), and N-methylpyrrolidone (1.2 mL) was reacted in a microwave reaction device at 180° C. for 1 hour. To the reaction mixture was added water, followed by extraction with ethyl acetate. The organic phase was dried over anhydrous magnesium sulfate and then the solvent was evaporated under reduced pressure. The residue was purified by silica gel column chromatography (eluent; chloroform:methanol:28% aqueous ammonia=1:0:0-100:10:1), and then washed with diisopropyl ether to obtain tert-butyl (3R)-3-{[5-carbamoyl-6-({-4-[4-(4-methylpiperazin-1-yl)piperidin-1-yl]phenyl}amino)-3-(prop-1-en-2-yl)pyrazin-2-yl]oxy}pyrrolidine-1-carboxylate (304 mg) as a yellow solid.

Preparation Example 33

To a mixture of tert-butyl (3R)-3-hydroxypyrrolidine-1-carboxylate (860 mg) and N,N-dimethylformamide (30 mL) was added 55% oily sodium hydride (200 mg) under ice-cooling. After stirring for 30 minutes under ice-cooling, 5-chloro-6-ethyl-3-({3-methyl-4-[4-(4-methylpiperazin-1-yl)piperidin-1-yl]phenyl}amino)pyrazine-2-carboxamide (1 g) was added thereto, followed by further stirring for 1 hour under ice-cooling. 55% oily sodium hydride (100 mg) was added thereto, followed by stirring at room temperature for 4 hours, and then 55% oily sodium hydride (100 mg) was added thereto, followed by stirring at room temperature overnight. The reaction mixture was poured into ice water, followed by extraction with ethyl acetate. The organic phase was washed with saturated brine and then dried over anhydrous magnesium sulfate. The solvent was evaporated under reduced pressure and the obtained residue was purified by silica gel column chromatography (eluent; chloroform:methanol:28% aqueous ammonia=1:0:0-100:10:1) to obtain tert-butyl (3R)-3-{[5-carbamoyl-3-ethyl-6-({3-methyl-4-[4-(4-methylpiperazin-1-yl)piperidin-1-yl]phenyl}amino)pyrazin-2-yl]oxy}pyrrolidine-1-carboxylate (284 mg).

Preparation Example 34

To a mixture of tert-butyl 3-[(5-carbamoyl-3-ethyl-6-{[4-(4-methylpiperazin-1-yl)phenyl]amino}pyrazin-2-yl)oxy]pyrrolidine-1-carboxylate (355 mg) and 1,2-dichloroethane (6 mL) was added trifluoroacetic acid (2 mL) under ice-cooling, followed by stirring at room temperature for 12 hours. The reaction mixture was concentrated, then diluted with chloroform, and neutralized with a 10% aqueous potassium carbonate solution. After extraction with chloroform, the organic phase was dried over anhydrous magnesium sulfate. The solvent was evaporated under reduced pressure and the obtained residue was purified by silica gel column chromatography (eluent; chloroform:methanol:28% aqueous ammonia=1:0:0-100:10:1), and dried under reduced pressure to obtain 6-ethyl-3-{[4-(4-methylpiperazin-1-yl)phenyl]amino}-5-(pyrrolidin-3-yloxy)pyrazine-2-carboxamide (212 mg) as a yellow solid.

Preparation Example 35

To a mixture of tert-butyl (3R)-3-{[5-carbamoyl-6-({4-[4-(4-methylpiperazin-1-yl)piperidin-1-yl]phenyl}amino)-3-(prop-1-en-2-yl)pyrazin-2-yl]oxy}pyrrolidine-1-carboxylate (300 mg), ethanol (6 mL), and tetrahydrofuran (6 mL) was added 10% palladium-supported carbon (50% wet product) (260 mg), followed by stirring at room temperature overnight under a hydrogen gas atmosphere (4 atm). The reaction mixture was filtered through celite, and then the solvent was evaporated under reduced pressure and washed with diisopropyl ether to obtain tert-butyl (3R)-3-{[5-carbamoyl-3-isopropyl-6-({4-[4-(4-methylpiperazin-1-yl)piperidin-1-yl]phenyl}amino)pyrazin-2-yl]oxy}pyrrolidine-1-carboxylate (253 mg) as a yellow solid.

Preparation Example 36

Under an argon atmosphere, to a mixture of 5-chloro-6-ethyl-3-({3-methyl-4-[4-(4-methylpiperazin-1-yl)piperidin-1-yl]phenyl}amino)pyrazine-2-carboxamide (500 mg), tert-butyl 4-(4,4,5,5-tetramethyl-1,3,2-dioxaboloran-2-yl)-3,6-dihydropyridine-1(2H)-carboxylate (328 mg), and dioxane (10 mL) were sequentially added tetrakistriphenylphosphine palladium (0) (61 mg), and a 2 M aqueous sodium carbonate solution (1.1 mL) in this order, followed by stirring at 80° C. overnight. After leaving to be cooled, ethyl acetate and a saturated aqueous sodium hydrogen carbonate solution were added thereto, and the organic phase was washed with saturated brine and dried over anhydrous magnesium sulfate. The solvent was evaporated under reduced pressure and the obtained residue was purified by silica gel column chromatography (chloroform:methanol:28% aqueous ammonia=1:0:0-200:10:1) to obtain tert-butyl 4-[5-carbamoyl-3-ethyl-6-({3-methyl-4-[4-(4-methylpiperazin-1-yl)piperidin-1-yl]phenyl}amino)pyrazin-2-yl]-3,6-dihydropyridine-1(2H)-carboxylate (610 mg) as a solid.

Preparation Example 37

To a mixture of tert-butyl 4-[5-carbamoyl-3-ethyl-6-({3-methyl-4-[4-(4-methylpiperazin-1-yl)piperidin-1-yl]phenyl}amino)pyrazin-2-yl]-3,6-dihydropyridine-1(2H)-carboxylate (600 mg) and 1,2-dichloroethane (6 mL) was added trifluoroacetic acid (742 µL), followed by stirring at room temperature for 3 hours. The mixture was subjected to liquid separation by the addition of a 5% aqueous potassium carbonate solution and chloroform. The organic phase was washed with saturated brine and then dried over anhydrous magnesium sulfate. The solvent was evaporated under reduced pressure and the obtained residue was purified by silica gel column chromatography (chloroform:methanol:28% aqueous ammonia=1:0:0-100:10:1) to obtain 6-ethyl-3-({3-methyl-4-[4-(4-methylpiperazin-1-yl)piperidin-1-yl]phenyl}amino)-5-(1,2,3,6-tetrahydropyridin-4-yl)pyrazine-2-carboxamide (460 mg) as an orange solid.

Preparation Example 38

A mixture of 6-ethyl-3-({3-methyl-4-[4-(4-methylpiperazin-1-yl)piperidin-1-yl]phenyl}amino)-5-(1,2,3,6-tetrahydropyridin-4-yl)pyrazine-2-carboxamide (100 mg), ethanol (3.9 mL), and tetrahydrofuran (1 mL) was reacted using a continuous hydrogenation reaction device (H-Cube (registered trademark); manufactured by ThalesNano) under the conditions of CatCart (registered trademark) 10% palladium-supported carbon (manufactured by ThalesNano), a flow rate of 1 mL/min, a temperature of 70° C., and a pressure of 1015 psi. The solvent was evaporated under reduced pressure to obtain 6-ethyl-3-({3-methyl-4-[4-(4-methylpiperazin-1-yl)piperidin-1-yl]phenyl}amino)-5-(piperidin-4-yl)pyrazine-2-carboxamide (87 mg) as a yellow solid.

Preparation Example 39

To a mixture of 3-nitrophenyl disulfide (2 g) and N,N-dimethylformamide (60 mL) was added potassium carbonate (1.79 g), followed by stirring at room temperature for 2 minutes, and then 3,5-dichloro-6-ethylpyrazine-2-carboxamide (3.14 g) and formaldehyde sodium sulfoxylate (2.3 g), and water were added thereto, followed by stirring at room temperature for 2 hours. To the reaction mixture was added water, and the precipitated solid was collected by filtration, washed with water and diisopropyl ether, and then dried under reduced pressure to obtain 3-chloro-6-ethyl-5-[(3-nitrophenyl)sulfanyl]pyrazine-2-carboxamide (3.9 g) as a white solid.

Preparation Example 40

A mixture of 4-(4-nitro-1H-pyrazol-1-yl)piperidine (100 mg), (1-ethoxycyclopropoxy) trimethylsilane (267 mg), acetic acid (292 µL), Molecular Sieve 3 A (100 mg), and sodium cyanoborohydride (96 mg), and methanol (3 mL) was stirred at 65° C. for 8 hours. After leaving to be cooled, the insoluble matter was separated by filtration and the filtrate was concentrated. The residue was dissolved in ethyl acetate, washed with a saturated aqueous sodium hydrogen carbonate solution and saturated brine, and then dried over anhydrous sodium sulfate. The solvent was evaporated under reduced pressure and the obtained residue was purified by silica gel column chromatography (eluent; chloroform:methanol=100:0-95:5) to obtain 1-cyclopropyl-4-(4-nitro-1H-pyrazol-1-yl)piperidine (110 mg) as a colorless solid.

Preparation Example 41

A mixture of 1-cyclopropyl-4-(4-nitro-1H-pyrazol-1-yl)piperidine (952 mg), ethanol (6 mL), water (2 mL), and ammonium chloride (108 mg) was heated to 80° C., and iron powder (1.13 g) was added thereto, followed by stirring at 80° C. for 3 hours. Chloroform and methanol were added thereto, followed by filtration through celite, and the organic phase was dried over anhydrous sodium sulfate. The solvent was evaporated under reduced pressure and the obtained residue was purified by silica gel column chromatography (eluent;

chloroform:methanol:28% aqueous ammonia=1:0:0-95:4.5: 0.5, NH2 type: eluent; hexane:ethyl acetate=3:7-0:1) to obtain 1-(1-cyclopropylpiperidin-4-yl)-1H-pyrazol-4-amine (558 mg) as a pale pink solid.

Preparation Example 42

To a mixture of 1-methyl-9-(4-nitrophenyl)-1,9-diazaspiro [5.5]undecane (680 mg), ethanol (10 mL), and tetrahydrofuran (10 mL) was added 10% palladium-supported carbon (50% wet product) (150 mg), followed by stirring for 5 hours under a hydrogen gas atmosphere (1 atm). The reaction mixture was filtered through celite and then the solvent was evaporated under reduced pressure to obtain 4-(1-methyl-1, 9-diazaspiro[5.5]undec-9-yl)aniline (0.6 g) as a pale purple solid.

Preparation Example 43

To a mixture of 1,9-diazaspiro[5.5]undecane dihydrochloride (640 mg), potassium carbonate (1.26 g), and N,N-dimethylformamide (7 mL) was added 1-fluoro-4-nitrobenzene (426 mg), followed by stirring at 60° C. overnight. To the reaction mixture was added water, and the precipitated solid was collected by filtration and then dried under reduced pressure to obtain 9-(4-nitrophenyl)-1,9-diazaspiro[5.5]undecane (0.69 g) as a yellow solid.

Preparation Example 44

To a mixture of 9-(4-nitrophenyl)-1,9-diazaspiro[5.5]undecane (680 mg), 37% aqueous formaldehyde solution (1 mL), and 1,2-dichloroethane (10 mL) was added sodium triacetoxyborohydride (1.57 g), followed by stirring at room temperature overnight. To the reaction mixture were added water and a saturated aqueous sodium hydrogen carbonate solution, followed by extraction with chloroform twice. The extract was dried over anhydrous sodium sulfate and then the solvent was evaporated under reduced pressure to obtain 1-methyl-9-(4-nitrophenyl)-1,9-diazaspiro[5.5]undecane (0.68 g) as a yellow solid.

Preparation Example 45

Under argon atmosphere, to a mixture of 5-bromo-3-(2,5-dimethyl-1H-pyrrol-1-yl)-1-methyl-1H-pyrazole (100 mg), 1-methyl-4-(4,4,5,5-tetramethyl-1,3,2-dioxaborolan-2-yl)-1,2,3,6-tetrahydropyridine (105 mg), and N,N-dimethylformamide (2 mL) were added a 1,1'-bis(diphenylphosphino) ferrocene-palladium (II) dichloride-dichloromethane complex (32 mg), and cesium carbonate (256 mg), followed by reacting them at 80° C. for 1 hour. After leaving to be cooled, ethyl acetate was added thereto, and the mixture was washed with water and saturated brine, and then dried over anhydrous sodium sulfate. The solvent was evaporated under reduced pressure and the obtained residue was purified by silica gel column chromatography (eluent; chloroform: methanol=1:0-9:1) to obtain 4-[3-(2,5-dimethyl-1H-pyrrol-1-yl)-1-methyl-1H-pyrazol-5-yl]-1-methyl-1,2,3,6-tetrahydropyridine (72 mg) as a brown oily substance.

Preparation Example 46

To a mixture of 4-[3-(2,5-dimethyl-1H-pyrrol-1-yl)-1-methyl-1H-pyrazol-5-yl]-1-methyl-1,2,3,6-tetrahydropyridine (1.06 g) and hydrochloric acid hydroxylamine (2.73 g) in ethanol (10 mL) and water (1 mL) was added triethylamine (1.10 mL), followed by stirring at 110° C. for 5 hours. After leaving to be cooled, the mixture was neutralized with a saturated aqueous sodium hydrogen carbonate solution, and then the solvent was evaporated under reduced pressure. The obtained residue was purified by silica gel column chromatography (NH2 type: eluent; chloroform:methanol=100:0-98:2) to obtain 1-methyl-5-(1-methyl-1,2,3,6-tetrahydropyridin-4-yl)-1H-pyrazol-3-amine (574 mg) as a pale brown solid.

Preparation Example 47

To a mixture of 1-methyl-5-(1-methyl-1,2,3,6-tetrahydropyridin-4-yl)-1H-pyrazol-3-amine (574 mg) and ethanol (10 mL) was added 10% palladium-supported carbon (50% wet product) (318 mg), followed by stirring for 5 hours under a hydrogen gas atmosphere (4 atm). The reaction mixture was filtered through celite and then the solvent was evaporated under reduced pressure. The obtained residue was purified by silica gel column chromatography (NH2 type, eluent; chloroform:methanol=100:0-95:5), and the obtained solid was washed with diisopropyl ether:ethyl acetate (10:1) to obtain 1-methyl-5-(1-methylpiperidin-4-yl)-1H-pyrazol-3-amine (367 mg) as a colorless solid.

Preparation Example 197

A mixture of 5-chloro-6-ethyl-3-{[4-(4-methylpiperazin-1-yl)phenyl]amino}pyrazine-2-carboxamide (200 mg), 1,3-phenylenediamine (288 mg), and N-methylpyrrolidone (0.8 mL) was reacted in a microwave device at 200° C. for 30 minutes. The mixture was subjected to liquid separation by the addition of ethyl acetate and a saturated aqueous sodium hydrogen carbonate solution were added thereto for extraction. The organic phase was washed with saturated brine and dried over anhydrous magnesium sulfate, and then the solvent was evaporated under reduced pressure. The obtained residue was purified by silica gel column chromatography (eluent; chloroform:methanol:28% aqueous ammonia=1:0:0-200:10: 1), and was washed with ethyl acetate to obtain 5-[(3-aminophenyl)amino]-6-ethyl-3-{[4-(4-methylpiperazin-1-yl) phenyl]amino}pyrazine-2-carboxamide (120 mg).

Preparation Example 198

A mixture of 5-chloro-6-ethyl-3-({3-methyl-4-[4-(4-methylpiperazin-1-yl)piperidin-1-yl]phenyl}amino)pyrazine-2-carboxamide (200 mg), 1,3-propanediamine (177 µL), and N-methylpyrrolidone (0.8 mL) was reacted in a microwave reaction device at 190° C. for 30 minutes. The mixture was subjected to liquid separation by the addition of chloroform and a saturated aqueous sodium hydrogen carbonate solution. The organic phase was washed with saturated brine and dried over anhydrous magnesium sulfate, and then the solvent was evaporated under reduced pressure. The obtained residue was purified by silica gel column chromatography (eluent; chloroform:methanol:28% aqueous ammonia=1:0:0-100:10:1) to obtain 5-[(3-aminopropyl)amino]-6-ethyl-3-({3-methyl-4-[4-(4-methylpiperazin-1-yl)piperidin-1-yl]phenyl}amino) pyrazine-2-carboxamide (123 mg) as a pale yellow solid.

Preparation Example 200

A mixture of 5-chloro-6-ethyl-3-({3-methyl-4-[4-(4-methylpiperazin-1-yl)piperidin-1-yl]phenyl}amino)pyrazine-2-carboxamide (200 mg), tert-butyl (3R)-3-aminopyrrolidine-1-carboxylate (360 µL), and N-methylpyrrolidone (0.8 mL) was reacted in a microwave reaction device at 190° C. for 30 minutes. The mixture was subjected to liquid separation by the addition of chloroform and a saturated aqueous sodium hydrogen carbonate solution. The organic phase was washed with saturated brine and dried over anhydrous magnesium sulfate. After filtration, the filtrate was concentrated. To the obtained residue and 1,2-dichloroethane (2.6 mL) were added trifluoroacetic acid (2.6 mL) under ice-cooling, followed by stirring at room temperature for 3 hours. The mixture was diluted with chloroform and neutralized with a 5% aqueous potassium carbonate solution. The organic phase was washed with saturated brine and dried over anhydrous magnesium sulfate, and then the solvent was evaporated under reduced pressure. The obtained residue was purified by silica gel column chromatography (eluent; chloroform:methanol:28% aqueous ammonia=1:0:0-100:10:1) to obtain 6-ethyl-3-({3-methyl-4-[4-(4-methylpiperazin-1-yl)piperidin-1-yl] phenyl}amino)-5-[(3R)-pyrrolidin-3-ylamino]pyrazine-2-carboxamide (109 mg) as a pale yellow solid.

Preparation Example 203

A mixture of 5-chloro-3-{[4-(1,4-dioxa-8-azaspiro[4.5] dec-8-yl)-3-methylphenyl]amino}pyrazine-2-carboxamide (1.7 g), tert-butyl (3R)-3-aminopyrrolidine-1-carboxylate (3.57 mL), and N-methylpyrrolidone (10.8 mL) was reacted in a microwave reaction device at 190° C. for 60 minutes. The reactant was left to be cooled, and then water and a saturated aqueous sodium hydrogen carbonate solution were added thereto, followed by extraction with ethyl acetate. The organic phase was dried over anhydrous magnesium sulfate and then the solvent was evaporated under reduced pressure. The obtained residue was purified by silica gel column chromatography (eluent; chloroform:methanol:28% aqueous ammonia=1:0:0-500:10:1) to obtain tert-butyl (3R)-3-[(5-carbamoyl-6-{[4-(1,4-dioxa-8-azaspiro[4.5]dec-8-yl)-3-methylphenyl]amino}pyrazin-2-yl)amino]pyrrolidine-1-carboxylate (1.71 g) as a yellow amorphous substance.

Preparation Example 204

Under an argon atmosphere, to a mixture of 5-chloro-6-ethyl-3-({3-methyl-4-[4-(4-methylpiperazin-1-yl)piperidin-1-yl]phenyl}amino)pyrazine-2-carboxamide (200 mg), 3-(4,4,5,5-tetramethyl-1,3,2-dioxaborolan-2-yl)aniline (93 mg), and N-methylpyrrolidone (2 mL) were added tetrakistriphenylphosphine palladium (0) (25 mg) and a 2 M aqueous sodium carbonate solution (424 µL), followed by stirring in a microwave reaction device at 100° C. for 1 hour. Water was added thereto, and the solid was collected by filtration. The obtained solid was purified by silica gel column chromatography (eluent: chloroform:methanol:28% aqueous ammonia=1:0:0-100:10:1) to obtain 5-(3-aminophenyl)-6-ethyl-3-({3-methyl-4-[4-(4-methylpiperazin-1-yl)piperidin-1-yl] phenyl}amino)pyrazine-2-carboxamide (125 mg) as an orange solid.

Preparation Example 210

A mixture of 3,5-dichloro-6-ethylpyrazine-2-carboxamide (500 mg), 5-methyl-6-(4-methylpiperazin-1-yl)pyridin-3-amine (470 mg), diisopropylethylamine (800 µL), and dioxane (10 mL) was stirred in a microwave reaction device at 150° C. for 30 minutes. After leaving to be cooled, water was added thereto, and the precipitated solid was collected by filtration and then dried under reduced pressure to obtain 5-chloro-6-ethyl-3-{[5-methyl-6-(4-methylpiperazin-1-yl) pyridin-3-yl]amino}pyrazine-2-carboxamide (210 mg) as a yellow solid.

Preparation Example 221

A mixture of 1-fluoro-4-nitrobenzene (750 µL), 1-(tetrahydro-2H-pyran-4-yl)piperazine dihydrochloride (2.1 g), potassium carbonate (3.2 g), and N,N-dimethylformamide (10 mL) was stirred at room temperature for 3 days. To the reactant was added water, and the precipitated solid was collected by filtration and then dried under reduced pressure to obtain 1-(4-nitrophenyl)-4-(tetrahydro-2H-pyran-4-yl)piperazine (1.83 g).

Preparation Example 223

To a mixture of 1-(4-nitrophenyl)-4-(tetrahydro-2H-pyran-4-yl)piperazine (1.5 g), ethanol (13 mL), and tetrahydrofuran (13 mL) was added 10% palladium-supported carbon (53% wet product) (150 mg), followed by stirring at room temperature for 2 hours under a hydrogen gas atmosphere (3 atm). The reactant was filtered through celite and then the solvent was evaporated under reduced pressure to obtain 4-[4-(tetrahydro-2H-pyran-4-yl)piperazin-1-yl]aniline (1.45 g).

Preparation Example 226

To a mixture of tert-butyl (3R)-3-[(5-carbamoyl-6-{[4-(1,4-dioxa-8-azaspiro[4.5]dec-8-yl)-3-methylphenyl] amino}pyrazin-2-yl)amino]pyrrolidine-1-carboxylate (1.16 g) and chloroform (35 mL) was added N-chlorosuccinimide (294 mg), followed by stirring at room temperature for 4 hours, and then N-chlorosuccinimide (84 mg) was added thereto, followed by stirring at room temperature for 1 hour. To the reactant was added silica gel, and then the solvent was evaporated under reduced pressure and then purified by silica gel column chromatography (eluent: chloroform) to obtain tert-butyl (3R)-3-[(5-carbamoyl-3-chloro-6-{[4-(1,4-dioxa-8-azaspiro[4.5]dec-8-yl)-3-methylphenyl]amino}pyrazin-2-yl)amino]pyrrolidine-1-carboxylate (851 mg) as a yellow solid.

Preparation Example 229

A mixture of tert-butyl (3R)-3-[(5-carbamoyl-3-chloro-6-{[4-(1,4-dioxa-8-azaspiro[4.5]dec-8-yl)-3-methylphenyl] amino}pyrazin-2-yl)amino]pyrrolidine-1-carboxylate (850 mg) and 3 M hydrochloric acid (9.6 mL) was stirred at 80° C. for 3 hours. The reactant was left to be cooled, and then a saturated aqueous sodium hydrogen carbonate solution and a 10% aqueous potassium carbonate solution were added thereto, followed by stirring at room temperature for 30 minutes. The precipitated solid was collected by filtration, washed with water, and then dried under reduced pressure to obtain 6-chloro-3-{[3-methyl-4-(4-oxopiperidin-1-yl)phenyl]amino}-5-[(3R)-pyrrolidin-3-ylamino]pyrazine-2-carboxamide (495 mg) as a pale yellow solid.

Preparation Example 231

To a mixture of 6-chloro-3-{[3-methyl-4-(4-oxopiperidin-1-yl)phenyl]amino}-5-[(3R)-pyrrolidin-3-ylamino]pyrazine-2-carboxamide (490 mg), tetrahydrofuran (9.8 mL) was added di-tert-butyl dicarbonate (289 mg), followed by stirring at room temperature for 30 minutes. The reactant was concentrated and then the obtained residue was purified by silica gel column chromatography (eluent; chloroform:methanol=100:1-30:1) to obtain tert-butyl (3R)-3-[(5-carbamoyl-3-chloro-6-{[3-methyl-4-(4-oxopiperidin-1-yl)phenyl]amino}pyrazin-2-yl)amino]pyrrolidine-1-carboxylate (578 mg) as a pale yellow amorphous substance.

Preparation Example 232

To a mixture of tert-butyl (3R)-3-[(5-carbamoyl-3-chloro-6-{[3-methyl-4-(4-oxopiperidin-1-yl)phenyl]amino}pyrazin-2-yl)amino]pyrrolidine-1-carboxylate (578 mg), 1-methylpiperazine (175 μL), and 1,2-dichloroethane (8.67 mL) was added sodium triacetoxyborohydride (338 mg), followed by stirring at room temperature for 3 hours. To the reactant was added 1-methylpiperazine (82 μL), followed by stirring at room temperature for 4 hours. To the reactant were added chloroform and a saturated aqueous sodium hydrogen carbonate solution, and followed by liquid separation. The organic phase was dried over anhydrous magnesium sulfate and then the solvent was evaporated under reduced pressure. The obtained residue was purified by silica gel column chromatography (eluent; chloroform:methanol:28% aqueous ammonia=1:0:0-300:10:1) to obtain tert-butyl (3R)-3-{[5-carbamoyl-3-chloro-6-({3-methyl-4-[4-(4-methylpiperazin-1-yl)piperidin-1-yl]phenyl}amino)pyrazin-2-yl]amino}pyrrolidine-1-carboxylate (560 mg) as a yellow amorphous substance.

Preparation Example 238

A mixture of 3,5-dichloro-6-ethylpyrazine-2-carboxamide (630 mg), 2-methyl-4-(morpholin-4-yl)aniline (500 mg), diisopropylethylamine (900 μL), and N-methylpyrrolidone (5 mL) was stirred at 110° C. overnight. The reactant was left to be cooled, and then water was added thereto, followed by extraction with ethyl acetate. The organic phase was dried over anhydrous sodium sulfate and then the solvent was evaporated under reduced pressure. The obtained residue was purified by silica gel column chromatography (eluent; hexane:ethyl acetate=8:2→5:5) to obtain 5-chloro-6-ethyl-3-{[2-methyl-4-(morpholin-4-yl)phenyl]amino}pyrazine-2-carboxamide (660 mg) as an orange solid.

Preparation Example 256

A mixture of 3,5-dichloro-6-ethylpyrazine-2-carboxamide (600 mg), 3-fluoro-4-(morpholin-4-yl)aniline (500 mg), diisopropylethylamine (880 μL), and N-methylpyrrolidone (2.5 mL) was reacted in a microwave reaction device at 180° C. for 1 hour. After leaving to be cooled, to the reactant was added water, and the precipitated solid was collected by filtration and then washed with ethanol to obtain 5-chloro-6-ethyl-3-{[3-fluoro-4-(morpholin-4-yl)phenyl]amino}pyrazine-2-carboxamide (640 mg) as a yellow solid.

Preparation Example 291

A mixture of 5-{[(3R)-1-benzylpyrrolidin-3-yl](methyl)amino}-6-ethyl-3-({3-methyl-4-[4-(4-methylpiperazin-1-yl)piperidin-1-yl]phenyl}amino)pyrazine-2-carboxamide (60 mg), and ethanol (21 mL) was reacted using a continuous hydrogenation reaction device (H-Cube (registered trademark); manufactured by ThalesNano) under the conditions of CatCart (registered trademark) 20% palladium hydroxide-supported carbon (manufactured by ThalesNano), a flow rate of 1 mL/min, a temperature of 50° C., and a pressure of 290 psi. The solvent was evaporated under reduced pressure to obtain 6-ethyl-3-(3-methyl-4-[4-(4-methylpiperazin-1-yl)piperidin-1-yl]phenyl amino)-5-{methyl[(3R)-pyrrolidin-3-yl]amino}pyrazine-2-carboxamide (38 mg) as a yellow solid.

Preparation Example 294

To a mixture of tert-butyl (3R)-3-[(5-carbamoyl-6-{[4-(1,4-dioxa-8-azaspiro[4.5]dec-8-yl)phenyl]amino}pyrazin-2-yl)amino]pyrrolidine-1-carboxylate (10 g), chloroform (200 mL) was added N-bromosuccinimide (3.46 g) under ice-cooling, followed by stirring for 1 hour. To the reactant was added silica gel, and the solvent was evaporated under reduced pressure and then purified by silica gel column chromatography (eluent; chloroform:methanol:28% aqueous ammonia=1:0:0-400:10:1) to obtain tert-butyl (3R)-3-[(3-bromo-5-carbamoyl-6-{[4-(1,4-dioxa-8-azaspiro[4.5]dec-8-yl)phenyl]amino}pyrazin-2-yl)amino]pyrrolidine-1-carboxylate (6.17 g) as a yellow amorphous substance.

Preparation Example 306

To a mixture of tert-butyl (3R)-3-{[3-bromo-5-carbamoyl-6-({4-[4-(4-methylpiperazin-1-yl)piperidin-1-yl]phenyl}amino)pyrazin-2-yl]amino}pyrrolidine-1-carboxylate (800 mg) was added 4 M hydrochloric acid (12.2 mL), followed by stirring at room temperature for 4 hours. To the reactant was added a 10% aqueous potassium carbonate solution, followed by extraction with a mixed solvent of chloroform:isopropanol (4:1). The organic phase was dried over anhydrous magnesium sulfate and filtered, and then the filtrate was concentrated to obtain 6-bromo-3-({4-[4-(4-methylpiperazin-1-yl)piperidin-1-yl]phenyl}amino)-5-[(3R)-pyrrolidin-3-ylamino]pyrazine-2-carboxamide (400 mg) as a yellow solid.

Preparation Example 309

A mixture of 5-chloro-6-ethyl-3-({3-methyl-4-[4-(4-methylpiperazin-1-yl)piperidin-1-yl]phenyl}amino)pyrazine-2-carboxamide (200 mg), rac-(1R,2R)-cyclopentane-1,2-diamine dihydrochloride (230 mg), diisopropylethylamine (480 μL), and N-methylpyrrolidone (0.8 mL) was reacted in a microwave device at 150° C. for 2 hours. Water and diisopropyl ether were added thereto, and the precipitated solid was filtered to obtain rac-5-{[(1R,2R)-2-aminocyclopentyl]amino}-6-ethyl-3-({3-methyl-4-[4-(4-methylpiperazin-1-yl)piperidin-1-yl]phenyl}amino)pyrazine-2-carboxamide (195 mg).

Preparation Example 312

Under an argon atmosphere, to a mixture of tert-butyl (3R)-3-{[3-bromo-5-carbamoyl-6-({4-[4-(4-methylpiperazin-1-yl)piperidin-1-yl]phenyl}amino)pyrazin-2-yl]amino}pyrrolidine-1-carboxylate (300 mg), pyridin-4-ylboronic acid (196 mg), and N-methylpyrrolidone (6 mL) were added tetrakistriphenylphosphine palladium (0) (79 mg) and a 2 M aqueous sodium carbonate solution (797 μL), followed by stirring at 100° C. for 4 hours. After leaving to be cooled, ethyl acetate and water were added thereto, followed by stirring, and then the insoluble matter was separated by filtration. The organic phase was washed with saturated brine and dried over anhydrous magnesium sulfate, and then the solvent was evaporated under reduced pressure. The obtained residue was purified by silica gel column chromatography (eluent; chloroform:methanol:28% aqueous ammonia=1:0:0-150:10:1) to obtain tert-butyl (3R)-3-{[5-carbamoyl-6-({4-[4-(4-methylpiperazin-1-yl)piperidin-1-yl]phenyl}amino)-3-(pyridin-4-yl)pyrazin-2-yl]amino}pyrrolidine-1-carboxylate (222 mg) as a yellow solid.

Preparation Example 314

Under an argon atmosphere, to a mixture of 6-bromo-3-({4-[4-(4-methylpiperazin-1-yl)piperidin-1-yl]phenyl}amino)-5-[(3R)-pyrrolidin-3-ylamino]pyrazine-2-carboxamide (257 mg), phenylboronic acid (196 mg), and N-methylpyrrolidone (5.14 mL) were added tetrakistriphenylphosphine palladium (0) (80 mg) and a 2 M aqueous sodium carbonate solution (805 µL), followed by stirring at 120° C. for 4 hours. After leaving to be cooled, chloroform and water were added thereto, followed by stirring, and the insoluble matter was separated by filtration. The filtrate was subjected to liquid separation, and the organic phase was washed with saturated brine and dried over anhydrous magnesium sulfate. Then, the solvent was evaporated under reduced pressure. The obtained residue was purified by silica gel column chromatography (eluent: chloroform:methanol: 28% aqueous ammonia=1:0:0-150:10:1) to obtain 3-({4-[4-(4-methylpiperazin-1-yl)piperidin-1-yl]phenyl}amino)-6-phenyl-5-[(3R)-pyrrolidin-3-ylamino]pyrazine-2-carboxamide (244 mg) as a yellow solid.

Preparation Example 317

To a mixture of tert-butyl (3R)-3-{[3-bromo-5-carbamoyl-6-({4-[4-(4-methylpiperazin-1-yl)piperidin-1-yl] phenyl}amino)pyrazin-2-yl]amino}pyrrolidine-1-carboxylate (500 mg) and pyridine (3 mL) was added cuprous cyanide (88 mg), followed by reacting at 140° C. for 3 hours. The reactant was left to be cooled, and then subjected to liquid separation by the addition of a mixed solvent of chloroform: methanol:28% aqueous ammonia (100:10:1) and a saturated aqueous sodium hydrogen carbonate solution. To the organic phase was added silica gel, and then the solvent was evaporated under reduced pressure. The obtained residue was purified by silica gel column chromatography (eluent; chloroform:methanol:28% aqueous ammonia=1:0:0-200:10:1) to obtain tert-butyl (3R)-3-{[5-carbamoyl-3-cyano-6-({4-[4-(4-methylpiperazin-1-yl)piperidin-1-yl]phenyl}amino) pyrazin-2-yl]amino}pyrrolidine-1-carboxylate (Preparation Example 317 a:154 mg), which is a low-polarity product, as a yellow amorphous substance and tert-butyl (3R)-3-{[3,5-dicarbamoyl-6-({4-[4-(4-methylpiperazin-1-yl)piperidin-1-yl]phenyl}amino)pyrazin-2-yl]amino}pyrrolidine-1-carboxylate (Preparation Example 317 b:130 mg), which is a high-polarity substance, as a brown amorphous substance.

Preparation Example 318

A mixture of 5-chloro-6-ethyl-3-({4-[4-(4-methylpiperazin-1-yl)piperidin-1-yl]phenyl}amino)pyrazine-2-carboxamide (200 mg), tert-butyl 4-(aminomethyl)piperidine-1-carboxylate (300 µL), diisopropylethylamine (240 µL), and N-methylpyrrolidone (0.8 mL) was reacted in a microwave reaction device at 160° C. for 2 hours. The mixture was subjected to liquid separation with ethyl acetate and water, and the organic phase was dried over magnesium sulfate, and then the solvent was evaporated under reduced pressure. The obtained residue was washed with diisopropyl ether to obtain tert-butyl 4-({[5-carbamoyl-3-ethyl-6-({4-[4-(4-methylpiperazin-1-yl)piperidin-1-yl]phenyl}amino)pyrazin-2-yl] amino}methyl)piperidine-1-carboxylate (195 mg) as a pale yellow solid.

Preparation Example 340

A mixture of 5-chloro-6-ethyl-3-({3-methyl-4-[4-(4-methylpiperazin-1-yl)piperidin-1-yl]phenyl}amino)pyrazine-2-carboxamide (350 mg), tert-butyl 3-(aminomethyl)azetidine-1-carboxylate (266 mg), potassium carbonate (154 mg), and N-methylpyrrolidone (7 mL) was reacted at 100° C. for 11.5 hours. To the mixture were added ethyl acetate and water, followed by liquid separation. The organic phase was washed with water and saturated brine, and dried over anhydrous magnesium sulfate, and then the solvent was evaporated under reduced pressure. The obtained residue was purified by silica gel column chromatography (eluent; chloroform:methanol=1:0-9:1) to obtain tert-butyl 3-({[5-carbamoyl-3-ethyl-6-({3-methyl-4-[4-(4-methylpiperazin-1-yl)piperidin-1-yl]phenyl}amino)pyrazin-2-yl] amino}methyl)azetidine-1-carboxylate (128 mg) as a yellow solid.

Preparation Example 343

A mixture of 5-[(5-bromopyridin-3-yl)oxy]-6-ethyl-3-{[4-(4-methylpiperazin-1-yl)phenyl]amino}pyrazine-2-carboxamide (370 mg), benzophenoneimine (145 µL), a tris (dibenzylideneacetone)dipalladium (0) chloroform complex (22 mg), di-tert-butyl (2',4',6'-triisopropylbiphenyl-2-yl) phosphine (28 mg), potassium phosphate (383 mg), and 1,2-dimethoxyethane (3 mL) was stirred at 80° C. for 10 hours under a nitrogen atmosphere. To the reactant was added N-methylpyrrolidone (3 mL), and a tris(dibenzylideneacetone)dipalladium (0) chloroform complex (22 mg) and di-tert-butyl (2',4',6'-triisopropylbiphenyl-2-yl)phosphine (28 mg) were added thereto, followed by stirring at 80° C. for 10 hours. Water was added thereto, followed by extraction with ethyl acetate. The organic phase was washed with saturated brine and dried over anhydrous magnesium sulfate, and then the solvent was evaporated under reduced pressure. The obtained residue was purified by silica gel column chromatography (eluent; chloroform:methanol=1:0-9:1) to obtain 5-({5-[(diphenylmethylene)amino]pyridin-3-yl}oxy)-6-ethyl-3-{[4-(4-methylpiperazin-1-yl)phenyl] amino}pyrazine-2-carboxamide (133 mg) as a brown amorphous substance.

Preparation Example 351

To a mixture of 5-({5-[(diphenylmethylene)amino]pyridin-3-yl}oxy)-6-ethyl-3-{[4-(4-methylpiperazin-1-yl)phenyl]amino}pyrazine-2-carboxamide (130 mg) and tetrahydrofuran (2.17 mL) was added 1 M hydrochloric acid (0.26 mL), followed by stirring at room temperature for 3 hours. To the residue obtained by evaporating the solvent was added ethyl acetate, followed by extraction with water. The aqueous phase was neutralized with a 1 M aqueous sodium hydroxide solution and extracted by the addition of a mixed solvent of chloroform:methanol (10:1). The organic phase was washed with saturated brine and dried over anhydrous magnesium sulfate, and then the solvent was evaporated under reduced pressure. The obtained residue was purified by silica gel column chromatography (NH2 type: eluent; chloroform: methanol=1:0-9:1) to obtain 5-[(5-aminopyridin-3-yl)oxy]-

6-ethyl-3-{[4-(4-methylpiperazin-1-yl)phenyl] amino}pyrazine-2-carboxamide (52 mg) as a yellow solid.

Preparation Example 352

To a mixture of tert-butyl 3-hydroxyazetidine-1-carboxylate (420 mg) and N,N-dimethylformamide (12.5 mL) was added potassium tert-butoxide (260 mg) under ice-cooling, followed by stirring for 1 hour, and then 3,5-dichloro-6-ethylpyrazine-2-carboxamide (500 mg) was added thereto, followed by stirring for 1 hour. The reaction mixture was poured into ice water, followed by extraction with ethyl acetate. The organic phase was washed with saturated brine and then dried over anhydrous magnesium sulfate, and the solvent was evaporated under reduced pressure. The obtained residue was purified by silica gel column chromatography (eluent; hexane:ethyl acetate), and then washed with a mixed solvent of hexane:diisopropyl ether to obtain tert-butyl 3-[(5-carbamoyl-6-chloro-3-ethylpyrazin-2-yl)oxy]azetidine-1-carboxylate (318 mg) as a white solid.

Preparation Example 358

A mixture of 1-fluoro-4-nitrobenzene (418 µL), [(2S)-1-methylpiperazin-2-yl]methanol dihydrochloride (0.8 g), potassium carbonate (2.45 g), and dimethylsulfoxide (8 mL) was stirred at 120° C. for 3 hours. To the reactant were added water and ethyl acetate, followed by liquid separation. The organic phase was washed with saturated brine and dried over anhydrous magnesium sulfate, and then the solvent was evaporated under reduced pressure. The obtained residue was purified by silica gel column chromatography (NH2 type: eluent; ethyl acetate) to obtain [(2S)-1-methyl-4-(4-nitrophenyl)piperazin-2-yl]methanol (590 mg) as a yellow solid.

Preparation Example 364

To a mixture of [(2S)-1-methyl-4-(4-nitrophenyl)piperazin-2-yl]methanol (315 mg) and ethanol (5.081 mL) was added 10% palladium-supported carbon (53% wet product) (267 mg), followed by stirring at room temperature for 4 hours under a hydrogen gas atmosphere (1 atm). The reactant was filtered through celite and then the solvent was evaporated under reduced pressure to obtain [(2S)-4-(4-aminophenyl)-1-methylpiperazin-2-yl]methanol (278 mg) as a solid.

Preparation Example 372

A mixture of 3,5-dichloro-2-iodopyrazine (2 g), cyclopropylboronic acid (750 mg), tetrakistriphenylphosphine palladium (0) (1.68 g), potassium phosphate (3.09 g), toluene (40 mL), and water (4 mL) was stirred at 110° C. overnight. After leaving to be cooled, the insoluble matter was removed by decantation, followed liquid separation by the addition of ethyl acetate and water. The organic phase was washed with saturated brine and dried over anhydrous magnesium sulfate, and then the solvent was evaporated under reduced pressure. The obtained residue was purified by silica gel column chromatography (eluent; hexane:ethyl acetate=98:2) to obtain 3,5-dichloro-2-cyclopropylpyrazine (784 mg) as a colorless oily material.

Preparation Example 380

A mixture of 5-chloro-6-ethyl-3-{[4-(4-methylpiperazin-1-yl)phenyl]amino}pyrazine-2-carboxamide (250 mg), 3-bromo-5-nitrophenol (170 mg), potassium carbonate (138 mg), and N-methylpyrrolidone (5 mL) was stirred at 100° C. for 4 hours. To the reactant was added water, followed by extraction with ethyl acetate. The organic phase was washed with water and saturated brine, and dried over anhydrous magnesium sulfate, and then the solvent was evaporated under reduced pressure. The obtained residue was purified by silica gel column chromatography (eluent; chloroform:methanol=1:0-9:1) to obtain 5-(3-bromo-5-nitrophenoxy)-6-ethyl-3-{[4-(4-methylpiperazin-1-yl)phenyl] amino}pyrazine-2-carboxamide (336 mg) as a yellow solid.

Preparation Example 381

To a mixture of 5-(3-aminophenoxy)-6-ethyl-3-({4-[(3S)-3-(hydroxymethyl)-4-methylpiperazin-1-yl]phenyl}amino) pyrazine-2-carboxamide (210 mg), diisopropylethylamine (301 µL), and dichloromethane (6.3 mL) was added acryloyl chloride (107 µL) under ice-cooling, followed by stirring for 2 hours. To the reactant were added water and chloroform, followed by liquid separation. The organic phase was washed with saturated brine and dried over anhydrous magnesium sulfate, and then the solvent was evaporated under reduced pressure. The obtained residue was purified by silica gel column chromatography (eluent; chloroform:methanol=95:5) to obtain {(2S)-4-[4-({6-[3-(acryloylamino)phenoxy]-3-carbamoyl-5-ethylpyrazin-2-yl}amino)phenyl]-1-methylpiperazin-2-yl}methyl acrylate (228 mg) as an amorphous substance.

Preparation Example 383

Under an argon atmosphere, to a mixture of tetrahydrofuran (6 mL) and diisopropylamine (258 µL) was added dropwise n-butyllithium (1.62 M n-hexane solution, 1.04 mL) under ice-cooling. After cooling to −100° C., a mixture of 3,5-dichloro-2-cyclopropylpyrazine (290 mg) and tetrahydrofuran (2 mL) was added dropwise thereto, followed by stirring for 10 minutes. The obtained reactant was added to dry ice (10 g) and tetrahydrofuran (5 mL), followed by stirring for 30 minutes in a water bath. To the reactant were added 1 M hydrochloric acid and a saturated aqueous ammonium chloride solution, followed by extraction with ethyl acetate. The organic phase was washed with saturated brine and dried over anhydrous magnesium sulfate. The solvent was evaporated under reduced pressure to obtain 3,5-dichloro-6-cyclopropylpyrazine-2-carboxylic acid (350 mg) as an oily material.

Preparation Example 384

A mixture of 5-chloro-6-ethyl-3-({4-[4-(4-methylpiperazin-1-yl)piperidin-1-yl]phenyl}amino)pyrazine-2-carboxamide (300 mg), [(2R)-1-benzylpyrrolidin-2-yl]methanol (251 mg), 18-crown-6 (346 mg), potassium t-butoxide (147 mg), and dioxane (3 mL) was stirred at 100° C. for 5 hours. To the mixture were added water and ethyl acetate, followed by liquid separation. The organic phase was washed with saturated brine and dried over anhydrous magnesium sulfate, and then the solvent was evaporated under reduced pressure. The obtained residue was purified by silica gel column chromatography (NH2 type: eluent; ethyl acetate:chloroform=1:1) to obtain 5-{[(2R)-1-benzylpyrrolidin-2-yl]methoxy}-6-ethyl-3-({4-[4-(4-methylpiperazin-1-yl)piperidin-1-yl] phenyl}amino)pyrazine-2-carboxamide (201 mg) as a yellow solid.

Preparation Example 386

A mixture of 3,5-dichloro-6-cyclopropylpyrazine-2-carboxylic acid (350 mg) and thionyl chloride (5 ml) was stirred at 90° C. for 30 minutes. After leaving to be cooled, the solvent was evaporated under reduced pressure and then azeotroped with toluene, and to the residue was added toluene (5 mL). After cooling to −40° C., a mixture of 28% aqueous ammonia (5 mL) and toluene (10 mL) was added dropwise thereto, followed by stirring for 15 minutes. The reactant was extracted with ethyl acetate, and the organic phase was washed with saturated brine and dried over anhydrous magnesium sulfate. Then, the solvent was evaporated under reduced pressure. The obtained residue was purified by silica gel column chromatography (eluent; chloroform:methanol=1:0-9:1) to obtain 3,5-dichloro-6-cyclopropylpyrazine-2-carboxamide (220 mg) as a pale brown solid.

Preparation Example 387

To a mixture of 5-{[(2R)-1-benzylpyrrolidin-2-yl]methoxy}-6-ethyl-3-({4-[4-(4-methylpiperazin-1-yl)piperidin-1-yl]phenyl}amino)pyrazine-2-carboxamide (182 mg), and acetic acid (3 mL) was added 10% palladium-supported carbon (53% wet product) (63 mg), followed by stirring for 6 hours under a hydrogen gas atmosphere (4 atm). The reactant was filtered through celite, then the mixture was concentrated under reduced pressure, and a saturated aqueous sodium hydrogen carbonate solution was added thereto, followed by extraction with a mixed solvent of chloroform:methanol=8:2. The organic phase was washed with saturated brine and dried over anhydrous magnesium sulfate, and then the solvent was evaporated under reduced pressure. The obtained residue was purified by silica gel column chromatography (NH2 type: eluent; chloroform:methanol=98:2) to obtain 6-ethyl-3-({4-[4-(4-methylpiperazin-1-yl)piperidin-1-yl]phenyl}amino)-5-[(2R)-pyrrolidin-2-ylmethoxy]pyrazine-2-carboxamide (138 mg) as a yellow solid.

Preparation Example 389

To a mixture of tert-butyl 4-{4-[(3-carbamoyl-6-chloro-5-ethylpyrazin-2-yl)amino]-1H-pyrazol-1-yl}piperidine-1-carboxylate (1.69 g), ethyl acetate (10 mL), and ethanol (10 mL) was added a 4 M hydrogen chloride ethyl acetate solution (20 mL), followed by stirring at room temperature for 2 hours. The mixture was subjected to liquid separation by the addition of a 1 M aqueous sodium hydroxide solution and chloroform. The organic phase was dried over anhydrous sodium sulfate and then filtered. The filtrate was concentrated under reduced pressure to obtain 5-chloro-6-ethyl-3-{[1-(piperidin-4-yl)-1H-pyrazol-4-yl]amino}pyrazine-2-carboxamide (1.32 g) as a yellow solid.

Preparation Example 391

Under an argon atmosphere, to a mixture of 5-(3-bromo-5-nitrophenoxy)-6-ethyl-3-{[4-(4-methylpiperazin-1-yl)phenyl]amino}pyrazine-2-carboxamide (312 mg), zinc powder (19 mg), biphenyl-2-yl (di-tert-butyl)phosphine (40 mg), zinc (II) cyanide (66 mg), and N,N-dimethylacetamide (6.13 mL) was added palladium trifluoroacetate (II) (20 mg), followed by heating at 100° C. for 4 hours. After leaving to be cooled, to the reactant was added water, followed by extraction with ethyl acetate. The organic phase was washed with saturated brine and dried over anhydrous magnesium sulfate, and then the solvent was evaporated under reduced pressure. The obtained residue was purified by silica gel column chromatography (eluent; chloroform:methanol=1:0-9:1) to obtain 5-(3-cyano-5-nitrophenoxy)-6-ethyl-3-{[4-(4-methylpiperazin-1-yl)phenyl]amino}pyrazine-2-carboxamide (250 mg) as a red solid.

Preparation Example 392

To a mixture of 5-chloro-6-ethyl-3-{[1-(piperidin-4-yl)-1H-pyrazol-4-yl]amino}pyrazine-2-carboxamide (350 mg) and diisopropylethylamine (685 µL) in N,N-dimethylformamide (3.5 mL) was added 2,2,2-trifluoroethyltrifluoromethanesulfonate (433 µL), followed by reacting at room temperature for 2 hours. The mixture was subjected to liquid separation by the addition of ethyl acetate and a saturated aqueous sodium hydrogen carbonate solution. The organic phase was washed with saturated brine and dried over anhydrous sodium sulfate, and then the solvent was evaporated under reduced pressure. The obtained residue was purified by silica gel column chromatography (chloroform:methanol=99:1-90:10) to obtain 5-chloro-6-ethyl-3-({1-[1-(2,2,2-trifluoroethyl)piperidin-4-yl]-1H-pyrazol-4-yl}amino)pyrazine-2-carboxamide (424 mg) as a yellow solid.

Preparation Example 395

To a mixture of 5-chloro-6-ethyl-3-{[1-(piperidin-4-yl)-1H-pyrazol-4-yl]amino}pyrazine-2-carboxamide (350 mg), diisopropylethylamine (685 µL), and N,N-dimethylformamide (3.5 mL) was added 2-bromoethylmethyl ether (282 µL), followed by reacting at 60° C. for 2 hours. The mixture was subjected to liquid separation by the addition of ethyl acetate and a saturated aqueous sodium hydrogen carbonate solution. The organic phase was washed with saturated brine and dried over anhydrous sodium sulfate, and then the solvent was evaporated under reduced pressure. The obtained residue was purified by silica gel column chromatography (eluent; chloroform:methanol=99:1-90:10) to obtain 5-chloro-6-ethyl-3-({1-[1-(2-methoxyethyl)piperidin-4-yl]-1H-pyrazol-4-yl}amino)pyrazine-2-carboxamide (225 mg) as a yellow solid.

Preparation Example 403

To a mixture of tert-butyl (3R)-3-hydroxypyrrolidine-1-carboxylate (151 mg) and dioxane (4 mL) were added potassium tert-butoxide (91 mg) and 5-chloro-6-cyclopropyl-3-({4-[4-(4-methylpiperazin-1-yl)piperidin-1-yl]phenyl}amino)pyrazine-2-carboxamide (190 mg), followed by stirring at 100° C. for 16 hours. After leaving to be cooled, water was added thereto, followed by extraction with ethyl acetate. The organic phase was washed with saturated brine and then dried over anhydrous magnesium sulfate, and the solvent was evaporated under reduced pressure. The obtained residue was purified by silica gel column chromatography (eluent; chloroform:methanol=1:0-9:1) to obtain tert-butyl (3R)-3-{[5-carbamoyl-3-cyclopropyl-6-({4-[4-(4-methylpiperazin-1-yl)piperidin-1-yl]phenyl}amino)pyrazin-2-yl]oxy}pyrrolidine-1-carboxylate (189 mg) as a yellow solid.

Preparation Example 405

To a mixture of 5-[2-(dibenzylamino)ethoxy]-6-ethyl-3-({4-[4-(4-methylpiperazin-1-yl)piperidin-1-yl]phenyl}amino)pyrazine-2-carboxamide (172 mg) and acetic acid (2.84 mL) was added 10% palladium-supported carbon (53% wet product) (55 mg), followed by stirring at room temperature for 6 hours under a hydrogen gas atmosphere (4 atm). The mixture was filtered through celite, and then 20% palladium hydroxide-supported carbon (36 mg) was added thereto, followed by stirring overnight under a hydrogen gas atmosphere (4 atm). The mixture was filtered through celite and then the filtrate was concentrated under reduced pressure. The obtained residue was purified by silica gel column chromatography (NH2 type: eluent; chloroform:methanol=99:1) to obtain 5-(2-aminoethoxy)-6-ethyl-3-({4-[4-(4-methylpiperazin-1-yl)piperidin-1-yl]phenyl}amino)pyrazine-2-carboxamide (123 mg) as a yellow solid.

Preparation Example 406

To a mixture of tert-butyl (3R)-3-(methoxymethyl)piperazine-1-carboxylate (206 mg), methanol (3.09 mL), and a 36% aqueous formaldehyde solution (187 mg) was added 10% palladium-supported carbon (50% wet product) (76 mg), followed by stirring at room temperature for 4 hours under a hydrogen gas atmosphere (1 atm). The reactant was filtered through celite and then the solvent was evaporated under reduced pressure to obtain tert-butyl (3R)-3-(methoxymethyl)-4-methylpiperazine-1-carboxylate (231 mg) as an oily material.

Preparation Example 407

To a mixture of tert-butyl (3R)-3-(methoxymethyl)-4-methylpiperazine-1-carboxylate (220 mg) and ethyl acetate (2.33 mL) was added a 4 M hydrogen chloride ethyl acetate solution (2.19 mL), followed by stirring at room temperature overnight. The reactant was concentrated under reduced pressure to obtain (2R)-2-(methoxymethyl)-1-methylpiperazine dihydrochloride (218 mg) as a white solid.

Preparation Example 410

To a mixture of 1-methyl-4-[1-(4-nitrophenyl)piperidin-4-yl]piperazine (4.84 g) and 1,2-dichloroethane (50 mL) was added 1-chloroethyl chloroformate (2.2 mL), followed by stirring at 90° C. for 3 hours. The solvent was evaporated under reduced pressure and then methanol (85 mL) was added thereto, followed by heating and refluxing for 1 hour. The solvent was evaporated under reduced pressure and the obtained residue was washed with ethyl acetate to obtain 1-[1-(4-nitrophenyl)piperidin-4-yl]piperazine monohydrochloride (3.74 g) as a yellow solid.

Preparation Example 415

A mixture of 1-[1-(4-nitrophenyl)piperidin-4-yl]piperazine monohydrochloride (1 g), oxetan-3-one (300 mg), sodium triacetoxyborohydride (1.02 g), dichloromethane (20 mL), acetic acid (1 mL), and chloroform (30 mL) was stirred at room temperature for 2 days. To the reactant were added a saturated aqueous sodium hydrogen carbonate solution and chloroform, followed by liquid separation. The organic phase was washed with saturated brine and dried over anhydrous magnesium sulfate, and then the solvent was evaporated under reduced pressure. The obtained residue was purified by silica gel column chromatography (eluent; chloroform:methanol=1:0-9:1) to obtain 1-[1-(4-nitrophenyl)piperidin-4-yl]-4-(oxetan-3-yl)piperazine (670 mg) as a yellow solid.

Preparation Example 422

Under an argon atmosphere, to a mixture of N-allylmorpholine (274 µL) and tetrahydrofuran (5 mL) was added 9-borabicyclo[3.3.1]nonane (0.5 M tetrahydrofuran solution 4.01 mL) under ice-cooling, followed by stirring at 60° C. for 1 hour. After leaving to be cooled, to the reactant were added a mixture of 5-(3-aminophenoxy)-3-{[3-bromo-4-(4-methylpiperazin-1-yl)phenyl]amino}pyrazine-2-carboxamide (1 g), N,N-dimethylformamide (10 mL), and potassium carbonate (1.39 g), water (1 mL), and a 1,1'-bis(diphenylphosphino)ferrocene palladium (II) dichloride-dichloromethane complex (164 mg), followed by stirring at 60° C. for 40 hours. The reactant was left to be cooled, and then chloroform was added thereto. Then, the insoluble matter was separated by filtration. The filtrate was washed with a saturated aqueous sodium hydrogen carbonate solution and saturated brine, and dried over anhydrous magnesium sulfate, and then the solvent was evaporated under reduced pressure. The obtained residue was purified by silica gel column chromatography (eluent: chloroform:methanol:28% aqueous ammonia=1000:10:1-150:10:1) to obtain 5-(3-aminophenoxy)-3-({4-(4-methylpiperazin-1-yl)-3-[3-(morpholin-4-yl) propyl]phenyl}amino)pyrazine-2-carboxamide (67 mg) as a pale yellow amorphous substance.

Preparation Example 427

A mixture of 5-chloro-6-ethyl-3-{[4-(4-methylpiperazin-1-yl)phenyl]amino}pyrazine-2-carboxamide (200 mg), 2-amino-4-pyridinol (118 mg), cesium carbonate (348 mg), and N-methylpyrrolidone (2 mL) was stirred at 120° C. for 3 hours. The reactant was purified by silica gel column chromatography (eluent; chloroform:methanol=95:5-80:20, NH2 type: eluent; chloroform:methanol=99:1-98:2) and then washed with ethyl acetate to obtain 5-[(2-aminopyridin-4-yl)oxy]-6-ethyl-3-{[4-(4-methylpiperazin-1-yl)phenyl]amino}pyrazine-2-carboxamide (104 mg) as a yellow solid.

Preparation Example 428

A mixture of 3,5-dichloro-6-(2-hydroxypropan-2-yl)pyrazine-2-carboxamide (2.0 g), 2-(4-amino-1H-pyrazol-1-yl)ethan-1-ol (1.12 g), diisopropylethylamine (2.79 mL), and dioxane (20 mL) was heated and refluxed for 2 hours. The reactant was cooled, and then a saturated aqueous sodium hydrogen carbonate solution was added thereto, followed by extraction with a mixture of chloroform:methanol (10:1). The organic phase was dried over anhydrous sodium sulfate, and then the solvent was evaporated under reduced pressure. The obtained residue was purified by silica gel column chromatography (eluent; chloroform:methanol=99:1-90:10) to obtain 5-chloro-3-{[1-(2-hydroxyethyl)-1H-pyrazol-4-yl]amino}-6-(2-hydroxypropan-2-yl)pyrazine-2-carboxamide (1.69 g) as a yellow solid.

Preparation Example 432

A mixture of 5-{[(1R,2S)-2-(1,3-dioxo-1,3-dihydro-2H-isoindol-2-yl)cyclopentyl]oxy}-6-ethyl-3-({4-[4-(4-methylpiperazin-1-yl)piperidin-1-yl]phenyl}amino)pyrazine-2-carboxamide (322 mg), hydrazine monohydrate (99 mg), tetrahydrofuran (6.44 mL), and ethanol (6.44 mL) was stirred at 80° C. overnight. The insoluble matter was separated by filtration and the filtrate was concentrated under reduced pressure. The obtained residue was purified by silica gel column chromatography (NH2 type: eluent; chloroform:methanol=99:1-97:3) to obtain 5-{[(1R,2S)-2-aminocyclopentyl]oxy}-6-ethyl-3-({4-[4-(4-methylpiperazin-1-yl)piperidin-1-yl]phenyl}amino)pyrazine-2-carboxamide (117 mg) as a pale yellow solid.

Preparation Example 435

A mixture of 5-chloro-3-{[1-(2-hydroxyethyl)-1H-pyrazol-4-yl]amino}-6-(2-hydroxypropan-2-yl)pyrazine-2-carboxamide (700 mg), tert-butyl (3R)-3-aminopyrrolidine-1-carboxylate (1.05 mL), diisopropylethylamine (1.06 mL), and N-methylpyrrolidone (2.5 mL) was reacted in a microwave reaction device at 180° C. for 1 hour. To the reactant was added a mixed solution of saturated brine:water (1:1), followed by extraction with ethyl acetate. The organic phase was dried over anhydrous sodium sulfate, and then the solvent was evaporated under reduced pressure. The obtained residue was purified by silica gel column chromatography (eluent; chloroform:methanol=99:1-90:10, NH2 type: eluent; chloroform:methanol=99:1-95:5) to obtain tert-butyl (3R)-3-{[5-carbamoyl-6-{[1-(2-hydroxyethyl)-1H-pyrazol-4-yl]amino}-3-(prop-1-en-2-yl)pyrazin-2-yl]amino}pyrrolidine-1-carboxylate (928 mg) as a yellow amorphous substance.

Preparation Example 438

A mixture of 5-chloro-3-{[1-(2-hydroxyethyl)-1H-pyrazol-4-yl]amino}-6-(2-hydroxypropan-2-yl)pyrazine-2-carboxamide (790 mg), 5-amino-2-fluorophenol (442 mg), potassium carbonate (641 mg), and N-methylpyrrolidone (8 mL) was reacted at 100° C. for 2 hours. To the reactant was added a mixed solution of saturated brine:water (1:1), followed by extraction with ethyl acetate. The organic phase was dried over anhydrous sodium sulfate and then the solvent was evaporated under reduced pressure. The obtained residue was purified by silica gel column chromatography (eluent; chloroform:methanol=99:1-80:20) to obtain 5-(5-amino-2-fluorophenoxy)-3-{[1-(2-hydroxyethyl)-1H-pyrazol-4-yl]amino}-6-(2-hydroxypropan-2-yl)pyrazine-2-carboxamide (523 mg) as a pale brown solid.

Preparation Example 441

A mixture of 5-(5-amino-2-fluorophenoxy)-3-{[1-(2-hydroxyethyl)-1H-pyrazol-4-yl]amino}-6-(2-hydroxypropan-2-yl)pyrazine-2-carboxamide (515 mg), diisopropylethylamine (409 μL), and N-methylpyrrolidone (3 mL) was reacted in a microwave reaction device at 200° C. for 4 hours. The mixture was purified by silica gel column chromatography (eluent; chloroform:methanol=98:2-90:10) to obtain 5-(5-amino-2-fluorophenoxy)-3-{[1-(2-hydroxyethyl)-1H-pyrazol-4-yl]amino}-6-(prop-1-en-2-yl)pyrazine-2-carboxamide (408 mg) as a yellow solid.

Preparation Example 442

To a mixture of tert-butyl [(1S,2R)-2-aminocyclohexyl]carbamate (500 mg) and ethanol (10 mL) was added 1H-benzotriazol-1-yl methanol (350 mg), followed by stirring at room temperature for 7 hours. Sodium borohydride (180 mg) was added thereto under ice-cooling, followed by stirring at room temperature for 15 hours. To the reactant were added ethyl acetate and a saturated aqueous sodium hydrogen carbonate solution, followed by liquid separation. The organic phase was dried over anhydrous magnesium sulfate and then the solvent was evaporated under reduced pressure. The obtained residue was purified by silica gel column chromatography (eluent; chloroform:methanol:28% aqueous ammonia=1:0:0-190:9:1) to obtain tert-butyl [(1S,2R)-2-(methylamino)cyclohexyl]carbamate (174 mg) as a pale yellow oily material.

Preparation Example 451

To a mixture of 5-{[(1R,2S)-2-aminocyclohexyl]amino}-6-ethyl-3-({4-[4-(4-methylpiperazin-1-yl)piperidin-1-yl]phenyl}amino)pyrazine-2-carboxamide (62 mg), ethanol (5 mL), and tetrahydrofuran (3 mL) were added 1H-benzotriazol-1-yl methanol (18 mg) and sodium acetate (15 mg), followed by stirring at room temperature for 7 hours. Sodium triacetoxyborohydride (50 mg) was added thereto under ice-cooling, followed by stirring at room temperature for 12 hours. To the reactant were added ethyl acetate and a saturated aqueous sodium hydrogen carbonate solution, followed by liquid separation. The organic phase was dried over anhydrous magnesium sulfate and then the solvent was evaporated under reduced pressure. The obtained residue was purified by silica gel column chromatography (eluent; chloroform:methanol:28% aqueous ammonia=500:10:1-200:10:1) to obtain 6-ethyl-5-{[(1R,2S)-2-(methylamino)cyclohexyl]amino}-3-({4-[4-(4-methylpiperazin-1-yl)piperidin-1-yl]phenyl}amino)pyrazine-2-carboxamide (43 mg) as a pale yellow solid.

Preparation Example 452

Under a nitrogen atmosphere, to a mixture of (1R,2S)-2-(benzylamino)cyclopentanol (1.36 g), 1,2-dichloroethane (34 mL), and a 37% aqueous formaldehyde solution (1.73 mL) was added sodium triacetoxyborohydride (4.52 g), followed by stirring at room temperature overnight. To the reactant was added a saturated aqueous sodium hydrogen carbonate solution, and then acidified by the addition of 1 M hydrochloric acid. The aqueous phase was washed with ethyl acetate. The water phase was basified with a 1 M aqueous sodium hydroxide solution, and then chloroform was added thereto, followed by liquid separation. The organic phase was washed with saturated brine and dried over anhydrous magnesium sulfate. The mixture was filtered and then the filtrate was concentrated under reduced pressure to obtain (1R,2S)-2-[benzyl(methyl)amino]cyclopentanol (1.38 g).

Preparation Example 456

To a mixture of tert-butyl (3R)-3-{[3-bromo-5-carbamoyl-6-({4-[4-(4-methylpiperazin-1-yl)piperidin-1-yl]phenyl}amino)pyrazin-2-yl]amino}pyrrolidine-1-carboxylate (220 mg), neopentyl glycol ester 2-cyano-3-methoxyphenylborate (164 mg), and tetrakistriphenylphosphine palladium (0) (39 mg), dioxane (8.8 mL) was added a 2 M aqueous sodium carbonate solution (836 μL), followed by stirring at 100° C. for 3 hours under an argon atmosphere. After leaving to be cooled, the mixture was subjected to liquid separation by the addition of ethyl acetate and water. The organic phase was dried over anhydrous magnesium sulfate and then the solvent was evaporated. The obtained residue was purified by silica gel column chromatography (eluent; chloroform:methanol:28% aqueous ammonia=1:0:0-200:10:1) to obtain tert-butyl (3R)-3-{[5-carbamoyl-3-(2-cyano-3-methoxyphenyl)-6-({4-[4-(4-methylpiperazin-1-yl)piperidin-1-yl]phenyl}amino)pyrazin-2-yl]amino}pyrrolidine-1-carboxylate (208 mg).

Preparation Example 460

A mixture of 5-{[2-(1,3-dioxo-1,3-dihydro-2H-isoindol-2-yl)benzyl]oxy}-6-ethyl-3-({4-[4-(4-methylpiperazin-1-yl)piperidin-1-yl]phenyl}amino)pyrazine-2-carboxamide (540 mg), tetrahydrofuran (10.8 mL), ethanol (10.8 mL), and hydrazine monohydrate (160 mg) was stirred at room temperature for 30 hours. The reactant was subjected to liquid separation by the addition of water and chloroform. The organic phase was washed with saturated brine and dried over anhydrous magnesium sulfate, and then the solvent was evaporated under reduced pressure. The obtained residue was purified by silica gel column chromatography (NH2 type: eluent; ethyl acetate, and then chloroform:methanol=97:3) to obtain 5-[(2-aminobenzyl)oxy]-6-ethyl-3-({4-[4-(4-methylpiperazin-1-yl)piperidin-1-yl]phenyl}amino)pyrazine-2-carboxamide (315 mg) as a brown solid.

Preparation Example 471

To a mixture of 5-chloro-6-(2-hydroxypropan-2-yl)-3-({4-[4-(4-methylpiperazin-1-yl)piperidin-1-yl]phenyl}amino)pyrazine-2-carboxamide (11.2 g) and trifluoroacetic acid (110 mL) was added triethylsilane (18.2 mL) under ice-cooling, and followed by stirring under ice-cooling for 10 minutes and at room temperature for 14 hours. The reactant was concentrated, then diluted with chloroform, and washed with a saturated aqueous sodium hydrogen carbonate solution. The organic phase was dried over anhydrous magnesium sulfate, and then the solvent was evaporated. The residue was purified by silica gel column chromatography (eluent; chloroform:methanol:28% aqueous ammonia=1:0:0-500:10:1) to obtain an orange solid. The obtained solid was heated and washed with ethyl acetate to obtain 5-chloro-6-isopropyl-3-({4-[4-(4-methylpiperazin-1-yl)piperidin-1-yl]phenyl}amino)pyrazine-2-carboxamide (9.2 g) as an orange solid.

The compounds shown in Tables 4 to 95 below were prepared by similar manner to the preparation methods of Preparation Examples shown above. Further, the preparation methods, the structures, and the physicochemical data for the respective compounds of Preparation Examples are shown in Tables 4 to 95.

Example 1

To a mixture of 5-(3-aminophenoxy)-6-ethyl-3-{[4-(4-methylpiperazin-1-yl)phenyl]amino}pyrazine-2-carboxamide (2 g), diisopropylethylamine (1.53 mL), and chloroform (100 mL) was added acryloyl chloride (508 μL) under ice-cooling, followed by stirring for 1 hour. Acryloyl chloride (363 μL) was added thereto, followed by stirring for 1 hour. The mixture was subject to liquid separation by the addition of chloroform and a saturated aqueous sodium hydrogen carbonate solution, and the organic phase was washed with saturated brine and then dried over anhydrous magnesium sulfate. The solvent was concentrated and the obtained residue was purified by silica gel column chromatography (chloroform:methanol:28% aqueous ammonia=1:0:0-200:10:1). Ethyl acetate was added thereto, the solid was collected by filtration and then dried under reduced pressure to obtain 5-[3-(acryloylamino)phenoxy]-6-ethyl-3-{[4-(4-methylpiperazin-1-yl)phenyl]amino}pyrazine-2-carboxamide (1.6 g) as a pale yellow solid.

Example 2

To a mixture of 4-bromocrotonic acid (632 mg) and acetonitrile (11 mL) were added oxalyl dichloride (308 μL) and N,N-dimethylformamide (2 droplets) under ice-cooling, followed by stirring at room temperature for 2 hours. To a mixture of 5-(3-aminophenoxy)-6-isopropyl-3-{[4-(4-methylpiperazin-1-yl)phenyl]amino}pyrazine-2-carboxamide (1.1 g) and N-methylpyrrolidone (22 mL) was added a solution of the acid chloride prepared above under ice-cooling, followed by stirring at room temperature overnight. To the reaction mixture was added a saturated aqueous sodium hydrogen carbonate solution, and the precipitated solid was collected by filtration and dried under reduced pressure. The obtained solid was purified by silica gel column chromatography (eluent; chloroform:methanol=1:0-9:1) to obtain 5-(3-{[(2E)-4-chlorobuta-2-enoyl]amino}phenoxy)-6-isopropyl-3-{[4-(4-methylpiperazin-1-yl)phenyl]amino}pyrazine-2-carboxamide (125 mg) as a solid.

Example 3

To a mixture of trans-4-dimethylaminocrotonic acid hydrochloride (113 mg) and acetonitrile (1.9 mL) were added oxalyl dichloride (55 μL) and N,N-dimethylformamide (2 droplets) under ice-cooling, followed by stirring at room temperature for 2 hours. To a mixture of 5-(3-aminophenoxy)-6-ethyl-3-{[4-(4-methylpiperazin-1-yl)phenyl]amino}pyrazine-2-carboxamide (190 mg) and N-methylpyrrolidone (3.8 mL) was added a solution of the acid chloride prepared above under ice-cooling, followed by stirring at room temperature overnight. The reaction mixture was diluted with ethyl acetate, and then washed with a saturated aqueous sodium hydrogen carbonate solution and saturated brine. The organic phase was dried over anhydrous magnesium sulfate and then the solvent was evaporated under reduced pressure. The residue was purified by silica gel column chromatography (eluent; chloroform:methanol:28% aqueous ammonia=1:0:0-100:10:1). Ethyl acetate was added thereto and the precipitated solid was collected by filtration and then dried under reduced pressure to obtain 5-(3-{[(2E)-4-(dimethylamino)buta-2-enoyl]amino}phenoxy)-6-ethyl-3-{[4-(4-methylpiperazin-1-yl)phenyl]amino}pyrazine-2-carboxamide (107 mg) as a pale yellow solid.

Example 4

To a mixture of 5-(3-{[(2E)-4-chlorobuta-2-enoyl]amino}phenoxy)-6-isopropyl-3-{[4-(4-methylpiperazin-1-yl)phenyl]amino}pyrazine-2-carboxamide (80 mg) and N,N-dimethylformamide (800 μL) were added diisopropylethylamine (25 μL) and morpholine (11 μL), followed by stirring at room temperature overnight. Water was added thereto, and the precipitated solid was collected by filtration and purified by silica gel column chromatography (eluent; chloroform:methanol:28% aqueous ammonia=1:0:0-100:10:1). Diisopropyl ether was added thereto and the precipitated solid was collected by filtration and then dried under reduced pressure to obtain 6-isopropyl-3-{[4-(4-methylpiperazin-1-yl)phenyl]amino}-5-(3-{[(2E)-4-(morpholin-4-yl)but-2-enoyl]amino}phenoxy)pyrazine-2-carboxamide (27 mg) as a solid.

Example 5

To a mixture of 5-[3-(acryloylamino)phenoxy]-6-ethyl-3-{[3-methyl-4-(4-oxopiperidin-1-yl)phenyl]amino}pyrazine-2-carboxamide (200 mg), morpholine (35 μL), and 1,2-dichloroethane (1.94 mL) was added sodium triacetoxyborohydride (100 mg), followed by stirring at room temperature overnight. To the reaction mixture were added a saturated aqueous sodium hydrogen carbonate solution and water, followed by extraction with chloroform twice. The extract was dried over anhydrous sodium sulfate and then the solvent was evaporated under reduced pressure. The residue was purified by silica gel column chromatography (eluent;

chloroform:methanol=100:0-99:1-97:3) to obtain 5-[3-(acryloylamino)phenoxy]-6-ethyl-3-({3-methyl-4-[4-(morpholin-4-yl)piperidin-1-yl]phenyl}amino)pyrazine-2-carboxamide (55 mg) as a solid.

Example 6

To a mixture of 6-ethyl-3-{[2-methoxy-4-(4-methylpiperazin-1-yl)phenyl]amino}-5-(3-nitrophenoxy)pyrazine-2-carboxamide (250 mg), ethanol (25 mL), and water (5 mL) were added ammonium chloride (1.05 g) and iron powder (550 mg), followed by stirring at 60° C. for 6 hours. Ammonium chloride (527 mg) and iron powder (275 mg) were added thereto, followed by stirring at 60° C. for 2 hours. After filtration through celite, the solvent was evaporated under reduced pressure, and the mixture was subjected to liquid separation by the additional chloroform and a saturated aqueous sodium hydrogen carbonate solution. The organic phase was washed with saturated brine and then dried over anhydrous magnesium sulfate, and the solvent was evaporated under reduced pressure. The obtained residue was purified by silica gel column chromatography (eluent; chloroform:methanol:28% aqueous ammonia=1:0:0-200:10:1). Diisopropyl ether was added thereto, and the solid was collected by filtration and then dried under reduced pressure. To a mixture of the obtained residue and chloroform (9.25 mL) was added diisopropylethylamine (133 µL), and acryloyl chloride (44 µL) was added thereto under ice-cooling, followed by stirring for 1 hour. Acryloyl chloride (32 µL) was added thereto, followed by stirring for 1 hour. A 1 M aqueous sodium hydroxide solution (1 mL) was added thereto under ice-cooling, and the mixture was subjected to liquid separation by the additional chloroform and a saturated aqueous sodium hydrogen carbonate solution. The organic phase was washed with saturated brine and then dried over anhydrous magnesium sulfate, and the solvent was evaporated under reduced pressure. The obtained residue was purified by silica gel column chromatography (eluent; chloroform:methanol:28% aqueous ammonia=1:0:0-200:10:1), and to the obtained residue was added ethyl acetate. The precipitated solid was collected by filtration and dried under reduced pressure to obtain 5-[3-(acryloylamino)phenoxy]-6-ethyl-3-{[2-methoxy-4-(4-methylpiperazin-1-yl)phenyl]amino}pyrazine-2-carboxamide (126 mg) as a yellow solid.

Example 7

To a mixture of 5-(3-aminophenoxy)-6-(2-hydroxypropan-2-yl)-3-{[4-(4-methylpiperazin-1-yl)phenyl]amino}pyrazine-2-carboxamide (27 mg), diisopropylethylamine (29 µL), and chloroform (5 ml) was added acryloyl chloride (7 µL) under ice-cooling, followed by stirring for 30 minutes. Further acryloyl chloride (7 µL) was added, followed by stirring under ice-cooling for 30 minutes. Diisopropylethylamine (29 µl) and acryloyl chloride (7 µL) were added thereto, followed by stirring for 30 minutes under ice-cooling. A saturated aqueous sodium hydrogen carbonate solution (10 mL) and tetrahydrofuran (20 mL) were added thereto under ice-cooling, followed by stirring for 10 minutes under ice-cooling. To the reaction mixture was added a 1 M aqueous sodium hydroxide solution (2 mL), followed by stirring at room temperature for 30 minutes. The reaction mixture was subjected to liquid separation and to the organic phase was added silica gel. Then, the solvent was evaporated under reduced pressure. The residue was purified by silica gel column chromatography (eluent; chloroform:methanol:28% aqueous ammonia=1:0:0-200:10:1), washed with ethyl acetate, and the solid was collected by filtration and then dried under reduced pressure to obtain 5-[3-(acryloylamino)phenoxy]-6-(2-hydroxypropan-2-yl)-3-{[4-(4-methylpiperazin-1-yl)phenyl]amino}pyrazine-2-carboxamide (18 mg) as a yellow solid.

Example 8

To a mixture of tert-butyl (2R,6S)-4-[4-({6-[3-(acryloylamino)phenoxy]-3-carbamoyl-5-ethylpyrazin-2-yl}amino)phenyl]-2,6-dimethylpiperazine-1-carboxylate (175 mg) and tetrahydrofuran (3 mL) was added a 4 M hydrogen chloride dioxane solution (3 mL), followed by stirring at room temperature for 2 hours. The solvent was evaporated under reduced pressure and the obtained residue was washed with ethyl acetate and then dried at room temperature to obtain 5-[3-(acryloylamino)phenoxy]-3-({4-[(3R,5S)-3,5-dimethylpiperazin-1-yl]phenyl}amino)-6-ethylpyrazine-2-carboxamide trihydrochloride (157 mg) as a yellow solid.

Example 75

To a mixture of 6-ethyl-3-{[4-(4-methylpiperazin-1-yl)phenyl]amino}-5-(1,2,3,6-tetrahydropyridin-4-yl)pyrazin-2-carboxamide (40 mg), diisopropylethylamine (75 µL), and chloroform (4 mL) was added under ice-cooling acryloyl chloride (25 µL), followed by stirring at room temperature overnight. To the reaction mixture was added saturated aqueous sodium hydrogen carbonate solution, followed by extraction with chloroform. The organic phase was washed with saturated aqueous sodium hydrogen carbonate solution and saturated brine, then dried over anhydrous magnesium sulfate, and the solvent was evaporated under reduced pressure. The obtained residue was purified by silica gel chromatography (eluent; chloroform:methanol:28% aqueous ammonia=1:0:0-100:10:1). To an ethyl acetate solution of the obtained oily substance was added 4 M hydrogen chloride ethyl acetate solution, followed by stirring for 5 hours. The solvent was evaporated under reduced pressure and the obtained solid was washed with diisopropyl ether to obtain 5-(1-acryloyl-1,2,3,6-tetrahydropyridin-4-yl)-6-ethyl-3-{[4-(4-methylpiperazin-1-yl)phenyl]amino}pyrazin-2-carboxamide monohydrochloride (21 mg) as an orange solid.

Example 122

To a mixture of tert-butyl 3-{[5-carbamoyl-3-ethyl-6-({4-[4-(4-methylpiperazin-1-yl)piperidin-1-yl]phenyl}amino)pyrazin-2-yl]amino}azetidine-1-carboxylate (130 mg), and dichloromethane (1 mL) was added trifluoroacetic acid (1 mL) at 0° C., followed by stirring for 2 hours. The solvent was evaporated, and subjected to liquid separation by the addition of chloroform and a saturated aqueous sodium hydrogen carbonate solution. The organic phase was dried over anhydrous magnesium sulfate. After filtration, the filtrate was concentrated under reduced pressure. To a mixture of the obtained residue and chloroform (4 mL) were added diisopropylethylamine (140 µL) and acryloyl chloride (40 µL) under ice-cooling, followed by stirring at room temperature for 8 hours. The reactant was subjected to liquid separation by the addition of a saturated aqueous sodium hydrogen carbonate solution. The organic phase was washed with a saturated aqueous sodium hydrogen carbonate solution, and saturated brine and dried over anhydrous magnesium sulfate, and then the solvent was evaporated under reduced pressure. The obtained residue was purified by silica gel column chromatography (eluent; chloroform:methanol:28% aqueous ammonia=1:0:0-100:10:

1) to obtain 5-[(1-acryloylazetidin-3-yl)amino]-6-ethyl-3-({4-[4-(4-methylpiperazin-1-yl)piperidin-1-yl]phenyl}amino)pyrazine-2-carboxamide (18 mg).

Example 192

To a mixture of {(2S)-4-[4-({6-[3-(acryloylamino)phenoxy]-3-carbamoyl-5-ethylpyrazin-2-yl}amino)phenyl]-1-methylpiperazin-2-yl}methylacryalte (197 mg) and tetrahydrofuran (5 mL) was added a 1 M aqueous sodium hydroxide solution (807 μL), followed by stirring at room temperature for 8 hours. The reactant was neutralized by the addition of 1 M hydrochloric acid (807 μL), and then water was added thereto. The mixture was extracted three times with a mixed solvent of methanol:chloroform (1:9). The organic phase was washed with saturated brine and dried over anhydrous magnesium sulfate, and then the solvent was evaporated under reduced pressure. The obtained residue was purified by silica gel column chromatography (NH2 type: eluent; chloroform:methanol=97:3-95:5) to obtain 5-[3-(acryloylamino)phenoxy]-6-ethyl-3-({4-[(3S)-3-(hydroxymethyl)-4-methylpiperazin-1-yl]phenyl}amino)pyrazine-2-carboxamide (41 mg) as a yellow solid.

Example 205

To a mixture of 5-(3-aminophenoxy)-6-ethyl-3-({4-[(3R)-3-(hydroxymethyl)-4-methylpiperazin-1-yl]phenyl}amino)pyrazine-2-carboxamide (227 mg), dichloromethane (6.8 mL), and diisopropylethylamine (326 μL) was added acryloyl chloride (116 μL) at 0° C., followed by stirring at the same temperature for 2 hours. To the mixture were added water and chloroform, followed by liquid separation. The separated organic phase was washed with saturated brine and dried over anhydrous magnesium sulfate. After concentration under reduced pressure, the obtained residue were added tetrahydrofuran (4.5 mL) and a 1 M aqueous sodium hydroxide solution (1.1 mL), followed by stirring at room temperature overnight. The mixture was neutralized by the addition of 1 M hydrochloric acid, and extracted with a mixed solvent of chloroform:methanol (9:1) three times. The separated organic phase was washed with saturated brine and dried over anhydrous magnesium sulfate. After concentration under reduced pressure, the obtained residue was purified by silica gel column chromatography (eluent; chloroform:methanol=9:1). A mixed solution of hexane:ethyl acetate (19:1) was added thereto, and the solid was collected by filtration, then washed, and dried under reduced pressure to obtain 5-[3-(acryloylamino)phenoxy]-6-ethyl-3-({4-[(3R)-3-(hydroxymethyl)-4-methylpiperazin-1-yl]phenyl}amino)pyrazine-2-carboxamide (27 mg) as a yellow solid.

Example 214

To a mixture of 3-{[1-(2-hydroxyethyl)-1H-pyrazol-4-yl]amino}-6-isopropyl-5-[(3R)-pyrrolidin-3-yloxy]pyrazine-2-carboxamide (476 mg), chloroform (5 mL), and diisopropylethylamine (867 μL) was added acryloyl chloride (226 μL) at 0° C., followed by stirring at the same temperature for 1 hour. The solvent of the reactant was evaporated, and then to the obtained residue were added tetrahydrofuran (5 mL) and a 1 M aqueous sodium hydroxide solution (5 mL), followed by stirring at 50° C. for 4 hours. After leaving to be cooled, the mixture was extracted by the addition of chloroform, and the organic phase was dried over anhydrous sodium sulfate. After concentration under reduced pressure, the obtained residue was purified by silica gel column chromatography (eluent; chloroform:methanol:28% aqueous ammonia=980:18:2-90:9:1), and then washed with diisopropyl ether to obtain 5-{[(3R)-1-acryloylpyrrolidin-3-yl]oxy}-3-{[1-(2-hydroxyethyl)-1H-pyrazol-4-yl]amino}-6-isopropylpyrazine-2-carboxamide (343 mg) as a yellow solid.

Example 231

A mixture of 5-chloro-6-ethyl-3-({4-[4-(4-methylpiperazin-1-yl)piperidin-1-yl]phenyl}amino)pyrazine-2-carboxamide (21 mg), tert-butyl (2-aminoethyl)methylcarbamate (31 mg), diisopropylethylamine (16 μL), and N-methylpyrrolidone (0.3 mL) was stirred at 140° C. for 2 hours and a half. To the reaction mixture was added PS-benzaldehyde (Biotage, 150 mg) at room temperature, N,N-dimethylformamide (1 mL) was added thereto, followed by stirring for 2 hours, and the insoluble matter was filtered. The filtrate was evaporated under reduced pressure and the obtained residue were added methanol (0.5 mL) and a 4 M hydrogen chloride-dioxane solution (0.45 mL), followed by stirring at room temperature for 8 hours. The solvent was evaporated under reduced pressure, and to the obtained residue were added tetrahydrofuran (0.9 mL) and a saturated aqueous sodium hydrogen carbonate solution (1 mL), followed by stirring at room temperature. Acryloyl chloride (8 μL) and tetrahydrofuran (0.1 mL) were added thereto at room temperature, followed by stirring for 4 hours. The reaction mixture was extracted with chloroform. The solvent of the organic phase was evaporated under reduced pressure and the obtained residue was purified by preparative HPLC (methanol/0.1% aqueous formic acid solution) to obtain 5-({2-[acryloyl (methyl)amino]ethyl}amino)-6-ethyl-3-({4-[4-(4-methylpiperazin-1-yl)piperidin-1-yl]phenyl}amino)pyrazine-2-carboxamide (1 mg).

Example 253

A mixture of 5-chloro-6-ethyl-3-({4-[4-(4-methylpiperazin-1-yl)piperidin-1-yl]phenyl}amino)pyrazine-2-carboxamide (21 mg), 2,7-diazaspiro[4.4]nonane-2-carboxylic acid-tert-butyl ester (41 mg), diisopropylethylamine (16 μL), and N-methylpyrrolidone (0.3 mL) was stirred at 140° C. for 2 hours and a half. To the reaction mixture was added PS-isocyanate (Biotage, 100 mg) at room temperature, N,N-dimethylformamide (1 mL) was added thereto, followed by stirring for 2 hours, and the insoluble matter was filtered. The filtrate was evaporated under reduced pressure and the obtained residue were added methanol (0.5 mL) and a 4 M hydrogen chloride-dioxane solution (0.45 mL), followed by stirring at room temperature for 8 hours. The solvent was evaporated under reduced pressure and the obtained residue were added tetrahydrofuran (0.9 mL) and a saturated aqueous sodium hydrogen carbonate solution (1 mL). Acryloyl chloride (8 μL) and tetrahydrofuran (0.1 mL) were added thereto at room temperature, followed by stirring for 4 hours. The reaction mixture was extracted with chloroform. The solvent of the organic phase was evaporated under reduced pressure and the obtained residue was purified by preparative HPLC (methanol/0.1% aqueous formic acid solution) to obtain 5-(7-acryloyl-2,7-diazaspiro[4.4]non-2-yl)-6-ethyl-3-({4-[4-(4-methylpiperazin-1-yl)piperidin-1-yl]phenyl}amino)pyrazine-2-carboxamide (2 mg).

Example 254

A mixture of 5-[3-(acryloylamino)phenoxy]-6-ethyl-3-{[4-(4-methylpiperazin-1-yl)phenyl]amino}pyrazine-2-carboxamide (100 mg) and acetonitrile (3 mL) was heated to 50°

C., and a 2 M aqueous methanesulfonic acid solution (100 µl) was added thereto, followed by stirring at 50° C. for 30 minutes. After leaving to be cooled to room temperature, the mixture was stirred at room temperature for 15 hours. The precipitated solid was collected by filtration and dried at 50° C. for 6 hours under reduced pressure to obtain 5-[3-(acryloylamino)phenoxy]-6-ethyl-3-{[4-(4-methylpiperazin-1-yl)phenyl]amino}pyrazine-2-carboxamide monomethanesulfonate (104 mg) as a pale yellow solid.

ESI+:502

1H-NMR (DMSO-d6): 1.32 (3H, t, J=7.5 Hz), 2.31 (3H, s), 2.76-2.90 (7H, m), 3.04-3.70 (6H, m), 5.78 (1H, dd, J=2.0, 10.0 Hz), 6.27 (1H, dd, J=2.0, 17.0 Hz), 6.44 (1H, dd, J=10.0, 17.0 Hz), 6.65 (2H, d, J=9.0 Hz), 6.96-7.01 (1H, m), 7.14 (2H, d, J=9.0 Hz), 7.46 (1H, t, J=8.1 Hz), 7.56 (1H, t, J=2.2 Hz), 7.67-7.72 (2H, m), 7.95-7.99 (1H, m), 9.50 (1H, brs), 10.34 (1H, s), 11.00 (1H, s)

A powder X-ray diffraction pattern of the compound of Example 254 is shown in FIG. 1.

Example 255

5-(3-{[(2E)-4-(dimethylamino)-2-butenolyl]amino}phenoxy)-6-ethyl-3-{[4-(4-methylpiperazin-1-yl)phenyl]amino}pyrazine-2-carboxamide monomethansulfonate (48 mg) was obtained as a yellow solid in a similar manner to Example 254 by using 5-(3-{[(2E)-4-(dimethylamino)-2-butenolyl]amino}phenoxy)-6-ethyl-3-{[4-(4-methylpiperazin-1-yl)phenyl]amino}pyrazine-2-carboxamide (80 mg).

ESI+:559

1H-NMR (DMSO-d6): 1.32 (3H, t, J=7.5 Hz), 2.32 (3H, s), 2.48-4.40 (22H, m), 6.37 (1H, d, J=15.4 Hz), 6.61 (2H, d, J=9.1 Hz), 6.69-6.78 (1H, m), 6.96-7.02 (1H, m), 7.10 (2H, d, J=9.1 Hz), 7.43-7.50 (1H, m), 7.59-7.72 (3H, m), 7.93-7.99 (1H, m), 10.38 (1H, brs), 10.96 (1H, s)

Figure 2:
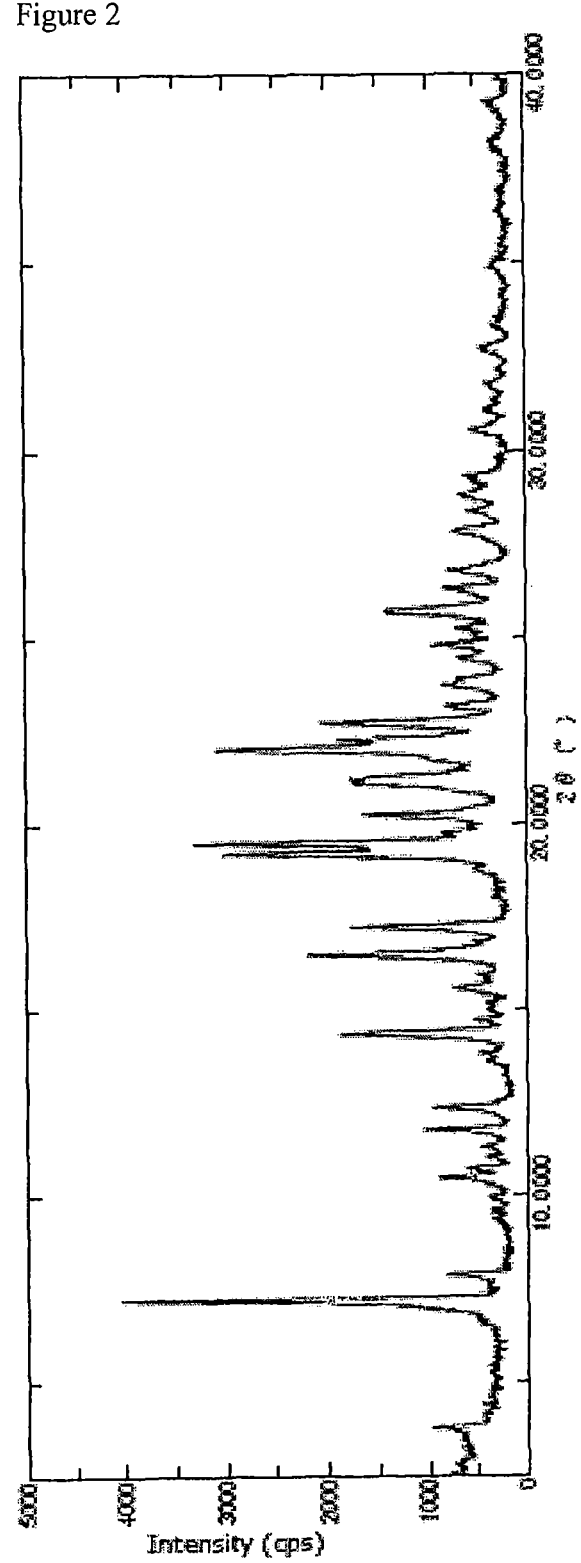
FIG. 2 shows a powder X-ray diffraction pattern of the compound of Example 255.

A powder X-ray diffraction pattern of the compound of Example 255 is shown in FIG. 2.

Example 256

5-[3-(acryloylamino)-2-methylphenoxy]-6-ethyl-3-{[4-(4-methylpiperazin-1-yl)phenyl]amino}pyrazine-2-carboxamide monomethansulfonate (34 mg) was obtained as a yellow solid in a similar manner to Example 254 by using 5-[3-(acryloylamino)-2-methylphenoxy]-6-ethyl-3-{[4-(4-methylpiperazin-1-yl)phenyl]amino}pyrazine-2-carboxamide (40 mg).

ESI+:516

1H-NMR (DMSO-d6): 1.34 (3H, t, J=7.5 Hz), 2.02 (3H, s), 2.31 (3H, s), 2.80-2.93 (7H, m), 3.02-3.90 (6H, m), 5.74-5.83 (1H, m), 6.29 (1H, dd, J=2.1, 17.0 Hz), 6.61 (1H, dd, J=10.0, 17.0 Hz), 6.68 (2H, d, J=9.0 Hz), 6.98-7.07 (3H, m), 7.32 (1H, t, J=8.2 Hz), 7.62-7.71 (2H, m), 7.93-7.99 (1H, m), 9.49 (1H, brs), 9.62 (1H, s), 10.99 (1H, s)

Figure 3:
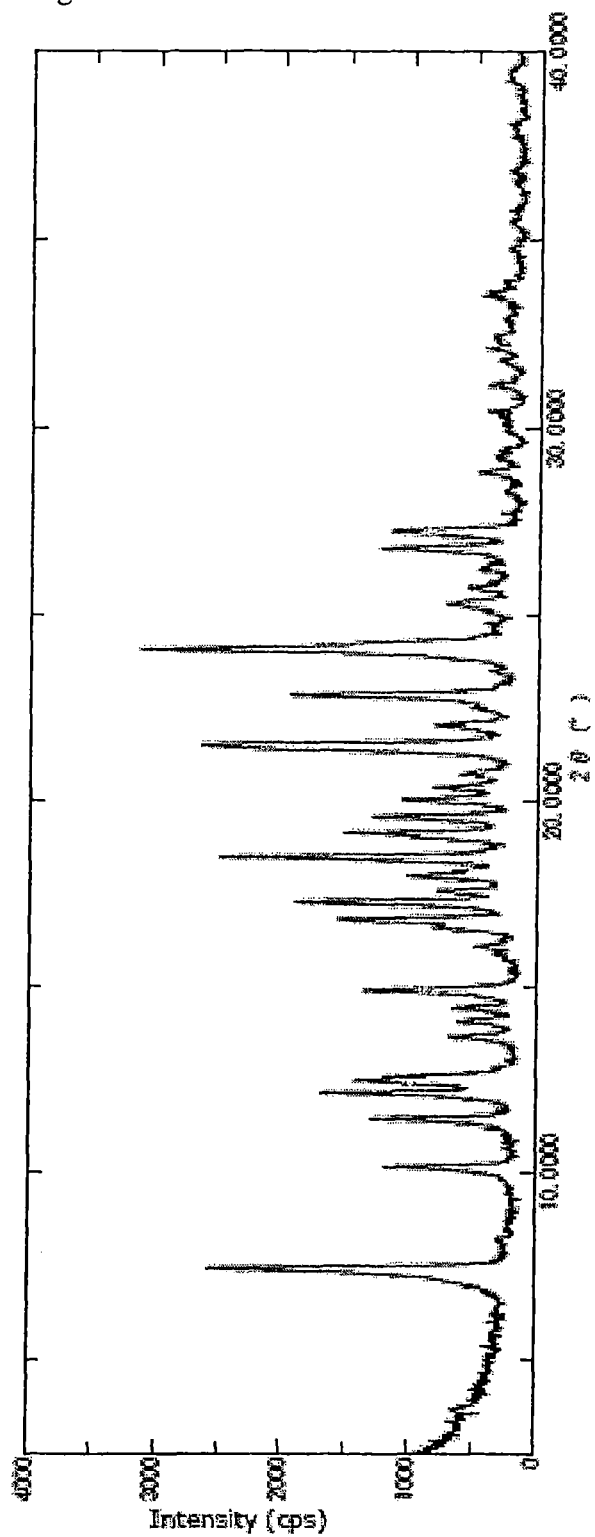
FIG. 3 shows a powder X-ray diffraction pattern of the compound of Example 256.

A powder X-ray diffraction pattern of the compound of Example 256 is shown in FIG. 3.

Example 257

5-[3-(acryloylamino)phenoxy]-6-isopropyl-3-{[4-(4-methylpiperazin-1-yl)phenyl]amino}pyrazine-2-carboxamide monomethansulfonate (80 mg) was obtained as a yellow solid in a similar manner to Example 254 by using 5-[3-(acryloylamino)phenoxy]-6-isopropyl-3-{[4-(4-methylpiperazin-1-yl)phenyl]amino}pyrazine-2-carboxamide (100 mg).

ESI+:516

1H-NMR (DMSO-d6): 1.33 (6H, d, J=6.8 Hz), 2.31 (3H, s), 2.76-2.91 (5H, m), 3.04-3.70 (7H, m), 5.78 (1H, dd, J=2.0, 10.0 Hz), 6.27 (1H, dd, J=2.0, 17.0 Hz), 6.44 (1H, dd, J=10.0, 17.0 Hz), 6.64 (2H, d, J=9.1 Hz), 6.96-7.01 (1H, m), 7.13 (2H, d, J=9.1 Hz), 7.46 (1H, t, J=8.2 Hz), 7.55 (1H, t, J=2.1 Hz), 7.67-7.75 (2H, m), 7.91-7.96 (1H, m), 9.50 (1H, brs), 10.33 (1H, s), 10.98 (1H, s)

Figure 4:
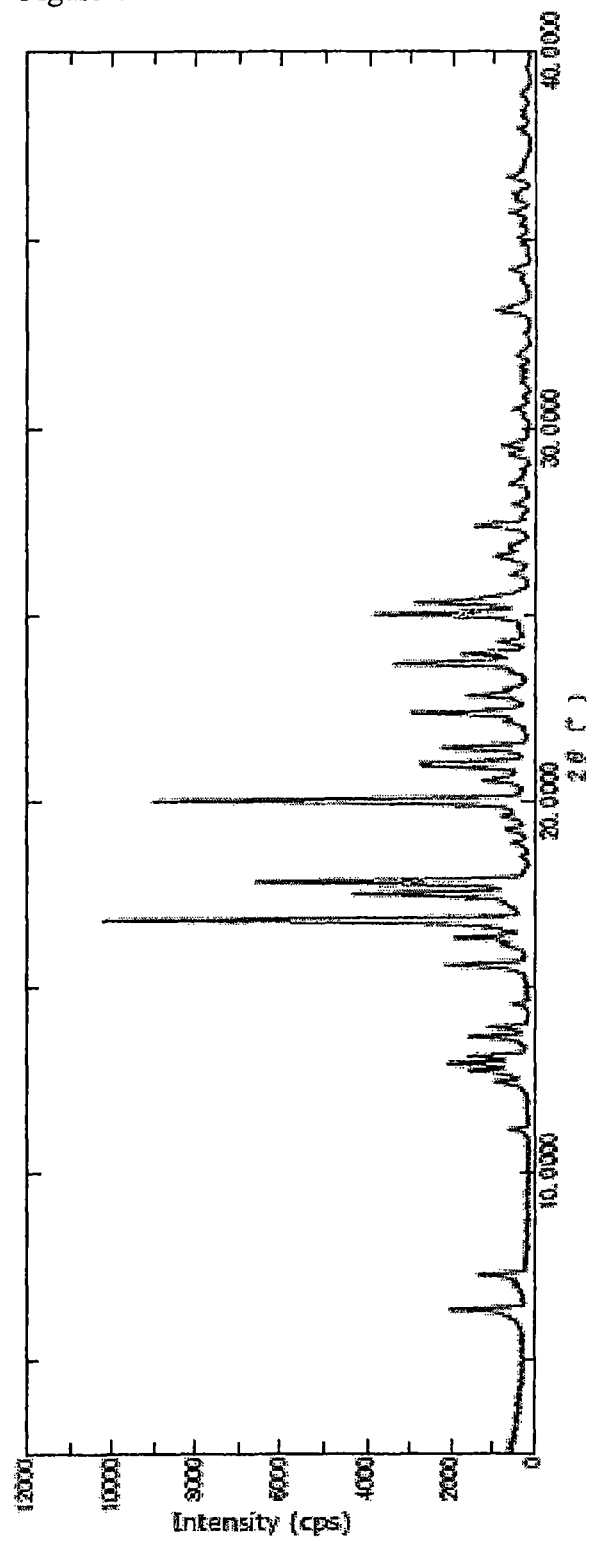
FIG. 4 shows a powder X-ray diffraction pattern of the compound of Example 257.

A powder X-ray diffraction pattern of the compound of Example 257 is shown in FIG. 4.

Example 258

5-(1-acryloylpiperidin-4-yl)-6-ethyl-3-({3-methyl-4-[4-(4-methylpiperazin-1-yl)piperidin-1-yl]phenyl}amino)pyrazine-2-carboxamide monomethansulfonate (20 mg) was obtained as a yellow solid in a similar manner to Example 254 by using 5-(1-acryloylpiperidin-4-yl)-6-ethyl-3-({3-methyl-4-[4-(4-methylpiperazin-1-yl)piperidin-1-yl]phenyl}amino)pyrazine-2-carboxamide (21 mg).

ESI+:575

1H-NMR (DMSO-d6): 1.25 (3H, t, J=7.5 Hz), 1.48-3.60 (35H, m), 4.14-4.24 (1H, m), 4.52-4.62 (1H, m), 5.68 (1H, dd, J=2.5, 10.5 Hz), 6.12 (1H, dd, J=2.5, 16.7 Hz), 6.87 (1H, dd, J=10.5, 16.7 Hz), 6.93 (1H, d, J=8.5 Hz), 7.27-7.35 (1H, m), 7.56-7.64 (1H, m), 7.78-7.88 (1H, m), 8.08-8.18 (1H, m), 9.00-9.40 (1H, m), 10.86 (1H, s)

Figure 5:
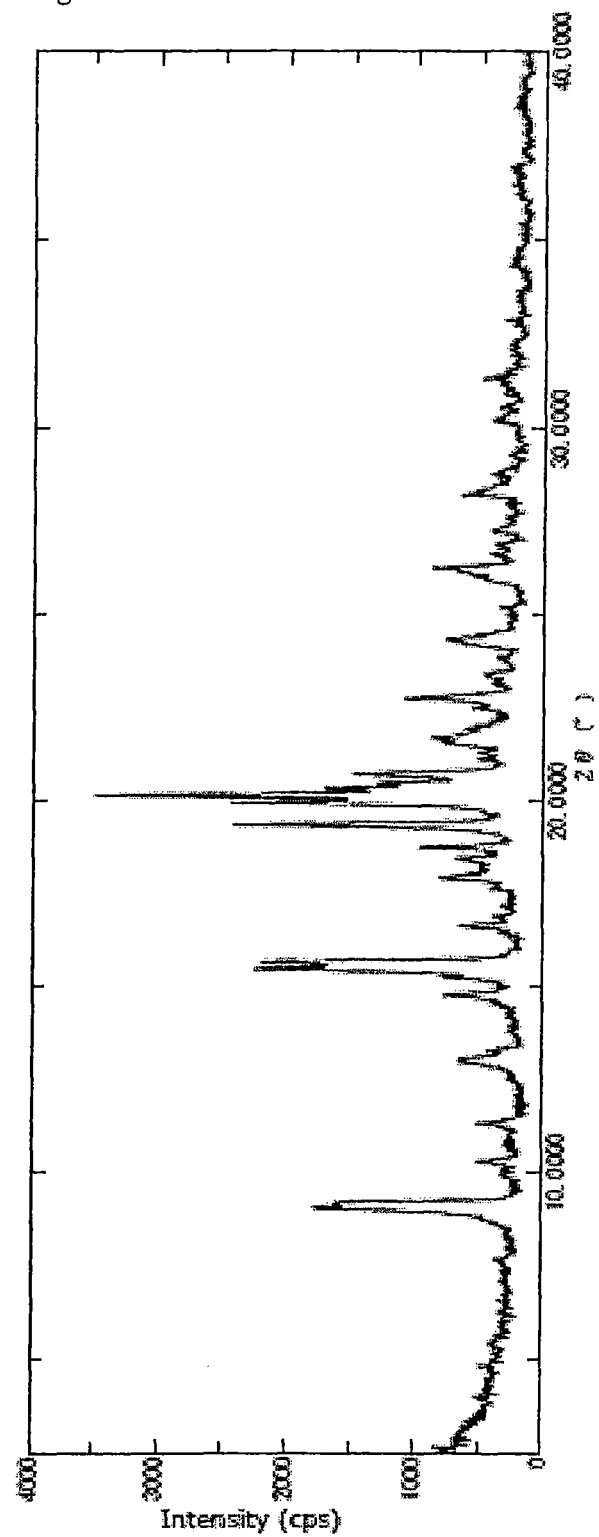
FIG. 5 shows a powder X-ray diffraction pattern of the compound of Example 258.

A powder X-ray diffraction pattern of the compound of Example 258 is shown in FIG. 5.

Example 259

5-[3-(acryloylamino)phenoxy]-3-{[4-(4-methylpiperazin-1-yl)phenyl]amino}pyrazine-2-carboxamide monomethansulfonate (102 mg) was obtained as a yellow solid in a similar manner to Example 254 by using 5-[3-(acryloylamino)phenoxy]-3-{[4-(4-methylpiperazin-1-yl)phenyl]amino}pyrazine-2-carboxamide (100 mg).

ESI+:474

1H-NMR (DMSO-d6): 2.32 (3H, s), 2.60-3.90 (11H, m), 5.78 (1H, dd, J=2.0, 10.0 Hz), 6.27 (1H, dd, J=2.0, 17.0 Hz), 6.45 (1H, dd, J=10.0, 17.0 Hz), 6.70 (2H, d, J=9.1 Hz), 6.98-7.03 (1H, m), 7.21 (2H, d, J=9.1 Hz), 7.46 (1H, t, J=8.2 Hz), 7.60 (1H, t, J=2.1 Hz), 7.64-7.75 (2H, m), 7.80 (1H, s), 8.12-8.15 (1H, m), 9.52 (1H, brs), 10.35 (1H, s), 11.23 (1H, s)

Figure 6:
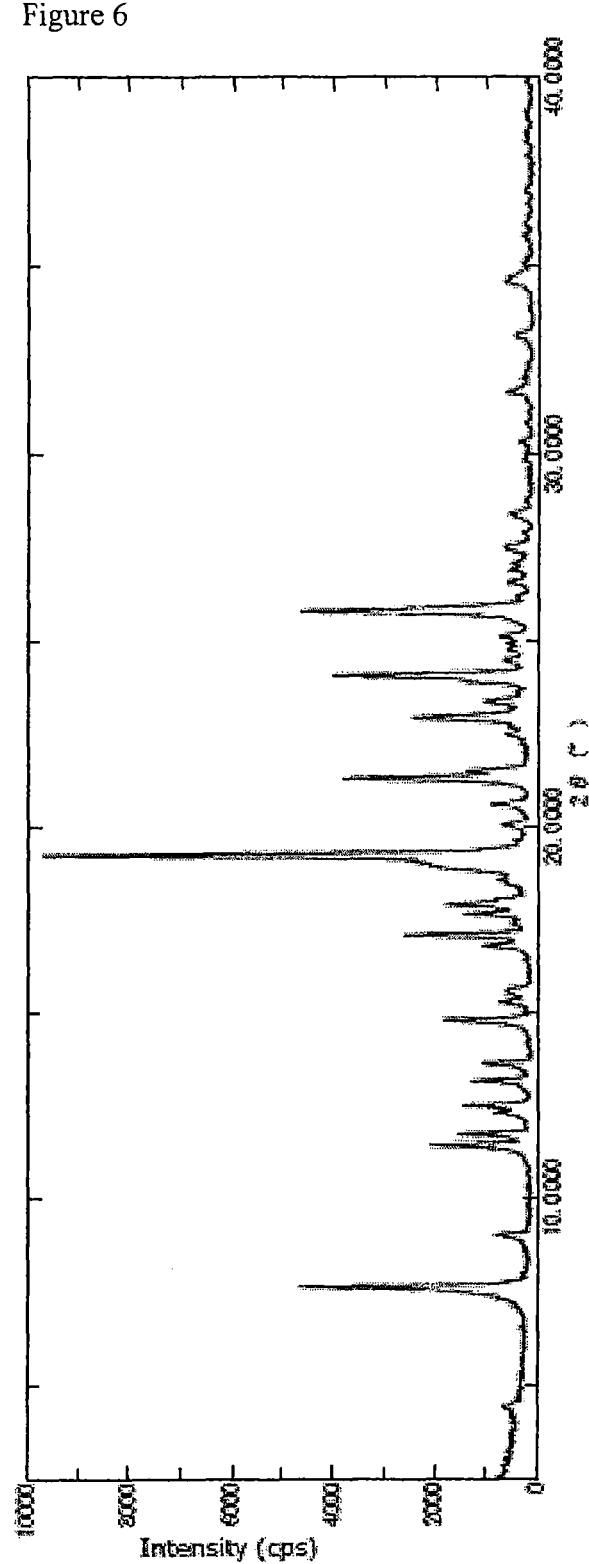
FIG. 6 shows a powder X-ray diffraction pattern of the compound of Example 259.

A powder X-ray diffraction pattern of the compound of Example 259 is shown in FIG. 6.

Example 260

5-[3-(acryloylamino)phenoxy]-6-ethyl-3-{[4-(4-ethylpiperazin-1-yl)phenyl]amino}pyrazine-2-carboxamide monomethansulfonate (42 mg) was obtained as a pale yellow solid in a similar manner to Example 254 by using 5-[3-(acryloylamino)phenoxy]-6-ethyl-3-{[4-(4-ethylpiperazin-1-yl)phenyl]amino}pyrazine-2-carboxamide (40 mg).

ESI+:516

1H-NMR (DMSO-d6): 1.25 (3H, t, J=7.3 Hz), 1.32 (3H, t, J=7.5 Hz), 2.31 (3H, s), 2.78-3.68 (12H, m), 5.78 (1H, dd, J=2.0, 10.0 Hz), 6.28 (1H, dd, J=2.0, 17.0 Hz), 6.44 (1H, dd, J=10.0, 17.0 Hz), 6.65 (2H, d, J=9.0 Hz), 6.96-7.01 (1H, m), 7.14 (2H, d, J=9.0 Hz), 7.46 (1H, t, J=8.2 Hz), 7.54-7.58 (1H, m), 7.65-7.72 (2H, m), 7.95-8.00 (1H, m), 9.25 (1H, brs), 10.33 (1H, s), 11.00 (1H, s)

Figure 7:
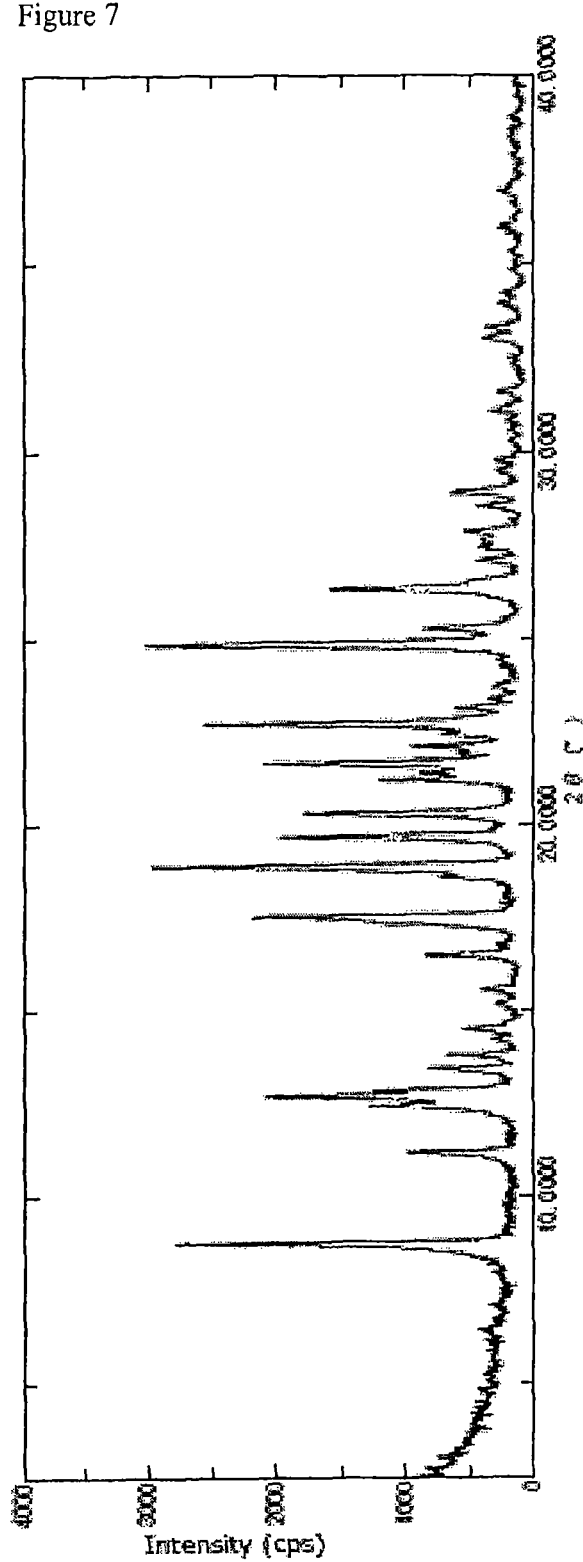
FIG. 7 shows a powder X-ray diffraction pattern of the compound of Example 260.

A powder X-ray diffraction pattern of the compound of Example 260 is shown in FIG. 7.

Example 261

5-{[(3R)-1-acryloylpyrrolidin-3-yl]oxy}-6-ethyl-3-({4-[4-(4-methylpiperazin-1-yl)piperidin-1-yl]phenyl}amino)pyrazine-2-carboxamide monomethansulfonate (97 mg) was obtained as a pale yellow solid in a similar manner to Example 254 by using 5-{[(3R)-1-acryloylpyrrolidin-3-yl]oxy}-6-ethyl-3-({4-[4-(4-methylpiperazin-1-yl)piperidin-1-yl]phenyl}amino)pyrazine-2-carboxamide (100 mg).

ESI+:563

1H-NMR (DMSO-d6): 1.16 (3H, t, J=7.5 Hz), 1.40-3.98 (31H, m), 5.46-5.57 (1H, m), 5.63-5.73 (1H, m), 6.11-6.19 (1H, m), 6.49-6.69 (1H, m), 6.89-7.01 (2H, m), 7.39-7.50 (2H, m), 7.53-7.61 (1H, m), 7.80-7.89 (1H, m), 9.00-9.38 (1H, m), 10.90-11.07 (1H, m)

Figure 8:
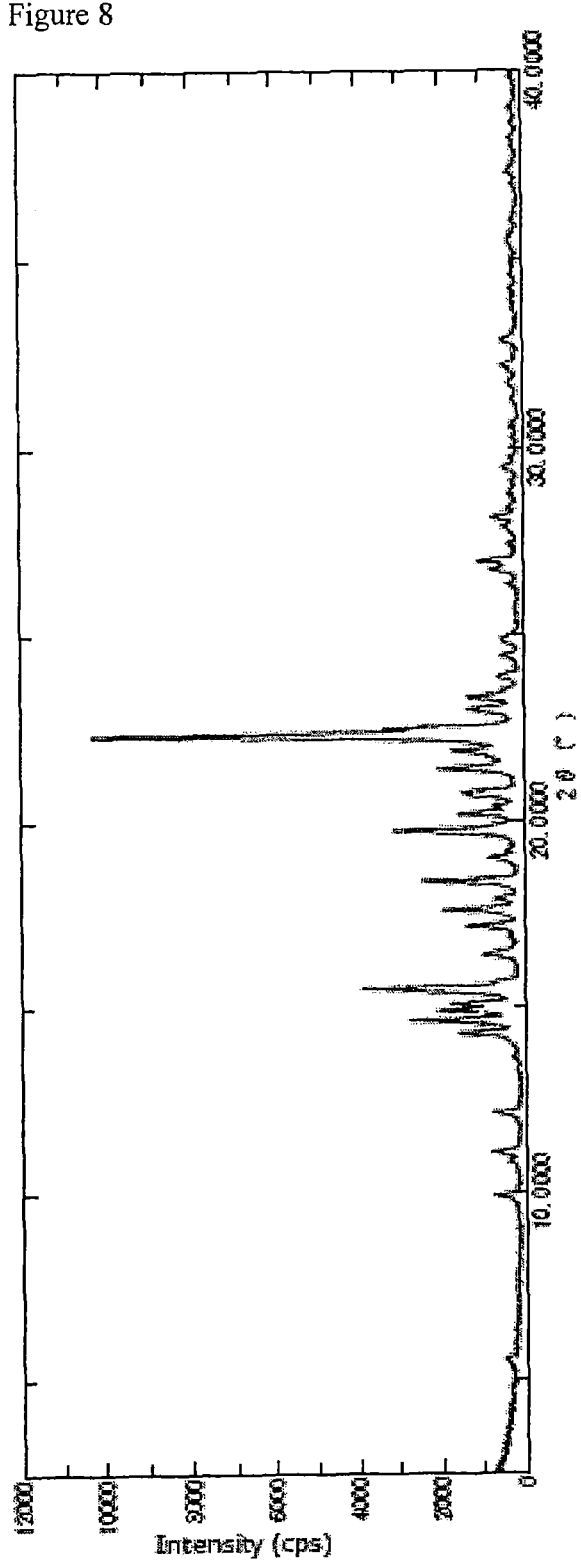
FIG. 8 shows a powder X-ray diffraction pattern of the compound of Example 261.

A powder X-ray diffraction pattern of the compound of Example 261 is shown in FIG. 8.

Example 262

5-[3-(acryloylamino)phenoxy]-6-isopropyl-3-{[1-(1-methylpiperidin-4-yl)-1H-pyrazol-4-yl]amino}pyrazine-2-carboxamide monomethansulfonate (15 mg) was obtained as a pale yellow solid in a similar manner to Example 254 by using 5-[3-(acryloylamino)phenoxy]-6-isopropyl-3-{[1-(1-methylpiperidin-4-yl)-1H-pyrazol-4-yl]amino}pyrazine-2-carboxamide (17 mg).

ESI+:505

1H-NMR (DMSO-d6): 1.33 (6H, d, J=6.8 Hz), 1.86-2.14 (4H, m), 2.31 (3H, s), 2.85 (3H, s), 3.06-3.60 (5H, m), 3.84-3.96 (1H, m), 5.79 (1H, dd, J=2.0, 10.0 Hz), 6.28 (1H, dd, J=2.0, 17.0 Hz), 6.43 (1H, dd, J=10.0, 17.0 Hz), 6.97-7.07 (2H, m), 7.38 (1H, s), 7.46-7.59 (2H, m), 7.66-7.73 (1H, m), 7.78-7.92 (2H, m), 9.31 (1H, brs), 10.38 (1H, s), 10.67 (1H, s)

Figure 9:
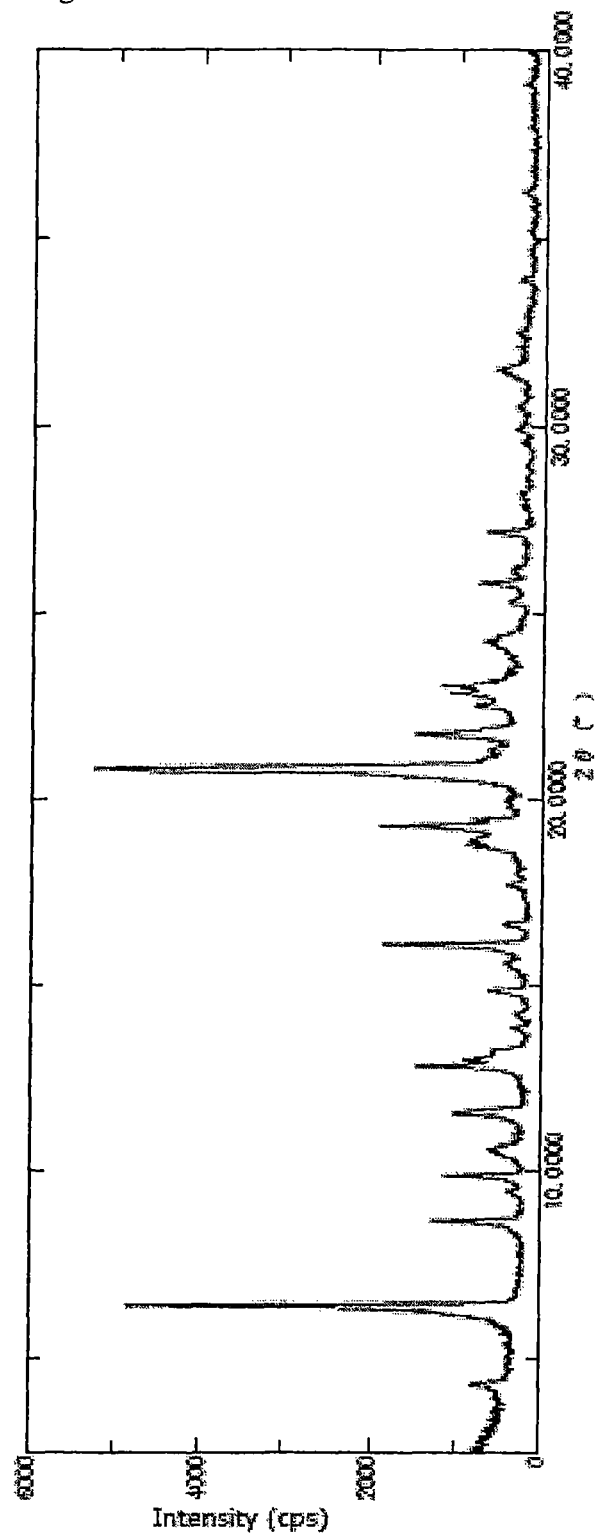
FIG. 9 shows a powder X-ray diffraction pattern of the compound of Example 262.

A powder X-ray diffraction pattern of the compound of Example 262 is shown in FIG. 9.

Example 263

5-[3-(acryloylamino)phenoxy]-3-({4-[(3S)-3,4-dimethylpiperazin-1-yl]phenyl}amino)-6-ethylpyrazine-2-carboxamide monomethansulfonate (72 mg) was obtained as a yellow solid in a similar manner to Example 254 by using 5-[3-(acryloylamino)phenoxy]-3-({4-[(3S)-3,4-dimethylpiperazin-1-yl]phenyl}amino)-6-ethylpyrazine-2-carboxamide (80 mg).

ESI+:516

1H-NMR (DMSO-d6): 1.26-1.38 (6H, m), 2.31 (3H, s), 2.50-3.80 (12H, m), 5.78 (1H, dd, J=2.0, 10.0 Hz), 6.27 (1H, dd, J=2.0, 17.0 Hz), 6.44 (1H, dd, J=10.0, 17.0 Hz), 6.65 (2H, d, J=9.0 Hz), 6.96-7.01 (1H, m), 7.13 (2H, d, J=9.0 Hz), 7.46 (1H, t, J=8.2 Hz), 7.53-7.57 (1H, m), 7.66-7.74 (2H, m), 7.94-8.01 (1H, m), 9.20-9.82 (1H, m), 10.34 (1H, s), 10.98 (1H, s)

Figure 10:
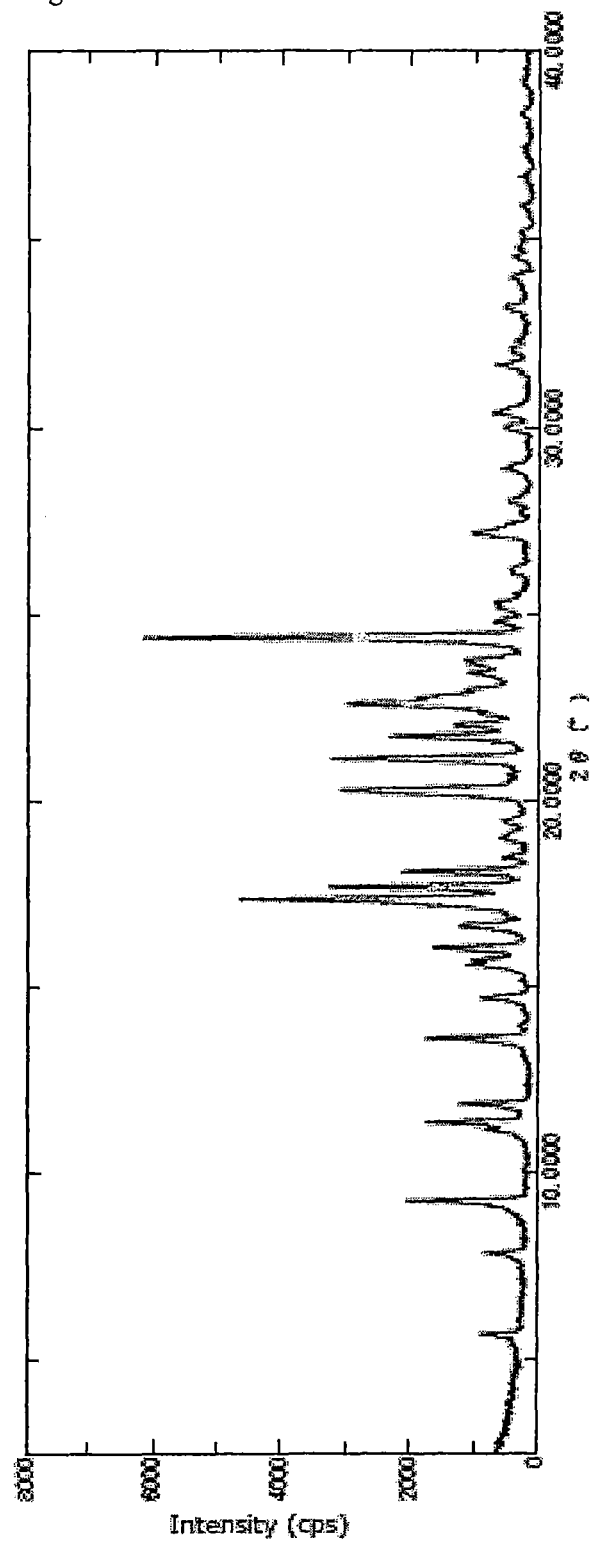
FIG. 10 shows a powder X-ray diffraction pattern of the compound of Example 263.

A powder X-ray diffraction pattern of the compound of Example 263 is shown in FIG. 10.

Example 264

5-[3-(acryloylamino)phenoxy]-3-({4-[(3R)-3,4-dimethylpiperazin-1-yl]phenyl}amino)-6-ethylpyrazine-2-carboxamide monomethansulfonate (58 mg) was obtained as a yellow solid in a similar manner to Example 254 by using 5-[3-(acryloylamino)phenoxy]-3-({4-[(3R)-3,4-dimethylpiperazin-1-yl]phenyl}amino)-6-ethylpyrazine-2-carboxamide (80 mg).

ESI+:516

1H-NMR (DMSO-d6): 1.28-1.36 (6H, m), 2.31 (3H, s), 2.50-3.80 (12H, m), 5.78 (1H, dd, J=2.0, 10.0 Hz), 6.27 (1H, dd, J=2.0, 17.0 Hz), 6.44 (1H, dd, J=10.0, 17.0 Hz), 6.65 (2H, d, J=9.0 Hz), 6.94-7.02 (1H, m), 7.14 (2H, d, J=9.0 Hz), 7.46 (1H, t, J=8.2 Hz), 7.53-7.57 (1H, m), 7.67-7.74 (2H, m), 7.94-7.99 (1H, m), 9.20-9.82 (1H, m), 10.34 (1H, s), 10.99 (1H, s)

Figure 11:
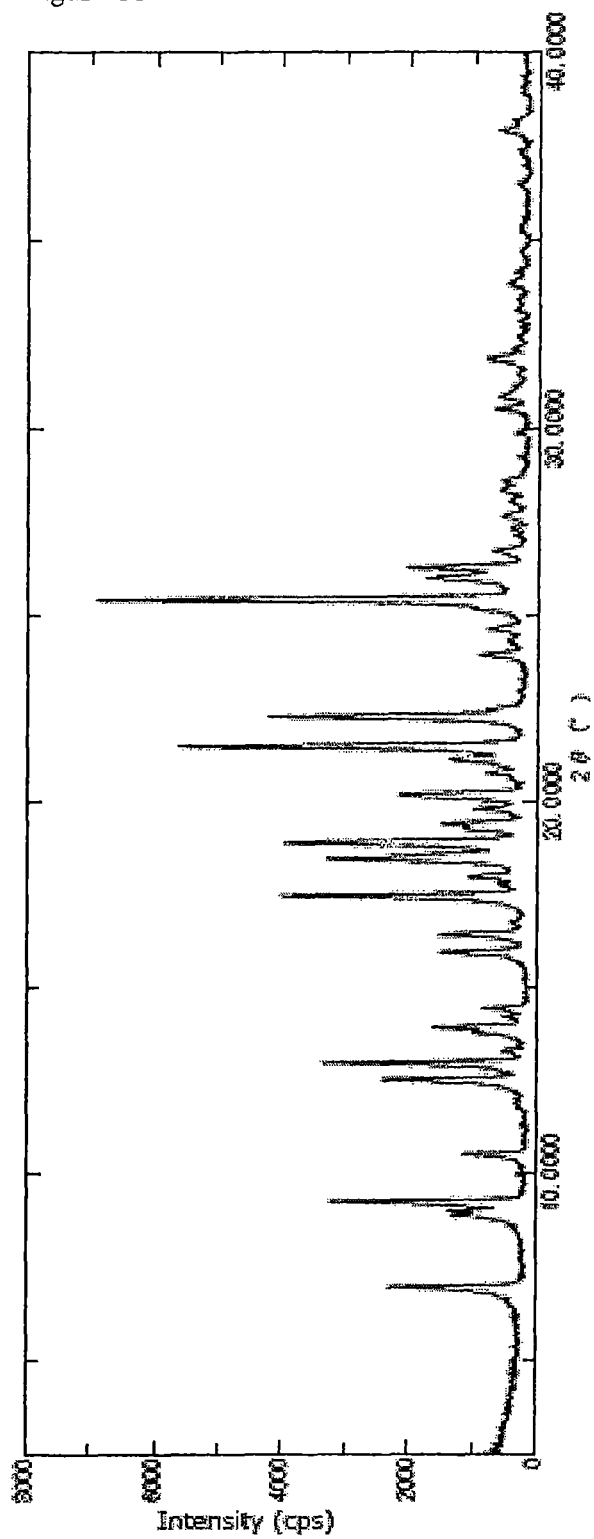
FIG. 11 shows a powder X-ray diffraction pattern of the compound of Example 264.

A powder X-ray diffraction pattern of the compound of Example 264 is shown in FIG. 11.

Example 265

5-[5-(acryloylamino)-2-fluorophenoxy]-6-ethyl-3-{[4-(4-methylpiperazin-1-yl)phenyl]amino}pyrazine-2-carboxamide monomethansulfonate (48 mg) was obtained as a yellow solid in a similar manner to Example 254 by using 5-[5-(acryloylamino)-2-fluorophenoxy]-6-ethyl-3-{[4-(4-methylpiperazin-1-yl)phenyl]amino}pyrazine-2-carboxamide (50 mg).

ESI+:520

1H-NMR (DMSO-d6): 1.32 (3H, t, J=7.5 Hz), 2.32 (3H, s), 2.80-2.97 (7H, m), 3.03-3.80 (6H, m), 5.79 (1H, dd, J=2.0, 10.0 Hz), 6.27 (1H, dd, J=2.0, 17.0 Hz), 6.42 (1H, dd, J=10.0, 17.0 Hz), 6.66 (2H, d, J=9.1 Hz), 7.09 (2H, d, J=9.1 Hz), 7.41-7.49 (1H, m), 7.67-7.77 (3H, m), 7.97-8.04 (1H, m), 9.51 (1H, brs), 10.37 (1H, s), 11.01 (1H, s)

Figure 12:
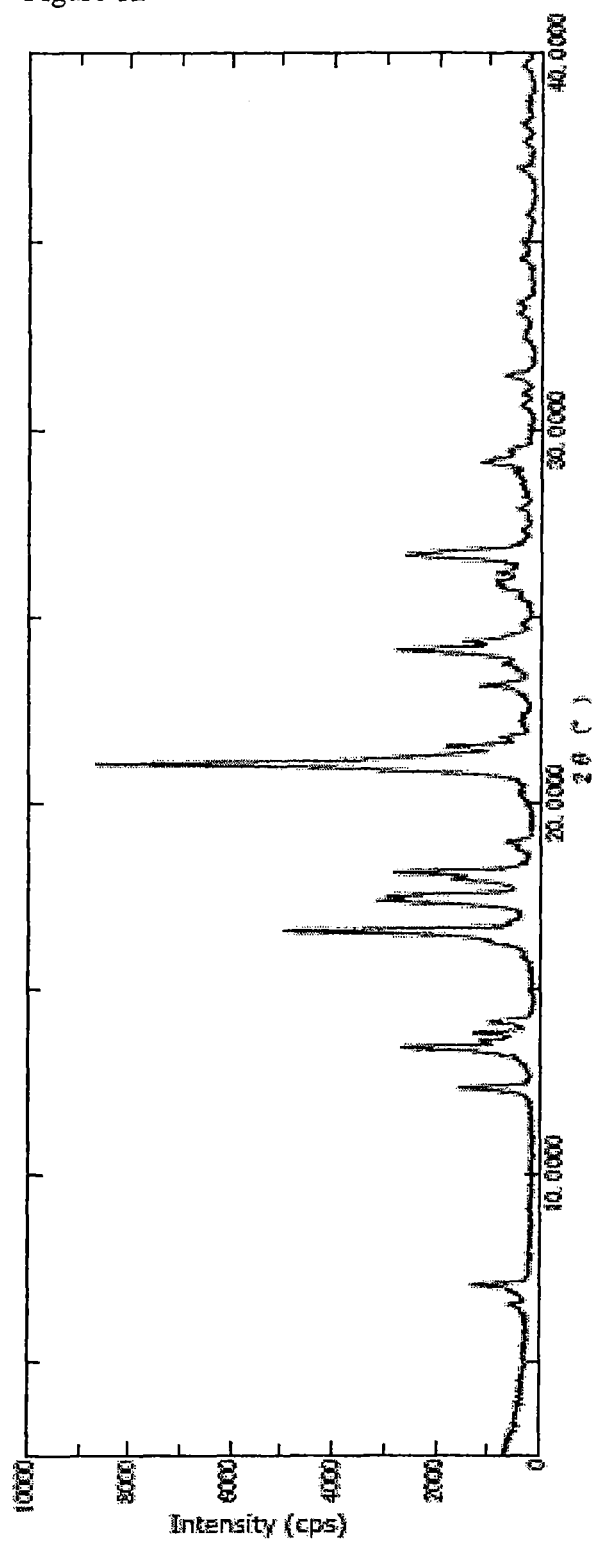
FIG. 12 shows a powder X-ray diffraction pattern of the compound of Example 265.

A powder X-ray diffraction pattern of the compound of Example 265 is shown in FIG. 12.

The compounds shown in Tables 96 to 150 below were prepared by similar manner to the preparation methods of Examples shown above. Further, for the respective compounds of Examples, except for Examples 254 to 265, the structures are shown in Tables 96 to 150, and the preparation methods and the physicochemical data are shown in Tables 151 to 160.

Furthermore, the structures of other compounds of the formula (I) are shown in Table 161. These can be easily prepared by using the preparation methods above or the methods described in Examples, and the methods apparent to a skilled person in the art or modified methods thereof.

TABLE 4

| PEx | PSyn | Str | Data |
|---|---|---|---|
| 1 | 1 | (structure: pyrazine with H$_2$N-C(=O)-, Et, Cl, N, O-phenyl-NO$_2$) | ESI+: 323, 325 |

TABLE 4-continued

| PEx | PSyn | Str | Data |
|---|---|---|---|
| 2 | 2 | (structure) | ESI+: 478 |
| 3 | 3 | (structure) | ESI+: 561 |
| 4 | 4 | (structure) | ESI+: 480 |
| 5 | 5 | (structure) | ESI+: 479 |
| 6 | 6 | (structure) | ESI+: 492 |

TABLE 5

| PEx | PSyn | Str | Data |
|---|---|---|---|
| 7 | 7 | (structure) | ESI+: 448 |
| 8 | 8 | (structure) | ESI+: 447 |

TABLE 5-continued

| PEx | PSyn | Str | Data |
|---|---|---|---|
| 9 | 9 | (structure) | APCI/ESI+: 462 |
| 10 | 10 | (structure) | ESI+: 462 |
| 11 | 11 | (structure) | ESI+: 449 |
| 12 | 12 | (structure) | ESI+: 478 |

TABLE 6

| PEx | PSyn | Str | Data |
|---|---|---|---|
| 13 | 13 | (structure) | ESI+: 466 |
| 14 | 14 | (structure) | APCI/ESI+: 490 |
| 15 | 15 | (structure) | ESI+: 479 |

TABLE 6-continued

| PEx | PSyn | Str | Data |
|---|---|---|---|
| 16 | 16 | (structure) | ESI+: 508 |
| 17 | 17 | (structure) | ESI+: 614, 616 |
| 18 | 18 | (structure) | ESI+: 570, 572 |

TABLE 7

| PEx | PSyn | Str | Data |
|---|---|---|---|
| 19 | 19 | (structure) | ESI+: 514, 516 |
| 20 | 20 | (structure) | ESI+: 446 |
| 21 | 21 | (structure) | ESI+: 528, 530 |
| 22 | 22 | (structure) | ESI+: 461 |

TABLE 7-continued

| PEx | PSyn | Str | Data |
|---|---|---|---|
| 23 | 23 | (structure) | ESI+: 527 |
| 24 | 24 | (structure) | ESI+: 475 |

TABLE 8

| PEx | PSyn | Str | Data |
|---|---|---|---|
| 25 | 25 | (structure) | ESI+: 529, 531 |
| 26 | 26 | (structure) | ESI+: 546 |
| 27 | 27 | (structure) | ESI+: 389, 391 |
| 28 | 28 | (structure) | ESI+: 467 |
| 29 | 29 | (structure) | ESI+: 371, 373 |

TABLE 8-continued

| PEx | PSyn | Str | Data |
|---|---|---|---|
| 30 | 30 | | ESI+: 526 |

TABLE 9

| PEx | PSyn | Str | Data |
|---|---|---|---|
| 31 | 31 | | APCI/ESI+: 609 |
| 32 | 32 | | ESI+: 621 |
| 33 | 33 | | APCI/ESI+: 623 |
| 34 | 34 | | ESI+: 426 |
| 35 | 35 | | ESI+: 623 |

TABLE 10

| PEx | PSyn | Str | Data |
|---|---|---|---|
| 36 | 36 | | ESI+: 619 |
| 37 | 37 | | ESI+: 519 |
| 38 | 38 | | ESI+: 521 |
| 39 | 39 | | ESI+: 339, 341 |
| 40 | 40 | | ESI+: 237 |
| 41 | 41 | | ESI+: 207 |

TABLE 11
| PEx | PSyn | Str | Data |
|---|---|---|---|
| 42 | 42 | 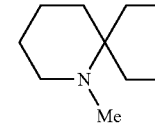 | ESI+: 260 |
| 43 | 43 | 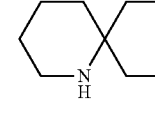 | ESI+: 276 |
| 44 | 44 | 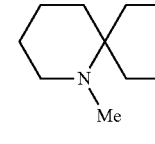 | ESI+: 290 |
| 45 | 45 | 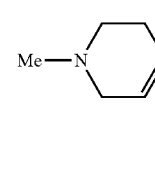 | ESI+: 271 |
| 46 | 46 | 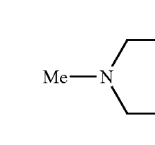 | ESI+: 193 |
| 47 | 47 | 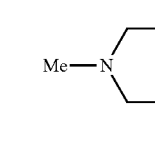 | ESI+: 195 |
| 48 | 1 | 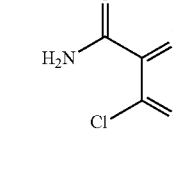 | ESI+: 323, 325 |
| 49 | 1 | 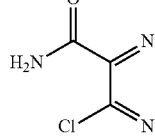 | ESI+: 323, 325 |
TABLE 12
| PEx | PSyn | Str | Data |
|---|---|---|---|
| 50 | 1 | 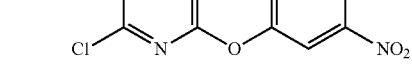 | ESI+: 337, 339 |
| 51 | 1 |  | ESI+: 337, 339 |
| 52 | 1 |  | ESI+: 337, 339 |
| 53 | 1 | 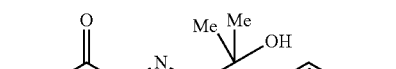 | ESI+: 353, 355 |
| 54 | 1 | 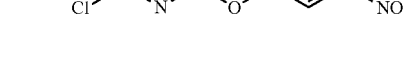 | ESI+: 295, 297 |
| 55 | 1 |  | ESI+: 391, 393 |
| 56 | 1 |  | ESI+: 393, 395 |

TABLE 13

| PEx | PSyn | Str | Data |
|---|---|---|---|
| 57 | 2 | | ESI+: 508 |
| 58 | 3 | | ESI+: 478 |
| 59 | 3 | | ESI+: 478 |
| 60 | 3 | | ESI+: 492 |
| 61 | 3 | | ESI+: 492 |
| 62 | 3 | | ESI+: 492 |

TABLE 14

| PEx | PSyn | Str | Data |
|---|---|---|---|
| 63 | 3 | | ESI+: 508 |

TABLE 14-continued
| PEx | PSyn | Str | Data |
|---|---|---|---|
| 64 | 3 | | ESI+: 492 |
| 65 | 3 | | ESI+: 546 |
| 66 | 3 | | ESI+: 496 |
| 67 | 3 | | ESI+: 575 |
| 68 | 3 | | ESI+: 450 |
TABLE 15
| PEx | PSyn | Str | Data |
|---|---|---|---|
| 69 | 3 | | ESI+: 546 |

TABLE 15-continued

| PEx | PSyn | Str | Data |
|---|---|---|---|
| 70 | 3 | (structure) | ESI+: 591 |
| 71 | 3 | (structure) | ESI+: 591 |
| 72 | 3 | (structure) | ESI+: 509 |
| 73 | 3 | (structure) | ESI+: 493 |
| 74 | 3 | (structure) | ESI+: 467 |

TABLE 16

| PEx | PSyn | Str | Data |
|---|---|---|---|
| 75 | 3 | (structure) | ESI+: 477 |

TABLE 16-continued

| PEx | PSyn | Str | Data |
|---|---|---|---|
| 76 | 3 | | ESI+: 478 |
| 77 | 4 | | ESI+: 508 |
| 78 | 4 | | ESI+: 492 |
| 79 | 5 | | ESI+: 499, 501 |
| 80 | 5 | | ESI+: 479 |

TABLE 17

| PEx | PSyn | Str | Data |
|---|---|---|---|
| 81 | 5 | | ESI+: 483 |
| 82 | 5 | | ESI+: 536 |

TABLE 17-continued

| PEx | PSyn | Str | Data |
|---|---|---|---|
| 83 | 5 | | ESI+: 535 |
| 84 | 5 | | ESI+: 451 |
| 85 | 5 | | ESI+: 449 |
| 86 | 5 | | ESI+: 477 |

TABLE 18

| PEx | PSyn | Str | Data |
|---|---|---|---|
| 87 | 5 | | ESI+: 410 |
| 88 | 5 | | ESI+: 507 |
| 89 | 5 | | ESI+: 492 |

TABLE 18-continued
| PEx | PSyn | Str | Data |
|---|---|---|---|
| 90 | 5 | 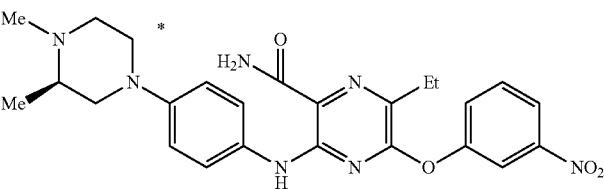 [SMILES: CCc1nc(C(N)=O)c(Nc2ccc(N3CCN(C)[C@H](C)C3)cc2)nc1Oc1cccc([N+](=O)[O-])c1] | ESI+: 492 |
| 91 | 5 | 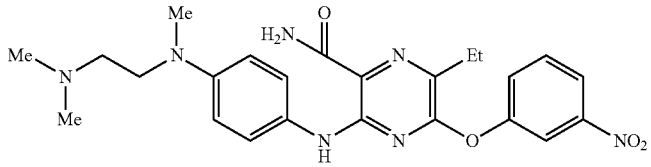 | ESI+: 480 |
| 92 | 5 | 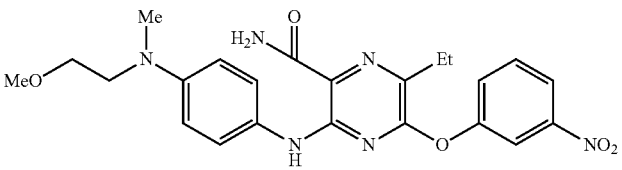 [SMILES: CCc1nc(C(N)=O)c(Nc2ccc(N(C)CCOC)cc2)nc1Oc1cccc([N+](=O)[O-])c1] | ESI+: 467 |
TABLE 19
| PEx | PSyn | Str | Data |
|---|---|---|---|
| 93 | 5 | 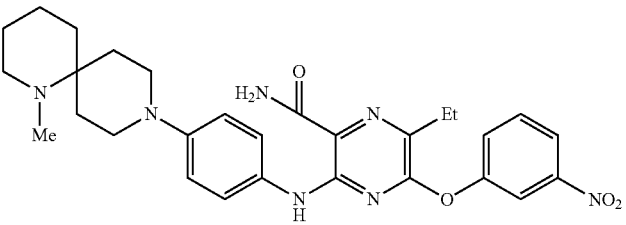 [SMILES: CCc1nc(C(N)=O)c(Nc2ccc(N3CCC4(CCCCN4C)CC3)cc2)nc1Oc1cccc([N+](=O)[O-])c1] | ESI+: 546 |
| 94 | 5 | 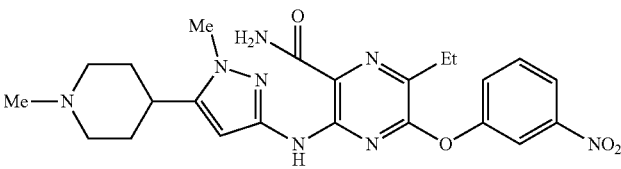 [SMILES: CCc1nc(C(N)=O)c(Nc2cc(C3CCN(C)CC3)n(C)n2)nc1Oc1cccc([N+](=O)[O-])c1] | ESI+: 481 |
| 95 | 5 | 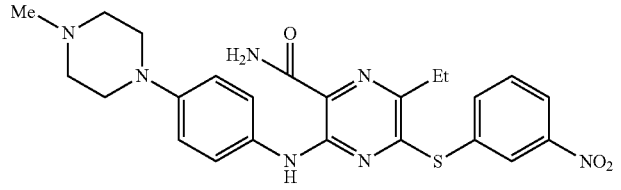 [SMILES: CCc1nc(C(N)=O)c(Nc2ccc(N3CCN(C)CC3)cc2)nc1Sc1cccc([N+](=O)[O-])c1] | ESI+: 494 |
| 96 | 5 | 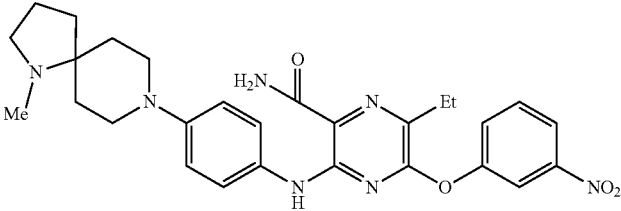 [SMILES: CCc1nc(C(N)=O)c(Nc2ccc(N3CCC4(CCCN4C)CC3)cc2)nc1Oc1cccc([N+](=O)[O-])c1] | ESI+: 532 |

TABLE 19-continued
| PEx | PSyn | Str | Data |
|---|---|---|---|
| 97 | 5 | 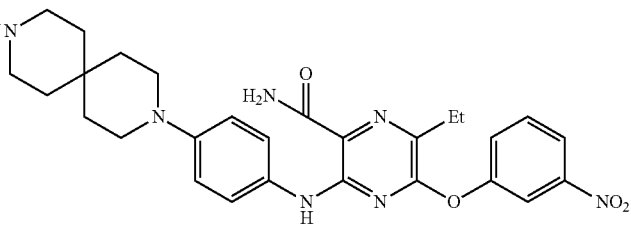 | ESI+: 546 |
| 98 | 6 | 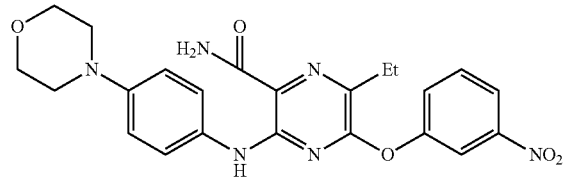 [SMILES: CCc1nc(C(N)=O)c(Nc2ccc(N3CCOCC3)cc2)nc1Oc1cccc([N+](=O)[O-])c1] | ESI+: 465 |
TABLE 20
| PEx | PSyn | Str | Data |
|---|---|---|---|
| 99 | 7 | 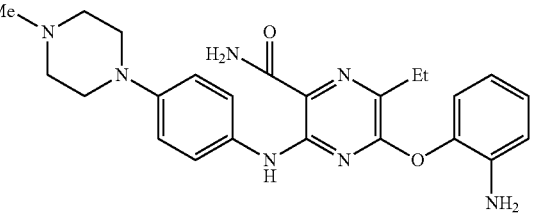 | ESI+: 448 |
| 100 | 7 | 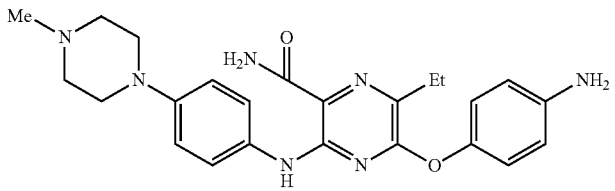 [SMILES: CCc1nc(C(N)=O)c(Nc2ccc(N3CCN(C)CC3)cc2)nc1Oc1ccc(N)cc1] | ESI+: 448 |
| 101 | 7 | 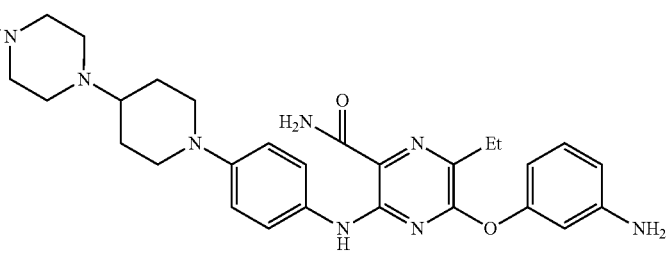 | ESI+: 531 |
| 102 | 7 | 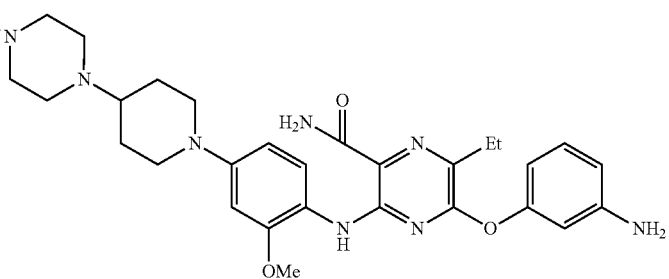 | ESI+: 561 |

TABLE 20-continued
| PEx | PSyn | Str | Data |
|---|---|---|---|
| 103 | 7 | 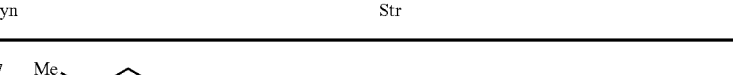 | ESI+: 561 |
TABLE 21
| PEx | PSyn | Str | Data |
|---|---|---|---|
| 104 | 7 | | ESI+: 462 |
| 105 | 7 | | ESI+: 462 |
| 106 | 7 | | ESI+: 462 |
| 107 | 7 | | ESI+: 478 |
| 108 | 7 | | ESI+: 462 |

TABLE 21-continued
| PEx | PSyn | Str | Data |
|---|---|---|---|
| 109 | 7 | 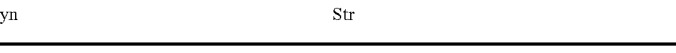 | ESI+: 516 |
TABLE 22
| PEx | PSyn | Str | Data |
|---|---|---|---|
| 110 | 7 | | ESI+: 466 |
| 111 | 7 | | ESI+: 545 |
| 112 | 7 | | ESI+: 420 |
| 113 | 7 | | ESI+: 516 |
| 114 | 7 | | ESI+: 479 |
| 115 | 7 | | ESI+: 463 |

TABLE 23

| PEx | PSyn | Str | Data |
|-----|------|-----|------|
| 116 | 7 | (structure) | ESI+: 437 |
| 117 | 7 | (structure) | ESI+: 450 |
| 118 | 7 | (structure) | ESI+: 478 |
| 119 | 7 | (structure) | ESI+: 462 |
| 120 | 7 | (structure) | ESI+: 454, 456 |
| 121 | 7 | (structure) | ESI+: 498, 500 |

TABLE 24

| PEx | PSyn | Str | Data |
|-----|------|-----|------|
| 122 | 7 | (structure) | ESI+: 421 |

TABLE 24-continued

| PEx | PSyn | Str | Data |
|---|---|---|---|
| 123 | 7 | (structure) | ESI+: 419 |
| 124 | 7 | (structure) | ESI+: 447 |
| 125 | 7 | (structure) | ESI+: 380 |
| 126 | 7 | (structure) | ESI+: 464 |
| 127 | 7 | (structure) | ESI+: 497 |

TABLE 25

| PEx | PSyn | Str | Data |
|---|---|---|---|
| 128 | 7 | (structure) | ESI+: 496 |
| 129 | 7 | (structure) | ESI+: 462 |

TABLE 25-continued
| PEx | PSyn | Str | Data |
|---|---|---|---|
| 130 | 7 | 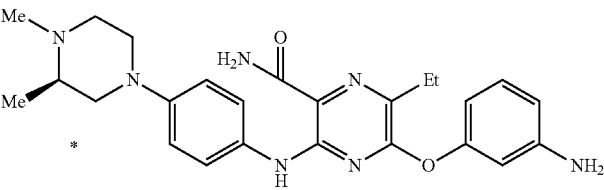 [SMILES: CCc1nc(C(N)=O)c(Nc2ccc(N3CCN(C)[C@H](C)C3)cc2)nc1Oc1cccc(N)c1] | ESI+: 462 |
| 131 | 7 | 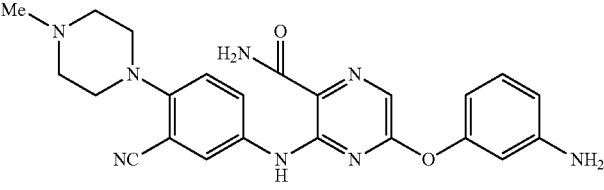 | ESI+: 445 |
| 132 | 7 | 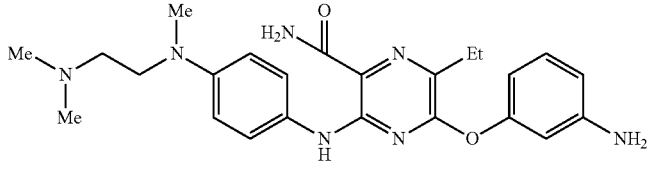 | ESI+: 450 |
| 133 | 7 | 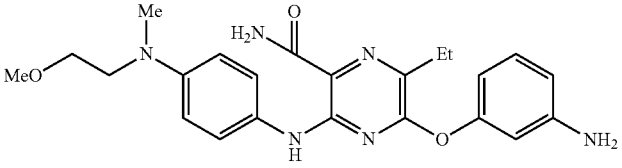 [SMILES: CCc1nc(C(N)=O)c(Nc2ccc(N(C)CCOC)cc2)nc1Oc1cccc(N)c1] | ESI+: 437 |
TABLE 26
| PEx | PSyn | Str | Data |
|---|---|---|---|
| 134 | 7 | 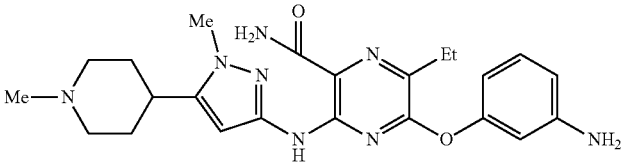 [SMILES: CCc1nc(C(N)=O)c(Nc2cc(C3CCN(C)CC3)n(C)n2)nc1Oc1cccc(N)c1] | ESI+: 451 |
| 135 | 7 | 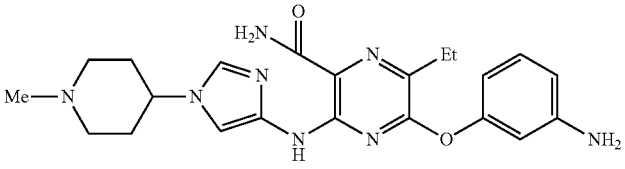 | ESI+: 437 |
| 136 | 8 | 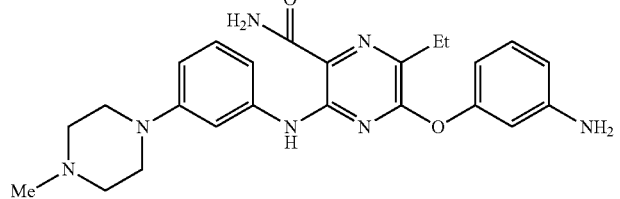 | ESI+: 448 |

107 108
TABLE 26-continued
| PEx | PSyn | Str | Data |
|---|---|---|---|
| 137 | 8 | 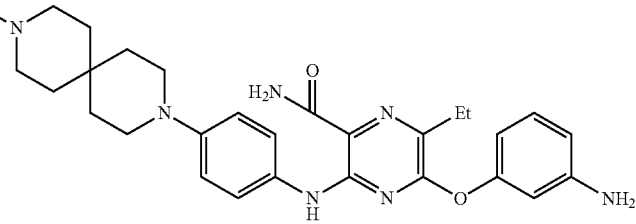 | ESI+: 516 |
| 138 | 9 | 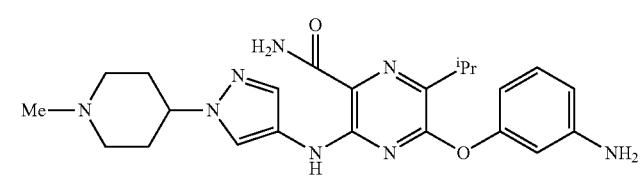 [SMILES: CC(C)c1nc(C(N)=O)c(Nc2cnn(C3CCN(C)CC3)c2)nc1Oc1cccc(N)c1] | ESI+: 451 |
| 139 | 9 | 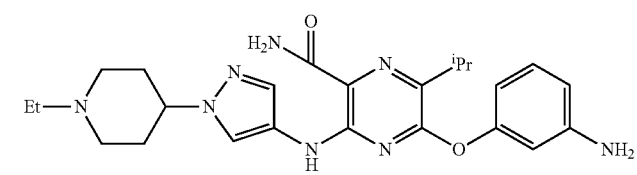 [SMILES: CCN1CCC(n2cc(Nc3nc(Oc4cccc(N)c4)c(C(C)C)nc3C(N)=O)cn2)CC1] | ESI+: 465 |
TABLE 27
| PEx | PSyn | Str | Data |
|---|---|---|---|
| 140 | 9 |  | ESI+: 477 |
| 141 | 10 | 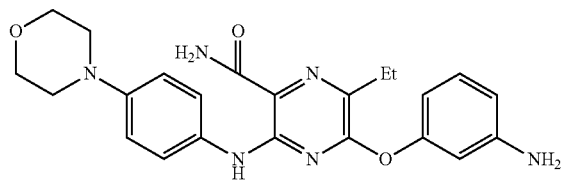 [SMILES: CCc1nc(C(N)=O)c(Nc2ccc(N3CCOCC3)cc2)nc1Oc1cccc(N)c1] | ESI+: 435 |
| 142 | 10 | 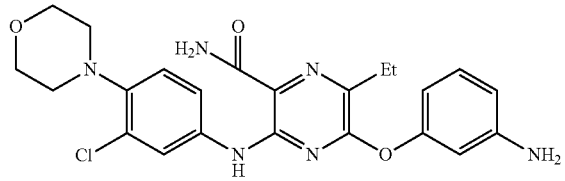 [SMILES: CCc1nc(C(N)=O)c(Nc2ccc(N3CCOCC3)c(Cl)c2)nc1Oc1cccc(N)c1] | ESI+: 469, 471 |
| 143 | 11 | 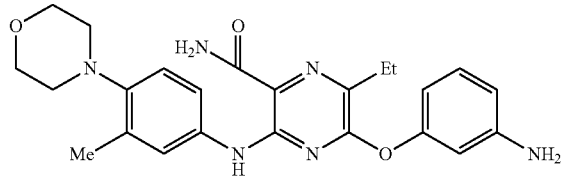 [SMILES: CCc1nc(C(N)=O)c(Nc2ccc(N3CCOCC3)c(C)c2)nc1Oc1cccc(N)c1] | ESI+: 449 |

TABLE 27-continued

| PEx | PSyn | Str | Data |
|---|---|---|---|
| 144 | 11 | | ESI+: 453 |
| 145 | 11 | | ESI+: 505 |

TABLE 28

| PEx | PSyn | Str | Data |
|---|---|---|---|
| 146 | 11 | | ESI+: 477 |
| 147 | 11 | | ESI+: 516 |
| 148 | 11 | | ESI+: 502 |
| 149 | 13 | | ESI+: 482, 484 |

TABLE 28-continued

| PEx | PSyn | Str | Data |
|---|---|---|---|
| 150 | 13 | | ESI+: 462 |
| 151 | 13 | | ESI+: 466 |

TABLE 29

| PEx | PSyn | Str | Data |
|---|---|---|---|
| 152 | 13 | | ESI+: 466 |
| 153 | 13 | | ESI+: 482, 484 |
| 154 | 13 | | ESI+: 449 |
| 155 | 13 | | ESI+: 437 |
| 156 | 13 | | ESI+: 534 |

TABLE 29-continued

| PEx | PSyn | Str | Data |
|---|---|---|---|
| 157 | 13 | (structure) | ESI+: 462 |

TABLE 30

| PEx | PSyn | Str | Data |
|---|---|---|---|
| 158 | 13 | (structure) | ESI+: 462 |
| 159 | 13 | (structure) | ESI+: 562 |
| 160 | 15 | (structure) | ESI+: 493 |
| 161 | 15 | (structure) | ESI+: 505 |
| 162 | 19 | (structure) | ESI+: 470, 472 |
| 163 | 21 | (structure) | ESI+: 484, 486 |

TABLE 31
| PEx | PSyn | Str | Data |
|---|---|---|---|
| 164 | 23 | 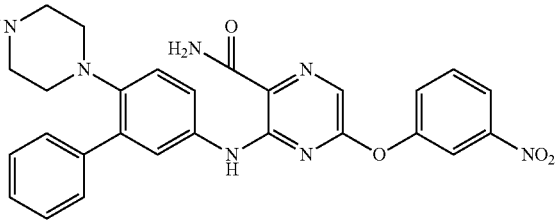 | ESI+: 526 |
| 165 | 27 | 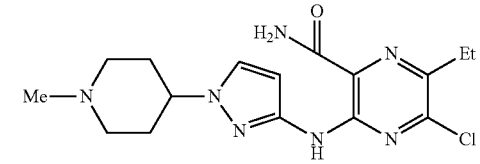 [SMILES: CCc1nc(C(N)=O)c(Nc2ccn(C3CCN(C)CC3)n2)nc1Cl] | ESI+: 364, 366 |
| 166 | 27 | 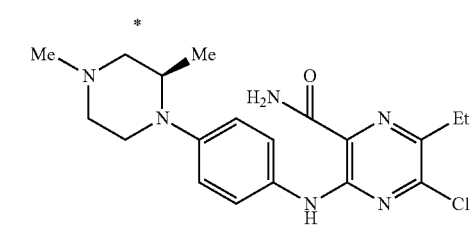 | ESI+: 389, 391 |
| 167 | 27 | 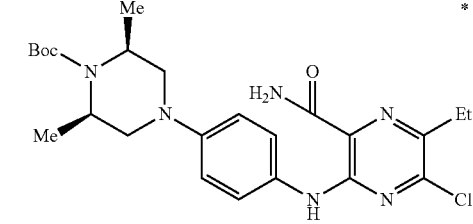 [SMILES: CCc1nc(C(N)=O)c(Nc2ccc(N3C[C@@H](C)N(C(=O)OC(C)(C)C)[C@@H](C)C3)cc2)nc1Cl] | ESI+: 489, 491 |
| 168 | 29 | 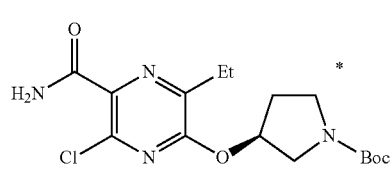 [SMILES: CCc1nc(C(N)=O)c(Cl)nc1O[C@H]1CCN(C(=O)OC(C)(C)C)C1] | ESI+: 371 |
| 169 | 29 | 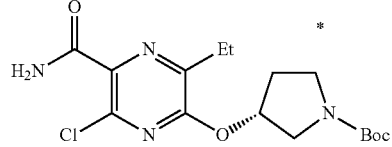 [SMILES: CCc1nc(C(N)=O)c(Cl)nc1O[C@@H]1CCN(C(=O)OC(C)(C)C)C1] | ESI+: 371 |
| 170 | 29 | 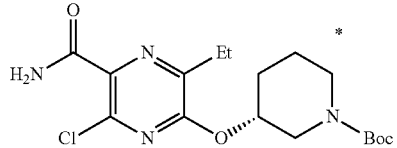 [SMILES: CCc1nc(C(N)=O)c(Cl)nc1O[C@@H]1CCCN(C(=O)OC(C)(C)C)C1] | ESI+: 385 |

TABLE 32

| PEx | PSyn | Str | Data |
|---|---|---|---|
| 171 | 29 | | ESI+: 401 |
| 172 | 30 | | APCI/ESI+: 526 |
| 173 | 30 | | APCI/ESI+: 526 |
| 174 | 31 | | ESI+: 623 |
| 175 | 31 | | ESI+: 637 |
| 176 | 32 | | ESI+: 635 |

TABLE 33
| PEx | PSyn | Str | Data |
|---|---|---|---|
| 177 | 34 | 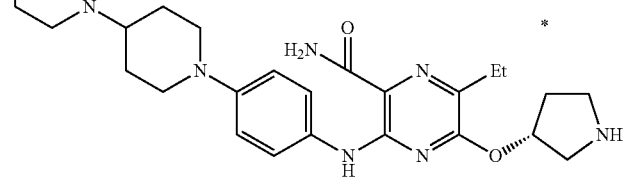 | APCI/ESI+: 509 |
| 178 | 34 | 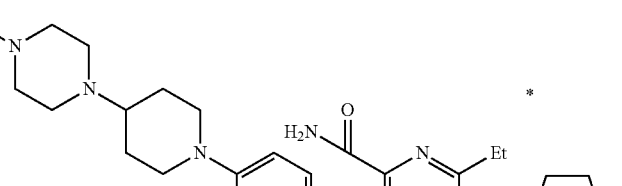 | APCI/ESI+: 523 |
| 179 | 34 | 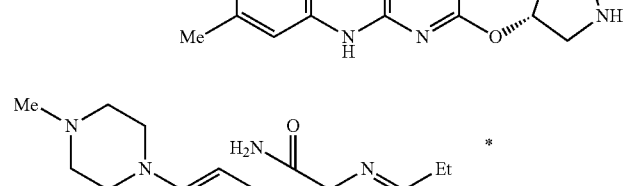 | APCI/ESI+: 426 |
| 180 | 34 | 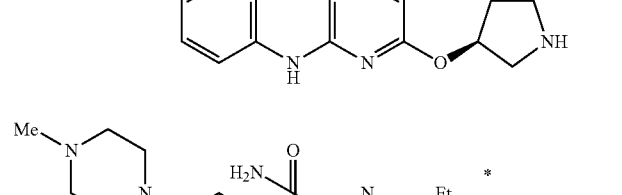 | APCI/ESI+: 426 |
| 181 | 34 | 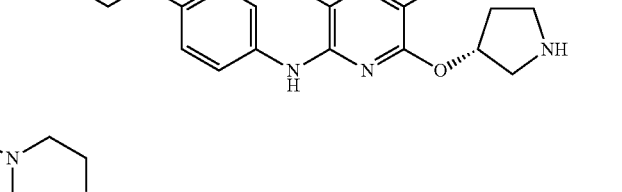 | ESI+: 523 |
TABLE 34
| PEx | PSyn | Str | Data |
|---|---|---|---|
| 182 | 34 | | ESI+: 537 |

TABLE 34-continued

| PEx | PSyn | Str | Data |
|---|---|---|---|
| 183 | 34 | | ESI+: 523 |
| 184 | 34 | | ESI+: 537 |
| 185 | 35 | | ESI+: 637 |
| 186 | 36 | | APCI/ESI+: 605 |

TABLE 35

| PEx | PSyn | Str | Data |
|---|---|---|---|
| 187 | 36 | | APCI/ESI+: 522 |

TABLE 35-continued

| PEx | PSyn | Str | Data |
|---|---|---|---|
| 188 | 37 | | APCI/ESI+: 505 |
| 189 | 37 | | ESI+: 422 |
| 190 | 38 | | APCI/ESI+: 507 |
| 191 | 42 | | ESI+: 246 |
| 192 | 43 | | ESI+: 262 |

TABLE 36

| PEx | PSyn | Str | Data |
|---|---|---|---|
| 193 | 44 | | ESI+: 276 |
| 194 | E1 | | ESI+: 588 |

TABLE 36-continued

| PEx | PSyn | Str | Data |
|---|---|---|---|
| 195 | E1 | | ESI+: 616 * |
| 196 | 198 | | ESI+: 496 |
| 197 | 197 | | ESI+: 447 |
| 198 | 198 | | ESI+: 510 |

TABLE 37

| PEx | PSyn | Str | Data |
|---|---|---|---|
| 199 | 197 | | ESI+: 544 |
| 200 | 200 | | ESI+: 522 * |

TABLE 37-continued
| PEx | PSyn | Str | Data |
|-----|------|-----|------|
| 201 | 200 | 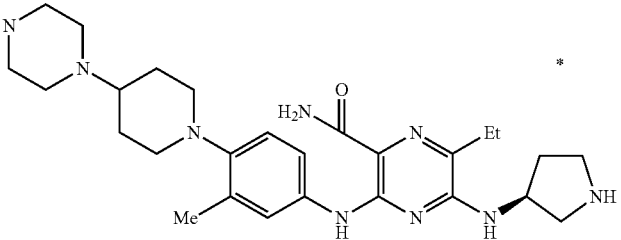 | ESI+: 522 |
| 202 | 200 | 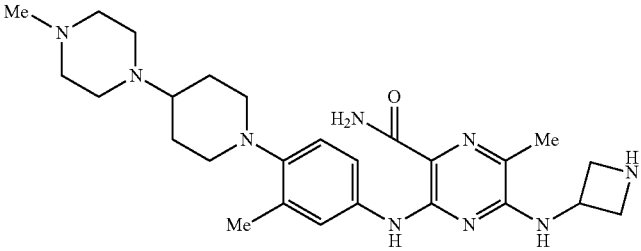 [SMILES: Cc1cc(Nc2nc(NC3CNC3)c(C)nc2C(N)=O)ccc1N1CCC(N2CCN(C)CC2)CC1] | ESI+: 508 |
TABLE 38
| PEx | PSyn | Str | Data |
|-----|------|-----|------|
| 203 | 203 | 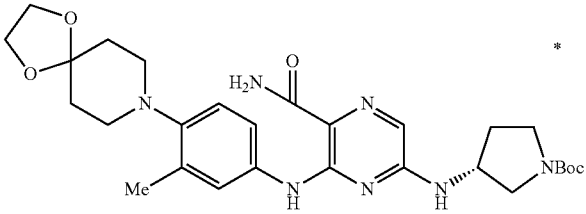 [SMILES: Cc1cc(Nc2nc(N[C@@H]3CCN(C(=O)OC(C)(C)C)C3)cnc2C(N)=O)ccc1N1CCC2(CC1)OCCO2] | ESI+: 554 |
| 204 | 204 | 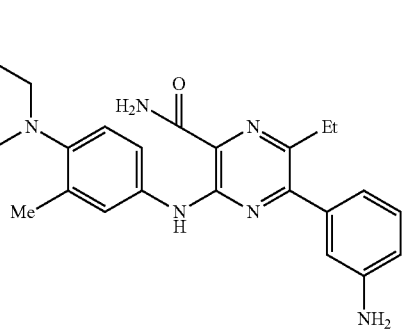 | ESI+: 529 |
| 205 | 200 | 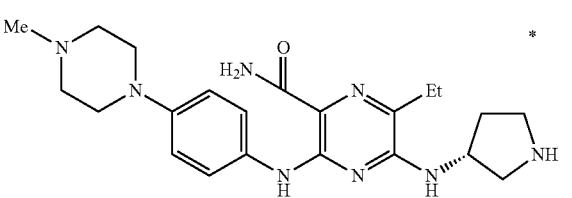 [SMILES: CCc1nc(C(N)=O)c(Nc2ccc(N3CCN(C)CC3)cc2)nc1N[C@@H]1CCNC1] | ESI+: 425 |

TABLE 38-continued

| PEx | PSyn | Str | Data |
|---|---|---|---|
| 206 | 198 | | APCI/ESI+: 508 |

TABLE 39

| PEx | PSyn | Str | Data |
|---|---|---|---|
| 207 | 198 | | APCI/ESI+: 455 |
| 208 | 198 | | APCI/ESI+: 538 |
| 209 | 198 | | ESI+: 536 |
| 210 | 210 | | APCI/ESI+: 390, 392 |

TABLE 40

| PEx | PSyn | Str | Data |
|---|---|---|---|
| 211 | 198 | (structure) | APCI/ESI+: 425 |
| 212 | 198 | (structure) | APCI/ESI+: 439 |
| 213 | 198 | (structure) | APCI/ESI+: 443 |
| 214 | 198 | (structure) | APCI/ESI+: 440 |
| 215 | 198 | (structure) | APCI/ESI+: 425 |

TABLE 41

| PEx | PSyn | Str | Data |
|---|---|---|---|
| 216 | 210 | (structure) | APCI/ESI+: 472 |

TABLE 41-continued

| PEx | PSyn | Str | Data |
|---|---|---|---|
| 217 | 198 | | APCI/ESI+: 412 |
| 218 | 198 | | APCI/ESI+: 424 |
| 219 | 198 | | APCI/ESI+: 522 |
| 220 | 210 | | APCI/ESI+: 389 |

TABLE 42

| PEx | PSyn | Str | Data |
|---|---|---|---|
| 221 | 221 | | APCI/ESI+: 292 |
| 222 | 198 | | APCI/ESI+: 439 |
| 223 | 223 | | APCI/ESI+: 262 |

TABLE 42-continued
| PEx | PSyn | Str | Data |
|---|---|---|---|
| 224 | 210 | 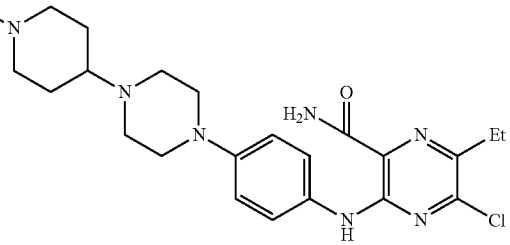 | APCI/ESI+: 458 |
| 225 | 210 | 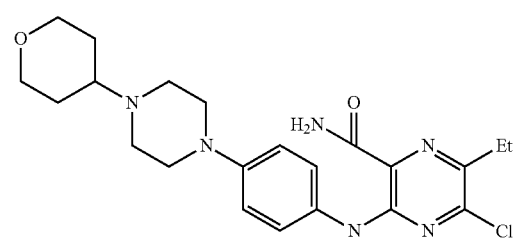 | APCI/ESI+: 445 |
| 226 | 226 | 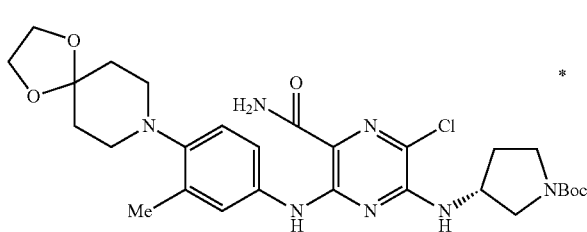 [SMILES: Cc1cc(Nc2nc(N[C@@H]3CCN(C(=O)OC(C)(C)C)C3)c(Cl)nc2C(N)=O)ccc1N1CCC2(CC1)OCCO2] | ESI+: 588 * |
TABLE 43
| PEx | PSyn | Str | Data |
|---|---|---|---|
| 227 | 198 | 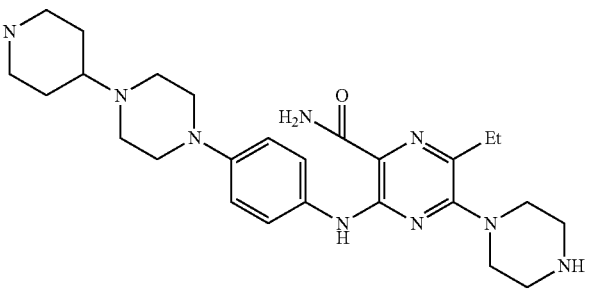 [SMILES: CCc1nc(C(N)=O)c(Nc2ccc(N3CCN(C4CCOCC4)CC3)cc2)nc1N1CCNCC1] | ESI+: 508 |
| 228 | 198 | 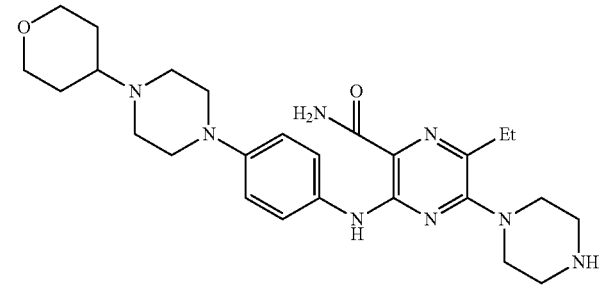 | APCI/ESI+: 495 |

TABLE 43-continued

| PEx | PSyn | Str | Data |
|---|---|---|---|
| 229 | 229 | | ESI+: 444, 446 |
| 230 | 198 | | APCI/ESI+: 511 |
| 231 | 231 | | ESI+: 544 |

TABLE 44

| PEx | PSyn | Str | Data |
|---|---|---|---|
| 232 | 232 | | ESI+: 628, 630 |
| 233 | 34 | | ESI+: 528, 530 |
| 234 | 203 | | APCI/ESI+: 608 |

TABLE 44-continued
| PEx | PSyn | Str | Data |
|---|---|---|---|
| 235 | 203 | 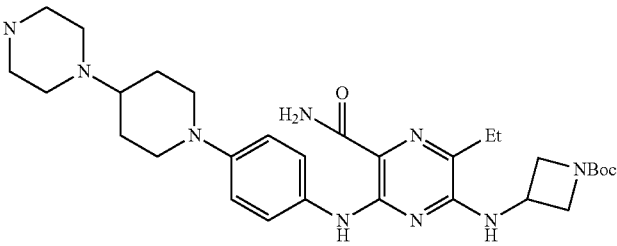 | APCI/ESI+: 594 |
TABLE 45
| PEx | PSyn | Str | Data |
|---|---|---|---|
| 236 | 203 | 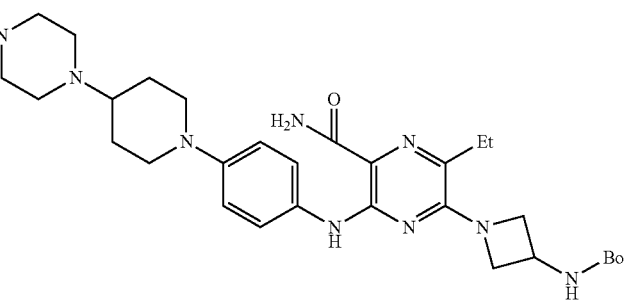 | APCI/ESI+: 594 |
| 237 | 203 | 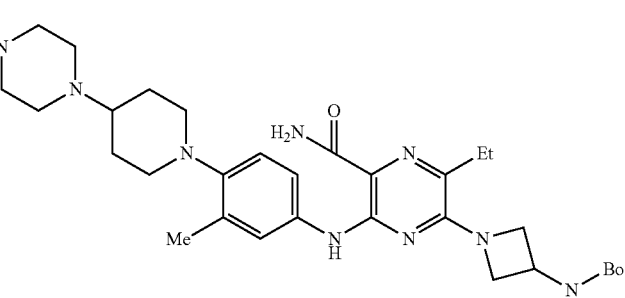 | APCI/ESI+: 608 |
| 238 | 238 | 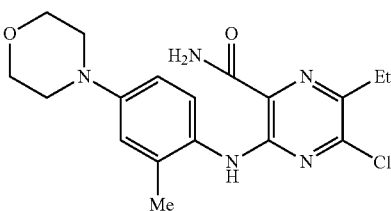 [SMILES: CCc1nc(C(N)=O)c(Nc2ccc(N3CCOCC3)cc2C)nc1Cl] | ESI+: 376, 378 |
| 239 | 238 | 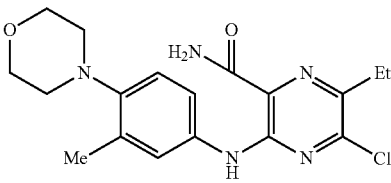 [SMILES: CCc1nc(C(N)=O)c(Nc2ccc(N3CCOCC3)c(C)c2)nc1Cl] | ESI+: 376, 378 |

TABLE 45-continued

| PEx | PSyn | Str | Data |
|---|---|---|---|
| 240 | 203 | | ESI+: 526 |

TABLE 46

| PEx | PSyn | Str | Data |
|---|---|---|---|
| 241 | 318 | | APCI/ESI+: 608 |
| 242 | 318 | | APCI/ESI+: 608 |
| 243 | 318 | | APCI/ESI+: 622 |
| 244 | 318 | | APCI/ESI+: 622 |

TABLE 46-continued

| PEx | PSyn | Str | Data |
|---|---|---|---|
| 245 | 34 | (morpholine-phenyl-Me, pyrazine-CONH2, Et, NH-pyrrolidine-NH) * | ESI+: 426 |

TABLE 47

| PEx | PSyn | Str | Data |
|---|---|---|---|
| 246 | 203 | (morpholine-phenyl-Me, pyrazine-CONH2, Et, NH-pyrrolidine-NBoc) * | ESI+: 526 |
| 247 | 34 | (Me-piperazine-piperidine-phenyl, pyrazine-CONH2, Et, pyrrolidine-NH2) * | APCI/ESI+: 508 |
| 248 | 34 | (Me-piperazine-piperidine-phenyl-Me, pyrazine-CONH2, Et, pyrrolidine-NH2) * | APCI/ESI+: 522 |
| 249 | 34 | (Me-piperazine-piperidine-phenyl, pyrazine-CONH2, Et, pyrrolidine-NH2) * | APCI/ESI+: 508 |

TABLE 47-continued
| PEx | PSyn | Str | Data |
|---|---|---|---|
| 250 | 34 | 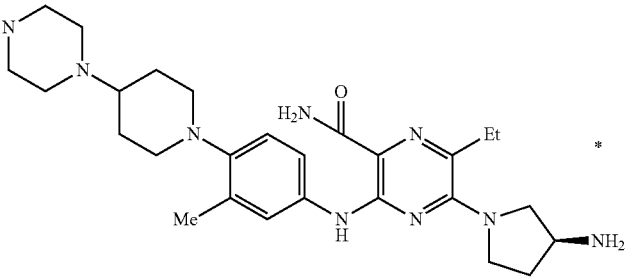 | APCI/ESI+: 522 |
TABLE 48
| PEx | PSyn | Str | Data |
|---|---|---|---|
| 251 | 318 | 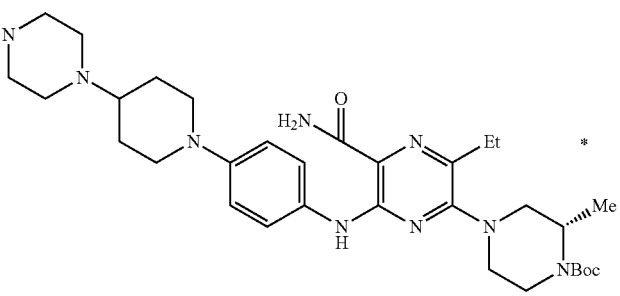 | APCI/ESI+: 622 |
| 252 | 318 | 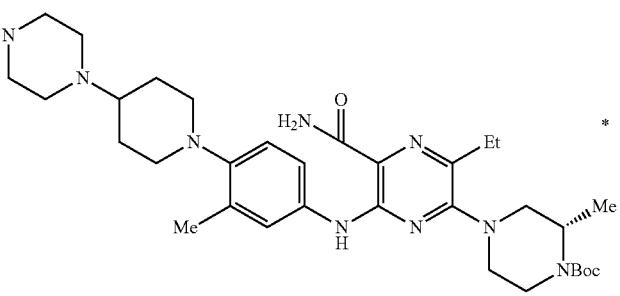 | APCI/ESI+: 636 |
| 253 | 318 | 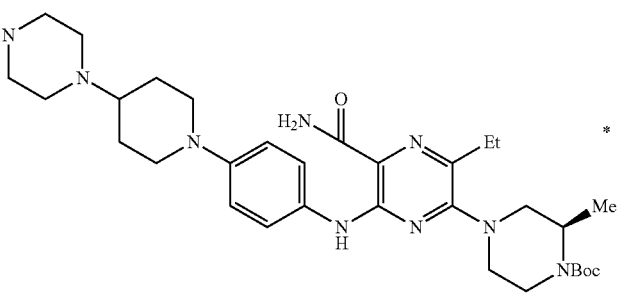 | ESI+: 622 |

TABLE 48-continued
| PEx | PSyn | Str | Data |
|---|---|---|---|
| 254 | 318 |  | ESI+: 636 |
TABLE 49
| PEx | PSyn | Str | Data |
|---|---|---|---|
| 255 | 34 | | APCI/ESI+: 426 |
| 256 | 256 | | ESI+: 380, 382 |
| 257 | 34 | | APCI/ESI+: 522 |
| 258 | 34 | | APCI/ESI+: 536 |

TABLE 49-continued
| PEx | PSyn | Str | Data |
|---|---|---|---|
| 259 | 34 | 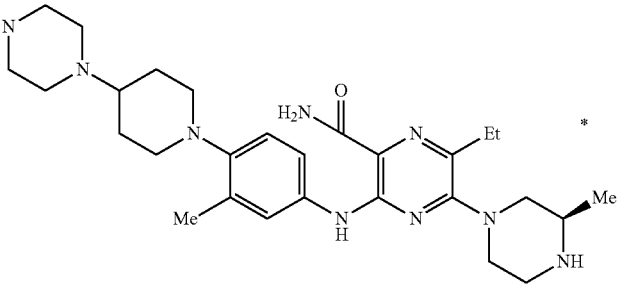 | APCI/ESI+: 522 |
TABLE 50
| PEx | PSyn | Str | Data |
|---|---|---|---|
| 260 | 34 | 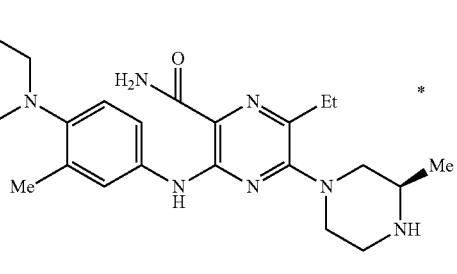 | APCI/ESI+: 536 |
| 261 | 203 | 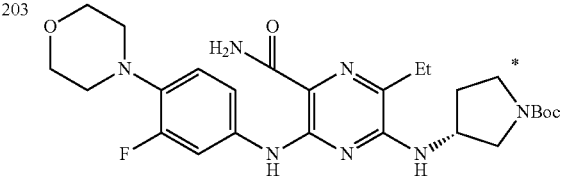 | ESI+: 530 |
| 262 | 318 | 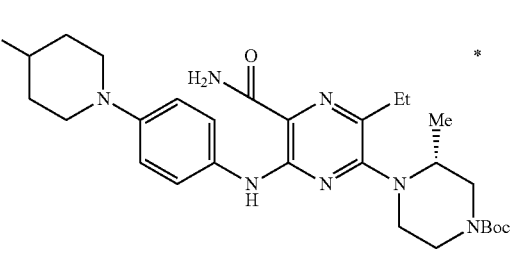 | ESI+: 622 |
| 263 | 318 | 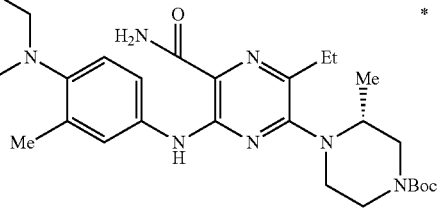 | APCI/ESI+: 636 |

TABLE 51

| PEx | PSyn | Str | Data |
|---|---|---|---|
| 264 | 318 | | APCI/ESI+: 622 |
| 265 | 318 | | APCI/ESI+: 636 |
| 266 | 34 | | ESI+: 430 |
| 267 | 198 | | ESI+: 522 |

TABLE 52

| PEx | PSyn | Str | Data |
|---|---|---|---|
| 268 | 34 | | APCI/ESI+: 522 |

TABLE 52-continued

| PEx | PSyn | Str | Data |
|-----|------|-----|------|
| 269 | 34 | | APCI/ESI+: 536 |
| 270 | 34 | | APCI/ESI+: 522 |
| 271 | 34 | | APCI/ESI+: 536 |

TABLE 53

| PEx | PSyn | Str | Data |
|-----|------|-----|------|
| 272 | 318 | | APCI/ESI+: 622 |
| 273 | 318 | | APCI/ESI+: 636 |

TABLE 53-continued

| PEx | PSyn | Str | Data |
|---|---|---|---|
| 274 | 318 | (structure) | APCI/ESI+: 622 |
| 275 | 318 | (structure) | APCI/ESI+: 636 |

TABLE 54

| PEx | PSyn | Str | Data |
|---|---|---|---|
| 276 | 34 | (structure) | APCI/ESI+: 522 |
| 277 | 34 | (structure) | APCI/ESI+: 522 |
| 278 | 34 | (structure) | APCI/ESI+: 536 |

TABLE 54-continued
| PEx | PSyn | Str | Data |
|---|---|---|---|
| 279 | 318 | 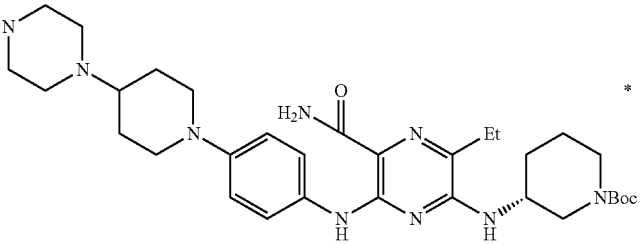 | APCI/ESI+: 622 |
TABLE 55
| PEx | PSyn | Str | Data |
|---|---|---|---|
| 280 | 318 | | APCI/ESI+: 636 |
| 281 | 34 | | APCI/ESI+: 522 |
| 282 | 34 | | APCI/ESI+: 536 |
| 283 | 203 | | APCI/ESI+: 626 |

TABLE 56

| PEx | PSyn | Str | Data |
|---|---|---|---|
| 284 | 318 | (structure) | ESI+: 636 |
| 285 | 318 | (structure) | ESI+: 622 |
| 286 | 198 | (structure) | APCI/ESI+: 522 |
| 287 | 198 | (structure) | APCI/ESI+: 536 |

TABLE 57

| PEx | PSyn | Str | Data |
|---|---|---|---|
| 288 | 198 | (structure) | APCI/ESI+: 550 |

TABLE 57-continued

| PEx | PSyn | Str | Data |
|---|---|---|---|
| 289 | 34 | | APCI/ESI+: 522 |
| 290 | 34 | | APCI/ESI+: 536 |
| 291 | 291 | | APCI/ESI+: 536 |

TABLE 58

| PEx | PSyn | Str | Data |
|---|---|---|---|
| 292 | 318 | | ESI+: 540 |
| 293 | 226 | | ESI+: 574, 576 |
| 294 | 294 | | ESI+: 618, 620 |

TABLE 58-continued

| PEx | PSyn | Str | Data |
|---|---|---|---|
| 295 | 4 | | ESI+: 536 |
| 296 | 17 | | ESI+: 614, 616 |

TABLE 59

| PEx | PSyn | Str | Data |
|---|---|---|---|
| 297 | 229 | | ESI+: 430, 432 |
| 298 | 231 | | ESI+: 530 |
| 299 | 232 | | ESI+: 614, 616 |
| 300 | 34 | | ESI+: 514, 516 |

TABLE 59-continued
| PEx | PSyn | Str | Data |
|---|---|---|---|
| 301 | 318 | 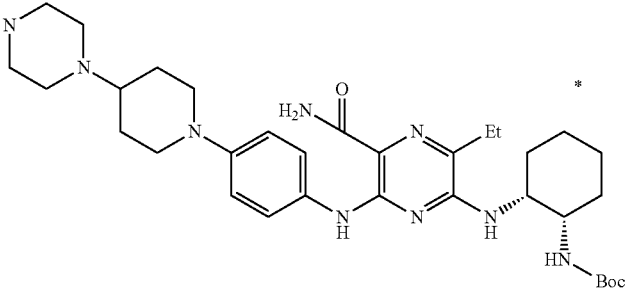 | APCI/ESI+: 636 |
TABLE 60
| PEx | PSyn | Str | Data |
|---|---|---|---|
| 302 | 318 | | APCI/ESI+: 650 |
| 303 | 229 | | ESI+: 474, 476 |
| 304 | 231 | | ESI+: 574 |
| 305 | 232 | | ESI+: 658, 660 |

TABLE 60-continued

| PEx | PSyn | Str | Data |
|---|---|---|---|
| 306 | 306 | (structure) | ESI+: 558, 560 |

TABLE 61

| PEx | PSyn | Str | Data |
|---|---|---|---|
| 307 | 34 | (structure) | APCI/ESI+: 536 |
| 308 | 34 | (structure) | APCI/ESI+: 550 |
| 309 | 309 | (structure) | APCI/ESI+: 536 |
| 310 | 309 | (structure) | APCI/ESI+: 522 |

TABLE 62
| PEx | PSyn | Str | Data |
|---|---|---|---|
| 311 | 309 | 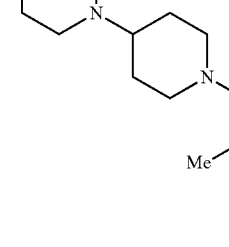 | APCI/ESI+: 536 |
| 312 | 312 | 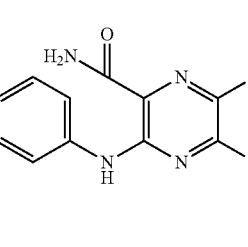 | ESI+: 657 |
| 313 | 306 | 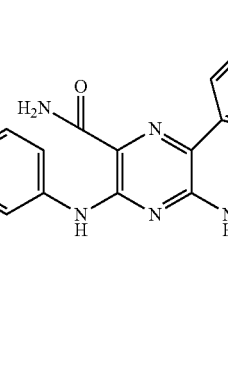 | ESI+: 557 |
| 314 | 314 | 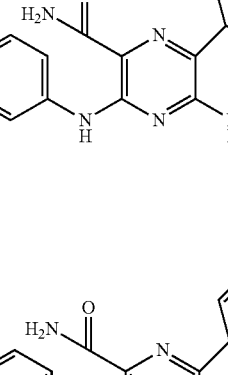 | ESI+: 556 |
TABLE 63
| PEx | PSyn | Str | Data |
|---|---|---|---|
| 316 | 34 | | ESI+: 523 |

TABLE 63-continued

| PEx | PSyn | Str | Data |
|---|---|---|---|
| 317a | 317 | (structure) | ESI+: 605 |
| 317b | 317 | (structure) | ESI+: 623 |
| 318 | 318 | (structure) | APCI/ESI+: 636 |

TABLE 64

| PEx | PSyn | Str | Data |
|---|---|---|---|
| 319 | 318 | (structure) | APCI/ESI+: 650 |
| 320 | 318 | (structure) | APCI/ESI+: 650 |

TABLE 64-continued
| PEx | PSyn | Str | Data |
|---|---|---|---|
| 321 | 34 | 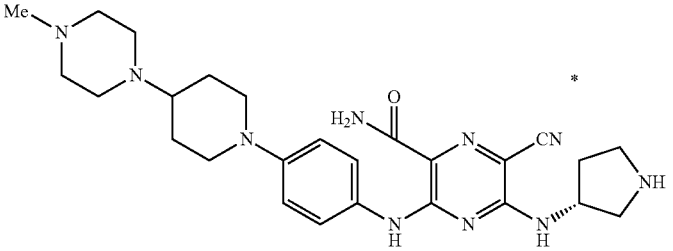 [SMILES: CN1CCN(C2CCN(c3ccc(Nc4nc(N[C@@H]5CCNC5)c(C#N)nc4C(N)=O)cc3)CC2)CC1] | ESI+: 505 |
| 322 | 318 | 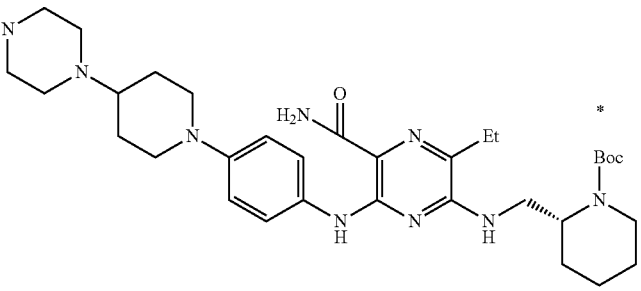 | ESI+: 636 |
TABLE 65
| PEx | PSyn | Str | Data |
|---|---|---|---|
| 323 | 318 | 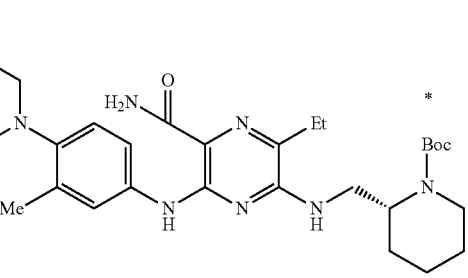 | ESI+: 650 |
| 324 | 34 | 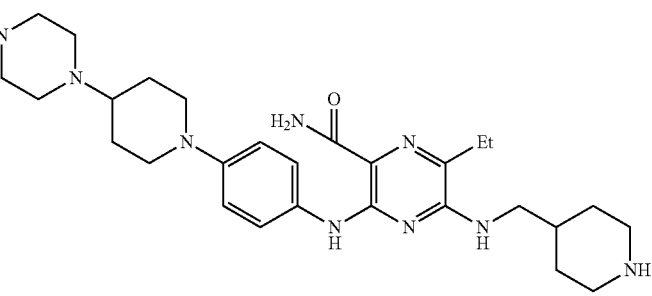 | APCI/ESI+: 536 |
| 325 | 34 | 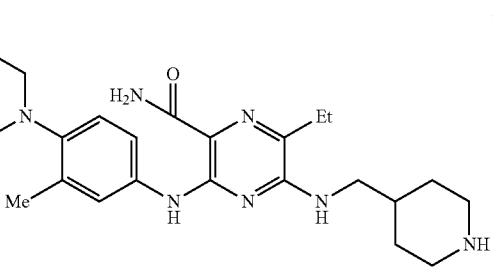 | APCI/ESI+: 550 |

TABLE 65-continued
| PEx | PSyn | Str | Data |
|---|---|---|---|
| 326 | 34 | 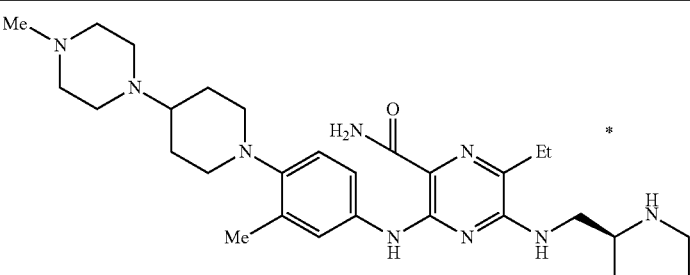 | APCI/ESI+: 550 |
TABLE 66
| PEx | PSyn | Str | Data |
|---|---|---|---|
| 327 | 34 | | APCI/ESI+: 536 |
| 328 | 34 | | APCI/ESI+: 550 |
| 329 | 380 | | ESI+: 562 |
| 330 | 306 | 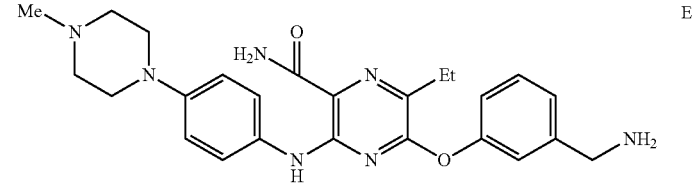 | ESI+: 462 |

TABLE 66-continued

| PEx | PSyn | Str | Data |
|---|---|---|---|
| 331 | 19 | | ESI+: 514, 516 |

TABLE 67

| PEx | PSyn | Str | Data |
|---|---|---|---|
| 332 | 21 | | ESI+: 528, 530 |
| 333 | 7 | | ESI+: 498, 500 |
| 334 | 318 | | ESI+: 637 |
| 335 | 34 | | ESI+: 537 |
| 336 | 318 | | ESI+: 680 |

TABLE 68
| PEx | PSyn | Str | Data |
|-----|------|-----|------|
| 337 | 318 | 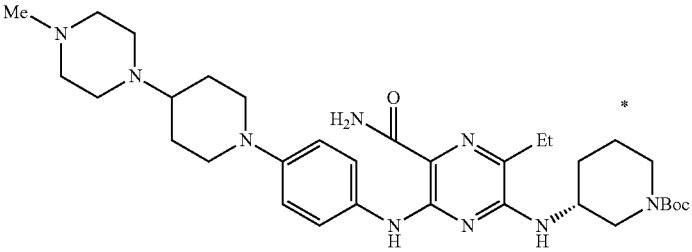 [SMILES: CCc1nc(C(N)=O)c(Nc2ccc(N3CCC(N4CCN(C)CC4)CC3)cc2)nc1N[C@@H]1CCCN(C(=O)OC(C)(C)C)C1] | ESI+: 622 |
| 338 | 27 | 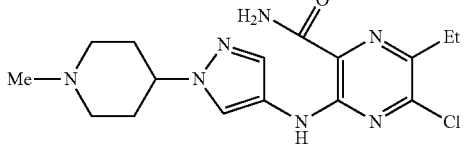 | ESI+: 364, 366 |
| 339 | 13 | 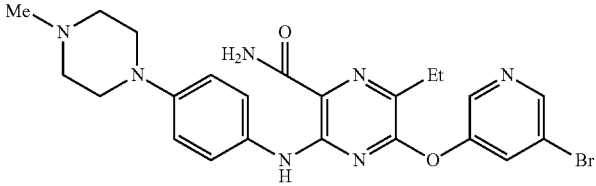 [SMILES: CCc1nc(C(N)=O)c(Nc2ccc(N3CCN(C)CC3)cc2)nc1Oc1cncc(Br)c1] | ESI+: 512, 514 |
| 340 | 340 | 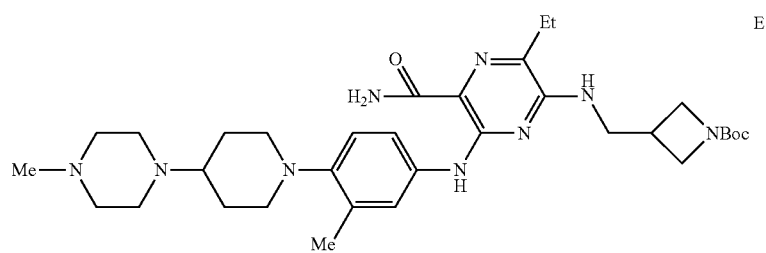 | ESI+: 622 |
| 341 | 318 | 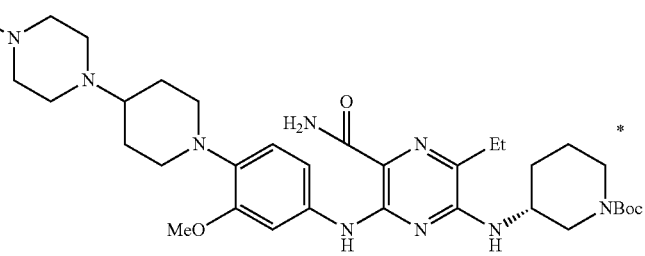 | ESI+: 652 |
TABLE 69
| PEx | PSyn | Str | Data |
|-----|------|-----|------|
| 342 | 318 | 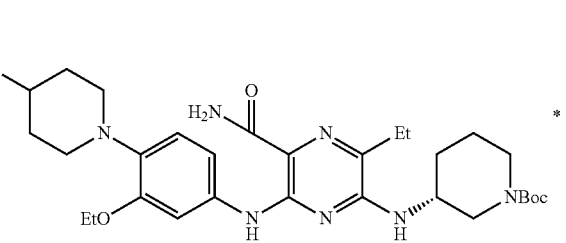 | ESI+: 666 |

181 182
TABLE 69-continued
| PEx | PSyn | Str | Data |
|---|---|---|---|
| 343 | 343 | 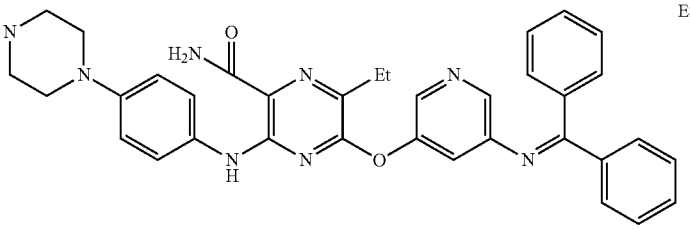 | ESI+: 613 |
| 344 | 13 | 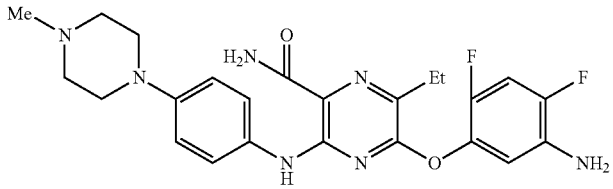 [SMILES: CCc1nc(C(N)=O)c(Nc2ccc(N3CCN(C)CC3)cc2)nc1Oc1cc(N)c(F)cc1F] | ESI+: 484 |
| 345 | 13 | 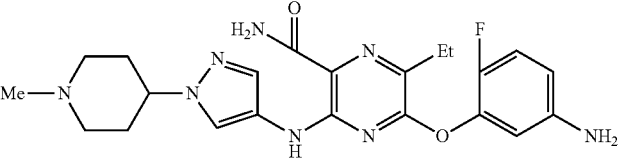 [SMILES: CCc1nc(C(N)=O)c(Nc2cnn(C3CCN(C)CC3)c2)nc1Oc1cc(N)ccc1F] | ESI+: 455 |
| 346 | 34 | 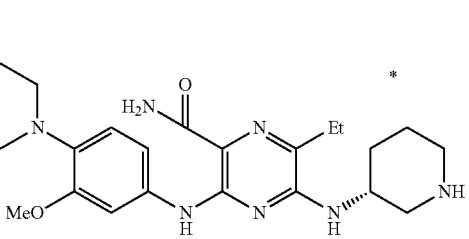 | ESI+: 552 |
TABLE 70
| PEx | PSyn | Str | Data |
|---|---|---|---|
| 347 | 34 | 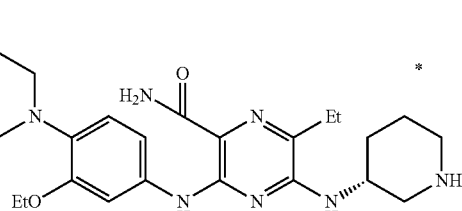 | ESI+: 566 |
| 348 | 34 | 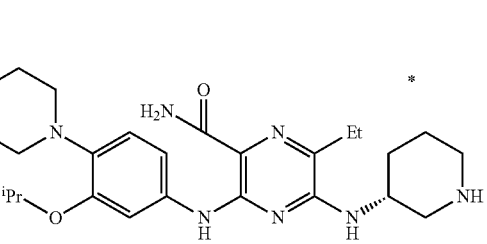 | ESI+: 580 |

TABLE 70-continued
| PEx | PSyn | Str | Data |
|---|---|---|---|
| 349 | 306 | 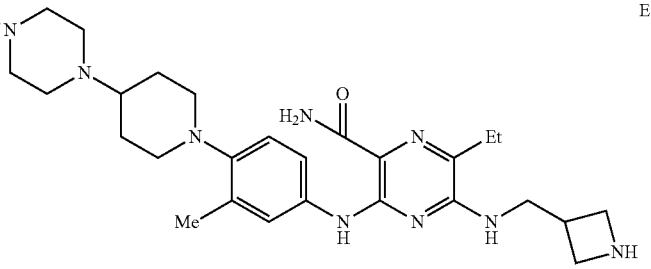 | ESI+: 522 |
| 350 | 34 | 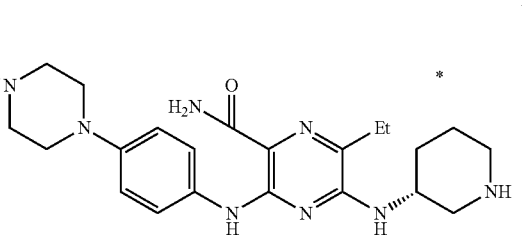 | ESI+: 522 |
| 351 | 351 | 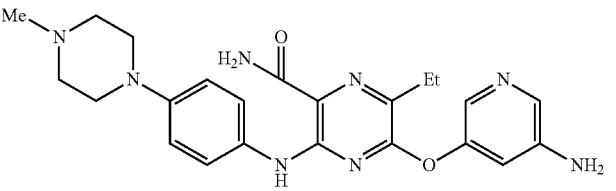 [SMILES: CCc1nc(C(N)=O)c(Nc2ccc(N3CCN(C)CC3)cc2)nc1Oc1cncc(N)c1] | ESI+: 449 |
TABLE 71
| PEx | PSyn | Str | Data |
|---|---|---|---|
| 352 | 352 | 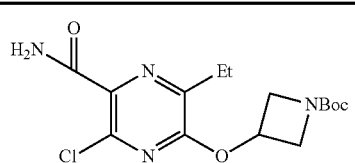 | ESI+: 357 |
| 353 | 13 | 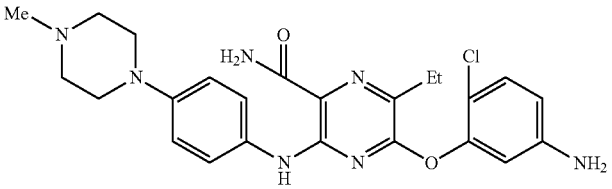 | ESI+: 482, 484 |
| 354 | 13 | 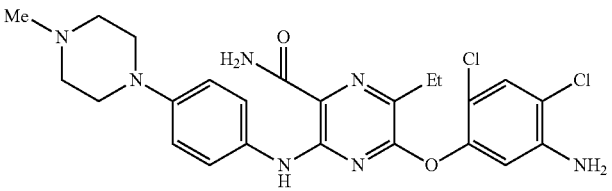 [SMILES: CCc1nc(C(N)=O)c(Nc2ccc(N3CCN(C)CC3)cc2)nc1Oc1cc(N)c(Cl)cc1Cl] | ESI+: 516, 518 |

TABLE 71-continued
| PEx | PSyn | Str | Data |
|---|---|---|---|
| 355 | 31 | 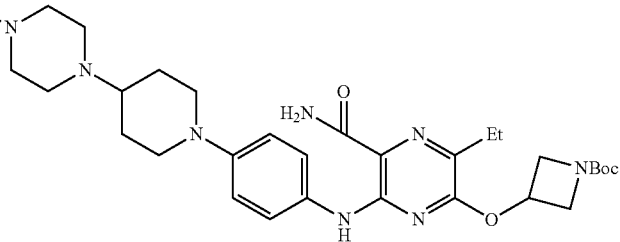 | ESI+: 595 |
| 356 | 31 | 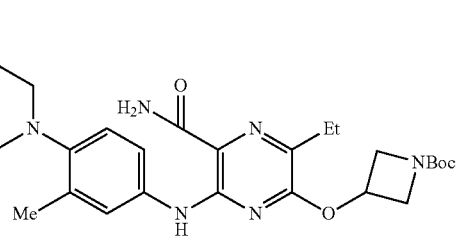 | ESI+: 609 |
TABLE 72
| PEx | PSyn | Str | Data |
|---|---|---|---|
| 357 | 340 | 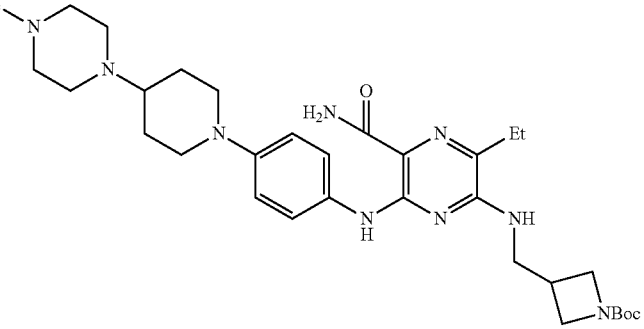 | ESI+: 608 |
| 358 | 358 | 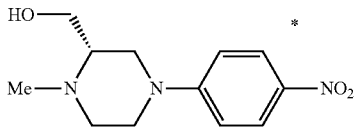 | ESI+: 252 |
| 359 | 34 | 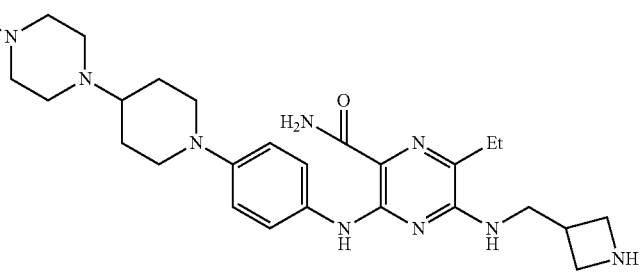 | ESI+: 508 |

TABLE 72-continued

| PEx | PSyn | Str | Data |
|---|---|---|---|
| 360 | 34 | | ESI+: 495 |
| 361 | 34 | | ESI+: 509 |

TABLE 73

| PEx | PSyn | Str | Data |
|---|---|---|---|
| 362 | 32 | | ESI+: 651 |
| 363 | 13 | | ESI+: 478 |
| 364 | 364 | | ESI+: 222 |
| 365 | 35 | | ESI+: 653 |

TABLE 73-continued
| PEx | PSyn | Str | Data |
|---|---|---|---|
| 366 | 13 | 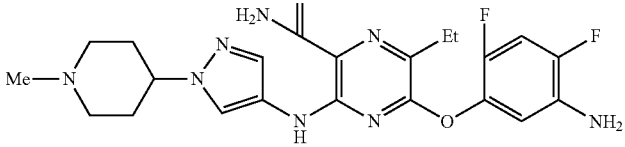 | ESI+: 473 |
TABLE 74
| PEx | PSyn | Str | Data |
|---|---|---|---|
| 367 | 27 | 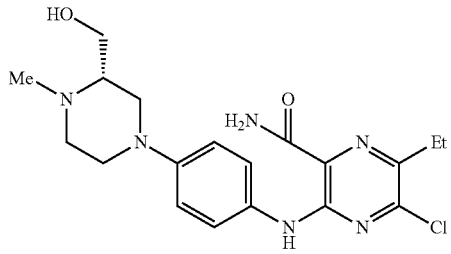 [SMILES: CCc1nc(C(N)=O)c(Nc2ccc(N3CCN(C)[C@H](CO)C3)cc2)nc1Cl] | ESI+: 405, 407 |
| 368 | 13 | 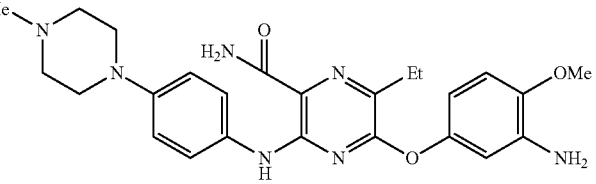 | ESI+: 478 |
| 369 | 13 | 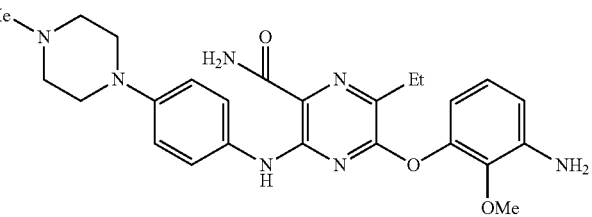 | ESI+: 478 |
| 370 | 13 | 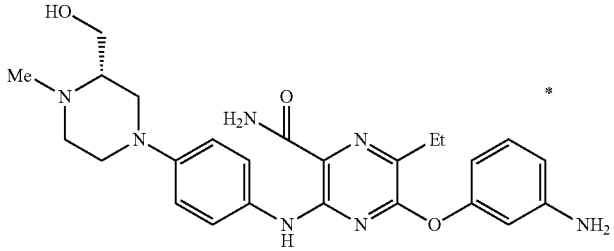 [SMILES: CCc1nc(C(N)=O)c(Nc2ccc(N3CCN(C)[C@H](CO)C3)cc2)nc1Oc1cccc(N)c1] | ESI+: 478 |
| 371 | 34 | 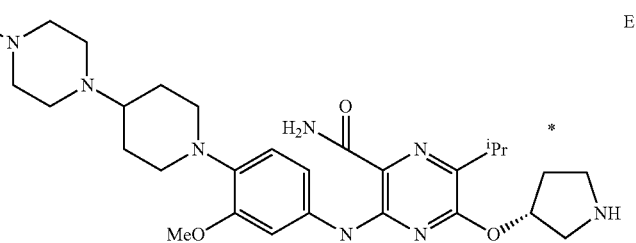 | ESI+: 553 |

TABLE 75

| PEx | PSyn | Str | Data |
|---|---|---|---|
| 372 | 372 | (structure: 2,6-dichloro-3-cyclopropylpyrazine) | 1H-NMR(CDCl3): 1.07-1.18(4H, m), 2.42-2.50(1H, m), 8.30(1H, s) |
| 373 | 27 | (structure) | ESI+: 281, 283 |
| 374 | 27 | (structure) | ESI+: 281, 283 |
| 375 | 27 | (structure) | ESI+: 389, 391 |
| 376 | 13 | (structure) | ESI+: 466 |
| 377 | 13 | (structure) | ESI+: 372 |

TABLE 76

| PEx | PSyn | Str | Data |
|---|---|---|---|
| 378 | 13 | (structure) | ESI+: 372 |
| 379 | 13 | (structure) | ESI+: 462 |

TABLE 76-continued
| PEx | PSyn | Str | Data |
|---|---|---|---|
| 380 | 380 | 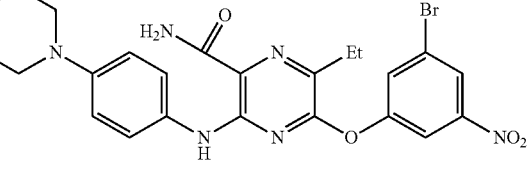 | ESI+: 556, 558 |
| 381 | 381 | | ESI+: 586 |
| 382 | 27 | | ESI+: 450, 452 |
TABLE 77
| PEx | PSyn | Str | Data |
|---|---|---|---|
| 383 | 383 | 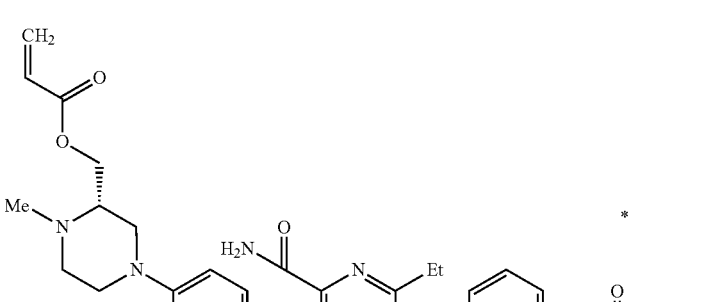 | ESI−: 231 |
| 384 | 384 | 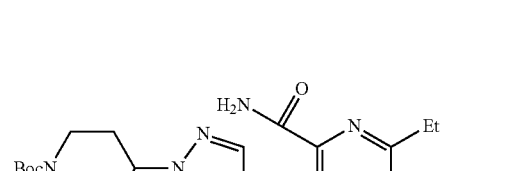 | ESI+: 613 |

TABLE 77-continued

| PEx | PSyn | Str | Data |
|---|---|---|---|
| 385 | 384 | | ESI+: 613 |
| 386 | 386 | | EI+: 231, 233 |

TABLE 78

| PEx | PSyn | Str | Data |
|---|---|---|---|
| 387 | 387 | | ESI+: 523 |
| 388 | 387 | | ESI+: 523 |
| 389 | 389 | | ESI+: 350, 352 |
| 390 | 27 | | ESI+: 470, 472 |

TABLE 78-continued
| PEx | PSyn | Str | Data |
|---|---|---|---|
| 391 | 391 | 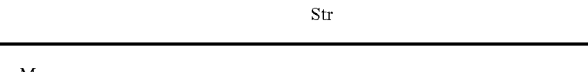 | ESI+: 503 |
TABLE 79
| PEx | PSyn | Str | Data |
|---|---|---|---|
| 392 | 392 | | ESI+: 432, 434 |
| 393 | 384 | | ESI+: 663 |
| 394 | 392 | | ESI+: 414, 416 |
| 395 | 395 | | ESI+: 408, 410 |
| 396 | 13 | | ESI+: 523 |

TABLE 80

| PEx | PSyn | Str | Data |
|---|---|---|---|
| 397 | 13 | | ESI+: 541 |
| 398 | 13 | | ESI+: 505 |
| 399 | 13 | | ESI+: 523 |
| 400 | 13 | | ESI+: 499 |
| 401 | 13 | | ESI+: 517 |
| 402 | 7 | | ESI+: 473 |

TABLE 81

| PEx | PSyn | Str | Data |
|---|---|---|---|
| 403 | 403 | | ESI+: 621 |

TABLE 81-continued
| PEx | PSyn | Str | Data |
|---|---|---|---|
| 404 | 34 | 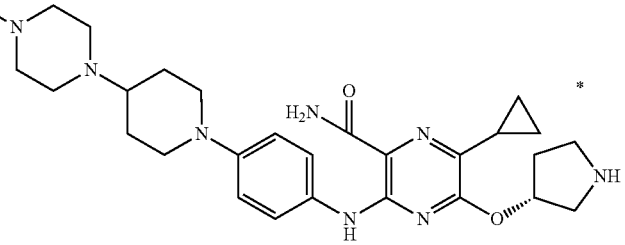 | ESI+: 521 |
| 405 | 405 | 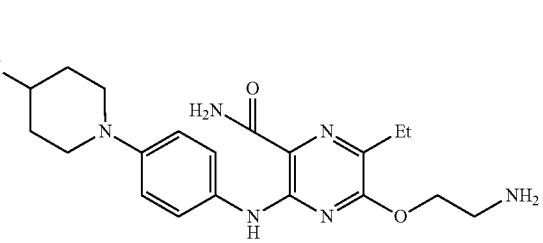 | ESI+: 483 |
| 406 | 406 | 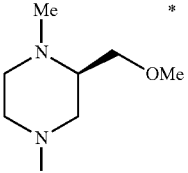 | ESI+: 245 |
| 407 | 407 | 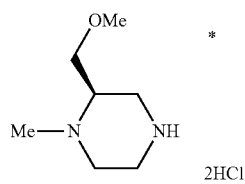 | ESI+: 145 |
TABLE 82
| PEx | PSyn | Str | Data |
|---|---|---|---|
| 408 | 358 | 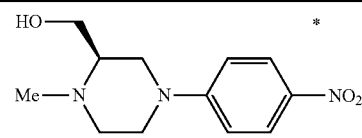 | ESI+: 252 |
| 409 | 358 | 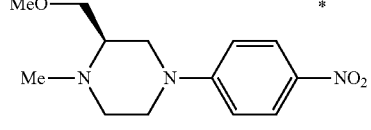 | ESI+: 266 |
| 410 | 410 |  | ESI+: 291 |
| 411 | 42 | 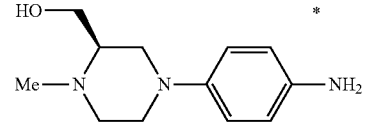 [SMILES: CN1CCN(c2ccc(N)cc2)C[C@@H]1CO] | ESI+: 222 |

TABLE 82-continued

| PEx | PSyn | Str | Data |
|---|---|---|---|
| 412 | 42 | | ESI+: 236 |
| 413 | 27 | | ESI+: 405, 407 |

TABLE 83

| PEx | PSyn | Str | Data |
|---|---|---|---|
| 414 | 27 | | ESI+: 419, 421 |
| 415 | 415 | | ESI+: 347 |
| 416 | 384 | | ESI+: 649 |
| 417 | 34 | | ESI+: 549 |
| 418 | 42 | | ESI+: 317 |

TABLE 84
| PEx | PSyn | Str | Data |
|---|---|---|---|
| 419 | 27 | 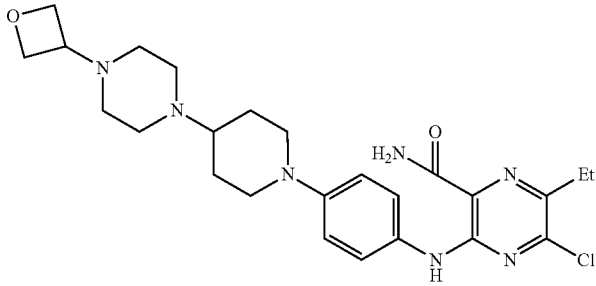 [SMILES: CCc1nc(C(N)=O)c(Nc2ccc(N3CCC(N4CCN(C5COC5)CC4)CC3)cc2)nc1Cl] | ESI+: 500, 502 |
| 420 | 13 | 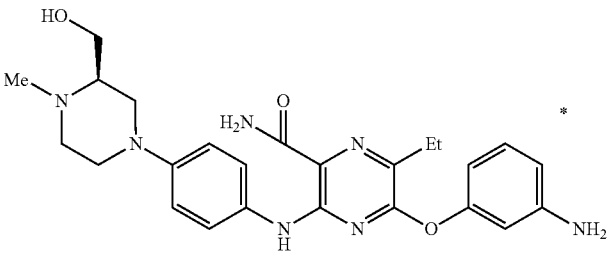 [SMILES: CCc1nc(C(N)=O)c(Nc2ccc(N3CCN(C)[C@@H](CO)C3)cc2)nc1Oc1cccc(N)c1] | ESI+: 478 |
| 421 | 13 | 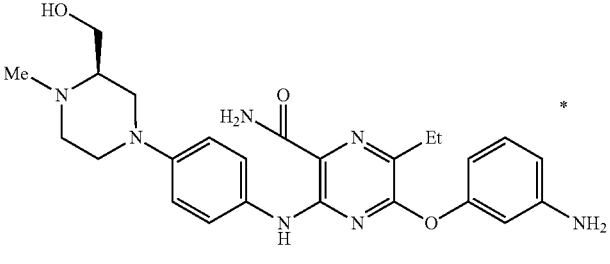 [SMILES: CCc1nc(C(N)=O)c(Nc2ccc(N3CCN(C)[C@@H](CO)C3)cc2)nc1Oc1cccc(N)c1] | ESI+: 492 |
| 422 | 422 | 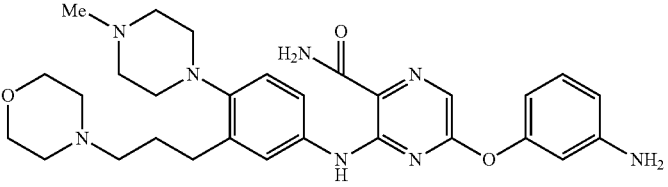 [SMILES: CN1CCN(c2ccc(Nc3nc(Oc4cccc(N)c4)cnc3C(N)=O)cc2CCCN2CCOCC2)CC1] | ESI+: 547 |
| 423 | 427 | 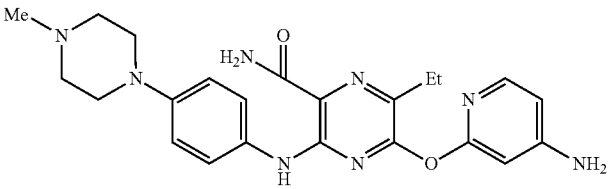 [SMILES: CCc1nc(C(N)=O)c(Nc2ccc(N3CCN(C)CC3)cc2)nc1Oc1cc(N)ccn1] | ESI+: 449 |

TABLE 85

| PEx | PSyn | Str | Data |
|---|---|---|---|
| 424 | 384 | (structure) | ESI+: 651 |
| 425 | 34 | (structure) | ESI+: 551 |
| 426 | 13 | (structure) | ESI+: 473 |
| 427 | 427 | (structure) | ESI+: 449 |
| 428 | 428 | (structure) | ESI+: 341, 343 |

TABLE 86

| PEx | PSyn | Str | Data |
|-----|------|-----|------|
| 429 | 384 | | ESI+: 653 |
| 430 | 13  | | ESI+: 473 |
| 431 | 384 | | ESI+: 653 |
| 432 | 432 | | ESI+: 523 |

TABLE 87
| PEx | PSyn | Str | Data |
|---|---|---|---|
| 433 | 198 | 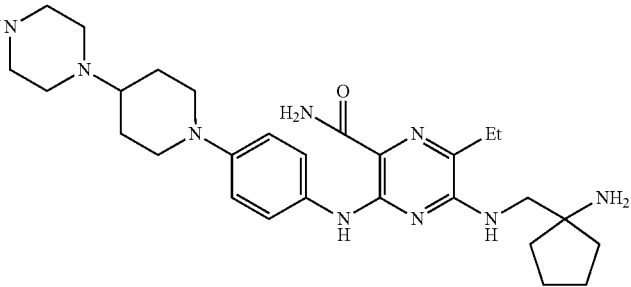 | ESI+: 536 |
| 434 | 32 | 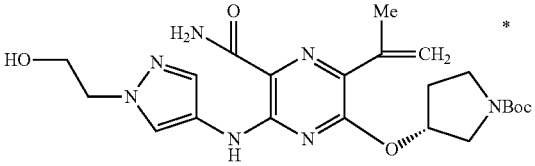 [SMILES: C=C(C)c1nc(C(N)=O)c(Nc2cnn(CCO)c2)nc1O[C@@H]1CCN(C(=O)OC(C)(C)C)C1] | ESI+: 474 |
| 435 | 435 | 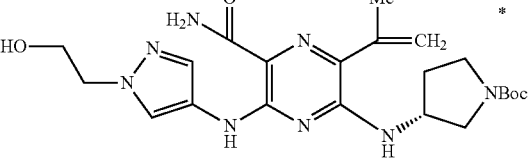 | ESI+: 473 |
| 436 | 35 | 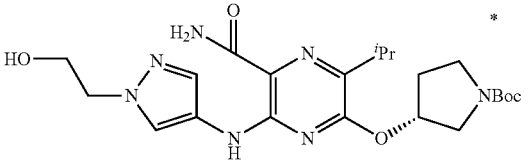 [SMILES: CC(C)c1nc(C(N)=O)c(Nc2cnn(CCO)c2)nc1O[C@@H]1CCN(C(=O)OC(C)(C)C)C1] | ESI+: 476 |
| 437 | 35 | 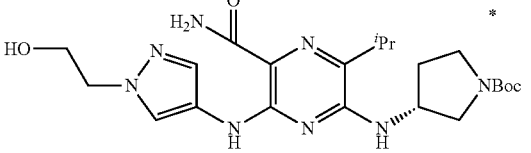 | ESI+: 475 |
TABLE 88
| PEx | PSyn | Str | Data |
|---|---|---|---|
| 438 | 438 | 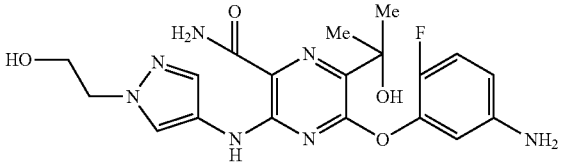 [SMILES: CC(C)(O)c1nc(C(N)=O)c(Nc2cnn(CCO)c2)nc1Oc1cc(N)ccc1F] | ESI+: 432 |
| 439 | 384 | 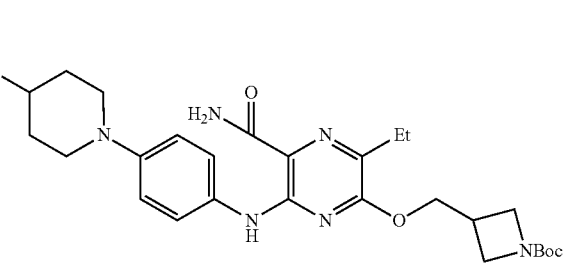 | ESI+: 609 |

TABLE 88-continued
| PEx | PSyn | Str | Data |
|---|---|---|---|
| 440 | 432 | 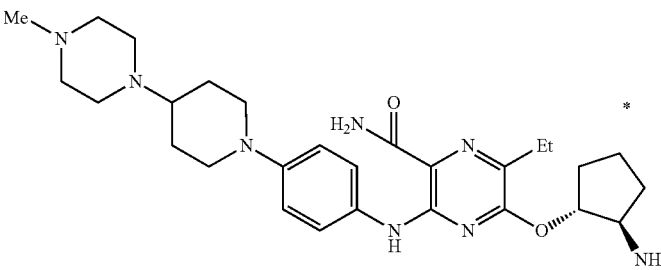 | ESI+: 523 |
| 441 | 441 | 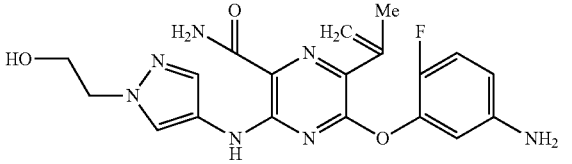 [SMILES: C=C(C)c1nc(C(N)=O)c(Nc2cnn(CCO)c2)nc1Oc1cc(N)ccc1F] | ESI+: 414 |
| 442 | 442 | 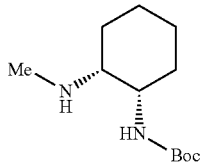 | APCI/ESI+: 229 |
TABLE 89
| PEx | PSyn | Str | Data |
|---|---|---|---|
| 443 | 34 | 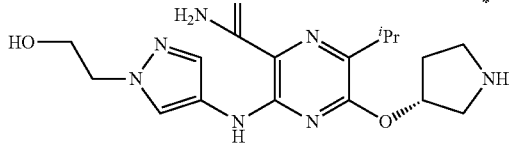 | ESI+: 376 |
| 444 | 34 | 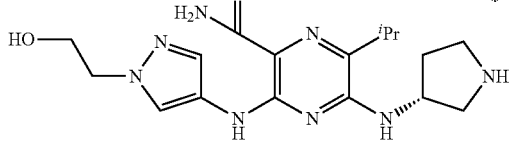 | ESI+: 375 |
| 445 | 35 | 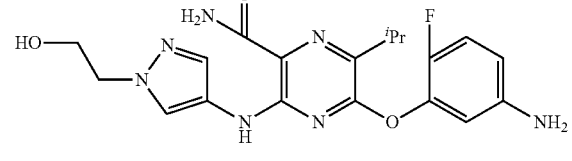 | ESI+: 416 |
| 446 | 34 | 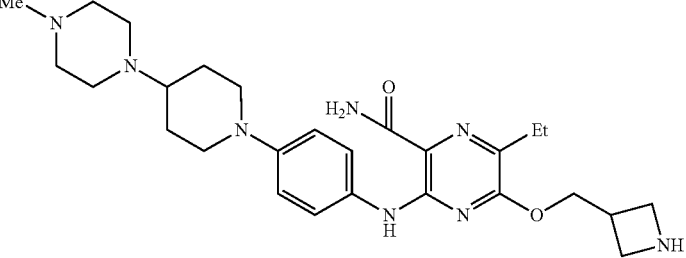 | ESI+: 509 |

TABLE 89-continued

| PEx | PSyn | Str | Data |
|---|---|---|---|
| 447 | 27 | (structure) | ESI+: 377, 379 |

TABLE 90

| PEx | PSyn | Str | Data |
|---|---|---|---|
| 448 | 318 | (structure) | APCI/ESI+: 650 |
| 449 | 13 | (structure) | ESI+: 468 |
| 450 | 34 | (structure) | ESI+: 550 |
| 451 | 451 | (structure) | APCI/ESI+: 550 |

TABLE 90-continued
| PEx | PSyn | Str | Data |
|---|---|---|---|
| 452 | 452 | 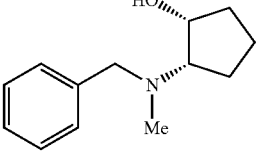 | ESI+: 206 |
TABLE 91
| PEx | PSyn | Str | Data |
|---|---|---|---|
| 453 | 384 | 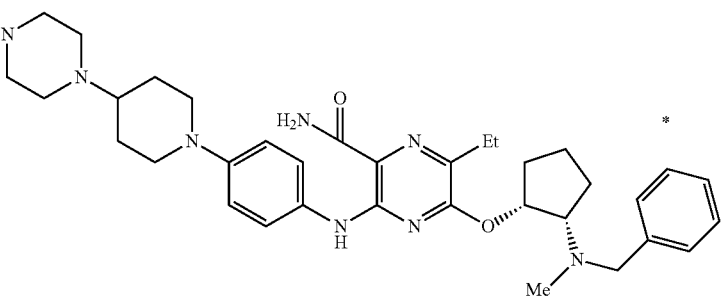 | ESI+: 627 |
| 454 | 387 | 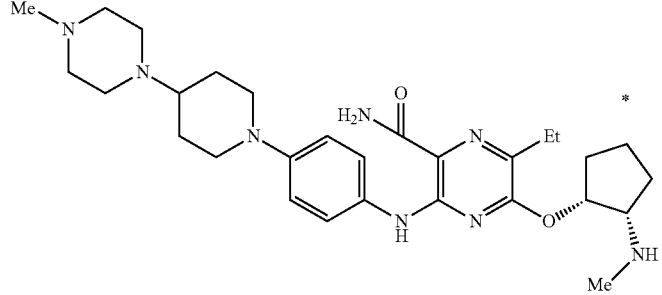 [SMILES: CCc1nc(C(N)=O)c(Nc2ccc(N3CCC(N4CCN(C)CC4)CC3)cc2)nc1O[C@@H]1CCC[C@@H]1NC] | ESI+: 537 |
| 455 | 27 | 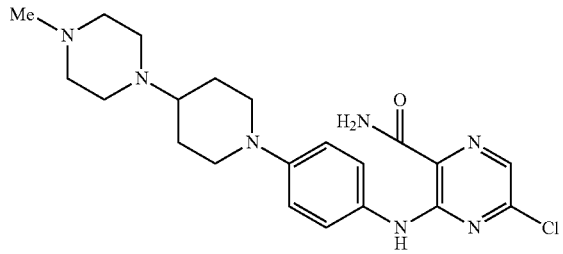 [SMILES: CN1CCN(C2CCN(c3ccc(Nc4nc(Cl)cnc4C(N)=O)cc3)CC2)CC1] | ESI+: 430, 432 |
| 456 | 456 | 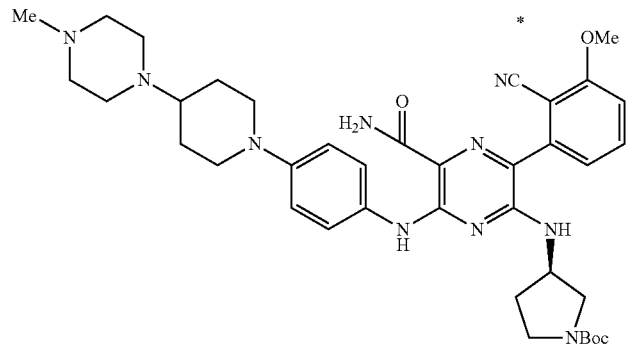 [SMILES: COc1cccc(-c2nc(C(N)=O)c(Nc3ccc(N4CCC(N5CCN(C)CC5)CC4)cc3)nc2N[C@@H]2CCN(C(=O)OC(C)(C)C)C2)c1C#N] | ESI+: 711 |

TABLE 92

| PEx | PSyn | Str | Data |
|---|---|---|---|
| 457 | 34 | | ESI+: 611 |
| 458 | 384 | | ESI+: 675 |
| 459 | 384 | | ESI+: 635 |
| 460 | 460 | | ESI+: 545 |

TABLE 93
| PEx | PSyn | Str | Data |
|---|---|---|---|
| 461 | 27 | 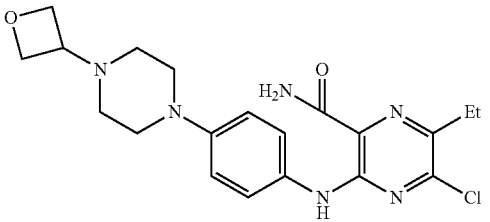 [SMILES: CCc1nc(C(N)=O)c(Nc2ccc(N3CCN(C4COC4)CC3)cc2)nc1Cl] | ESI+: 417, 419 |
| 462 | 34 | 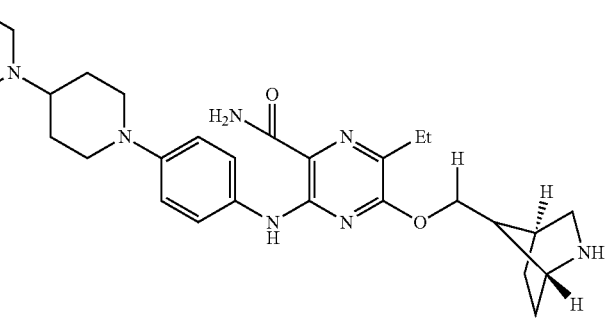 | ESI+: 535 |
| 463 | 403 | 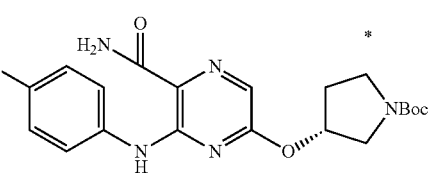 | ESI+: 581 |
| 464 | 384 | 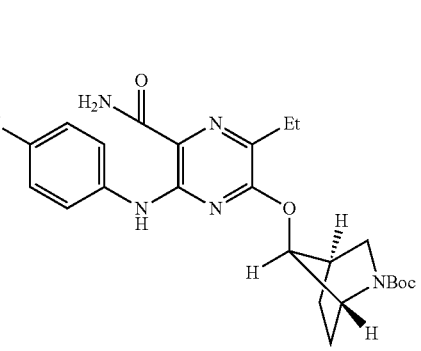 | ESI+: 635 |

TABLE 94

| PEx | PSyn | Str | Data |
|---|---|---|---|
| 465 | 34 | (structure) | ESI+: 535 |
| 466 | 34 | (structure) | ESI+: 481 |
| 467 | 403 | (structure) | ESI+: 568 |
| 468 | 34 | (structure) | ESI+: 468 |

TABLE 95

| PEx | PSyn | Str | Data |
|---|---|---|---|
| 469 | 34 | (structure) | APCI/ESI+: 536 |

TABLE 95-continued
| PEx | PSyn | Str | Data |
|---|---|---|---|
| 470 | 407 | 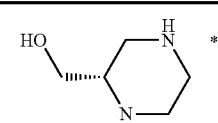 | ESI+: 131 |
| 471 | 471 | 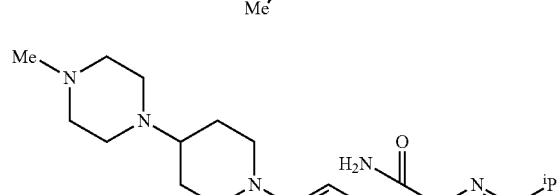 | ESI+: 472, 474 |
TABLE 96
| Ex | Str |
|---|---|
| 1 | ![structure] |
| 2 | ![structure] |
| 3 | ![structure] |
| 4 | ![structure] |
| 5 | ![structure] |

TABLE 96-continued
| Ex | Str |
|---|---|
| 6 | 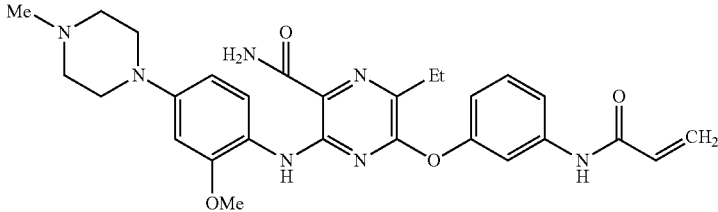 [SMILES: C=CC(=O)Nc1cccc(Oc2nc(Nc3ccc(N4CCN(C)CC4)cc3OC)c(C(N)=O)nc2CC)c1] |
TABLE 97
| Ex | Str |
|---|---|
| 7 | 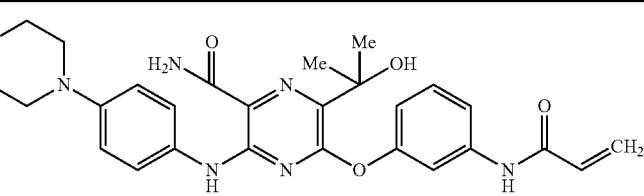 |
| 8 | 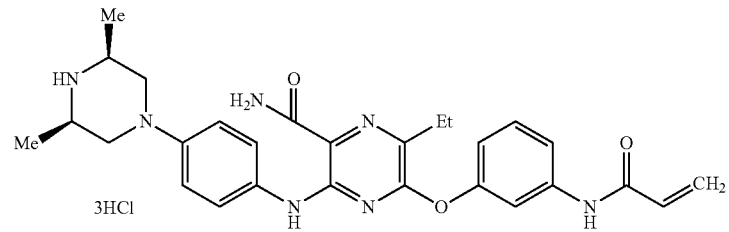 [SMILES: C=CC(=O)Nc1cccc(Oc2nc(Nc3ccc(N4C[C@@H](C)N[C@@H](C)C4)cc3)c(C(N)=O)nc2CC)c1] |
| 9 | 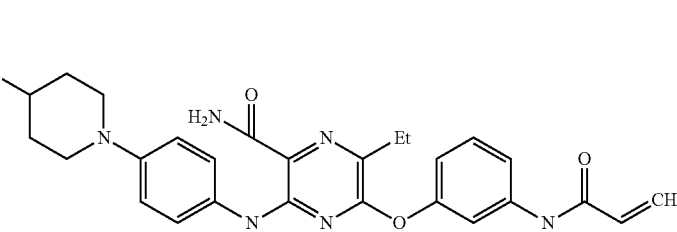 |
| 10 | 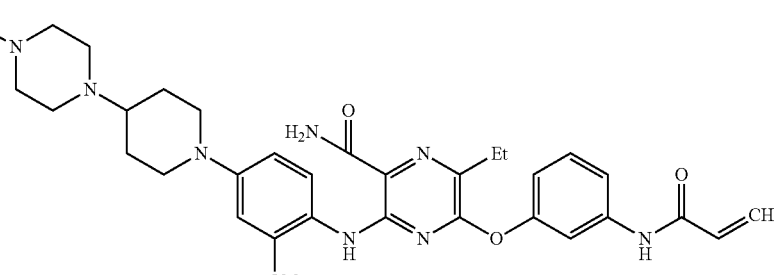 |
| 11 | 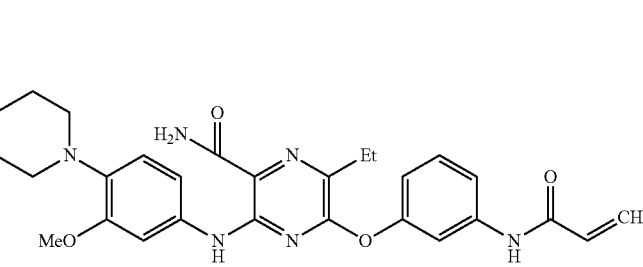 |

TABLE 98

| Ex | Str |
|---|---|
| 12 | (structure) |
| 13 | (structure) |
| 14 | (structure) |
| 15 | (structure) |
| 16 | (structure) |
| 17 | (structure) |

TABLE 99

| Ex | Str |
|---|---|
| 18 | (structure) |
| 19 | (structure) |
| 20 | (structure) |
| 21 | (structure) |
| 22 | (structure) |

TABLE 100

| Ex | Str |
|---|---|
| 23 | (structure) |

TABLE 100-continued

| Ex | Str |
|---|---|
| 24 | |
| 25 | |
| 26 | |
| 27 | |

TABLE 101

| Ex | Str |
|---|---|
| 28 | |
| 29 | |

TABLE 101-continued

| Ex | Str |
|---|---|
| 30 | (structure) |
| 31 | (structure) |
| 32 | (structure) |
| 33 | (structure) |

TABLE 102

| Ex | Str |
|---|---|
| 34 | (structure) |
| 35 | (structure) |
| 36 | (structure) |

TABLE 102-continued
| Ex | Str |
|---|---|
| 37 | 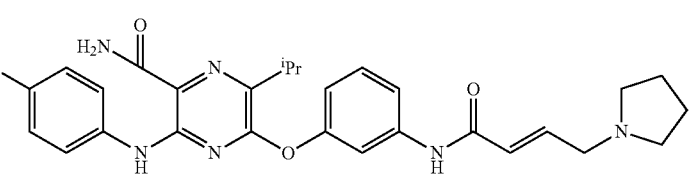 |
| 38 | 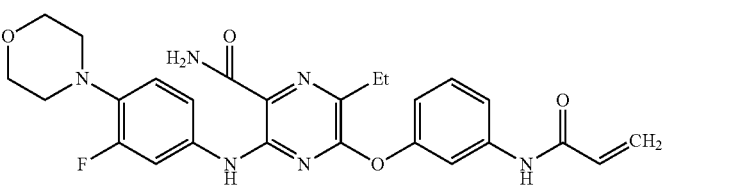 [SMILES: C=CC(=O)Nc1cccc(Oc2nc(Nc3ccc(N4CCOCC4)c(F)c3)c(C(N)=O)nc2CC)c1] |
| 39 | 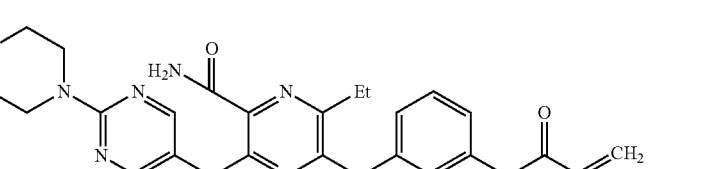 |
TABLE 103
| Ex | Str |
|---|---|
| 40 | 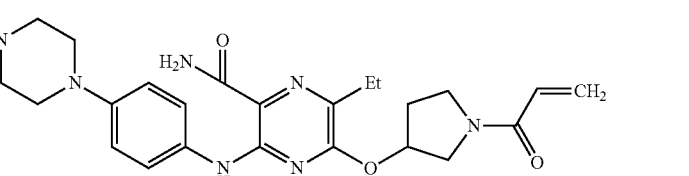 |
| 41 | 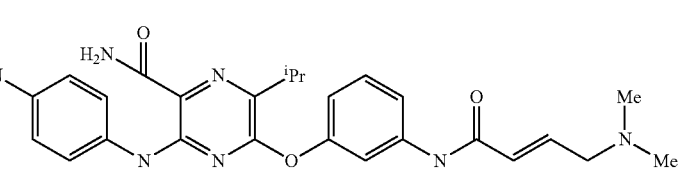 |
| 42 | 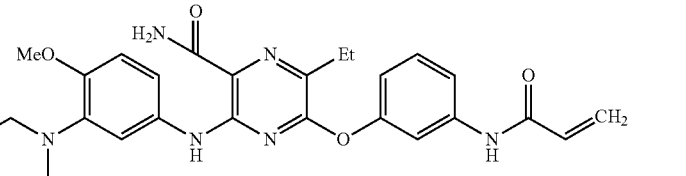 |
| 43 | 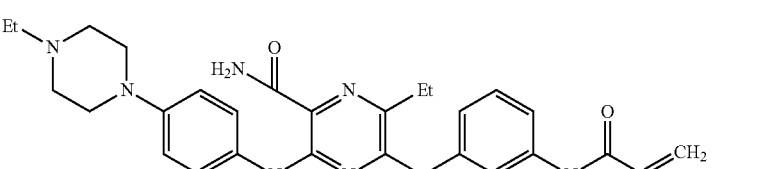 |

TABLE 103-continued

| Ex | Str |
|---|---|
| 44 | (structure) |
| 45 | (structure) |

TABLE 104

| Ex | Str |
|---|---|
| 46 | (structure) |
| 47 | (structure) |
| 48 | (structure) |
| 49 | (structure) |
| 50 | (structure) |

TABLE 104-continued
| Ex | Str |
|---|---|
| 51 | 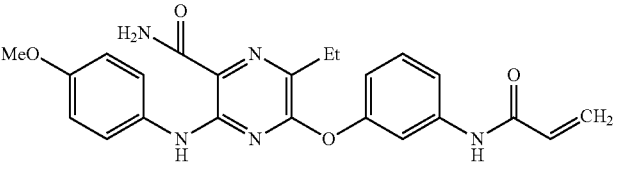 [SMILES: C=CC(=O)Nc1cccc(Oc2nc(Nc3ccc(OC)cc3)c(C(N)=O)nc2CC)c1] |
TABLE 105
| Ex | Str |
|---|---|
| 52 | 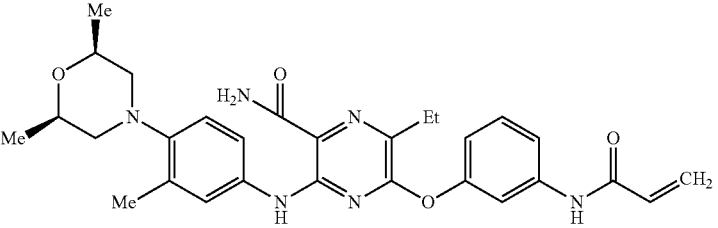 [SMILES: C=CC(=O)Nc1cccc(Oc2nc(Nc3ccc(N4C[C@@H](C)O[C@@H](C)C4)c(C)c3)c(C(N)=O)nc2CC)c1] |
| 53 | 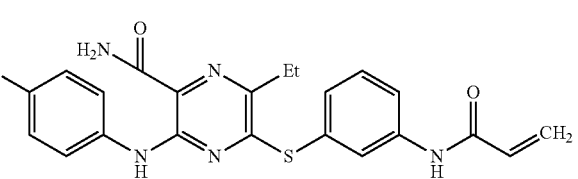 |
| 54 | 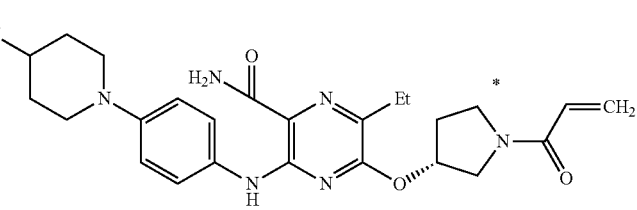 |
| 55 | 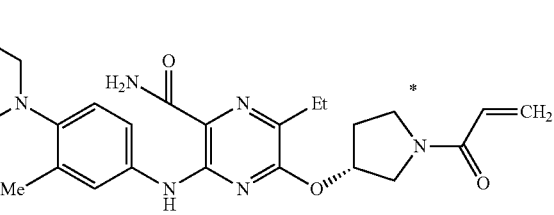 |
| 56 | 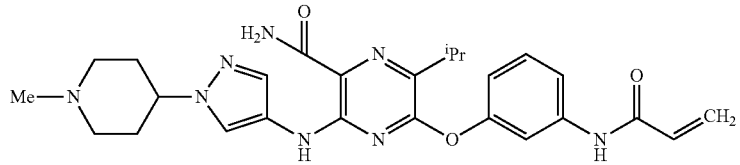 [SMILES: C=CC(=O)Nc1cccc(Oc2nc(Nc3cnn(C4CCN(C)CC4)c3)c(C(N)=O)nc2C(C)C)c1] |

TABLE 105-continued
| Ex | Str |
|---|---|
| 57 | 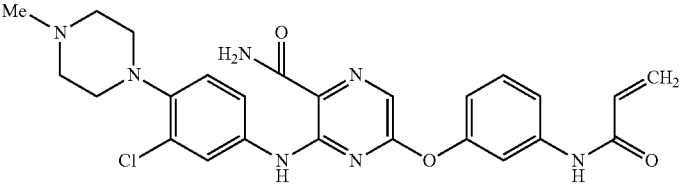 [SMILES: C=CC(=O)Nc1cccc(Oc2cnc(C(N)=O)c(Nc3ccc(N4CCN(C)CC4)c(Cl)c3)n2)c1] |
TABLE 106
| Ex | Str |
|---|---|
| 58 | 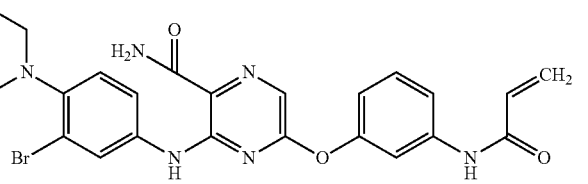 |
| 59 | 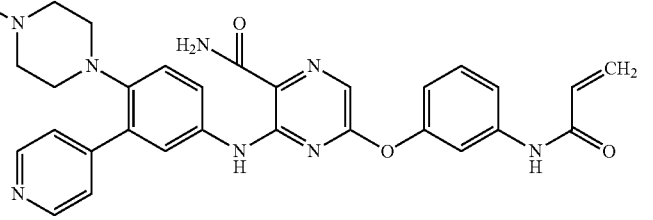 |
| 60 | 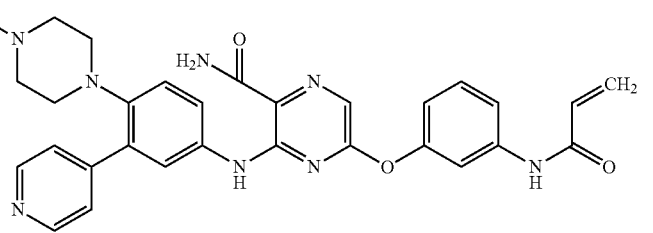 |
| 61 | 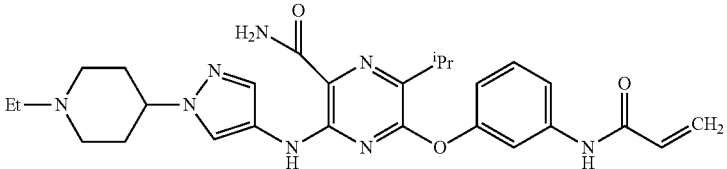 [SMILES: C=CC(=O)Nc1cccc(Oc2nc(Nc3cnn(C4CCN(CC)CC4)c3)c(C(N)=O)nc2C(C)C)c1] |
| 62 | 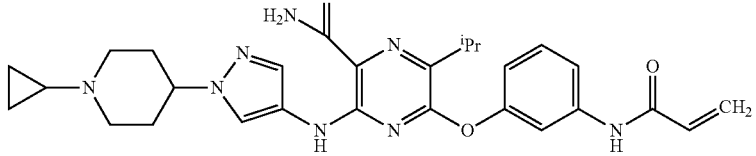 |
| 63 | 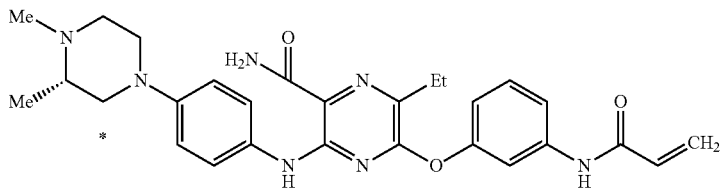 [SMILES: C=CC(=O)Nc1cccc(Oc2nc(Nc3ccc(N4CCN(C)[C@@H](C)C4)cc3)c(C(N)=O)nc2CC)c1] |

TABLE 107

| Ex | Str |
|---|---|
| 64 | (structure) |
| 65 | (structure) |
| 66 | (structure) |
| 67 | (structure) |
| 68 | (structure) |

TABLE 108

| Ex | Str |
|---|---|
| 69 | (structure) |

TABLE 108-continued
| Ex | Str |
|---|---|
| 70 | 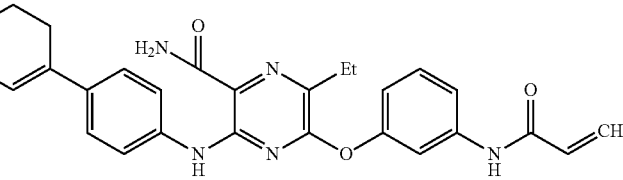 |
| 71 | 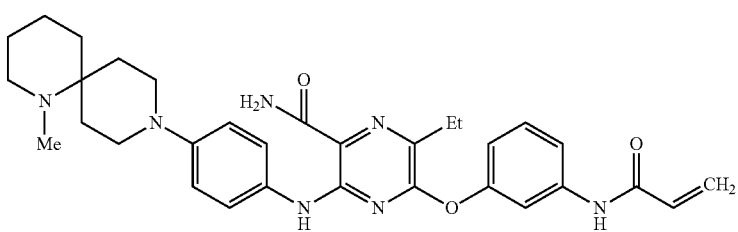 [SMILES: C=CC(=O)Nc1cccc(Oc2nc(Nc3ccc(N4CCC5(CCCCN5C)CC4)cc3)c(C(N)=O)nc2CC)c1] |
| 72 | 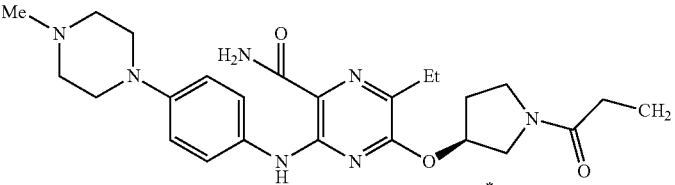 |
| 73 | 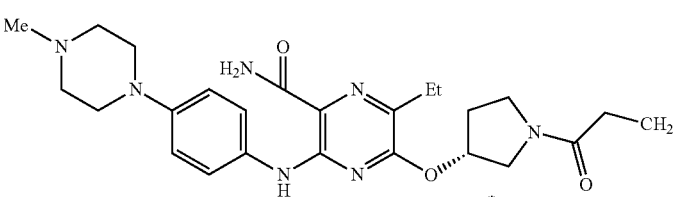 |
TABLE 109
| Ex | Str |
|---|---|
| 74 | 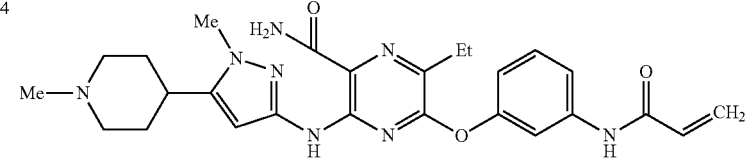 |
| 75 | 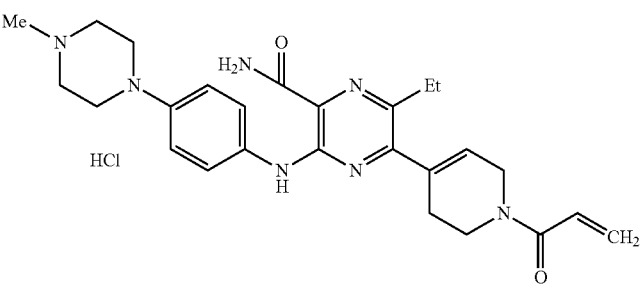 [SMILES: C=CC(=O)N1CC=C(c2nc(Nc3ccc(N4CCN(C)CC4)cc3)c(C(N)=O)nc2CC)CC1 ; Cl] |

TABLE 109-continued
| Ex | Str |
|---|---|
| 76 | 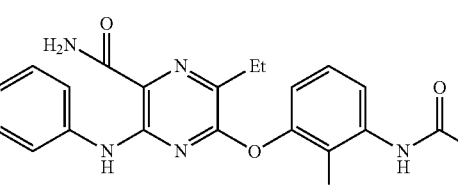 |
| 77 | 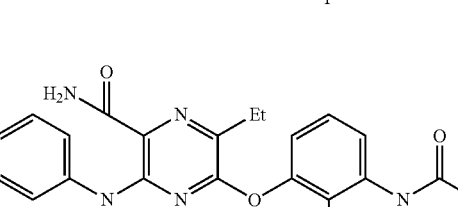 |
| 78 | 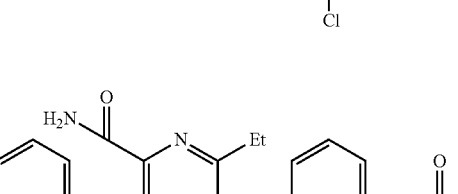 |
TABLE 110
| Ex | Str |
|---|---|
| 79 | 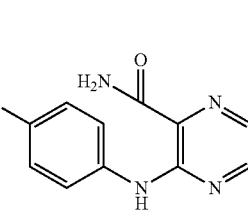 |
| 80 | 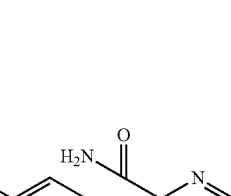 |
| 81 | 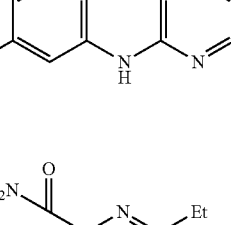 |

TABLE 110-continued
| Ex | Str |
|---|---|
| 82 | 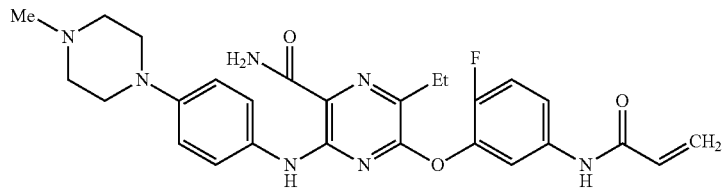 [SMILES: C=CC(=O)Nc1ccc(F)c(Oc2nc(Nc3ccc(N4CCN(C)CC4)cc3)c(C(N)=O)nc2CC)c1] |
| 83 | 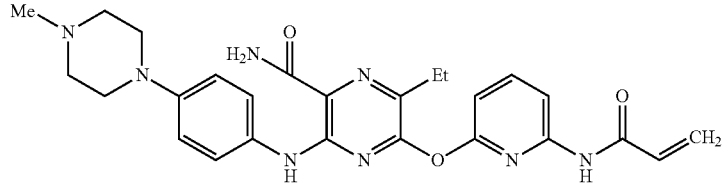 [SMILES: C=CC(=O)Nc1cccc(Oc2nc(Nc3ccc(N4CCN(C)CC4)cc3)c(C(N)=O)nc2CC)n1] |
TABLE 111
| Ex | Str |
|---|---|
| 84 | 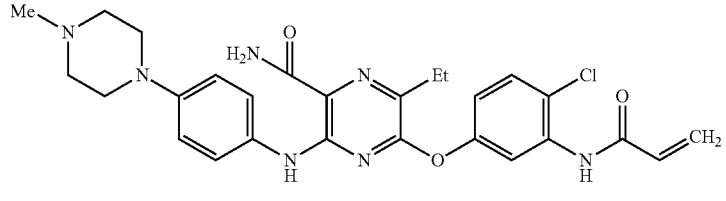 [SMILES: C=CC(=O)Nc1cc(Oc2nc(Nc3ccc(N4CCN(C)CC4)cc3)c(C(N)=O)nc2CC)ccc1Cl] |
| 85 | 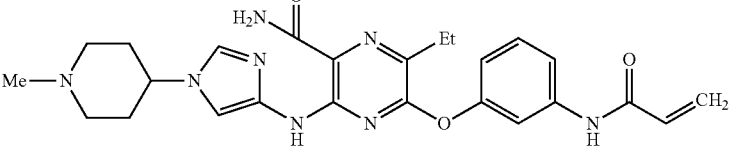 |
| 86 | 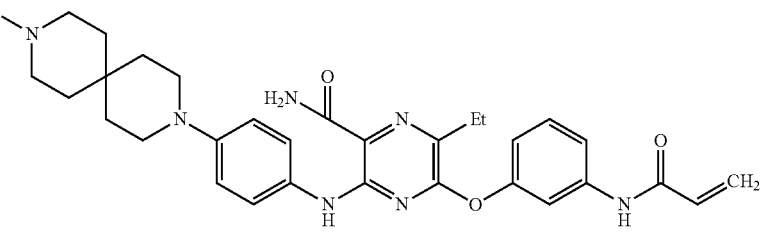 |
| 87 | 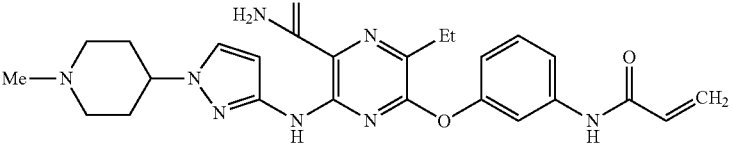 |
| 88 | 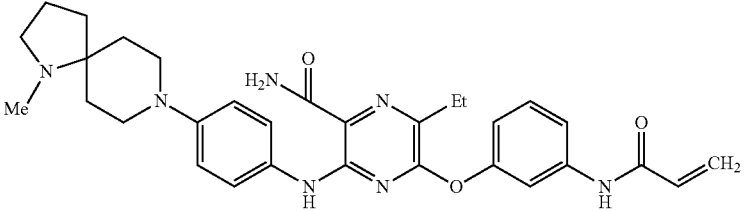 [SMILES: C=CC(=O)Nc1cccc(Oc2nc(Nc3ccc(N4CCC5(CCCN5C)CC4)cc3)c(C(N)=O)nc2CC)c1] |

TABLE 111-continued
| Ex | Str |
|---|---|
| 89 | 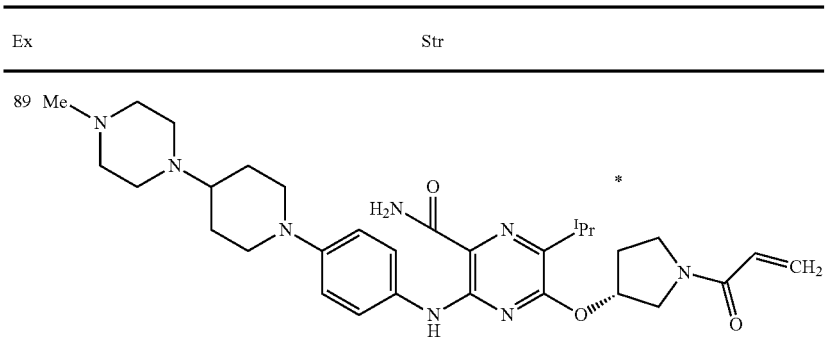 |
TABLE 112
| Ex | Str |
|---|---|
| 90 | |
| 91 | |
| 92 | |
| 93 | |
| 94 | |

TABLE 113

| Ex | Str |
|---|---|
| 95 | (structure) |
| 96 | (structure) |
| 97 | (structure) |
| 98 | (structure) |
| 99 | (structure) |

TABLE 114

| Ex | Str |
|---|---|
| 100 | (structure) |

TABLE 114-continued
| Ex | Str |
|---|---|
| 101 | 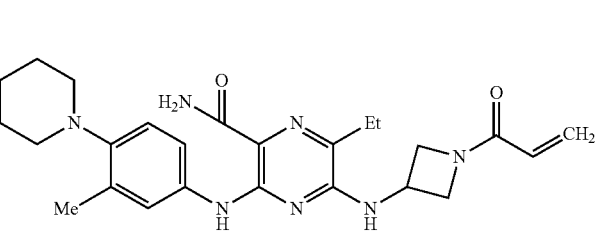 |
| 102 | 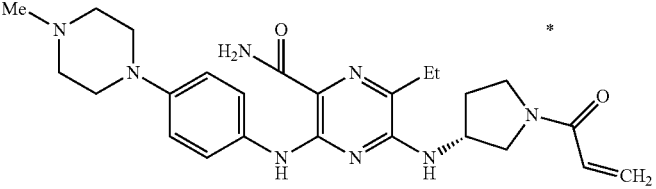 [SMILES: C=CC(=O)N1CC[C@@H](Nc2nc(Nc3ccc(N4CCN(C)CC4)cc3)c(C(N)=O)nc2CC)C1] |
| 103 | 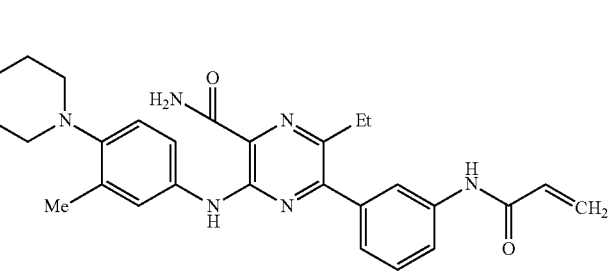 |
TABLE 115
| Ex | Str |
|---|---|
| 104 | 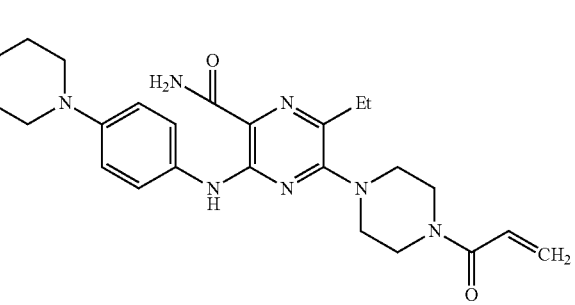 |
| 105 | 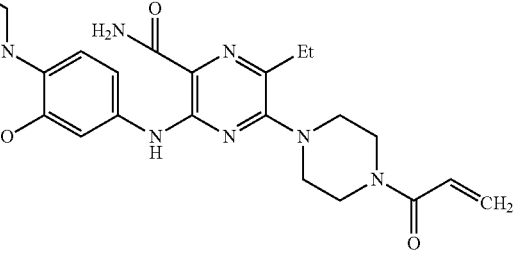 |

TABLE 115-continued
| Ex | Str |
|---|---|
| 106 | 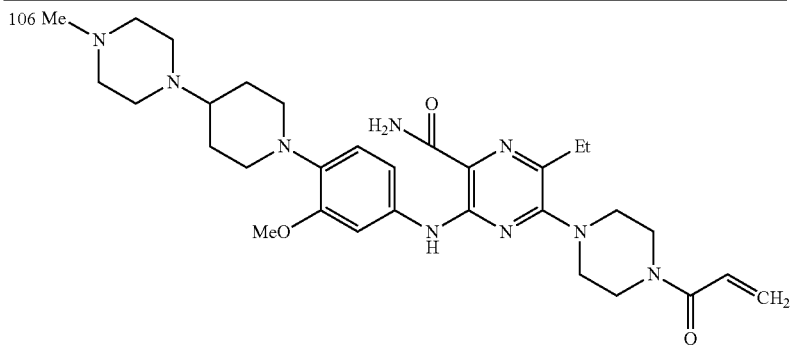 |
| 107 | 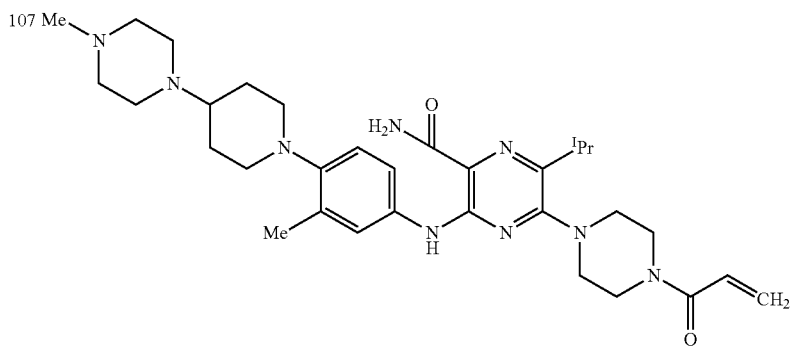 |
TABLE 116
| Ex | Str |
|---|---|
| 108 | 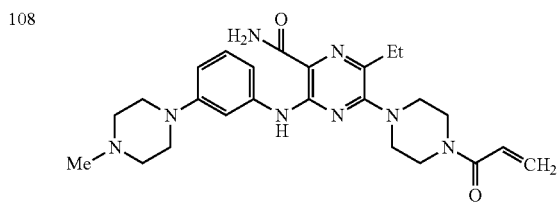 |
| 109 | 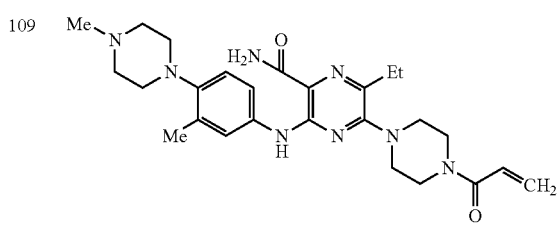 |
TABLE 116-continued
| Ex | Str |
|---|---|
| 110 | 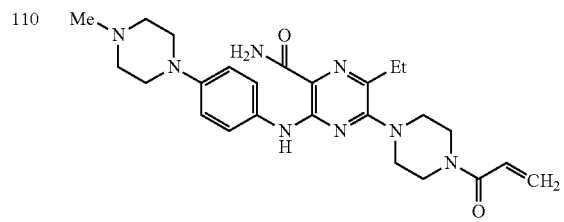 |
| 111 | 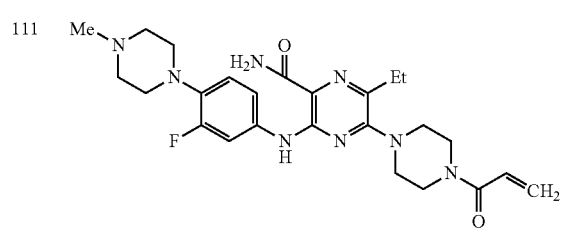 |

TABLE 117

| Ex | Str |
|---|---|
| 112 | (structure) |
| 113 | (structure) |
| 114 | (structure) |
| 115 | (structure) |

TABLE 118

| Ex | Str |
|---|---|
| 116 | (structure) |

TABLE 118-continued
| Ex | Str |
|---|---|
| 117 | 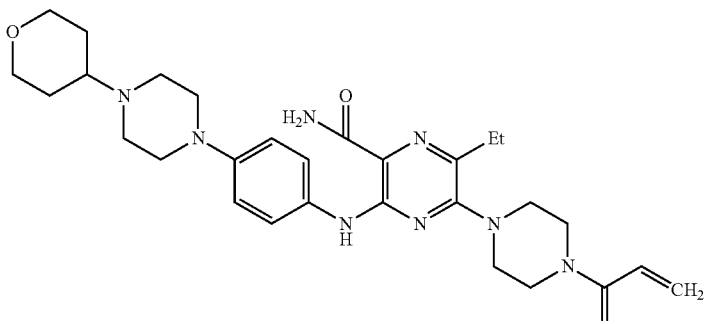 |
| 118 | 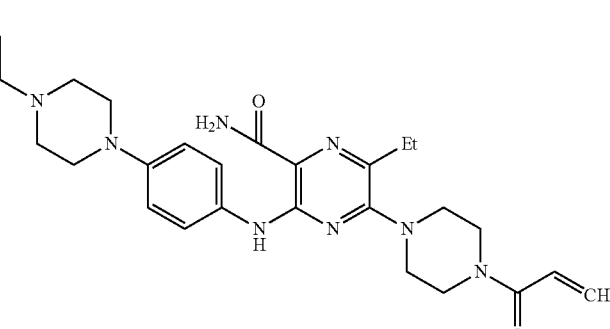 |
| 119 | 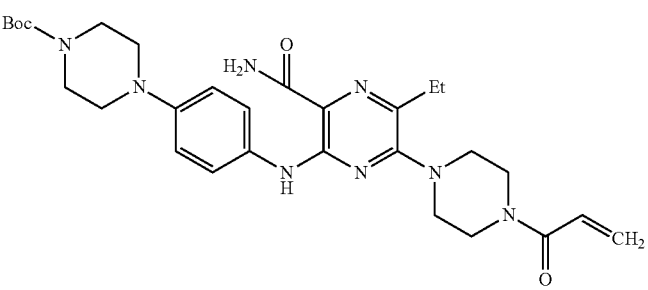 [SMILES: C=CC(=O)N1CCN(c2nc(Nc3ccc(N4CCN(C(=O)OC(C)(C)C)CC4)cc3)c(C(N)=O)nc2CC)CC1] |
TABLE 119
| Ex | Str |
|---|---|
| 120 | 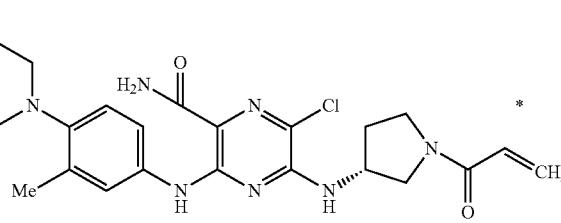 |

TABLE 119-continued
| Ex | Str |
|---|---|
| 121 | 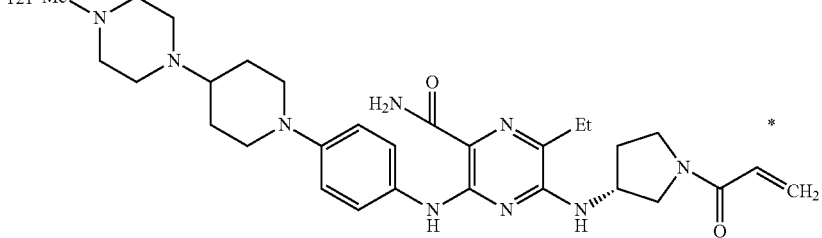 |
| 122 | 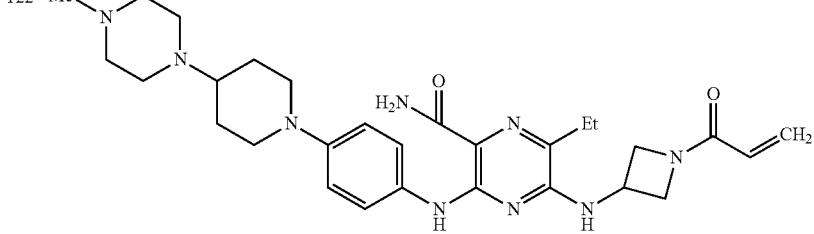 |
| 123 | 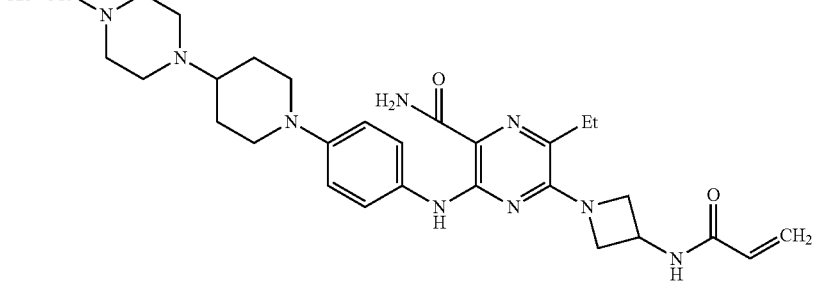 |
TABLE 120
| Ex | Str |
|---|---|
| 124 | 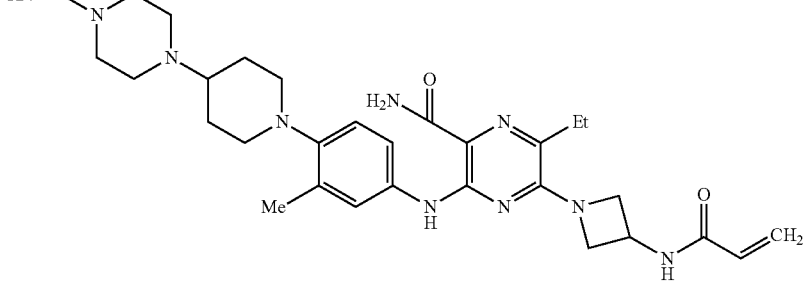 |
| 125 | 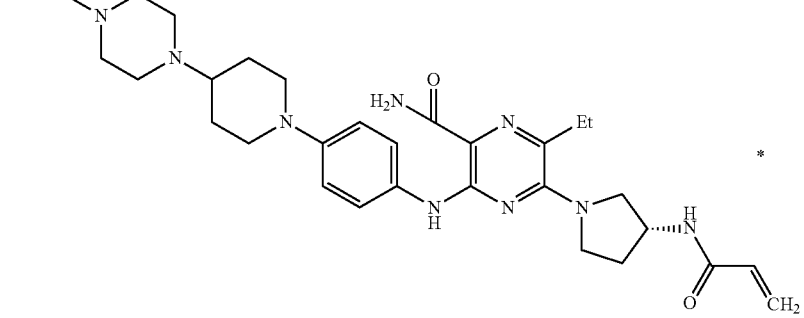 |

TABLE 120-continued
| Ex | Str |
|---|---|
| 126 | 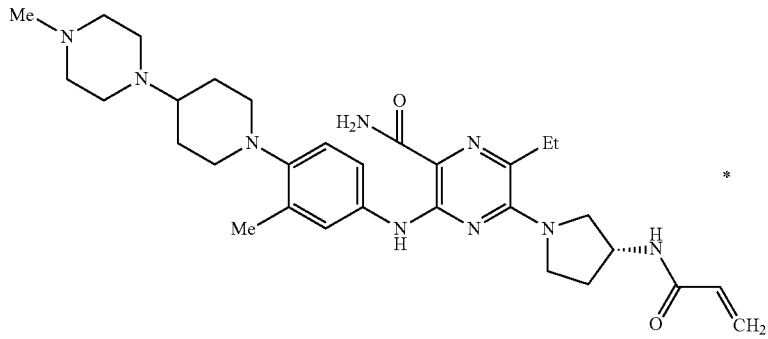 [SMILES: C=CC(=O)N[C@@H]1CCN(c2nc(Nc3ccc(N4CCC(N5CCN(C)CC5)CC4)c(C)c3)c(C(N)=O)nc2CC)C1] |
| 127 | 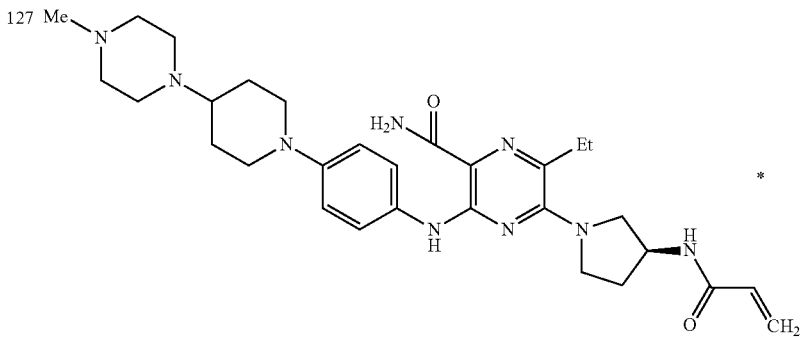 |
TABLE 121
| Ex | Str |
|---|---|
| 128 | 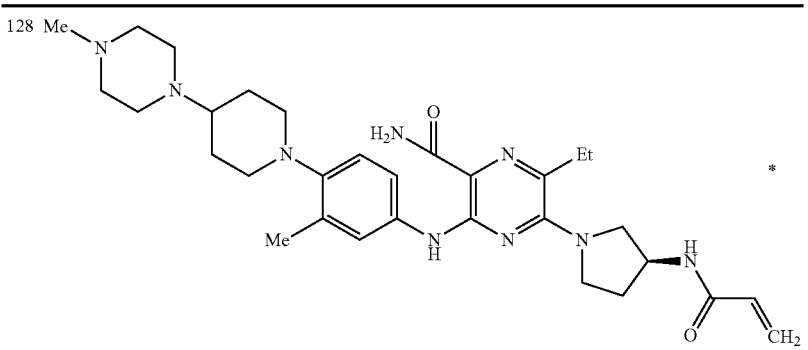 |
| 129 | 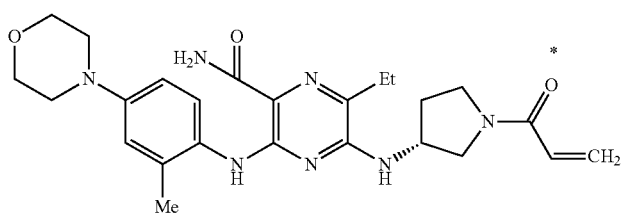 |
| 130 | 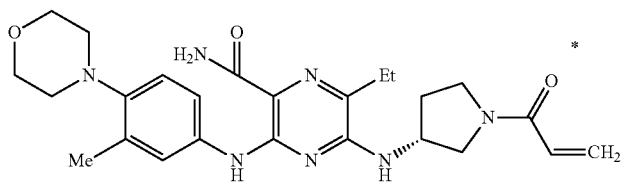 |

TABLE 121-continued

| Ex | Str |
|---|---|
| 131 | (structure) |

TABLE 122

| Ex | Str |
|---|---|
| 132 | (structure) |
| 133 | (structure) |
| 134 | (structure) |

TABLE 122-continued
| Ex | Str |
|---|---|
| 135 | 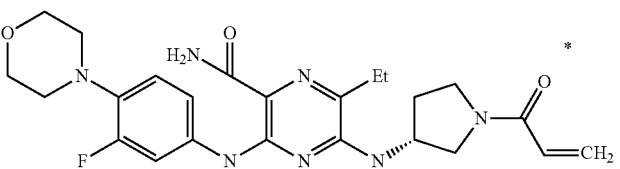 |
TABLE 123
| Ex | Str |
|---|---|
| 136 | 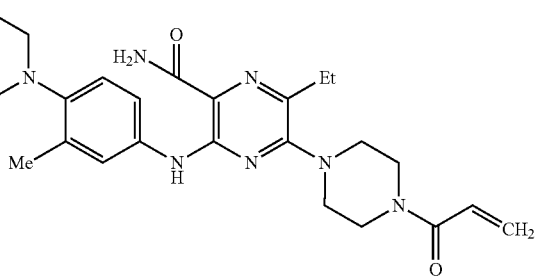 |
| 137 | 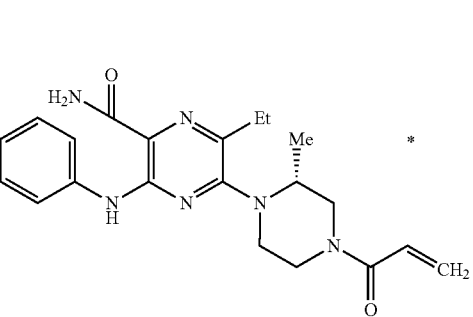 |
| 138 | 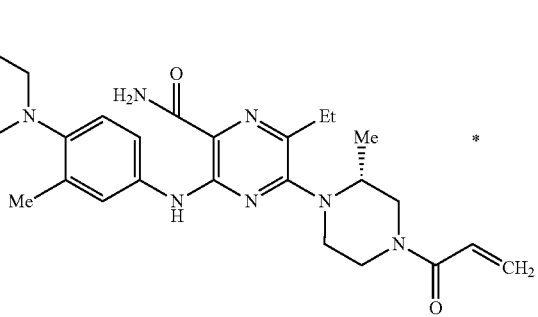 |

TABLE 123-continued
| Ex | Str |
|---|---|
| 139 | 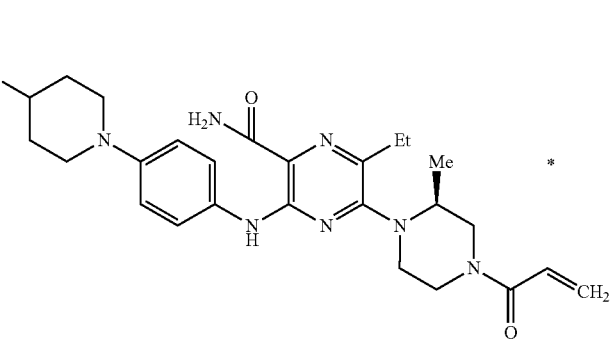 |
TABLE 124
| Ex | Str |
|---|---|
| 140 | 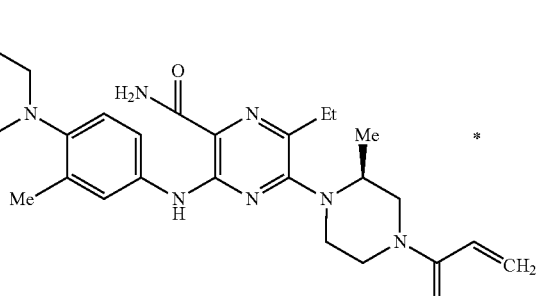 |
| 141 | 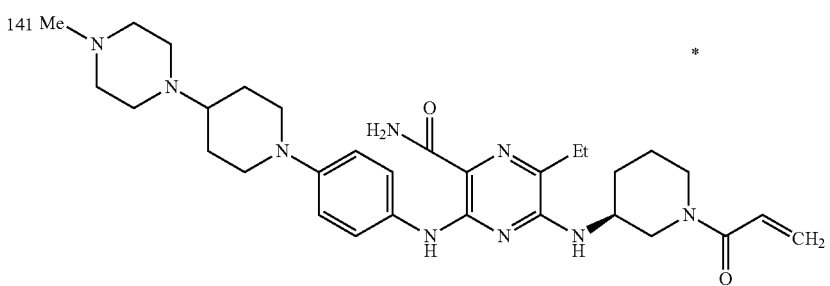 |
| 142 | 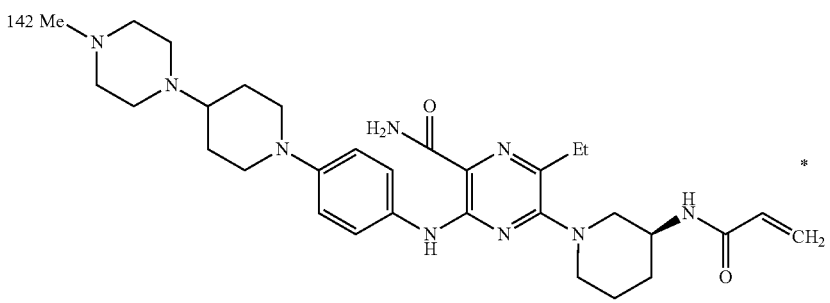 |

TABLE 124-continued
| Ex | Str |
|---|---|
| 143 | 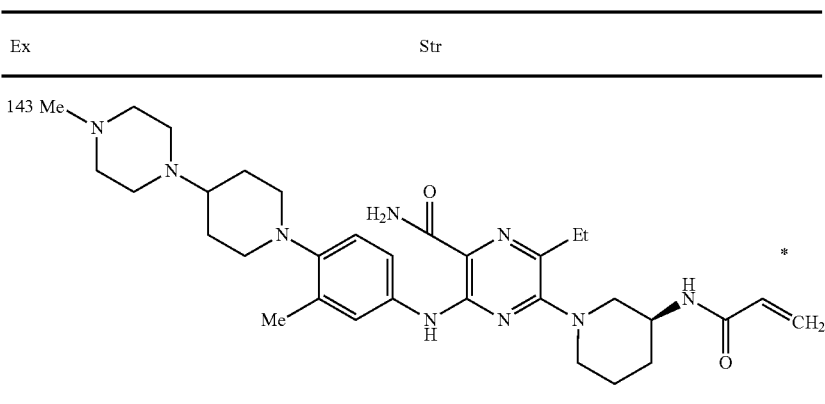 |
TABLE 125
| Ex | Str |
|---|---|
| 144 | 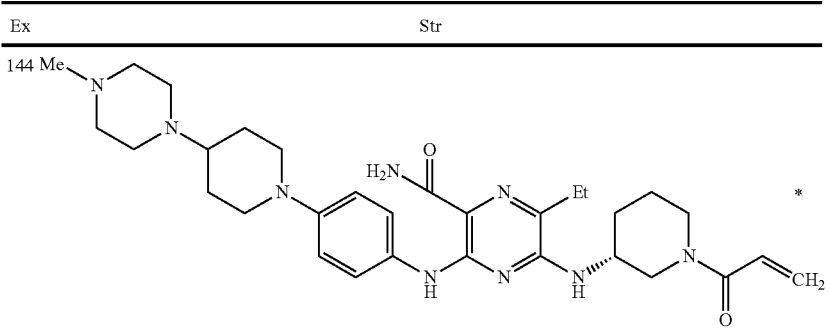 |
| 145 | 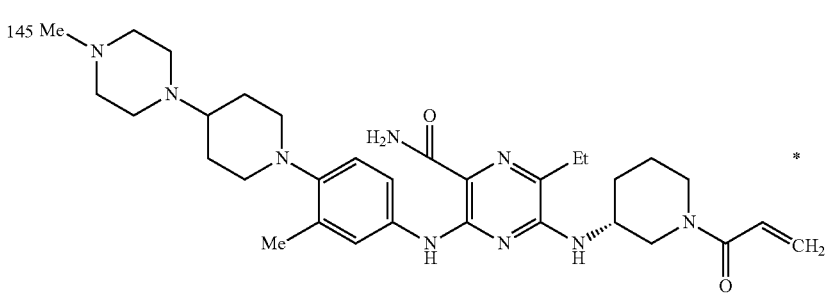 |
| 146 | 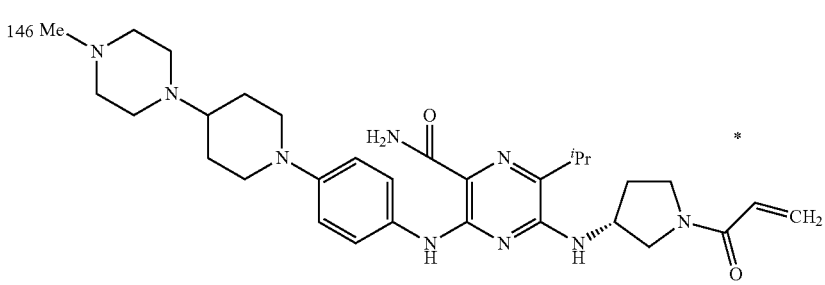 |
| 147 | 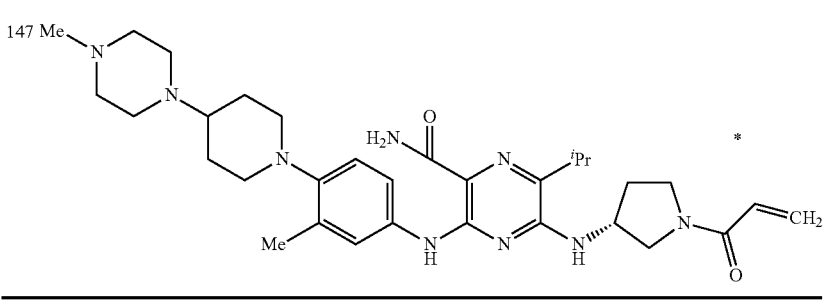 |

TABLE 126
| Ex | Str |
|---|---|
| 148 | 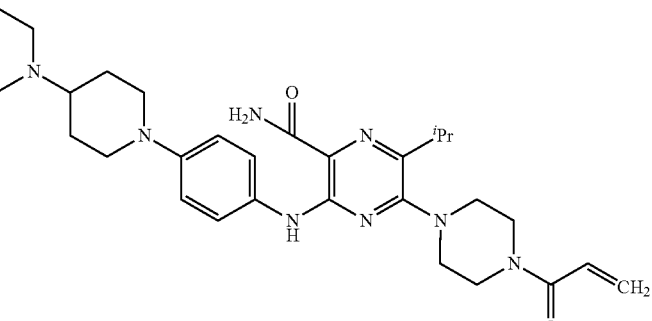 |
| 149 | 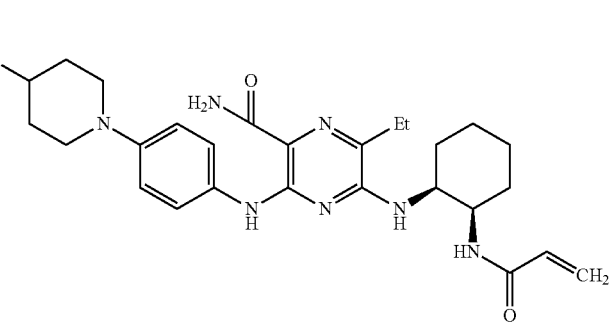 |
| 150 | 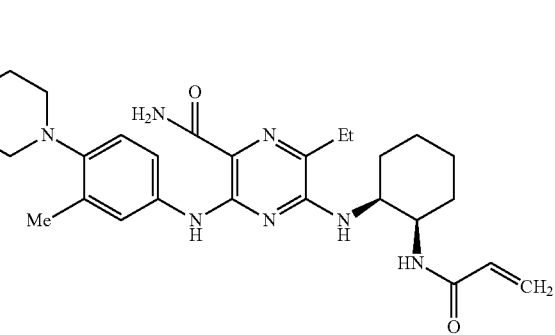 |
| 151 | 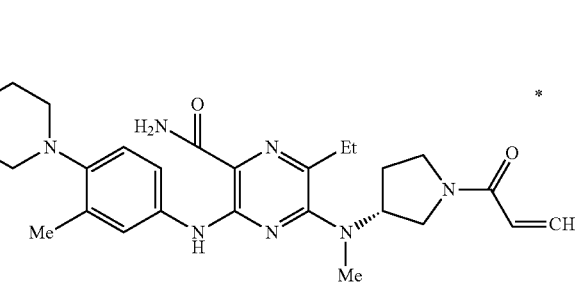 |

TABLE 127
| Ex | Str |
|---|---|
| 152 | 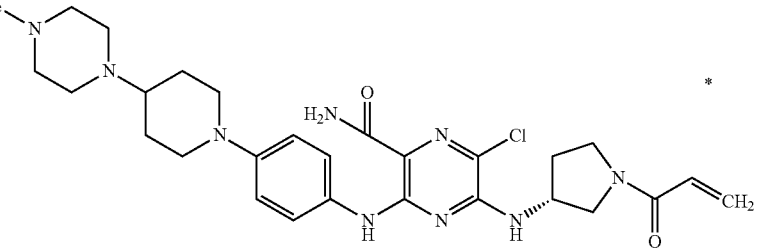 |
| 153 | 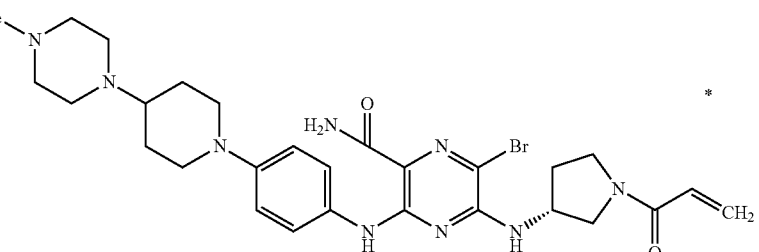 |
| 154 | 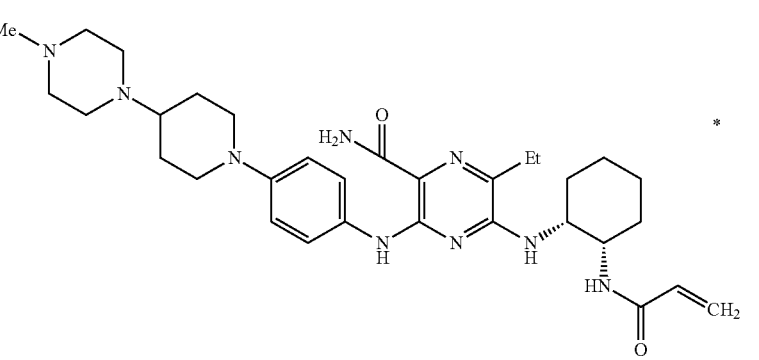 |
| 155 | 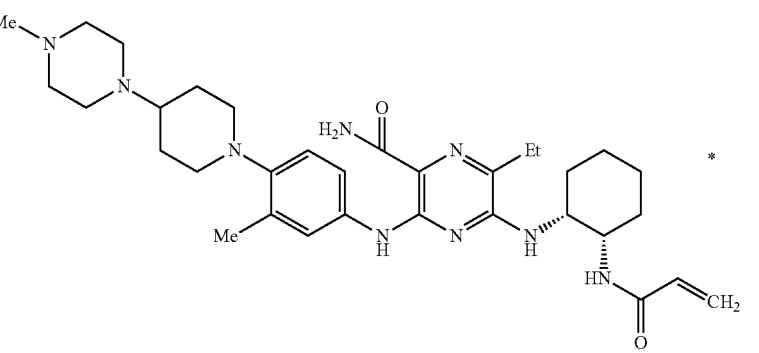 |
TABLE 128
| Ex | Str |
|---|---|
| 156 | 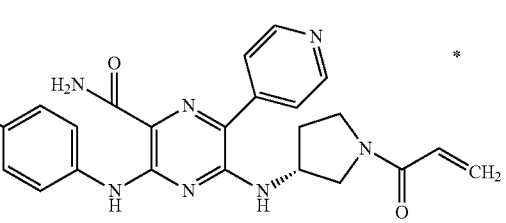 |

TABLE 128-continued

| Ex | Str |
|---|---|
| 157 | (structure) |
| 158 | (structure) |
| 159 | (structure) |

TABLE 129

| Ex | Str |
|---|---|
| 160 | (structure) * |

TABLE 129-continued
| Ex | Str |
|---|---|
| 161 | 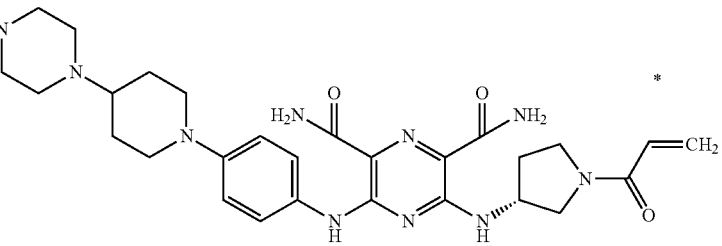 |
| 162 | 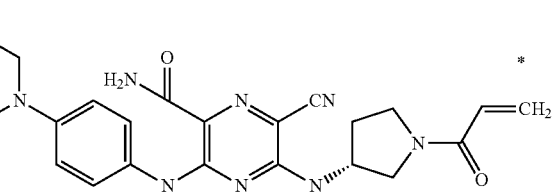 |
| 163 | 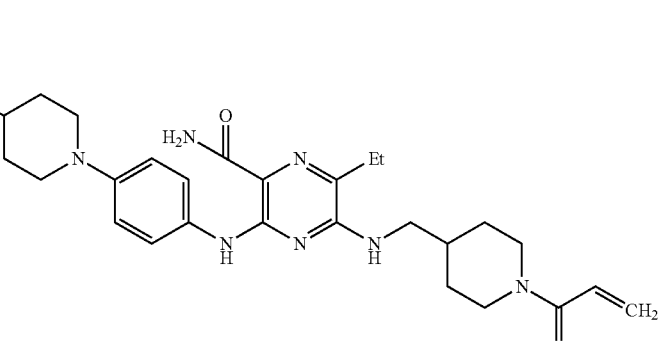 |
TABLE 130
| Ex | Str |
|---|---|
| 164 | 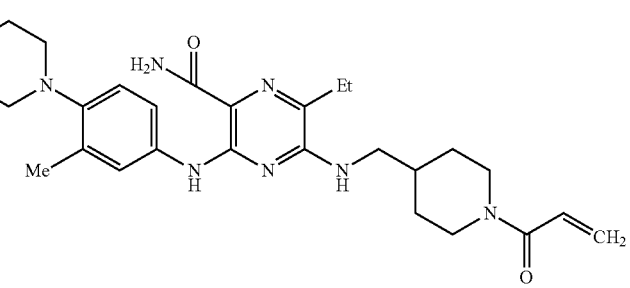 |

TABLE 130-continued
| Ex | Str |
|---|---|
| 165 | 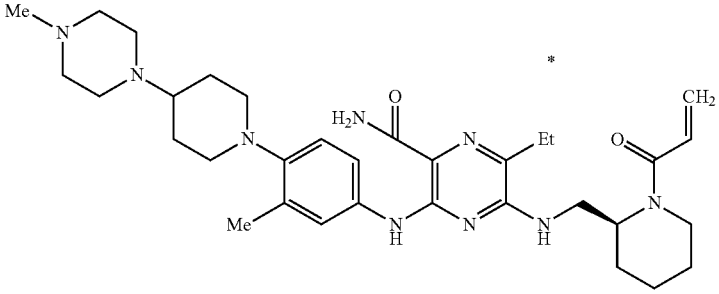 |
| 166 | 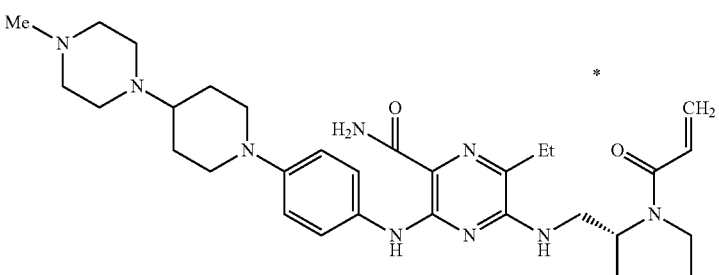 |
| 167 | 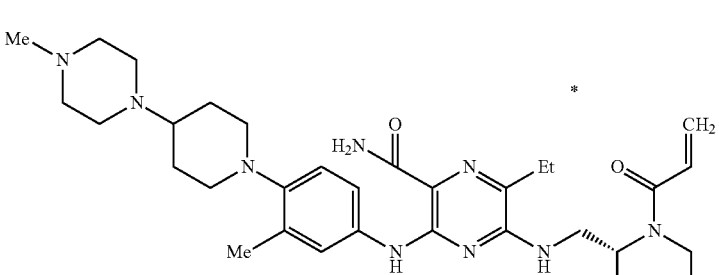 |
TABLE 131
| Ex | Str |
|---|---|
| 168 | 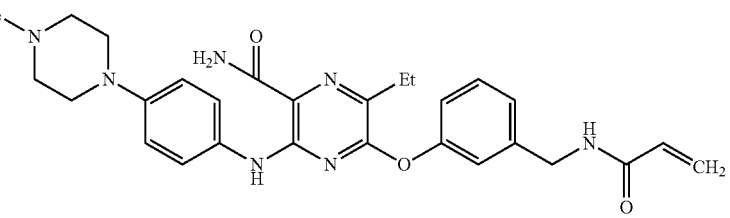 |
| 169 | 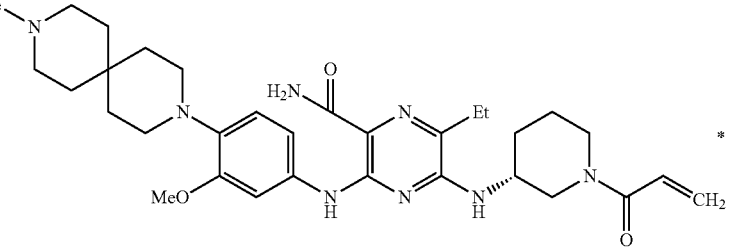 |

TABLE 131-continued
| Ex | Str |
|---|---|
| 170 | 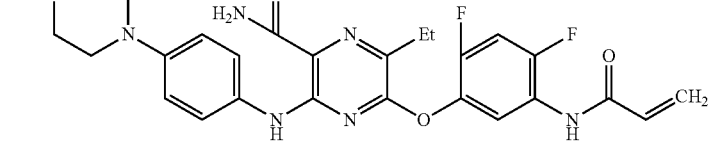 |
| 171 | |
| 172 | |
TABLE 132
| Ex | Str |
|---|---|
| 173 | 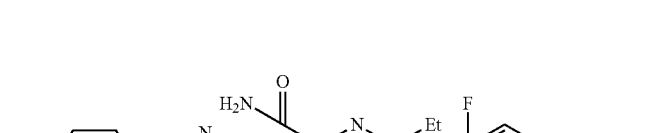 |
| 174 | 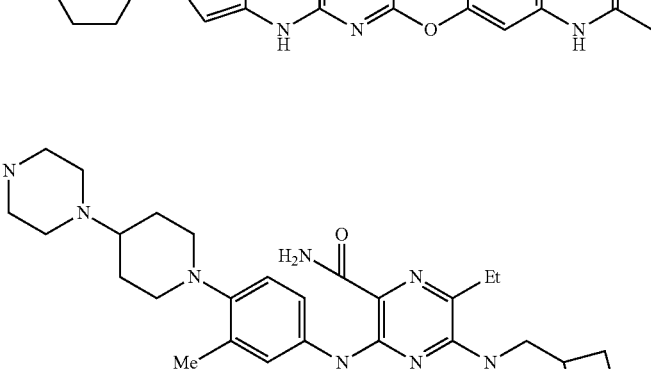 |

TABLE 132-continued

| Ex | Str |
|---|---|
| 175 | (structure) |
| 176 | (structure) |

TABLE 133

| Ex | Str |
|---|---|
| 177 | (structure) |
| 178 | (structure) |
| 179 | (structure) |

TABLE 133-continued
| Ex | Str |
|---|---|
| 180 | 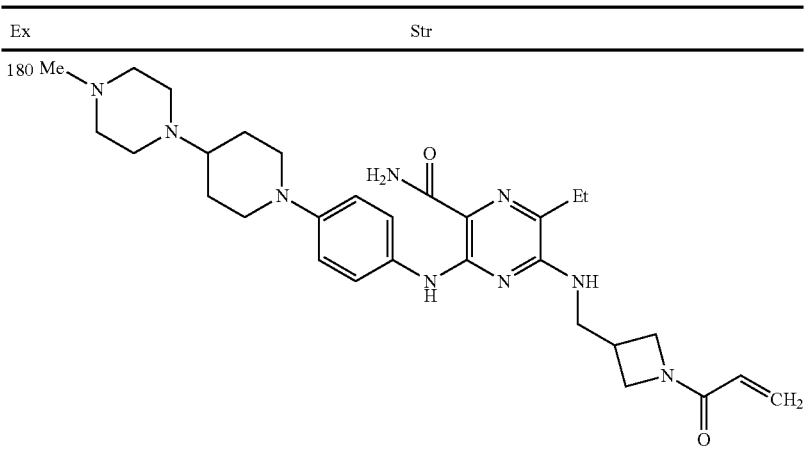 |
| 181 | 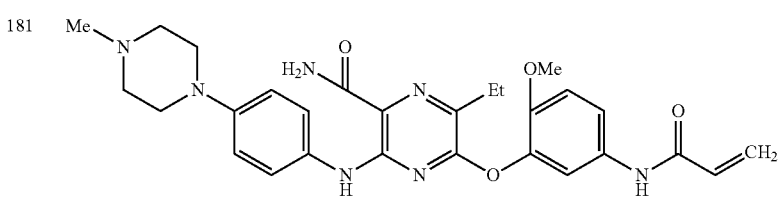 |
TABLE 134
| Ex | Str |
|---|---|
| 182 | 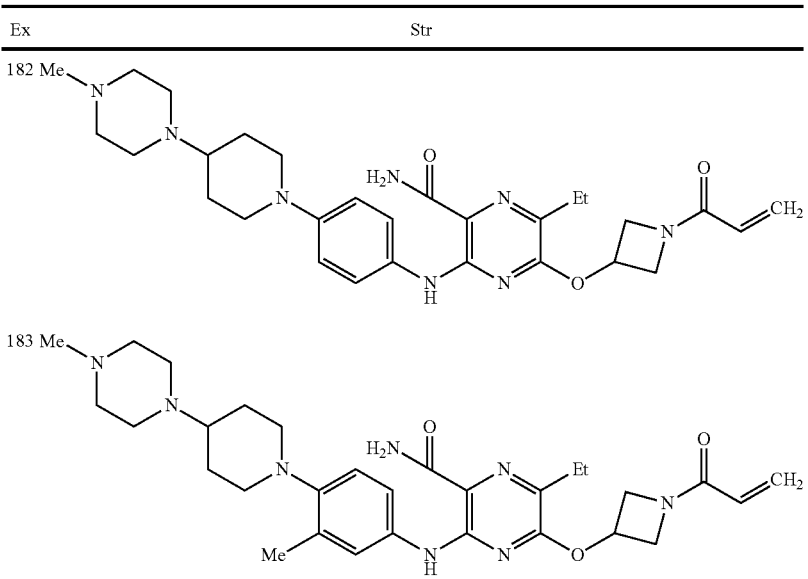 |
| 183 | |
| 184 | 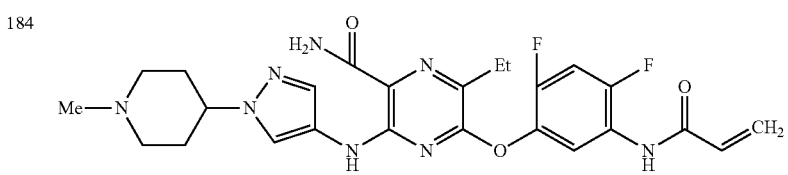 |
| 185 | 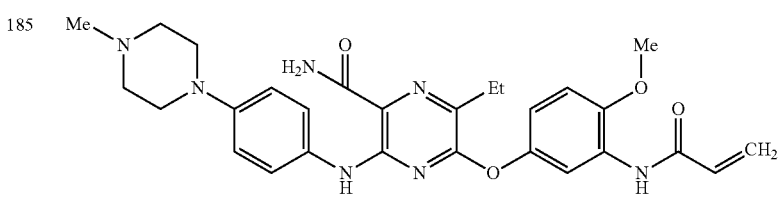 |

TABLE 134-continued
| Ex | Str |
|---|---|
| 186 | 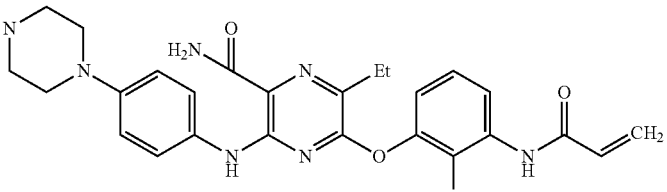 |
TABLE 135
| Ex | Str |
|---|---|
| 187 | 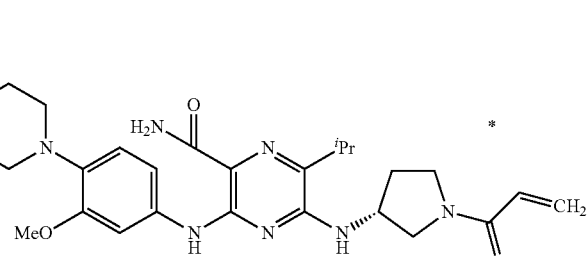 |
| 188 | 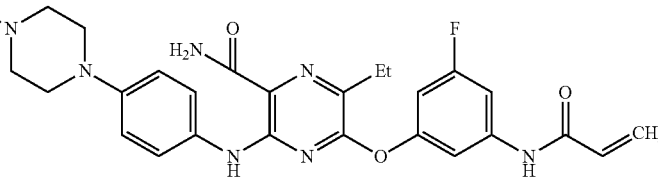 |
| 189 | 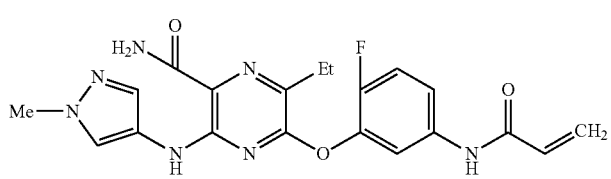 [SMILES: C=CC(=O)Nc1ccc(F)c(Oc2nc(Nc3cnn(C)c3)c(C(N)=O)nc2CC)c1] |
| 190 | 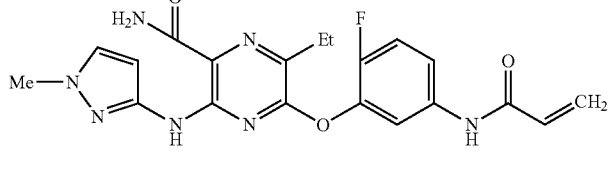 |
| 191 | 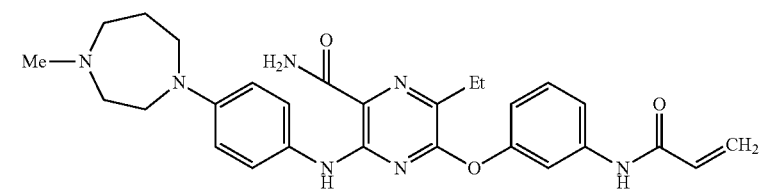 [SMILES: C=CC(=O)Nc1cccc(Oc2nc(Nc3ccc(N4CCCN(C)CC4)cc3)c(C(N)=O)nc2CC)c1] |

TABLE 136
| Ex | Str |
|---|---|
| 192 | 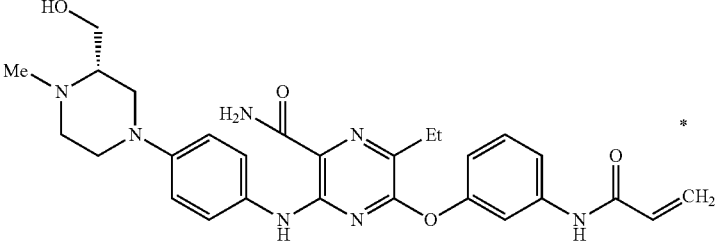 [SMILES: C=CC(=O)Nc1cccc(Oc2nc(Nc3ccc(N4CCN(C)[C@H](CO)C4)cc3)c(C(N)=O)nc2CC)c1] |
| 193 | 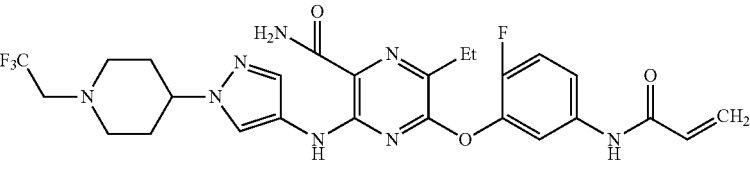 [SMILES: C=CC(=O)Nc1ccc(F)c(Oc2nc(Nc3cnn(C4CCN(CC(F)(F)F)CC4)c3)c(C(N)=O)nc2CC)c1] |
| 194 | 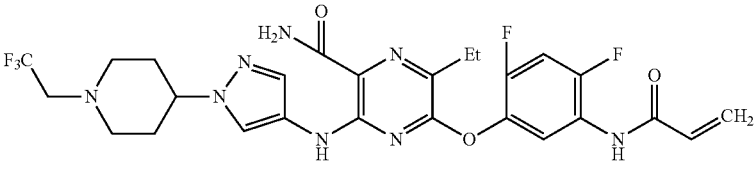 [SMILES: C=CC(=O)Nc1cc(Oc2nc(Nc3cnn(C4CCN(CC(F)(F)F)CC4)c3)c(C(N)=O)nc2CC)c(F)cc1F] |
| 195 | 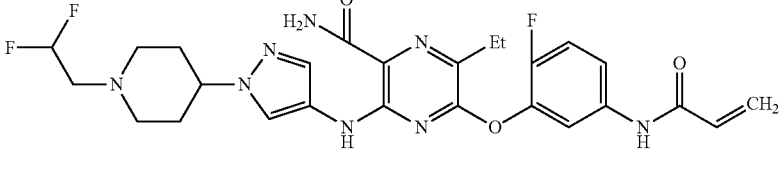 |
| 196 | 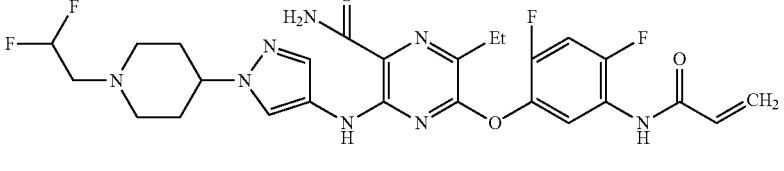 |
| 197 | 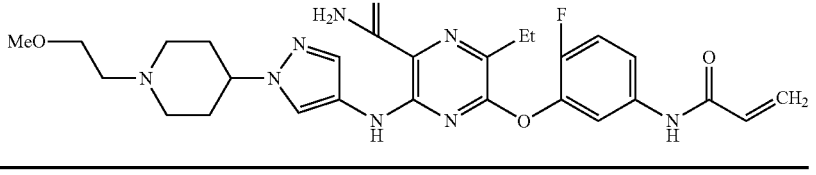 |
TABLE 137
| Ex | Str |
|---|---|
| 198 | 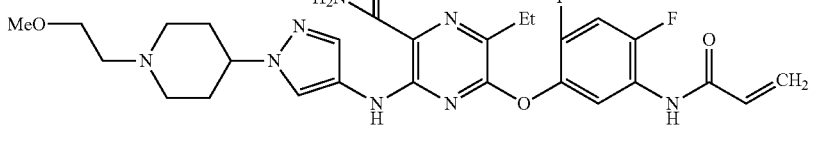 |

TABLE 137-continued
| Ex | Str |
|---|---|
| 199 | 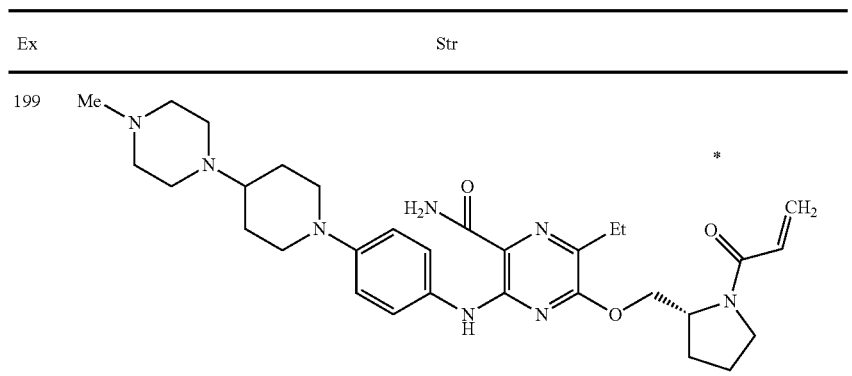 |
| 200 | 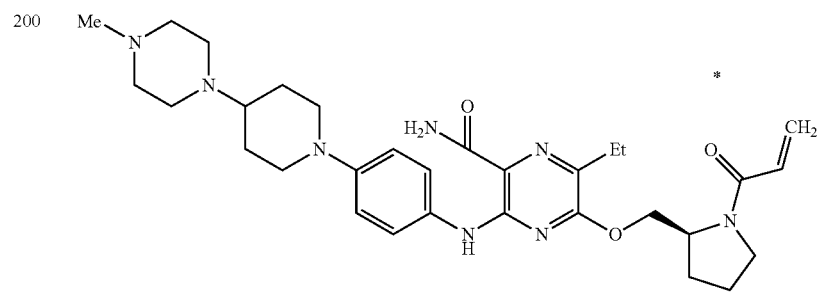 |
| 201 | 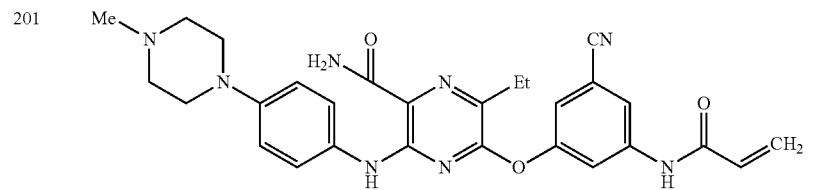 |
| 202 | 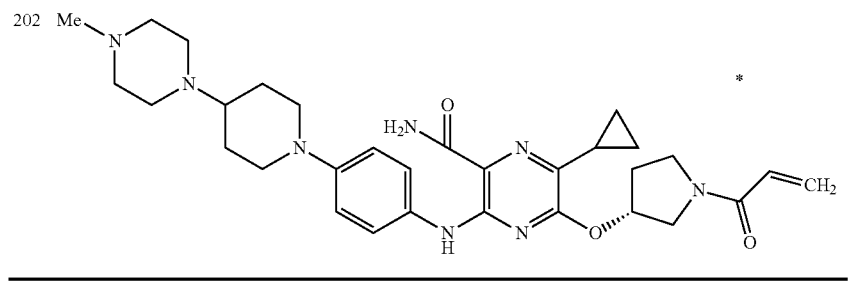 |
TABLE 138
| Ex | Str |
|---|---|
| 203 | 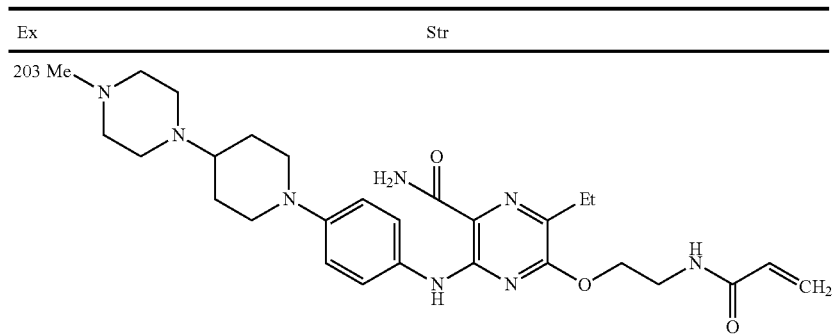 |

TABLE 138-continued
| Ex | Str |
|---|---|
| 204 | 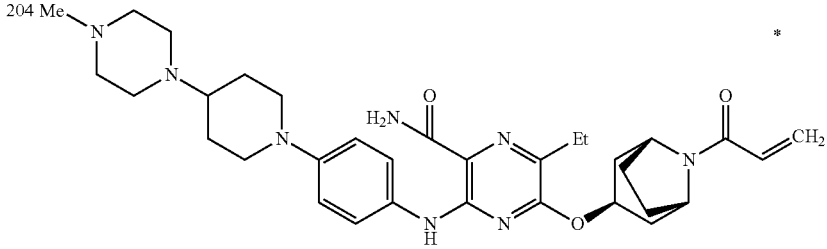 |
| 205 | 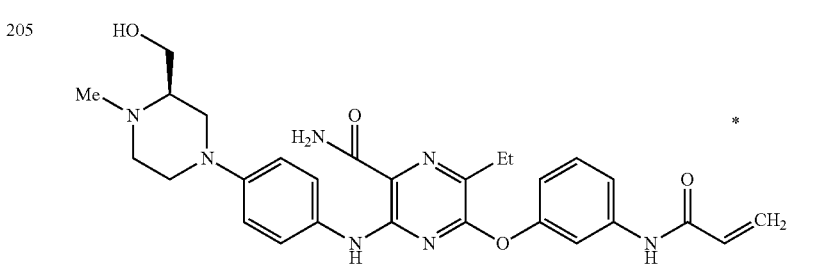 |
| 206 | 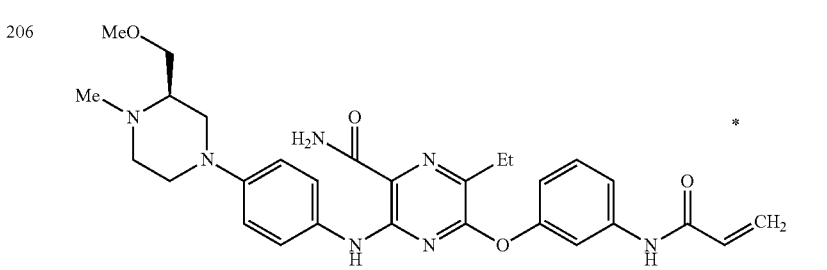 |
| 207 | 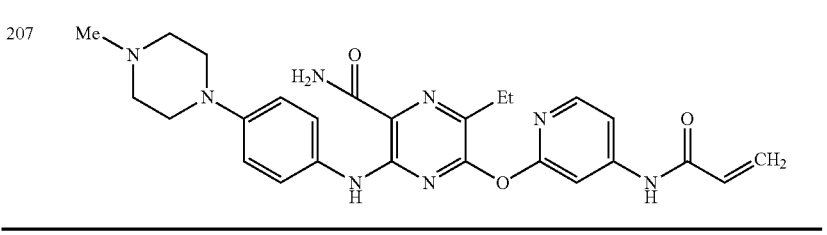 |
TABLE 139
| Ex | Str |
|---|---|
| 208 | 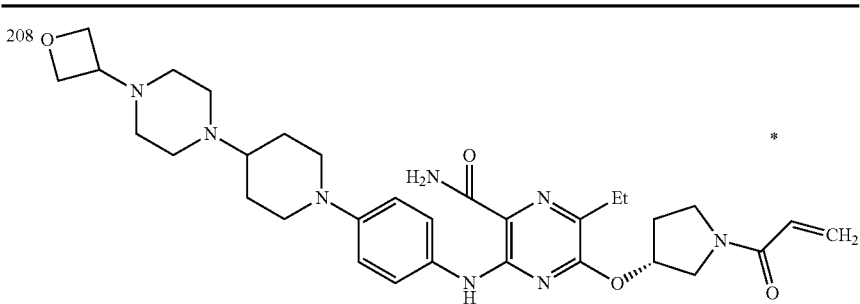 |

TABLE 139-continued

| Ex | Str |
|---|---|
| 209 | (structure) |
| 210 | (structure) |
| 211 | (structure) |
| 212 | (structure) |

TABLE 140

| Ex | Str |
|---|---|
| 213 | (structure) |

TABLE 140-continued
| Ex | Str |
|---|---|
| 214 | 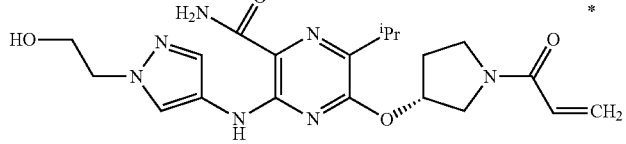 |
| 215 | 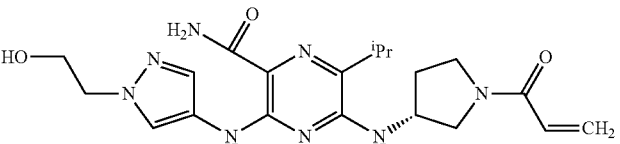 |
| 216 | 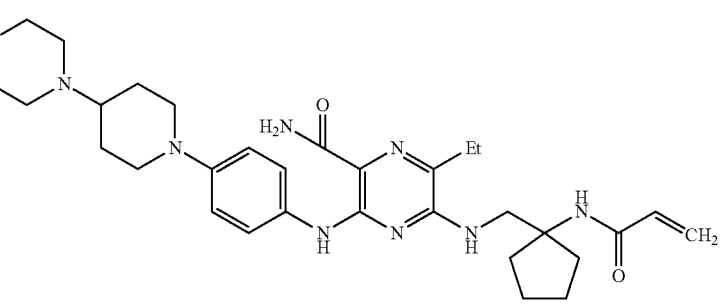 |
| 217 | 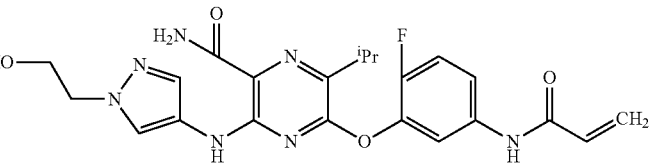 |
TABLE 141
| Ex | Str |
|---|---|
| 218 | 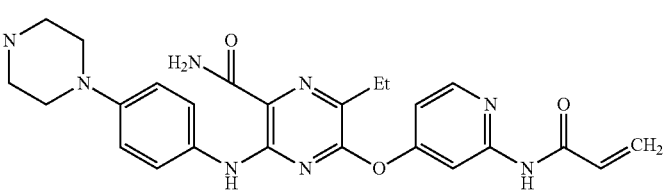 |
| 219 | 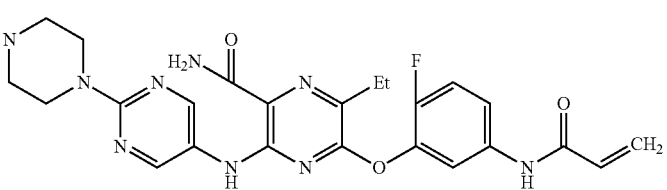 |

TABLE 141-continued

| Ex | Str |
|---|---|
| 220 | (structure) |
| 221 | (structure) |

TABLE 142

| Ex | Str |
|---|---|
| 222 | (structure) |
| 223 | (structure) |

TABLE 142-continued

| Ex | Str |
|---|---|
| 224 | (structure) |
| 225 | (structure) |

TABLE 143

| Ex | Str |
|---|---|
| 226 | (structure) |
| 227 | (structure) * |
| 228 | (structure) * |

TABLE 143-continued

| Ex | Str |
|---|---|
| 229 | (structure) |

TABLE 144

| Ex | Str |
|---|---|
| 230 | (structure) |
| 231 | (structure) |
| 232 | (structure) |

TABLE 144-continued

| Ex | Str |
|---|---|
| 233 | (structure) |

TABLE 145

| Ex | Str |
|---|---|
| 234 | (structure) |
| 235 | (structure) |
| 236 | (structure) |

TABLE 145-continued
| Ex | Str |
|---|---|
| 237 | 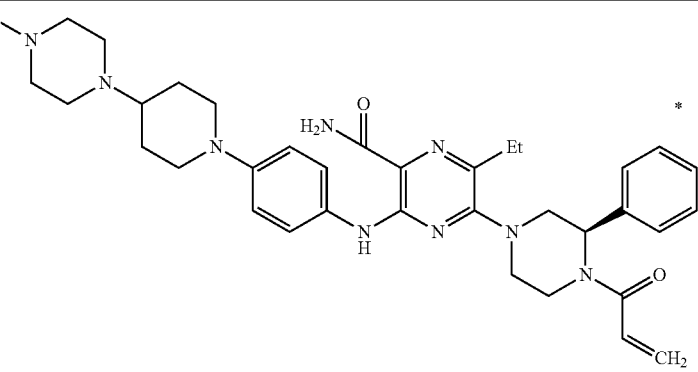 |
TABLE 146
| Ex | Str |
|---|---|
| 238 | 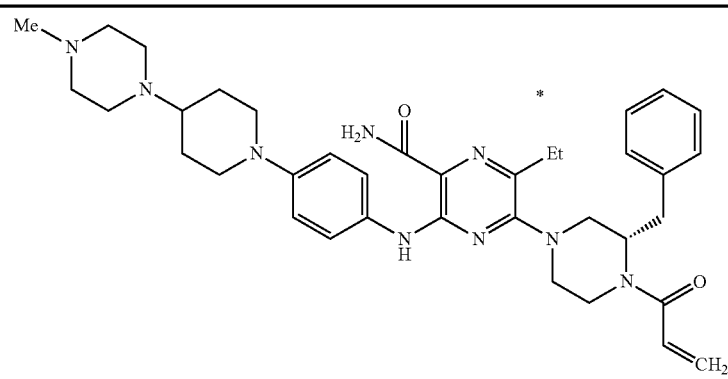 |
| 239 | 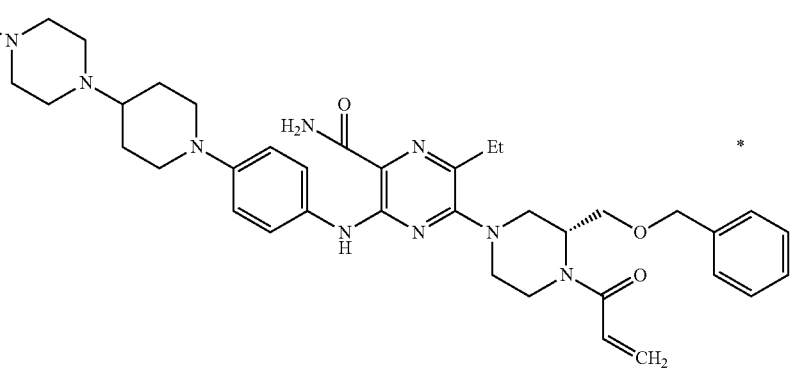 |
| 240 | 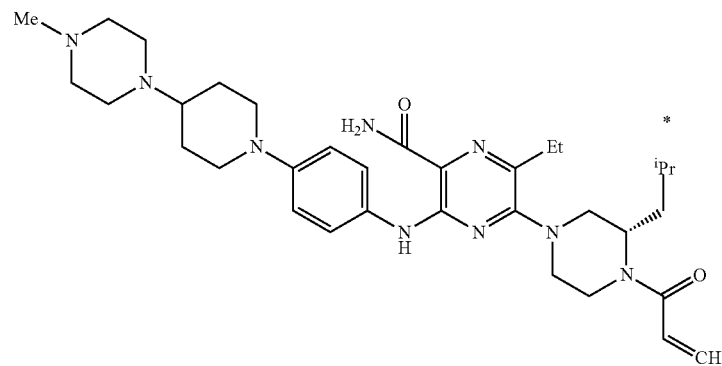 |

TABLE 147
| Ex | Str |
|---|---|
| 241 | 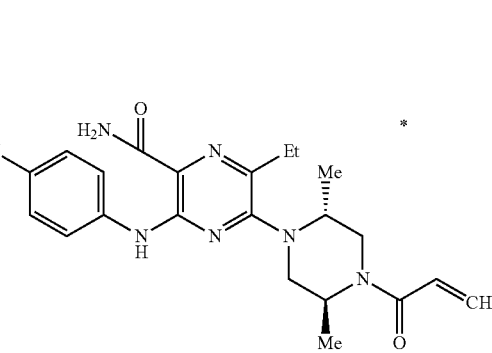 |
| 242 | 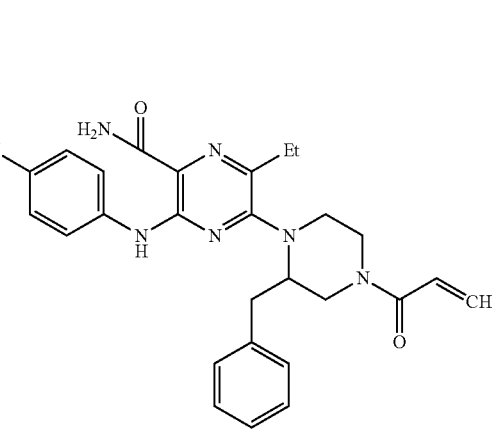 |
| 243 | 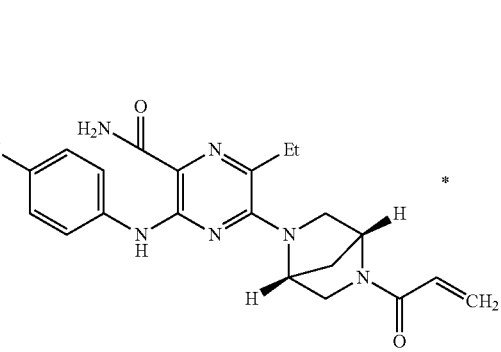 |
TABLE 148
| Ex | Str |
|---|---|
| 244 | 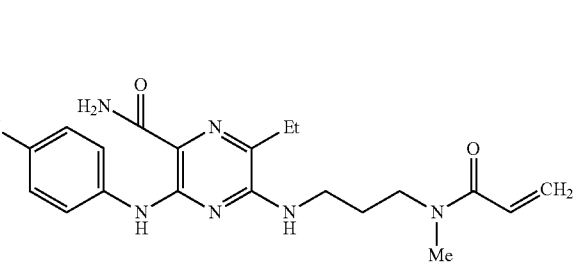 |

TABLE 148-continued
| Ex | Str |
|---|---|
| 245 | 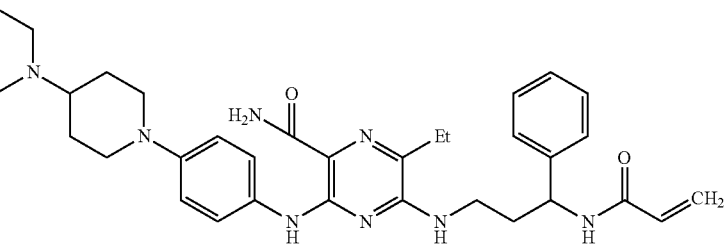 |
| 246 | 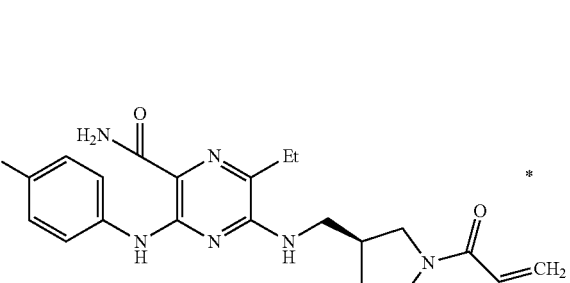 |
| 247 | 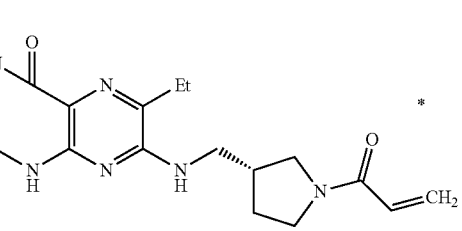 |
TABLE 149
| Ex | Str |
|---|---|
| 248 | 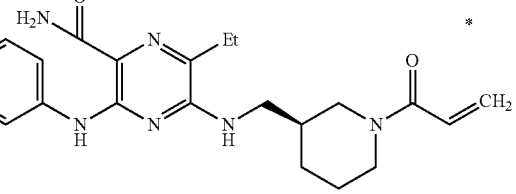 |
| 249 | 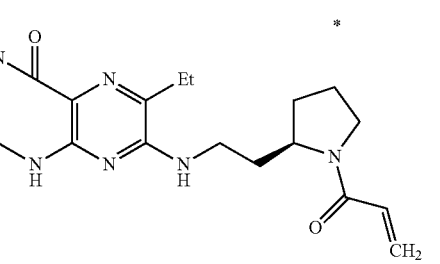 |

TABLE 149-continued
| Ex | Str |
|----|-----|
| 250 | 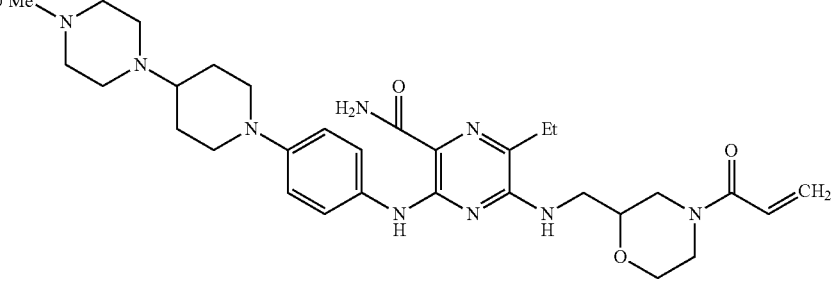 |
| 251 | 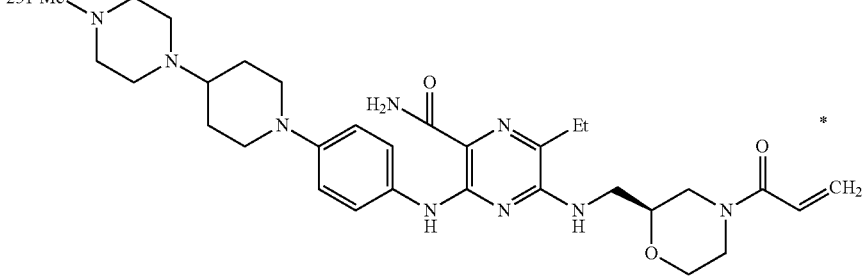 |
TABLE 150
| Ex | Str |
|----|-----|
| 252 | 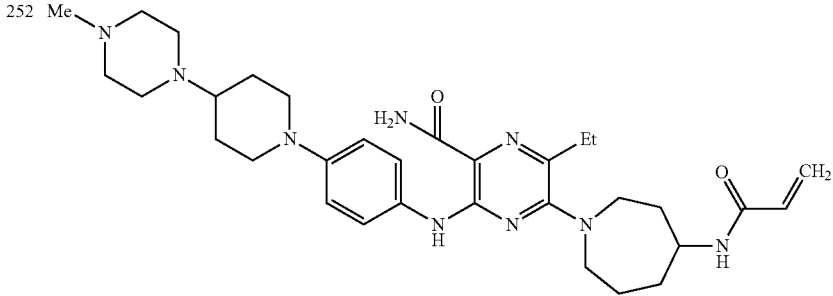 |
| 253 | 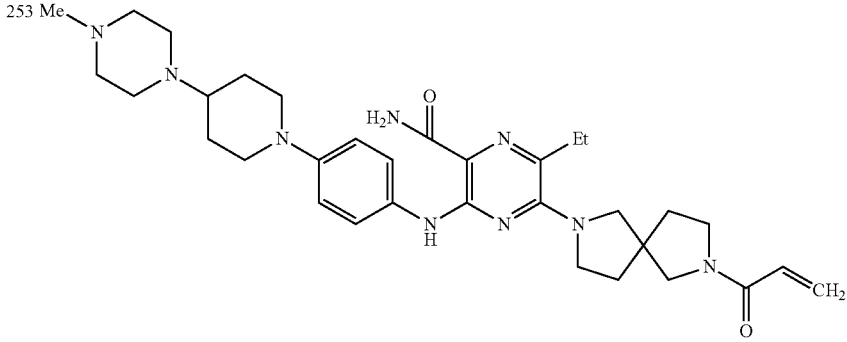 |

TABLE 150-continued

| Ex | Str |
|---|---|
| 254 | Me-N(piperazine)-N-(piperidine)-N-phenyl-NH-[pyrazine with H2N-C(=O), Et, and NH-CH2CH2-N(cyclopropyl)-C(=O)-CH=CH2 substituents] |

TABLE 151

| Ex | Syn | Data |
|---|---|---|
| 1 | E1 | ESI+: 502<br>1H-NMR(DMSO-d6): 1.32(3H, t, J = 7.5 Hz), 2.22(3H, s), 2.38-2.47(4H, m), 2.84(2H, q, J = 7.5 Hz), 2.92-3.00(4H, m), 5.77(1H, dd, J = 2.0, 10.0 Hz), 6.26 (1H, dd, J = 2.0, 16.9 Hz), 6.43(1H, dd, J = 10.0, 16.9 Hz), 6.57(2H, d, J = 9.1 Hz), 6.94-6.99(1H, m), 7.08(2H, d, J = 9.1 Hz), 7.42-7.49(1H, m), 7.63-7.69(3H, m), 7.93-7.97(1H, m), 10.34(1H, s), 10.93(1H, s) |
| 2 | E2 | ESI+: 564, 566 |
| 3 | E3 | ESI+: 559<br>1H-NMR(DMSO-d6):1.32(3H, t, J = 7.5 Hz), 2.16(6H, s), 2.21(3H, s), 2.38-2.43(4H, m), 2.84(2H, q, J = 7.5 Hz), 2.92-2.98(4H, m), 3.02-3.07(2H, m), 6.23-6.30(1H, m), 6.57(2H, d, J = 9.1 Hz), 6.69-6.78(1H, m), 6.91-6.96(1H, m), 7.07(2H, d, J = 9.1 Hz), 7.43(1H, t, J = 8.1 Hz), 7.59-7.69(3H, m), 7.92-7.96(1H, m), 10.25(1H, s), 10.92(1H, s) |
| 4 | E4 | ESI+: 615 |
| 5 | E5 | ESI+: 586 |
| 6 | E6 | ESI+: 532 |
| 7 | E7 | ESI+: 532 |
| 8 | E8 | ESI+: 516 |
| 9 | E1 | ESI+: 585 |
| 10 | E1 | ESI+: 615 |
| 11 | E1 | ESI+: 615 |
| 12 | E1 | ESI+: 502 |
| 13 | E1 | ESI+: 502 |
| 14 | E1 | ESI+: 516 |
| 15 | E1 | ESI+: 516<br>1H-NMR(DMSO-d6): 1.34(3H, t, J = 7.5 Hz), 2.01(3H, s), 2.20(3H, s), 2.37-2.45(4H, m), 2.88(2H, q, J = 7.5 Hz), 2.93-3.02(4H, m), 5.72-5.82(1H, m), 6.27(1H, dd, J = 2.1, 17.0 Hz), 6.53-6.66(3H, m), 6.96(2H, d, J = 9.1 Hz), 7.03(1H, d, J = 7.7 Hz), 7.32(1H, t, J = 8.1 Hz), 7.62-7.72(2H, m), 7.91-7.97 (1H, m), 9.60(1H, s), 10.95(1H, s) |
| 16 | E1 | ESI+: 516 |
| 17 | E1 | ESI+: 532 |
| 18 | E1 | ESI+: 516 |
| 19 | E1 | ESI+: 570 |
| 20 | E1 | ESI+: 520 |
| 21 | E1 | ESI+: 599 |

TABLE 152

| Ex | Syn | Data |
|---|---|---|
| 22 | E1 | ESI+: 516<br>1H-NMR(DMSO-d6): 1.33(6H, d, J = 6.9 Hz), 2.21(3H, s), 2.38-2.44(4H, m), 2.92-2.99(4H, m), 3.31-3.41(1H, m), 5.75-5.79(1H, m), 6.26(1H, dd, J = 2.0, 17.0 Hz), 6.43(1H, dd, J = 10.0, 17.0 Hz), 6.57(2H, d, J = 9.1 Hz), 6.94-6.98(1H, m), 7.07(2H, d, J = 9.1 Hz), 7.42-7.49(1H, m), 7.62-7.72(3H, m), 7.88-7.92(1H, m), 10.34(1H, s), 10.91(1H, s) |
| 23 | E1 | ESI+: 573 |
| 24 | E1 | ESI+: 575<br>1H-NMR(DMSO-d6): 1.25(3H, t, J = 7.5 Hz), 1.48-1.88(8H, m), 2.17 (3H, s), 2.18(3H, s), 2.20-2.60(11H, m), 2.76-2.86(3H, m), 2.97-3.06(2H, m), 3.20-3.32(2H, m), 4.15-4.24(1H, m), 4.52-4.61(1H, m), 5.69(1H, dd, J = 2.5, 10.4 Hz), 6.12(1H, dd, J = 2.5, 16.7 Hz), 6.86(1H, dd, J = 10.4, 16.7H z), 6.92(1H, d, J = 8.6 Hz), 7.30(1H, dd, J = 2.5, 8.6 Hz), 7.58(1H, d, J = 2.5 Hz), 7.81-7.85(1H, m), 8.10-8.14(1H, m), 10.85(1H, s) |
| 25 | E1 | ESI+: 570 |
| 26 | E1 | ESI+: 474<br>1H-NMR(DMSO-d6): 2.21(3H, s), 2.36-2.46(4H, m), 2.91-3.04(4H, m), 5.78(1H, dd, J = 2.0, 10.1 Hz), 6.26(1H, dd, J = 2.0, 17.0 Hz), 6.44(1H, dd, J = 10.1, 17.0 Hz), 6.62(2H, d, J = 9.1 Hz), 6.94-7.01(1H, m), 7.15(2H, d, J = 9.1 Hz), 7.41-7.49(1H, m), 7.60-7.73(3H, m), 7.78(1H, s), 8.07-8.15(1H, m), 10.35(1H, s), 11.17(1H, s) |
| 27 | E1 | ESI+: 501 |
| 28 | E1 | ESI+: 502 |
| 29 | E1 | ESI+: 516 |
| 30 | E1 | ESI+: 489 |
| 31 | E1 | ESI+: 533 |
| 32 | E1 | ESI+: 503 |
| 33 | E1 | ESI+: 503 |
| 34 | E1 | ESI+: 523, 525 |

TABLE 152-continued

| Ex | Syn | Data |
|----|-----|------|
| 35 | E1 | ESI+: 517 |
| 36 | E1 | ESI+: 491 |
| 37 | E4 | ESI+: 599 |
| 38 | E1 | ESI+: 507 |
| 39 | E1 | ESI+: 504 |
| 40 | E1 | ESI+: 480 |
| 41 | E3 | ESI+: 573 |

TABLE 153

| Ex | Syn | Data |
|----|-----|------|
| 42 | E1 | ESI+: 532<br>1H-NMR(DMSO-d6): 1.30(3H, t, J = 7.5 Hz), 2.17(3H, s), 2.30-2.40(4H, m), 2.69-2.77(4H, m), 2.83(2H, q, J = 7.5 Hz), 3.66(3H, s), 5.76(1H, dd, J = 2.0, 10.1 Hz), 6.25(1H, dd, J = 2.0, 17.0 Hz), 6.43(1H, dd, J = 10.1, 17.0 Hz), 6.51(1H, d, J = 8.9 Hz), 6.70(1H, d, J = 2.6 Hz), 6.86(1H, dd, J = 2.5, 8.8 Hz), 6.93(1H, ddd, J = 0.8, 2.3, 8.1 Hz), 7.40(1H, t, J = 8.1 Hz), 7.54-7.58(1H, m), 7.63(1H, t, J = 2.1 Hz), 7.69-7.72(1H, m), 7.97-8.00(1H, m), 10.29(1H, s), 11.00(1H, s) |
| 43 | E1 | ESI+: 516<br>1H-NMR(DMSO-d6): 1.03(3H, t, J = 7.2 Hz), 1.32(3H, t, J = 7.5 Hz), 2.35 (2H, q, J = 7.2 Hz), 2.42-2.48(4H, m), 2.84(2H, q, J = 7.5 Hz), 2.93 -2.98(4H, m), 5.77(1H, dd, J = 2.0, 10.1 Hz), 6.26(1H, dd, J = 2.0, 17.0 Hz), 6.43(1H, dd, J = 10.1, 17.0 Hz), 6.57(2H, d, J = 9.1 Hz), 6.96(1H, ddd, J = 1.0, 2.2, 8.1 Hz), 7.07(2H, d, J = 9.1 Hz), 7.45(1H, t, J = 8.4 Hz), 7.62-7.69(3H, m), 7.91 -7.97 (1H, m), 10.33(1H, s), 10.92(1H, s) |
| 44 | E1 | ESI+: 559 |
| 45 | E4 | ESI+: 587 |
| 46 | E4 | ESI+: 613 |
| 47 | E1 | ESI+: 515 |
| 48 | E1 | ESI+: 475 |
| 49 | E1 | ESI+: 473 |
| 50 | E1 | ESI+: 501 |
| 51 | E1 | ESI+: 434 |
| 52 | E1 | ESI+: 531 |
| 53 | E1 | ESI+: 518 |
| 54 | E1 | ESI+:563<br>1H-NMR(DMSO-d6): 1.16(3H, t, J = 7.5 Hz), 1.42-1.58(2H, m), 1.78-1.89 (2H, m), 2.07-2.71(18H, m), 3.20-3.99(6H, m), 5.46-5.57(1H, m), 5.62-5.72(1H, m), 6.10-6.19(1H, m), 6.49-6.68(1H, m), 6.90-6.96(2H, m), 7.40-7.47(2H, m), 7.54-7.58(1H, m), 7.81-7.85(1H, m), 10.94-11.00 (1H, m) |
| 55 | E1 | ESI+: 577 |
| 56 | E1 | ESI+: 505<br>1H-NMR(DMSO-d6): 1.32(6H, d, J = 6.9 Hz), 1.58-1.75(4H, m), 1.93-2.02 (2H, m), 2.20(3H, s), 2.74-2.83(2H, m), 3.31-3.41(1H, m), 3 .55-3 .65 (1H, m), 5.77(1H, dd, J = 2.0, 10.1 Hz), 6.25(1H, dd, J = 2.0, 17.0 Hz), 6.42 (1H, dd, J = 10.1, 17.0 Hz), 6.96-7.01(1H, m), 7.09-7.12(1H, m), 7.29-7.31 (1H, m), 7.46-7.52(1H, m), 7.62-7.71(3H, m), 7.84-7.90(1H, m), 10.34 (1H, s), 10.69(1H, s) |

TABLE 154

| Ex | Syn | Data |
|----|-----|------|
| 57 | E1 | ESI+: 508, 510 |
| 58 | E1 | ESI+: 552, 554 |
| 59 | E1 | ESI+: 551 |
| 60 | E1 | ESI+: 550 |
| 61 | E1 | ESI+: 519 |
| 62 | E1 | ESI+: 531 |
| 63 | E1 | ESI+: 516<br>1H-NMR(DMSO-d6): 1.03(3H, d, J = 6.1 Hz), 1.32(3H, t, J = 7.5 Hz), 2.04-2.13(1H, m), 2.16-2.26(5H, m), 2.54-2.63(1H, m), 2.73-2.79(1H, m), 2.84(2H, q, J = 7.5 Hz), 3.25-3.35(2H, m), 5.77(1H, dd, J = 2.0, 10.0 Hz), 6.26 (1H, dd, J = 2.0, 17.0 Hz), 6.44(1H, dd, J = 10.0, 17.0 Hz), 6.57(2H, d, J = 9.1 Hz), 6.96(1H, ddd, J = 0.9, 2.3, 8.1 Hz), 7.07(2H, d, J = 9.1 Hz), 7.45(1H, t, J = 8.1 Hz), 7.61-7.71(3H, m), 7.91-7.97(1H, m), 10.33(1H, s), 10.92(1H, s) |

TABLE 154-continued

| Ex | Syn | Data |
|---|---|---|
| 64 | E1 | ESI+: 516<br>1H-NMR(DMSO-d6): 1.03(3H, d, J = 6.1 Hz), 1.32(3H, t, J = 7.5 Hz), 2.04-2.13(1H, m), 2.16-2.26(5H, m), 2.54-2.63(1H, m), 2.73-2.79(1H, m), 2.84(2H, q, J = 7.5 Hz), 3.25-3.35(2H, m), 5.77(1H, dd, J = 2.0, 10.0 Hz), 6.26(1H, dd, J = 2.0, 17.0 Hz), 6.44(1H, dd, J = 10.0, 17.0 Hz), 6.57(2H, d, J = 9.1 Hz), 6.96(1H, ddd, J = 0.9, 2.3, 8.1 Hz), 7.07(2H, d, J = 9.1 Hz), 7.45(1H, t, J = 8.1 Hz), 7.61-7.71(3H, m), 7.91-7.97(1H, m), 10.33(1H, s), 10.92(1H, s) |
| 65 | E1 | ESI+: 499 |
| 66 | E1 | ESI+: 559 |
| 67 | E1 | ESI+: 504 |
| 68 | E1 | ESI+: 491 |
| 69 | E1 | ESI+: 561<br>1H-NMR(DMSO-d6): 1.25(3H, t, J = 7.6 Hz), 1.42-1.89(8H, m), 2.14(3H, s), 2.20-2.38(5H, m), 2.43-3.03(9H, m), 3.18-3.67(4H, m), 4.12-4.23(1H, m), 4.51-4.60(1H, m), 5.68(1H, dd, J = 2.5 Hz, 10.4 Hz), 6.12(1H, dd, J = 2.5 Hz, 16.6 Hz), 6.82-6.93(3H, m), 7.46(2H, d, J = 9.1 Hz), 7.78-7.81(1H, m), 8.07-8.12(1H, m), 10.78(1H, s) |
| 70 | E1 | ESI+: 500 |
| 71 | E1 | ESI+: 570 |
| 72 | E1 | ESI+: 480 |
| 73 | E1 | ESI+: 480<br>1H-NMR(DMSO-d6): 1.16(3H, t, J = 7.5 Hz), 2.14-2.37(5H, m), 2.42-2.69(6H, m), 3.04-3.12(4H, m), 3.40-3.99(4H, m), 5.47-5.57(1H, m), 5.62-5.72(1H, m), 6.10-6.19(1H, m), 6.49-6.68(1H, m), 6.94(2H, d, J = 9.0 Hz), 7.41-7.49(2H, m), 7.54-7.59(1H, m), 7.81-7.86(1H, m), 10.95-11.02(1H, m) |

TABLE 155

| Ex | Syn | Data |
|---|---|---|
| 74 | E1 | ESI+: 505 |
| 75 | E75 | ESI+: 476 |
| 76 | E1 | ESI+: 520 |
| 77 | E1 | ESI+: 536, 538 |
| 78 | E1 | ESI+: 516 |
| 79 | E1 | ESI+: 577<br>1H-NMR(DMSO-d6): 1.13(3H, t, J = 7.4 Hz), 1.42-2.08(8H, m), 2.14(3H, s), 2.20-2.70(13H, m), 3.01-4.14(6H, m), 5.02-5.11(1H, m), 5.45-5.72(1H, m), 5.97-6.12(1H, m), 6.47-6.95(3H, m), 7.35-7.44(2H, m), 7.51-7.57(1H, m), 7.78-7.85(1H, m), 10.92-10.99(1H, m) |
| 80 | E1 | ESI+: 591<br>1H-NMR(DMSO-d6): 1.13(3H, t, J = 7.4 Hz), 1.47-2.07(8H, m), 2.14(3H, s), 2.19-2.69(16H, m), 2.98-4.23(6H, m), 5.06-5.13(1H, m), 5.43-5.72(1H, m), 5.95-6.11(1H, m), 6.48-6.92(1H, m), 6.97(1H, d, J = 8.6 Hz), 7.28-7.35(1H, m), 7.38-7.42(1H, m), 7.55-7.60(1H, m), 7.82-7.86(1H, m), 11.04-11.08(1H, m) |
| 81 | E1 | ESI+: 520 |
| 82 | E1 | ESI+: 520<br>1H-NMR(DMSO-d6): 1.32(3H, t, J = 7.5 Hz), 2.21(3H, s), 2.38-2.45(4H, m), 2.86(2H, q, J = 7.5 Hz), 2.93-3.01(4H, m), 5.78(1H, dd, J = 2.1, 10.0 Hz), 6.26(1H, dd, J = 2.1, 17.0 Hz), 6.41(1H, dd, J = 10.0, 17.0 Hz), 6.59(2H, d, J = 9.1 Hz), 7.02(2H, d, J = 9.1 Hz), 7.45(1H, dd, J = 9.1, 10.1 Hz), 7.62-7.67(1H, m), 7.69-7.73(1H, m), 7.78(1H, dd, J = 2.5, 7.2 Hz), 7.95-8.01(1H, m), 10.36(1H, s), 10.93(1H, s) |
| 83 | E1 | ESI+: 503 |
| 84 | E1 | ESI+: 536, 538 |
| 85 | E1 | ESI+: 491 |
| 86 | E1 | ESI+: 570 |
| 87 | E1 | ESI+: 491 |
| 88 | E1 | ESI+: 556 |
| 89 | E1 | ESI+: 577 |
| 90 | E1 | ESI+: 591 |
| 91 | E8 | ESI+: 488 |
| 92 | E1 | ESI+: 516 |
| 93 | E1 | ESI+: 516 |
| 94 | E1 | ESI+: 550 |
| 95 | E1 | ESI+: 501 |
| 96 | E3 | ESI+: 558 |
| 97 | E1 | ESI+: 564 |

TABLE 156

| Ex | Syn | Data |
|---|---|---|
| 98 | E1 | ESI+: 598 |
| 99 | E1 | ESI+: 576 |
| 100 | E1 | ESI+: 576 |
| 101 | E1 | ESI+: 562 |
| 102 | E1 | ESI+: 479 |
| 103 | E1 | ESI+: 583 |
| 104 | E1 | ESI+: 562 |
| 105 | E1 | ESI+: 509 |
| 106 | E1 | ESI+: 592 |
| 107 | E1 | ESI+: 590 |
| 108 | E1 | ESI+: 479 |
| 109 | E1 | ESI+: 493 |
| 110 | E1 | ESI+: 479 |
| 111 | E1 | ESI+: 497 |
| 112 | E1 | ESI+: 494 |
| 113 | E1 | ESI+: 466 |
| 114 | E1 | ESI+: 478 |
| 115 | E1 | ESI+: 576 |
| 116 | E1 | ESI+: 493 |
| 117 | E1 | ESI+: 549 |
| 118 | E1 | ESI+: 562 |
| 119 | E1 | ESI+: 565 |
| 120 | E1 | ESI+: 582, 584 |
| 121 | E122 | ESI+: 562 |
| 122 | E122 | ESI+: 548 |
| 123 | E122 | ESI+: 548 |
| 124 | E122 | ESI+: 562 |
| 125 | E1 | ESI+: 562 |
| 126 | E1 | ESI+: 576 |
| 127 | E1 | ESI+: 562 |
| 128 | E1 | ESI+: 576 |
| 129 | E1 | ESI+: 480 |
| 130 | E1 | ESI+: 480 |
| 131 | E1 | ESI+: 576 |
| 132 | E1 | ESI+: 590 |
| 133 | E1 | ESI+: 576 |
| 134 | E1 | ESI+: 590 |

TABLE 157

| Ex | Syn | Data |
|---|---|---|
| 135 | E1 | ESI+: 484 |
| 136 | E1 | ESI+: 576 |
| 137 | E1 | ESI+: 576 |
| 138 | E1 | ESI+: 590 |
| 139 | E1 | ESI+: 576 |
| 140 | E1 | ESI+: 590 |
| 141 | E1 | ESI+: 576 |
| 142 | E1 | ESI+: 576 |
| 143 | E1 | ESI+: 590 |
| 144 | E1 | ESI+: 576 |
| 145 | E1 | ESI+: 590 |
| 146 | E1 | ESI+: 576 |
| 147 | E1 | ESI+: 590 |
| 148 | E1 | ESI+: 576 |
| 149 | E1 | ESI+: 590 |
| 150 | E1 | ESI+: 604 |
| 151 | E1 | ESI+: 590 |
| 152 | E1 | ESI+: 568, 570 |
| 153 | E1 | ESI+: 612, 614 |
| 154 | E1 | ESI+: 590 |
| 155 | E1 | ESI+: 604 |
| 156 | E1 | ESI+: 611 |
| 157 | E1 | ESI+: 590 |
| 158 | E1 | ESI+: 576 |
| 159 | E1 | ESI+: 590 |
| 160 | E1 | ESI+: 610 |
| 161 | E1 | ESI+: 577 |
| 162 | E1 | ESI+: 559 |
| 163 | E1 | ESI+: 590 |
| 164 | E1 | ESI+: 604 |

TABLE 157-continued

| Ex | Syn | Data |
|---|---|---|
| 165 | E1 | ESI+: 604 |
| 166 | E1 | ESI+: 590 |
| 167 | E1 | ESI+: 604 |
| 168 | E1 | ESI+: 516 |
| 169 | E1 | ESI+: 591 |
| 170 | E1 | ESI+: 538 |
| 171 | E1 | ESI+: 509 |
| 172 | E1 | ESI+: 576 |

TABLE 158

| Ex | Syn | Data |
|---|---|---|
| 173 | E1 | ESI+: 606 |
| 174 | E1 | ESI+: 620 |
| 175 | E1 | ESI+: 634 |
| 176 | E1 | ESI+: 576 |
| 177 | E1 | ESI+: 503 |
| 178 | E1 | ESI+: 536, 538 |
| 179 | E1 | ESI+: 570, 572 |
| 180 | E1 | ESI+: 562 |
| 181 | E1 | ESI+: 532 |
| 182 | E1 | ESI+: 549 |
| 183 | E1 | ESI+: 563 |
| 184 | E1 | ESI+: 527 |
| 185 | E1 | ESI+: 532 |
| 186 | E1 | ESI+: 532 |
| 187 | E1 | ESI+: 607 |
| 188 | E1 | ESI+: 520 |
| 189 | E1 | ESI+: 426 |
| 190 | E1 | ESI+: 426 |
| 191 | E1 | ESI+: 516 |
| 192 | E192 | ESI+: 532 |
| 193 | E1 | ESI+: 577 |
| 194 | E1 | ESI+: 595 |
| 195 | E1 | ESI+: 559 |
| 196 | E1 | ESI+: 577 |
| 197 | E1 | ESI+: 553 |
| 198 | E1 | ESI+: 571 |
| 199 | E1 | ESI+: 577 |
| 200 | E1 | ESI+: 577 |
| 201 | E1 | ESI+: 527 |
| 202 | E1 | ESI+: 575 |
| 203 | E1 | ESI+: 537 |
| 204 | E1 | ESI+: 603 |
| 205 | E205 | ESI+: 532 |
| 206 | E1 | ESI+: 546 |
| 207 | E1 | ESI+: 503 |
| 208 | E1 | ESI+: 605 |
| 209 | E1 | ESI+: 527 |
| 210 | E1 | ESI+: 601 |

TABLE 159

| Ex | Syn | Data |
|---|---|---|
| 211 | E1 | ESI+: 527 |
| 212 | E1 | ESI+: 577 |
| 213 | E1 | ESI+: 577 |
| 214 | E214 | ESI+: 430 |
| 215 | E214 | ESI+: 429 |
| 216 | E1 | ESI+: 590 |
| 217 | E214 | ESI+: 470 |
| 218 | E1 | ESI+: 503 |
| 219 | E1 | ESI+: 522 |
| 220 | E1 | ESI+: 604 |
| 221 | E1 | ESI+: 604 |
| 222 | E1 | ESI+: 591 |
| 223 | E1 | ESI+: 563 |
| 224 | E1 | ESI+: 589 |

TABLE 159-continued
| Ex | Syn | Data |
|---|---|---|
| 225 | E1 | ESI+: 599 |
| 226 | E1 | ESI+: 589 |
| 227 | E1 | ESI+; 535 |
| 228 | E1 | ESI+: 522 |
| 229 | E1 | ESI+: 665 |
| 230 | E1 | ESI+: 590 |
| 231 | E231 | ESI+: 550 |
| 232 | E231 | ESI+: 576 |
| 233 | E231 | ESI+: 592 |
| 234 | E231 | ESI+: 626 |
| 235 | E231 | ESI+: 578 |
| 236 | E253 | ESI+: 576 |
| 237 | E253 | ESI+: 638 |
| 238 | E253 | ESI+: 652 |
| 239 | E253 | ESI+: 682 |
| 240 | E253 | ESI+: 618 |
| 241 | E253 | ESI+: 590 |
| 242 | E253 | ESI+: 652 |
| 243 | E253 | ESI+: 574 |
TABLE 159-continued
| Ex | Syn | Data |
|---|---|---|
| 244 | E231 | ESI+: 564 |
| 245 | E231 | ESI+: 626 |
| 246 | E231 | ESI+: 576 |
| 247 | E231 | ESI+: 576 |
| 248 | E231 | ESI+: 590 |
TABLE 160
| Ex | Syn | Data |
|---|---|---|
| 249 | E231 | ESI+: 590 |
| 250 | E231 | ESI+: 592 |
| 251 | E231 | ESI+: 592 |
| 252 | E253 | ESI+: 590 |
| 253 | E253 | ESI+: 602 |
| 254 | E231 | ESI+: 576 |
TABLE 161
| No | Str |
|---|---|
| A1 | 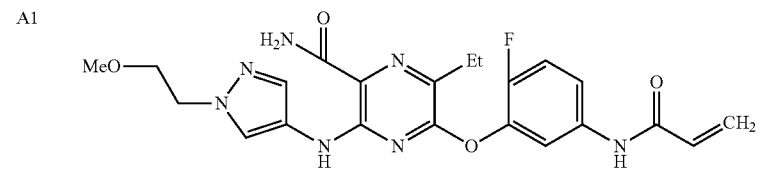 |
| A2 | 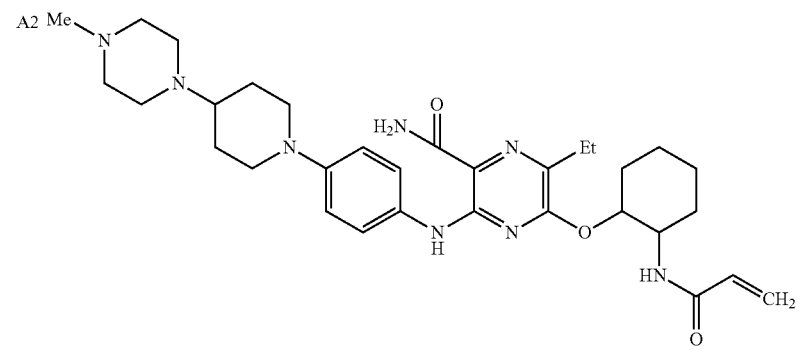 |
| A3 | 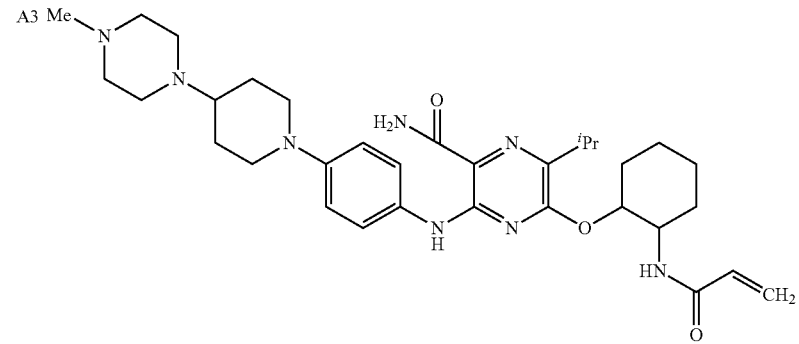 |

INDUSTRIAL APPLICABILITY

The compound of the formula (I) or a salt thereof has an inhibitory action on an EGFR T790M mutation kinase and an inhibitory action on EGFR T790M mutation protein-dependent cell proliferation, and can be used for treatment or the like of EGFR T790M mutation positive cancer, in another embodiment, EGFR T790M mutation positive lung cancer, in still another embodiment, EGFR T790M mutation positive non-small cell lung cancer, in further still another embodiment, EGFR T790M mutation protein positive cancer, in further still another embodiment, EGFR T790M mutation protein positive lung cancer, and the like.

Since the EGFR T790M mutation positive cancer exhibits resistance to the existing EGFR tyrosine kinase inhibitors such as gefitinib and erlotinib, in another embodiment, the compound of the formula (I) or a salt thereof of the present invention can be used for treatment or the like of EGFR tyrosine kinase inhibitor-resistant cancer, in another embodiment, EGFR tyrosine kinase inhibitor-resistant lung cancer, in a still other embodiment, EGFR tyrosine kinase inhibitor-resistant non-small cell lung cancer, and the like.

The invention claimed is:
1. A compound represented by formula (I):

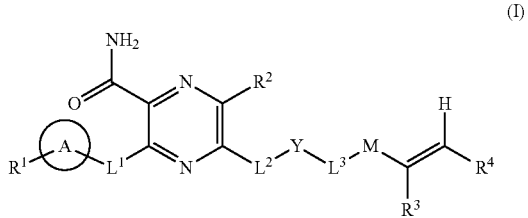

wherein

R$^1$ is lower alkyl which may be substituted, —O-lower alkyl which may be substituted, —NH$_2$, —NH-lower alkyl which may be substituted, —N(lower alkyl which may be substituted)$_2$, -L$^4$-cycloalkyl which may be substituted, -L$^4$-aryl which may be substituted, -L$^4$-aromatic heterocyclic group which may be substituted, or -L$^4$-non-aromatic heterocyclic group which may be substituted, Ring A is arene which may be substituted or aromatic heterocycle which may be substituted, L$^1$ is —O— or —NH—, R$^2$ is H, halogen, —OH, —NR$^5$R$^6$, —CONH$_2$, —CN, -L$^4$-cycloalkyl which may be substituted, -L$^4$-aryl which may be substituted, -L$^4$-aromatic heterocyclic group which may be substituted, -L$^4$-non-aromatic heterocyclic group which may be substituted, lower alkyl which may be substituted, lower alkenyl which may be substituted, or lower alkynyl which may be substituted, L$^2$ is —O—, —S(O)$_P$—, —NH—, —N(CH$_3$)—, —NHCH$_2$—, —NHCH$_2$CH$_2$—, —OCH$_2$—, or a bond, Y is Ring X or a bond, Ring X is cycloalkane which may be substituted, arene which may be substituted, an aromatic heterocycle which may be substituted, or a non-aromatic heterocycle which may be substituted, L$^3$ is —O—, —NH—, —N(lower alkyl which may be substituted)-, —N(cycloalkyl which may be substituted), -lower alkylene which may be substituted-, -lower alkylene which may be substituted-NH—, —NH-lower alkylene which may be substituted-, -lower alkylene which may be substituted-N(lower alkyl which may be substituted)-, —N(lower alkyl which may be substituted)-lower alkylene which may be substituted-, or a bond, M is —C(O)— or —S(O)$_2$—, R$^3$ is H or lower alkyl which may be substituted, R$^4$ is lower alkyl which may be substituted with one or more substituents selected from the group consisting of —OH, halogen, —NH$_2$, —NH-(lower alkyl which may be substituted), —N(lower alkyl which may be substituted)$_2$, and a non-aromatic heterocyclic group which may be substituted, or H, R$^5$ and R$^6$ are the same or different and are each independently H or lower alkyl which may be substituted, each L$^4$ is the same or different and each is independently lower alkylene which may be substituted-, —NH—, —O—, —O-lower alkylene which may be substituted-, -lower alkylene which may be substituted-O—, or a bond, and p represents 0, 1, or 2, or a pharmaceutically acceptable salt thereof.

2. The compound or pharmaceutically acceptable salt thereof according to claim 1, wherein R$^2$ is H, halogen, —OH, —NR$^5$R$^6$, —CN, -L$^4$-cycloalkyl which may be substituted, -L$^4$-aryl which may be substituted, -L$^4$-aromatic heterocyclic group which may be substituted, -L$^4$-non-aromatic heterocyclic group which may be substituted, lower alkyl which may be substituted, lower alkenyl which may be substituted or lower alkynyl which may be substituted, L$^2$ is —O—, —S(O)$_P$— or a bond, and Y is Ring X.

3. The compound or pharmaceutically acceptable salt thereof according to claim 2, wherein R$^2$ is a non-aromatic heterocyclic group which may be substituted, L' is —NH—, R$^2$ is H or lower alkyl, and M is —C(O)—.

4. The compound or pharmaceutically acceptable salt thereof according to claim 3, wherein R$^1$ is piperazinyl which is substituted with lower alkyl, piperidinyl which is substituted with lower alkyl, or piperidinyl substituted with piperazinyl which may be substituted with lower alkyl, Ring A is benzene which may be substituted with one or more substituents selected from the group consisting of halogen, lower alkyl which may be substituted with one or more halogen atoms, and —O-lower alkyl, pyrazole which may be substituted with lower alkyl, imidazole which may be substituted with lower alkyl, or pyrimidine which may be substituted with lower alkyl, and R$^3$ and R$^4$ are each H.

5. The compound or pharmaceutically acceptable salt thereof according to claim 4, wherein L$^2$ is —O— or a bond, Ring X is an aromatic heterocycle, a non-aromatic heterocycle, cycloalkane, or benzene which may be substituted, and L$^3$ is —NH—, —N(lower alkyl)-, or a bond.

6. The compound or pharmaceutically acceptable salt thereof according to claim 5, wherein L$^2$ is —O—, Ring X is an aromatic heterocycle, or benzene which may be substituted, and L$^3$ is —NH— or —N(lower alkyl)-.

7. The compound or pharmaceutically acceptable salt thereof according to claim 5, wherein L$^2$ is —O—, Ring X is a non-aromatic heterocycle, and L$^3$ is a bond.

8. The compound or pharmaceutically acceptable salt thereof according to claim 5, wherein L$^2$ is a bond, Ring X is a non-aromatic heterocycle, and L$^3$ is a bond.

9. The compound or pharmaceutically acceptable salt thereof according to claim 6, wherein Ring X is benzene which may be substituted with lower alkyl, and L$^3$ is —NH—.

10. The compound or pharmaceutically acceptable salt thereof according to claim 7, wherein Ring X is pyrrolidine or piperidine.

11. The compound or pharmaceutically acceptable salt thereof according to claim 8, wherein Ring X is piperidine or tetrahydropyridine.

12. The compound or pharmaceutically acceptable salt thereof according to claim 1, which is
- 5-[3-(acryloylamino)phenoxy]-6-ethyl-3-{[4-(4-methylpiperazin-1-yl)phenyl]amino}pyrazine-2-carboxamide,
- 5-(3-{[(2E)-4-(dimethylamino)-2-butenoyl]amino}phenoxy)-6-ethyl-3-{[4-(4-methylpiperazin-1-yl)phenyl]amino}pyrazine-2-carboxamide,
- 5-[3-(acryloylamino)-2-methylphenoxy]-6-ethyl-3-{[4-(4-methylpiperazin-1-yl)phenyl]amino}pyrazine-2-carboxamide,
- 5-[3-(acryloylamino)phenoxy]-6-isopropyl-3-{[4-(4-methylpiperazin-1-yl)phenyl]amino}pyrazine-2-carboxamide,
- 5-(1-acryloylpiperidin-4-yl)-6-ethyl-3-({3-methyl-4-[4-(4-methylpiperazin-1-yl)piperidin-1-yl]phenyl}amino)pyrazine-2-carboxamide,
- 5-[3-(acryloylamino)phenoxy]-3-{[4-(4-methylpiperazin-1-yl)phenyl]amino}pyrazine-2-carboxamide,
- 5-[3-(acryloylamino)phenoxy]-6-ethyl-3-{[4-methoxy-3-(4-methylpiperazin-1-yl)phenyl]amino}pyrazine-2-carboxamide,
- 5-[3-(acryloylamino)phenoxy]-6-ethyl-3-{[4-(4-ethylpiperazin-1-yl)phenyl]amino}pyrazine-2-carboxamide,
- 5-{[(3R)-1-acryloylpyrrolidin-3-yl]oxy}-6-ethyl-3-({4-[4-(4-methylpiperazin-1-yl)piperidin-1-yl]phenyl}amino)pyrazine-2-carboxamide,
- 5-[3-(acryloylamino)phenoxy]-6-isopropyl-3-{[1-(1-methylpiperidin-4-yl)-1H-pyrazol-4-yl]amino}pyrazine-2-carboxamide,
- 5-[3-(acryloylamino)phenoxy]-3-({4-[(3S)-3,4-dimethylpiperazin-1-yl]phenyl}amino)-6-ethylpyrazine-2-carboxamide,
- 5-[3-(acryloylamino)phenoxy]-3-({4-[(3R)-3,4-dimethylpiperazin-1-yl]phenyl}amino)-6-ethylpyrazine-2-carboxamide,
- 5-(1-acryloylpiperidin-4-yl)-6-ethyl-3-({4-[4-(4-methylpiperazin-1-yl)piperidin-1-yl]phenyl}amino)pyrazine-2-carboxamide,
- 5-{[(3R)-1-acryloylpyrrolidin-3-yl]oxy}-6-ethyl-3-{[4-(4-methylpiperazin-1-yl)phenyl]amino}pyrazine-2-carboxamide,
- 5-{[(3R)-1-acryloylpiperidin-3-yl]oxy}-6-ethyl-3-({4-[4-(4-methylpiperazin-1-yl)piperidin-1-yl]phenyl}amino)pyrazine-2-carboxamide,
- 5-{[(3R)-1-acryloylpiperidin-3-yl]oxy}-6-ethyl-3-({3-methyl-4-[4-(4-methylpiperazin-1-yl)piperidin-1-yl]phenyl}amino)pyrazine-2-carboxamide, or
- 5-[5-(acryloylamino)-2-fluorophenoxy]-6-ethyl-3-{[4-(4-methylpiperazin-1-yl)phenyl]amino}pyrazine-2-carboxamide, or a pharmaceutically acceptable salt thereof.

13. A pharmaceutical composition, comprising a compound or pharmaceutically acceptable salt thereof according to claim 12 and a pharmaceutically acceptable excipient.

14. A method for treating cancer in a patient expressing the EGFR T790M mutation, comprising administering an effective amount of a compound or pharmaceutically acceptable salt thereof according to claim 12 to a subject in need thereof.

15. A method for treating lung cancer in a patient expressing the EGFR T790M mutation, comprising administering an effective amount of a compound or pharmaceutically acceptable salt thereof according to claim 12 to a subject in need thereof.

16. A method for treating non-small cell lung cancer in a patient expressing the EGFR T790M mutation, comprising administering an effective amount of a compound or pharmaceutically acceptable salt thereof according to claim 12 to a subject in need thereof.

17. The compound or pharmaceutically acceptable salt thereof according to claim 12, which is
- 5-[3-(acryloylamino)phenoxy]-6-isopropyl-3-{[4-(4-methylpiperazin-1-yl)phenyl]amino}pyrazine-2-carboxamide or a pharmaceutically acceptable salt thereof.

18. The compound or pharmaceutically acceptable salt thereof according to claim 12, which is
- 5-(1-acryloylpiperidin-4-yl)-6-ethyl-3-({3-methyl-4-[4-(4-methylpiperazin-1-yl)piperidin-1-yl]phenyl}amino)pyrazine-2-carboxamide or a pharmaceutically acceptable salt thereof.

19. The compound or pharmaceutically acceptable salt thereof according to claim 12, which is
- 5-{[(3R)-1-acryloylpyrrolidin-3-yl]oxy}-6-ethyl-3-({4-[4-(4-methylpiperazin-1-yl)piperidin-1-yl]phenyl}amino)pyrazine-2-carboxamide or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 9,085,540 B2 | Page 1 of 1 |
| APPLICATION NO. | : 13/990006 | |
| DATED | : July 21, 2015 | |
| INVENTOR(S) | : Matsuya et al. | |

It is certified that error appears in the above-identified patent and that said Letters Patent is hereby corrected as shown below:

In the claims

Column 332, lines 34-35, claim 3:
"wherein $R^2$ is a non-aromatic heterocyclic group which may be substituted, L' is -NH-, $R^2$ is H or lower alkyl, and M is -C(O)-." should read -- wherein $R^1$ is a non-aromatic heterocyclic group which may be substituted, $L^1$ is -NH-, $R^2$ is H or lower alkyl, and M is -C(O)-. --

Signed and Sealed this
Twenty-second Day of December, 2015

Michelle K. Lee
*Director of the United States Patent and Trademark Office*